US007008904B2

(12) United States Patent
Crockett et al.

(10) Patent No.: US 7,008,904 B2
(45) Date of Patent: Mar. 7, 2006

(54) HERBICIDAL COMPOSITIONS CONTAINING GLYPHOSATE AND BIPYRIDILIUM

(75) Inventors: Ron P. Crockett, Vancouver, WA (US); Andrew Dyszlewski, St. Louis, MO (US); Richard M. Kramer, St. Louis, MO (US); Domingo C. Riego, Carmel, IN (US); Joseph J. Sandbrink, St. Louis, MO (US); Donald L. Suttner, Chesterfield, MO (US); Dennis H. Williamson, Morrisville, NC (US); Daniel R. Wright, St. Louis, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 107 days.

(21) Appl. No.: 10/204,094

(22) PCT Filed: Feb. 13, 2001

(86) PCT No.: PCT/US01/28617

§ 371 (c)(1),
(2), (4) Date: Dec. 2, 2002

(87) PCT Pub. No.: WO02/21924

PCT Pub. Date: Mar. 21, 2002

(65) Prior Publication Data
US 2005/0239652 A1 Oct. 27, 2005

Related U.S. Application Data

(60) Provisional application No. 60/232,508, filed on Sep. 13, 2000.

(51) Int. Cl.
*A01N 43/40* (2006.01)
*A01N 43/90* (2006.01)
*A01N 57/02* (2006.01)

(52) U.S. Cl. .................. 504/128; 504/206; 504/235; 504/250

(58) Field of Classification Search ................ 504/128, 504/206, 235, 250
See application file for complete search history.

(56) References Cited

U.S. PATENT DOCUMENTS

| 2,764,602 | A | 9/1956 | Ahlbrecht |
| 2,764,603 | A | 9/1956 | Ahlbrecht |
| 2,803,656 | A | 8/1957 | Ahlbrecht et al. |
| 3,147,064 | A | 9/1964 | Brown, et al. |
| 3,255,131 | A | 6/1966 | Ahlbrecht |
| 3,450,755 | A | 6/1969 | Ahlbrecht |
| 3,505,377 | A | 4/1970 | Morehouse |
| 3,799,758 | A | 3/1974 | Franz |
| 4,042,522 | A | 8/1977 | Falk |
| 4,069,158 | A | 1/1978 | Bertocchio et al. |
| 4,069,244 | A | 1/1978 | Mueller |
| 4,090,967 | A | 5/1978 | Falk |
| 4,161,602 | A | 7/1979 | Mueller |
| 5,196,044 | A | 3/1993 | Caulder et al. |
| 5,389,598 | A | 2/1995 | Berk et al. |
| 5,504,054 | A | 4/1996 | Murphy |
| 5,532,205 | A | 7/1996 | Baylis |
| 5,536,700 | A | 7/1996 | Woodard et al. |
| 5,558,806 | A | 9/1996 | Policello et al. |
| 5,561,099 | A | 10/1996 | Murphy et al. |
| 5,563,111 | A | 10/1996 | Hioki et al. |
| 5,622,911 | A | 4/1997 | Hasebe et al. |
| 5,658,852 | A | 8/1997 | Murphy et al. |
| 5,665,679 | A | 9/1997 | McInnes |
| 5,703,015 | A | 12/1997 | Berger et al. |
| 5,750,468 | A | 5/1998 | Wright et al. |
| 5,849,663 | A | 12/1998 | Hasebe et al. |
| 5,863,909 | A | 1/1999 | Kurita et al. |
| 5,985,794 | A | 11/1999 | Hasebe et al. |
| 5,985,798 | A | 11/1999 | Crudden |
| 5,998,331 | A | 12/1999 | Policello |
| 5,998,332 | A | 12/1999 | Sato et al. |
| 6,030,923 | A | 2/2000 | Okano et al. |
| 6,040,272 | A | 3/2000 | Riego et al. |
| 6,063,733 | A | 5/2000 | Berger et al. |
| 6,093,679 | A | 7/2000 | Azuma et al. |
| 6,117,820 | A | 9/2000 | Cutler et al. |
| 2002/0123430 | A1 * | 9/2002 | Xu et al. .................... 504/206 |

FOREIGN PATENT DOCUMENTS

| CN | 1232614 | * 10/1999 |
| CN | 1232614 A | 10/1999 |
| EP | 0 483 095 A2 | 4/1992 |
| EP | 0 531 269 A2 | 3/1993 |
| GB | 785732 | 11/1957 |

(Continued)

OTHER PUBLICATIONS

Translation of Chinese Patent 1232614A, Oct. 26, 1999.*

(Continued)

*Primary Examiner*—S. Mark Clardy
(74) *Attorney, Agent, or Firm*—Senniger Powers; Joseph A. Schaper

(57) ABSTRACT

Herbicidal compositions are provided which cause rapid symptomology while delivering long term control of regrowth of plants. The herbicidal compositions comprise N-phosphonomethylglycine or a herbicidal derivative thereof, a bipyridilium or a herbicidal derivative thereof, and at least one surfactant. A herbicidal spray composition is preparable from a particulate solid concentrate or a liquid concentrate. Also provided is a method for killing or controlling the growth of plants comprising the step of contacting the foliage of said plants with an aqueous herbicidal composition of the invention.

115 Claims, No Drawings

FOREIGN PATENT DOCUMENTS

| GB | 2 169 806 A | 7/1986 |
|---|---|---|
| JP | 10-1679915 A | 6/1998 |
| WO | WO 96/31121 A1 | 10/1996 |
| WO | WO 97/23281 | 7/1997 |
| WO | WO 97/31535 | 9/1997 |
| WO | WO 98/35561 | 8/1998 |
| WO | WO 01/89302 A2 | 11/2001 |

OTHER PUBLICATIONS

Gaskin, R., et al., "Antagonism of the Foliar Uptake of Glyphosate into Grasses by Organosilicone Surfantants. Part 1: Effects of Plant Species, Formulation, Concentrations and Timing of Application", Pestic. Sci. (1993), 38, pp. 185-192, 0031-613X/93/S06.00, New Zealand Forest Research Institute, Private Bag 3020, Rotorua, New Zealand.

Gaskin, R., et al., "Antagonism of the Foliar Uptake of Glyphosate into Grasses by Organosilicone Surfactants. Part 2: Effects of Surfactant Structure and Glycerol Addition", Pestic. Sci. (1993), 38, pp. 193-200, 0031-613X/93/S06.00, New Zealand Forest Research Institute, Private Bag 3020, Rotorua, New Zealand.

Stevens, P., et al., "Contributions of Stomatal Infiltration and Cuticular Penetration to Enhancements of Foliar Uptake by Surfactants", Pestic. Sci. (1991), 33, pp. 371-382, 0031-613X/91/S03.50, Forest Research Institute, Private Bag 3020, Rotorua, New Zealand.

Stevens, P., "Organosilicone Surfactants as Adjuvants for Agrochemicals", Pestic. Sci. (1993), 38, pp. 103-122, New Zealand Forest Research Institute, Private Bag 3020, Rotorua, New Zealand.

Field, R., et al., "Promotion of Stomatal Infiltration of Glyphosate by an Organosilicone Surfactant Reduces the Critical Rainfall Period", Pestic. Sci. (1988), 24, pp. 55-62, Plant Science Department, Lincoln College, Canterbury, New Zealand.

* cited by examiner

HERBICIDAL COMPOSITIONS CONTAINING GLYPHOSATE AND BIPYRIDILIUM

CROSS-REFERENCE TO RELATED APPLICATIONS

This application is a 35 U.S.C. §371 application of PCT/US01/28617, filed Sep. 13, 2001, which claims priority from U.S. Provisional Patent Application Ser. No. 60/232,508, filed Sep. 13, 2000.

The present invention relates to herbicidal compositions and methods for killing or controlling the growth and proliferation of unwanted plants. The herbicidal compositions of this invention cause early visual symptoms of treatment and/or enhanced effectiveness when applied to the foliage of plants. These compositions comprise N-phosphonomethylglycine, or derivatives thereof, and a bipyridilium or derivatives thereof, with one or more suitable surfactants. The herbicidal compositions found to be useful for this purpose, as well as methods for using them, are described herein.

BACKGROUND OF THE INVENTION

Herbicidal compositions comprising the herbicide N-phosphonomethylglycine or derivatives thereof ("glyphosate") are useful for suppressing the growth of or killing unwanted plants such as grasses, weeds, and the like. Glyphosate typically is applied to the foliage of the target plant. After application the glyphosate is absorbed by the foliar tissue of the plant and translocated throughout the plant. Glyphosate noncompetitively blocks an important biochemical pathway which is common to virtually all plants, but which is absent in animals. Although glyphosate is very effective in killing or controlling the growth of unwanted plants, the uptake (i.e., absorption) of glyphosate by the plant foliar tissue and translocation of glyphosate throughout the plant is relatively slow. Visual symptoms that a plant has been treated with glyphosate may not appear until one week or more after treatment.

Although early visual symptoms of plant treatment generally can be achieved using compositions comprising glyphosate and the contact herbicide pelargonic acid, such compositions have several drawbacks. First, they require high application rates of the pelargonic acid. Second, they often do not permanently kill plants. Pelargonic acid attacks the plant very rapidly so that the glyphosate may have insufficient time to translocate into the plant and completely kill the plant. This drawback is particularly evident when the compositions are used to treat perennial plants such as, but not limited to, Johnsongrass. Third, the compositions are difficult to prepare in a stable formulation; the formulations frequently settle or solidify. Even a tank mix requires essentially constant agitation to prevent the pelargonic acid from separating out. Fourth, pelargonic acid is difficult to formulate in a concentrate, therefore, compositions of glyphosate and pelargonic acid are typically sold in dilute "ready-to-use" formulations.

U.S. Pat. No. 5,196,044 discloses herbicidal compositions comprising, for example, glyphosate that are claimed to reduce the time required for systemic phytotoxic symptoms to appear on the target weed. These herbicidal compositions comprise a first ingredient comprising a fatty acid or mixture of fatty acids such as pelargonic acid, also known as nonanoic acid, (the active ingredient in the contact herbicide SCYTHE®) and a second ingredient selected from a group of herbicides including glyphosate and paraquat. Scythe® has been observed to rapidly burn plant foliage. A too rapid burn may not allow for the complete translocation of glyphosate throughout the plant. As a result, the plant may later recover and continue growing.

Compositions comprising glyphosate are generally formulated with one or more surfactants to enhance their effectiveness for foliar application. When water is added to a composition formulated with surfactants, the resulting sprayable composition more easily and effectively covers the foliage (e.g., the leaves or other photosynthesizing organs) of plants. Glyphosate salts, for example, have been formulated with surfactants such as polyoxyalkylene-type surfactants including, among other surfactants, polyoxyalkylene alkylamines. Commercial formulations of glyphosate herbicide marketed under the trademark ROUNDUP® have been formulated by Monsanto with such a polyoxyalkylene alkylamine, in particular a polyoxyethylene tallowamine, identified as MON 0818. Glyphosate similarly has been formulated with polyoxyalkylene polysiloxane surfactants, in particular polyoxyethylene trisiloxane surfactants, such as the commercial organosilicone surfactant Silwet®L-77, available from Crompton Corporation. Among the numerous studies of the foliar uptake of glyphosate herbicide combined with Silwet® L-77 are those reported by Field & Bishop in *Pesticide Science,* 1988, Vol. 24, pp. 55–62; Stevens et al. in *Pesticide Science,* 1991, Vol. 33, pp. 371–82; Gaskin & Stevens in *Pesticide Science,* 1993, Vol. 38, pp. 185–92; and Gaskin & Stevens in *Pesticide Science,* 1993, Vol. 38, pp. 193–200. An extensive review of 160 references relating to the use of organosilicones as adjuvants for agrochemicals was provided by Stevens in *Pesticide Science,* 1993, Vol. 38, pp. 103–22. In fact, so many studies are reported in this area that OSi Specialties has published a *Bibliography of Silwet® Organosilicone Surfactants As Agricultural Adjuvants* (1996), which is indexed for computer searching. This reference lists hundreds of published studies of commercial organosilicone surfactants in agricultural applications. This bibliography is available to the public through the publisher's office in Tarrytown, N.Y.

WO 98/35561 discloses aqueous herbicidal compositions useful for controlling woody plants when applied to the bark. These compositions comprise glyphosate and a surfactant composition that comprises one or more polyoxyalkylene trisiloxane surfactants and one or more glycols or glycol ethers.

WO 97/23281 discloses surfactant blends comprising organosilicone compounds and a water-soluble surfactant characterized by hydrophobic groups having from about 4 to about 12 atoms. These surfactant blends are useful as spreading agents for the delivery of agriculturally active ingredients such as herbicides.

EP 0 483 095 A2 discloses aqueous compositions comprising glyphosate, the organosilicone SILWET L-77®, and either propylene glycol, dipropylene glycol or polyethylene glycol.

EP 0 531 269 A2 discloses aqueous compositions comprising glyphosate, the organosilicone SILWET L-77®, and an acetylenic diol.

Herbicidal compositions comprising the herbicide dihydrodipyrido(1,2-a:2',1'-c)pyrazinediium or derivatives thereof ("diquat") or another bipyridilium, paraquat, also are useful for suppressing the growth of or killing unwanted grasses, weeds, and the like. This contact herbicide typically is applied to the foliage of the target plant and causes rapid disruption of plant cell membranes. It primarily is used as a herbicide to control weeds in noncrop and aquatic areas. Visual symptoms that a plant has been treated with diquat typically appear within 1 to 3 days of application, depending on environmental conditions.

Herbicidal compositions comprising diquat may comprise one or more surfactants. For example, U.S. Pat. No. 5,665,679 discloses compositions containing diquat dibromide and organosilicone surfactants such as Kinetic™, an organosilicone surfactant available from Setre Chemical.

U.S. Pat. Nos. 5,561,099 and 5,658,852 disclose an oil-based agricultural adjuvant comprising an organosilicone compound and a carrier oil. The adjuvant can be used as a spreading agent in combination with herbicides including, but not limited to, glyphosate and diquat.

U.S. Pat. No. 5,504,054 discloses a group of low foaming, superspreading trisiloxane silicone surfactants useful in aqueous spray mixtures comprising herbicides including, but not limited to, glyphosate and diquat.

U.S. Pat. No. 5,558,806 discloses a polyalkyleneoxide polysiloxane surfactant useful as an adjuvant for dispersing, wetting, spreading, and enhancing the efficacy of a herbicide, including, but not limited to, glyphosate and diquat.

U.S. Pat. No. 5,536,700 discloses herbicidal compositions comprising an aryl-5-haloalkylpyrazole and glyphosate, diquat, paraquat or other herbicides.

U.S. Pat. No. 5,532,205 describes herbicidal compositions containing glyphosate, paraquat or diquat, and a photosystem II inhibitor herbicide. The composition is said to provide early burndown symptoms without excessive reduction in regrowth control as compared to a herbicidal composition containing glyphosate and paraquat or diquat. A composition containing glyphosate and diquat or paraquat in a weight ratio of 20:1 is reported to have produced some early burndown symptoms at the cost of long term or regrowth control. A composition containing significantly less diquat or paraquat is said to provide little by way of visible early burndown symptoms.

Chinese Patent Publication No. 1232614 is said to describe a herbicidal composition containing 41% IPA glyphosate salt and paraquat in a ratio of glyphosate salt to paraquat cation of 25:1 to 2.5:1.

It is an object of the present invention to provide novel herbicidal compositions of glyphosate, a bipyridilium (such as diquat or paraquat) and a surfactant that is of a type and present in a concentration sufficient to allow the plant to uptake a herbicidally effective amount of the glyphosate prior to the substantial onset of bipyridilium induced leaf damage that would prevent or severely reduce further uptake of glyphosate by the plant. Use of such novel compositions for the control of unwanted plants provides rapid bipyridilium symptomology (e.g. rapid burndown) yet with the long term control expected of glyphosate based herbicides.

It is a further object of the invention to provide concentrate liquid and particulate solid formulations of glyphosate, a bipyridilium, and suitable surfactant. Such concentrates can be employed to easily prepare the novel herbicidal compositions of the present invention. A still further object of the present invention is to provide a method of controlling or killing unwanted plants by utilizing the novel herbicidal compositions of the present invention.

SUMMARY OF THE INVENTION

In one aspect, the invention comprises a herbicidal composition useful for controlling vegetation, the composition comprising (a) glyphosate or a herbicidal derivative thereof; and (b) a bipyridilium, such as diquat or paraquat, or a herbicidal derivative thereof; and (c) a suitable surfactant composition comprising one or more surfactant(s). When applied to target foliage the herbicidal composition is characterized by more rapid initial burndown than treatment with glyphosate alone but with comparable long term control.

The herbicidal compositions of the invention can be prepared on site by the end-user shortly before application to the foliage of the vegetation to be killed or controlled by mixing in aqueous solution a glyphosate containing composition; a bipyridilium containing composition, and a suitable surfactant. Such compositions are typically referred to as "tank-mix" compositions.

Alternatively, the compositions of the invention may be provided to the end-user already formulated, either at the desired dilution for application ("ready to use" compositions) or requiring dilution, dispersion, or dissolution in water by the end-user ("concentrate" compositions). Such preformulated concentrates can be liquids or particulate solids.

Suitable surfactant compositions useful in the present inventions are of a type and present in a concentration sufficient to allow the plant to uptake a herbicidally effective amount of the glyphosate prior to the substantial onset of bipyridilium induced leaf damage that would prevent or severely reduce further uptake and translocation of glyphosate by the plant. Particularly preferred surfactants are of the "superspreading" or "superwetting" type described in more detail herein.

An additional aspect of the invention comprises a method for preparation of the particulate solid concentrates of the invention.

A method of use of the herbicidal compositions of the invention for controlling the growth and/or proliferation of unwanted plants is also provided.

DETAILED DESCRIPTION OF THE INVENTION

According to the present invention, herbicidal compositions containing glyphosate, a bipyridilium and a suitable surfactant are provided that allow for rapid uptake by the target plant, early visual symptoms of plant treatment, and control of a broad spectrum of plant species. The following discussion sets forth in detail the compositions and methods of the present invention, through which good control of growth and proliferation of plants is achieved by foliar application of a herbicidal composition comprising glyphosate, a bipyridilium, and one or more suitable surfactants, as more fully described below.

These compositions further provide other advantages in addition to early visual symptoms of treatment. For example, the novel compositions enhance the potency of the bipyridilium applied. As a result, lower application rates can be used for the bipyridilium and/or the surfactants applied without a loss of effectiveness of plant control.

In addition, the novel compositions can be prepared as spray compositions such as ready-to-use or tank mixes or from concentrates. These concentrates can be either liquid or a particulate solid. Additionally, both glyphosate and diquat separately have aquatic clearance, i.e. are approved for use on foliage in water. Further, the novel compositions of the invention provide better long term control and less regrowth than glyphosate-nonanoic acid compositions.

The compositions of the present invention comprise at least two herbicides (glyphosate and a bipyridilium), and at least one surfactant. A first component of the compositions of the present invention is N-phosphonomethylglycine ("glyphosate"), a salt, adduct or ester thereof, or a compound which is converted to glyphosate in plant tissues or which otherwise provides glyphosate ion. The term "glyphosate" when used herein is to be understood to encompass such derivatives unless the context requires otherwise.

Glyphosate salts that can be used according to this invention include but are not restricted to alkali metal salts, for example the mono-, di-, and trisodium salts and the mono-, di-, and tripotassium salts; monoammonium and diammonium salts; alkylamine salts, for example $C_{1-6}$ alkylamine salts such as the dimethylamine and isopropylamine salts; alkylammonium salts, for example $C_{1-16}$ alkylammonium salts such as the dimethylammonium and isopropylammonium salts; alkanolamine salts, for example $C_{1-6}$ alkanolamine salts such as the monoethanolamine salt; alkylsulfonium salts, for example the trimethylsulfonium salt; sulfoxonium salts; and mixtures thereof. The herbicidal compositions sold by Monsanto Company as the ACCORD® herbicide contain the monoisopropylamine ("IPA") salt of N-phosphonomethylglycine. The herbicidal compositions sold by Monsanto Company as ROUNDUP GEOFORCE® contain the monosodium salt of N-phosphonomethylglycine. The herbicidal compositions sold by Monsanto Company as ROUNDUP FULL® and ROUNDUP MAX® contain the monoethanolamine salt of glyphosate. The herbicidal compositions sold by Syngenta Corporation as TOUCHDOWN® contain the trimethylsulfonium salt of N-phosphonomethylglycine and TOUCHDOWN IQ® contains the diammonium salt of N-phosphonomethylglycine. Especially preferred glyphosate salts include the potassium salt, isopropylamine salt, ammonium salt, monoethanolamine salt, and trimethylsulfonium salt. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Various salts of N-phosphonomethylglycine are commercially significant in part because they are water soluble. Many of the salts listed immediately above are highly water soluble, thereby allowing for highly concentrated solutions that can be diluted at the site of use. In accordance with the methods of this invention as they pertain to glyphosate herbicide, a solution containing a herbicidally effective amount of glyphosate and other components in accordance with the invention is applied to foliage of plants.

The relative amount of glyphosate present in a contemplated herbicidal composition, particulate solid concentrate, or liquid concentrate will vary depending upon many factors including the plant species to be controlled and the method of application. The glyphosate concentration present in the herbicidal compositions of the invention is sufficient to provide at least 70% control of plant regrowth within 50 days after application of the composition to a plant, and more preferably at least 75%, 80% or 85% control or more within 50 to 55 days after application to the plant.

A bipyridilium is the second component of the compositions of the present invention. Bipyridiliums are the general class of herbicides that include diquat and paraquat. Compounds in this class are characterized by very rapid symptomology. It is believed that the rapid symptomology of the bipyridiliums is a result of their ability to react with photosynthetic mechanisms in plants. The production of superoxides and hydrogen peroxides leads to massive disruption of cells and their physiological processes in any tissues that are contacted. The mode of action of diquat and other members of this class is described in the Herbicide Handbook of WSSA, $7^{th}$ Edition, 1994. Both diquat and paraquat are tightly bound to soil.

The preferred bipyridilium present in the herbicidal compositions of the present invention is Diquat [6,7-dihydrodipyrido (1,2-a:2', 1'-c)pyrazinediium], a salt or adduct thereof, or a compound which otherwise provides the diquat cation. The term "diquat" when used herein is to be understood to encompass such derivatives unless the context requires otherwise. Other commercial names for diquat include Aquacide™, Dextrone™, Reward®, Reglone®, and Weedtrine D™. Diquat salts that can be used according to this invention include but are not restricted to halide salts, for example the dichloride, difluoride and dibromide salts; and mixtures thereof. For example, and not by way of limitation, Syngenta Corporation sells the dibromide salt of dihydrodipyrido (1,2-a:2',1'-c)pyrazinediium ("diquat dibromide") under the name REWARD® or REGLONE® in the form of a composition comprising 37.3% diquat dibromide and 62.7% inert ingredients wherein two pounds of diquat cation are found in a solution having 3.73 pounds of diquat dibromide per gallon. The herbicidal properties of diquat and its derivatives were disclosed on pages 108–110 of WSSA Herbicide Handbook, 1994 (7th Edition) and patented in British Patent 785,732 (1955). The disclosures of both of these references are hereby incorporated by reference.

Salts of diquat are commercially significant in part because they are water soluble. The salts listed immediately above are highly water soluble, thereby allowing for highly concentrated solutions that can be diluted at the site of use. In accordance with the methods of this invention, a herbicidal composition containing glyphosate, diquat, surfactant and optionally other components in accordance with the invention is applied to foliage of plants.

The relative amount of diquat present in a contemplated herbicidal spray composition, particulate solid concentrate, or liquid concentrate varies depending upon many factors including the plant species to be controlled and the method of application. The mixtures or coformulations of the present invention likewise may employ another herbicide in addition to glyphosate and diquat, such as glufosinate and/or paraquat.

In lieu of diquat, a less preferred bipyridilium that may be used is 1,1'-Dimethyl-4,4'-bipyridinium dichloride (paraquat dichloride), a salt or adduct thereof, or a compound which otherwise provides the paraquat cation. The term "paraquat" when used herein is to be understood to encompass such derivatives unless the context requires otherwise. Other commercial names for paraquat include Crisquat™, Cyclone™, Dexuron™, Gramoxone Extra™, Herbaxone™, Ortho™ Weed and Spot Killer and Sweep™. Paraquat has been formulated with other herbicides, including Simazine and diquat dibromide. The dimethyl sulfate salt of paraquat has been commercialized. Paraquat has been widely used for weed control. It also has been employed as a crop desiccant and defoliant, and as a terrestrial herbicide.

The relative amount of paraquat present in a contemplated herbicidal spray composition, particulate solid concentrate or liquid concentrate varies depending upon many factors including the plant species to be controlled and the method of application. The mixtures or coformulations of the present invention likewise may employ another herbicide in addition to glyphosate and paraquat, such as glufosinate and/or diquat. The bipyridilium concentration present in the herbicidal compositions of the invention is sufficient to provide visual symptoms of herbicidal treatment within 3 days after application of the composition to a plant, and more preferably within 2 days or 24 hours after application to the plant. However, the bipyridilium concentration is also such that it is not substantially antagonistic to the herbicidal activity of the glyphosate within the herbicidal composition. The bipyridilium concentration present in the herbicidal compositions of the invention is sufficient to provide visual symptoms of herbicidal treatment within 3 days after application of the composition to a plant, and more preferably within 2 days or 24 hours after application to the plant. However, the bipyridilium concentration is also such that it is not substantially antagonistic to the herbicidal activity of the glyphosate within the herbicidal composition.

The surfactant component of the composition of the present invention when applied with the above-mentioned herbicidal components of the invention is of the type and present in a sufficient concentration to allow the plant to uptake and translocate a herbicidally effective amount of glyphosate prior to the substantial onset of bipyridilium induced leaf damage that would prevent or severely reduce further uptake and translocation of glyphosate by the plant. One way to accomplish this is to provide more intimate contact between the applied herbicidal composition and the microtopographically rough surface of the plant, for example by flattening the contact angle of the composition, so as to permit the composition to spread into crevices and pores in the plant. However, other modes of enhancement are also possible. For example, the surfactant composition should preferably also enhance sticking or adhesion to a plant surface when used in aqueous solution, and it should allow the solution to dry on a time scale that is effective to permit penetration. It has been found that surfactant compositions containing either polyoxyalkylene trisiloxane surfactants, with optional additional ingredients, or certain combinations of a polyoxyalkylene trisiloxane surfactant and one or more glycols, with optional additional ingredients, can meet these requirements. It has also been found that surfactant compositions including alkoxylated alkylamines, alkoxylated etheramines or alkoxylated etheramine oxides in combination with other surfactants can meet these requirements.

Various surfactants have been found to be effective in formulating herbicidal compositions and concentrates of the invention, particularly in formulating compositions and concentrates containing potassium, ammonium or diammonium glyphosate.

Cationic surfactants effective in forming herbicide formulations include:

(a) aminated alkoxylated alcohol having the formula:

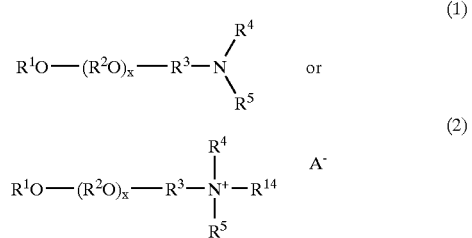

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, —$(R^6)_n$—$(R^2O)_yR^7$, —C(=NR$^{11}$)NR$^{12}$R$^{13}$, —C(=O)NR$^{12}$R$^{13}$, —C(=S)NR$^{12}$R$^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, —$(R^6)_n$—$(R^2O)_yR^7$, —C(=NR$^{11}$)NR$^{12}$R$^{13}$, —C(=O)NR$^{12}$R$^{13}$, —C(=S)NR$^{12}$R$^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, —$(6)_n$—$(R^2O)_yR^7$, —C(=NR$^{11}$)NR$^{12}$R$^{13}$, —C(=O)NR$^{12}$R$^{13}$, or —C(=S)NR$^{12}$R$^{13}$, n is 0 or 1, x and y are independently an average number from 1 to about 60, and A— is an agriculturally acceptable anion. In this context, preferred $R^1$, $R^3$, $R^4$, $R^5$, $R^6$, $R^{11}$, $R^{12}$ and $R^{13}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^3$ is linear alkylene, preferably ethylene, and $R^1$, $R^2$, $R^4$ and $R^5$ are as previously defined. In another embodiment, $R^4$ is H, alkyl, or —$R^2OR^7$ and $R^1$, $R^2$, $R^3$, $R^5$ and $R^7$ are as previously defined. In yet another embodiment, $R^1$ is a linear or branched alkyl or linear or branched alkenyl group having from about 8 to about 25 carbon atoms, $R^2$ in each of the x ($R^2O$) groups is independently $C_2$–$C_4$ alkylene, $R^3$ is a linear or branched alkylene group having from 1 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 1 to about 4 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are methyl, and x is an average number from about 4 to about 20. Compounds of formula (2) have the preferred groups as described above and $R^{14}$ is preferably hydrogen or a linear or branched alkyl or alkenyl group, more preferably alkyl, and most preferably methyl. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{16-18}$ ether dimethyl propylamines and PEG 10, 15 or 20 or 25 $C_{16-18}$ ether dimethyl propylamines (from Tomah).

(b) hydroxylated amines having the formula:

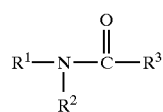

(3)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl. In this context, preferred $R^1$ and $R^2$ hydrocarbyl groups are linear or branched alkyl, linear or branched alkenyl, linear or branched alkynyl, aryl, or aralkyl groups. Preferably, the hydroxylated amines have the formula:

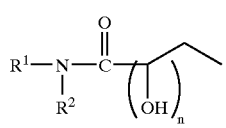

(4)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and n is 1 to about 8. In this context, preferred $R^1$ and $R^2$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ is hydrogen, a linear or branched alkyl or linear or branched alkenyl group having from 1 to about 30 carbon atoms, and n is about 4 to about 8; or $R^1$ and $R^2$ are independently linear or branched alkyl or linear or branched alkenyl groups having from about 4 to about 30 carbon atoms and n is about 4 to about 8. More preferably, $R^1$ is a linear or branched alkyl or linear or branched alkenyl group having from about 8 to about 22 carbon atoms, $R^2$ is hydrogen or a linear or branched alkyl or linear or branched alkenyl group having from 1 to about 6 carbon atoms, and n is about 4 to about 8; or $R^1$ and $R^2$ are independently linear or branched alkyl or linear or branched alkenyl groups having from about 4 to about 8 carbon atoms, and n is about 4 to about 8.

(c) diamines having the formula:

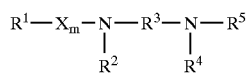

(5)

wherein $R^1$, $R^2$ and $R^5$ are independently hydrogen or hydrocarbyl or substituted hydrocarbyl having from 1 to about 30 carbon atoms or —$R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is —C(O)— or —SO$_2$—. In this context, preferred $R^1$, $R^2$, $R^3$, $R^4$, $R^5$ and $R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$ and $R^5$ are independently hydrogen, a linear or branched alkyl or alkenyl group having from 1 to about 6 carbon atoms, and $R^3$ is a linear or branched alkylene having from 2 to about 6 carbon atoms. More preferably, $R^1$, $R^2$, $R^4$ and $R^5$ are independently hydrogen, or a linear or branched alkyl group having from 1 to about 6 carbon atoms, and $R^3$ is a linear or branched alkylene having from 2 to about 6 carbon atoms. Most preferably, $R^1$, $R^2$, $R^4$, and $R^5$ are independently hydrogen or methyl, and $R^3$ is ethylene or propylene.

(d) mono- or di-ammonium salts having the formula:

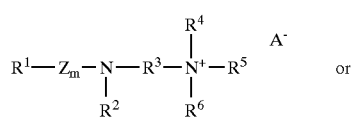

(6)

or

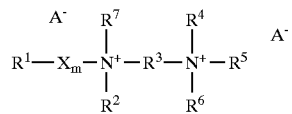

(7)

wherein $R^1$, $R^2$, $R^4$, $R^5$ and $R^7$ are independently hydrogen or hydrocarbyl or substituted hydrocarbyl having from 1 to about 30 carbon atoms or —$R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is C(O)— or —SO$_2$—, Z is —C(O)—, and A$^-$ is an agriculturally acceptable anion. In this context, preferred $R^1$–$R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$, $R^5$ and $R^7$ are independently hydrogen, or a linear or branched alkyl or alkenyl group having from 1 to about 6 carbon atoms, $R^6$ is a linear or branched alkyl or alkenyl group having from about 8 to about 30 carbon atoms, m is 0 or 1, and $R^3$ is a linear or branched alkylene having from 2 to about 6 carbon atoms. More preferably, $R^1$, $R^2$, $R^4$, $R^5$ and $R^7$ are independently hydrogen, or a linear or branched alkyl group having from 1 to about 6 carbon atoms, $R^6$ is a linear or branched alkyl group having from about 8 to about 22 carbon atoms, m is 0 or 1, and $R^3$ is a linear or branched alkylene having from 2 to about 6 carbon atoms. Most preferably, $R^1$, $R^2$, $R^4$, $R^5$ and $R^7$ are independently hydrogen or methyl, $R^6$ is a linear or branched alkyl group having from about 8 to about 18 carbon atoms, m is 0 or 1, and $R^3$ is ethylene or propylene.

(e) poly(hydroxyalkyl)amines having the formula:

(8)

wherein $R^1$ is hydrocarbyl or substituted hydrocarbyl having from about 4 to about 30 carbon atoms or —$R^4OR^5$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, and $R^5$ is hydrogen or hydrocarbyl or substituted hydrocarbyl having from 1 to about 30 carbon atoms. Preferably, the poly(hydroxyalkyl)amines have the formula:

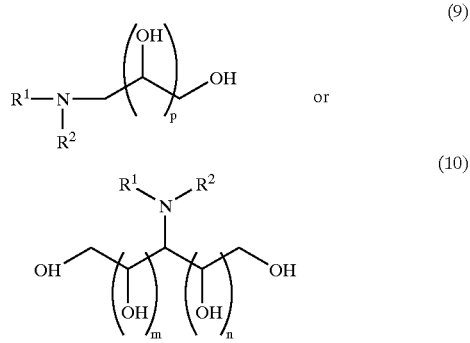
(9)

or (10)

wherein $R^1$ is hydrocarbyl or substituted hydrocarbyl having from about 4 to about 30 carbon atoms or —$R^3OR^4$; $R^2$ is hydrogen or hydrocarbyl or substituted hydrocarbyl having from 1 to about 30 carbon atoms, $R^3$ is hydrocarbylene or substituted hydrocarbylene having from 2 to about 18 carbon atoms, $R^4$ is hydrogen or hydrocarbyl or substituted hydrocarbyl having from 1 to about 30 carbon atoms, m and n are independently integers from 0 to about 7, the sum of m and n is not greater than about 7, and p is an integer from 1 to about 8. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 30 carbon atoms or —$R^3OR^4$, $R^2$ is hydrogen, a linear or branched alkyl or linear or branched alkenyl group having from 1 to about 30 carbon atoms, $R^3$ is a linear or branched alkylene or alkenylene group having from 2 to about 6 carbon atoms, $R^4$ is a linear or branched alkyl or alkenyl group having from about 8 to about 22 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 30 carbon atoms, m and n are independently integers from 0 to about 7, the sum of m and n is from about 3 to 7, and p is an integer from about 4 to about 8. More preferably, $R^1$ is a linear or branched alkyl or linear or branched alkenyl group having from about 8 to about 22 carbon atoms or —$R^3OR^4$, $R^2$ is hydrogen or a linear or branched alkyl or linear or branched alkenyl group having from 1 to about 6 carbon atoms, $R^3$ is a linear or branched alkylene or alkenylene group having from 2 to about 6 carbon atoms, $R^4$ is a linear or branched alkyl or alkenyl group having from about 8 to about 18 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms or —$R^3OR^4$, $R^2$ is hydrogen or methyl, m and n are independently integers from 0 to about 4, $R^3$ is a linear or branched alkylene group having from 2 to about 6 carbon atoms, $R^4$ is a linear or branched alkyl group having from about 8 to about 18 carbon atoms, the sum of m and n is about 4, and p is an integer of about 4. Most preferably, $R^1$ is a linear or branched alkyl group having from about 8 to about 18 carbon atoms or —$R^3OR^4$, $R^2$ is methyl, $R^3$ is ethylene, propylene, hydroxyethylene or 2-hydroxypropylene, $R^4$ is a linear or branched alkyl group having from about 8 to about 18 carbon atoms, m and n are independently integers from 0 to about 4, the sum of m and n is about 4, and p is an integer of about 4. Such compounds are commercially available from Aldrich and Clariant.

(f) alkoxylated poly(hydroxyalkyl)amines having the formula:

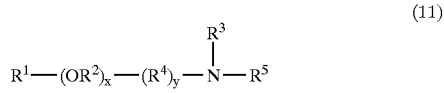
(11)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferred alkoxylated poly(hydroxyalkyl)amines have the formula:

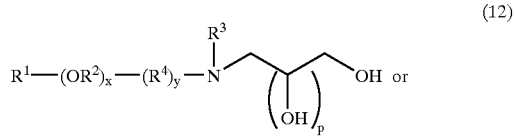
(12)

or

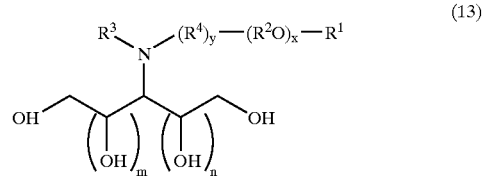
(13)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, m and n are independently integers from 0 to about 7, the sum of m and n is not greater than about 7, p is an integer from 1 to about 8, x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferably, $R^1$ is a linear or branched alkyl or linear or branched alkenyl group having from about 8 to about 30 carbon atoms; $R^2$ in each of the x ($R^2O$) groups is independently $C_2$–$C_4$ alkylene; $R^3$ is hydrogen, a linear or branched alkyl or linear or branched alkenyl group having from 1 to about 30 carbon atoms; $R^4$ is a linear or branched alkylene having from 1 to about 30 carbon atoms, m and n are independently integers from 0 to about 7, the sum of m and n is from about 3 to 7, p is an integer from 1 to about 8, x is an average number from 0 to about 30, and y is 0 or 1. More preferably, $R^1$ is a linear or branched alkyl group having from about 8 to about 22 carbon atoms; $R^2$ in each of the x ($R^2O$) groups is independently ethylene or propylene; $R^3$ is hydrogen, or a linear or branched alkyl group having from 1 to about 6 carbon atoms; $R^4$ is a linear or branched alkylene having from 1 to about 6 carbon atoms, m and n are independently integers from 0 to about 7, the sum of m and n is from about 3 to 7, p is an integer from 1 to about 8, x is an average number from 0 to about 30, and y is 0 or 1. Most preferably, $R^1$ is a linear or branched alkyl group having from about 8 to about 18 carbon atoms; $R^2$ in each of the x ($R^2O$) groups is independently ethylene or propylene; $R^3$ is hydrogen or methyl; m and n are independently integers from 0 to about 7, the sum of m and n is from about 3 to 7, p is an integer from 1 to about 8, x is an average number from 0 to about 30, and y is 0.

(g) di-poly(hydroxyalkyl)amine having the formula:

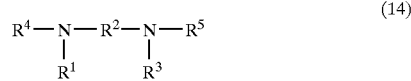

(14)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, the di-poly(hydroxyalkyl)amine has the formula:

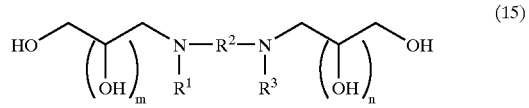

(15)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ arc independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(h) quaternary poly(hydroxyalkyl)amine salts having the formula:

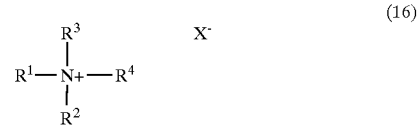

(16)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, and X— is an agriculturally acceptable anion. In this context, preferred $R^1$, $R^2$, and $R^3$ hydrocarbyl groups are linear or branched alkyl, linear or branched alkenyl, linear or branched alkynyl, aryl, or aralkyl groups. Preferably, the quaternary poly(hydroxyalkyl) amine salts have the formula:

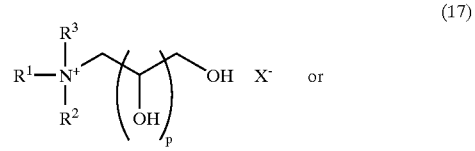

(17) or

-continued

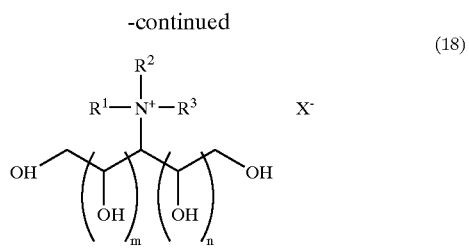

(18)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, m and n are independently integers from 0 to about 7, the sum of m and n is not greater than about 7, p is an integer from 1 to about 8, and X— is an agriculturally acceptable anion. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ and $R^3$ are independently hydrogen or a linear or branched alkyl or linear or branched alkenyl group having from 1 to about 30 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 30 carbon atoms, m and n are independently integers from 0 to about 7, the sum of m and n is not greater than about 7, and p is an integer from about 4 to about 8. More preferably, $R^1$ is a linear or branched alkyl or linear or branched alkenyl group having from about 8 to about 22 carbon atoms, $R^2$ and $R^3$ are independently hydrogen or a linear or branched alkyl or linear or branched alkenyl group having from 1 to about 6 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms, $R^2$ and $R^3$ are independently hydrogen or methyl, m and n are independently integers from 0 to about 4, the sum of m and n is about 4, and p is an integer of about 4. Most preferably, $R^1$ is a linear or branched alkyl group having from about 8 to about 18 carbon atoms, $R^2$ and $R^3$ are methyl, m and n are independently integers from 0 to about 4, the sum of m and n is about 4, and p is an integer of about 4.

(i) triamines having the formula:

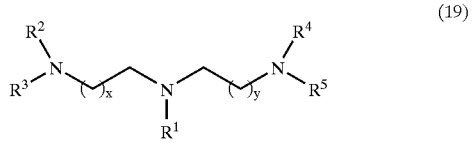

(19)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or —$(R^8)_s$ $(R^7O)_nR^6$; $R^6$ is hydrogen or a linear or branched alkyl group having from 1 to about 4 carbon atoms, $R^7$ in each of the n $(R^7O)$ groups is independently $C_2$–$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4. In this context, preferred $R^1$, $R^2$, $R^3$, $R^4$, $R^5$, and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or —$(R^7O)_nR^6$, $R^6$ is hydrogen, methyl or ethyl; $R^7$ in each of the n $(R^7O)$ groups is independently $C_2$–$C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or —$(R^7O)_nR^6$, $R^6$ is hydrogen or methyl, $R^7$ in each of the n $(R^{7o})$ groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or —$(R^7O)_nR^6$, $R^6$ is hydrogen, $R^7$ in each of the n $(R^7O)$ groups is independently ethylene or propylene, n is an average number from 1 to about 5, and x and y are independently an integer from 1 to about 4. Commercially available triamines include Acros and Clariant Genamin 3119.

(i) diamines having the formula:

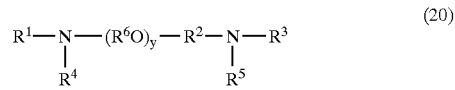

(20)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, C(=NR$^{11}$)NR$^{12}$R$^{13}$—, —C(=O) NR$^{12}$R$^{13}$—, —C(S)NR$^{12}$R$^{13}$, —C(=NR$^{12}$)—, —C(S)—, or —C(O)—, $R^6$ in each of the x $(R^6O)$ and y $(R^6O)$ groups is independently $C_2$–$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60. In this context, preferred $R^1$, $R^2$, $R^3$, $R^4$, and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$ and $R^5$ are independently hydrogen or a linear or branched alkyl or linear or branched alkenyl group having from 1 to about 22 carbon atoms or —$(R^6O)_x$ $R^7$, $R^2$ is a linear or branched alkylene or linear or branched alkenylene group having from 1 to about 6 carbon atoms, $R^6$ in each of the $x(R^6O)$ and $y (R^6O)$ groups is independently $C_2$–$C_4$ alkylene, $R^7$ is hydrogen, or a linear or branched alkyl group having from 1 to about 4 carbon atoms, x is an average number from 1 to about 30, and y is an average number from 0 to about 60. More preferably, $R^1$, $R^3$, $R^4$ and $R^5$ are independently hydrogen or a linear or branched alkyl group having from about 1 to about 18 carbon atoms or —$(R^6O)_x$ $R^7$, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 15, and y is an average number from 0 to about 60. Most preferably, $R^1$ and $R^3$ are independently linear or branched alkyl groups having from about 8 to about 18 carbon atoms and $R^4$ and $R^5$ are independently hydrogen, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 0 to about 50.

(j) mono- or di-quaternary ammonium salts having the formula:

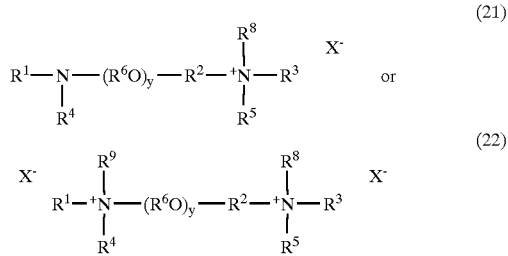

(21)

(22)

wherein $R^1$, $R^3$, $R^4$, $R^5$, $R^8$ and $R^9$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and $X^{31}$ is an agriculturally acceptable anion. In this context, preferred $R^1$, $R^2$, $R^3$, $R^4$, $R^5$, $R^8$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$, $R^5$, $R^8$ and $R^9$ are independently hydrogen or a linear or branched alkyl or alkenyl group having from about 1 to about 22 carbon atoms or —$(R^6O)_xR^7$, $R^2$ is a linear or branched alkylene or alkenylene group having from about 1 to about 6 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$, $R^5$, $R^8$ and $R^9$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$, $R^5$, $R^8$ and $R^9$ are independently hydrogen or methyl, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 10 to about 50.

(k) a secondary or tertiary amine having the formula:

(23)

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl or ethyl. In one embodiment of the amine of formula (23), $R^1$ is a linear or branched alkyl group having from about 12 to about 22 carbon atoms, and $R^2$ and $R^3$ are independently linear or branched hydroxyalkyl groups having from 1 to about 6 carbon atoms.

In one embodiment, the surfactant has the formula (23) wherein $R^1$ is hydrocarbyl or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or polyhydroxyalkyl)alkyl. In this context, preferred $R_1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

(l) monoalkoxylated amines having the formula:

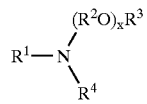

(24)

wherein $R^1$ and $R^4$ are independently hydrocarbyl or substituted hydrocarbyl groups having from 1 to about 30 carbon atoms or $-R^5SR^6$, $R^2$ in each of the x ($R^2O$) groups is independently $C_2$–$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x ($R^2O$) groups is independently $C_2$–$C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear pr branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

(n) dialkoxylated quaternary ammonium salts having the formula:

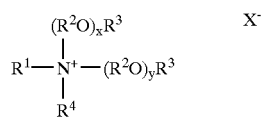

(25)

wherein $R^1$ is hydrocarbyl or substituted hydrocarbyl having from 1 to about 30 carbon atoms, $R^2$ in each of the x ($R^2O$) and y ($R^2O$) groups is independently $C_2$–$C_4$ alkylene, $R^1$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion. In this context preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, R in each of the x ($R^2O$) and y ($R^2O$) groups is independently $C_2$–$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x any y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^1$ in each of the x ($R^2O$) and y ($R^2O$) groups is independently ethylene or propylene, $R^3$ is hydrogen or methyl, and x is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and x is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and x is an average number from about 5 to about 15. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

(o) monoalkoxylated quaternary ammonium salts having the formula:

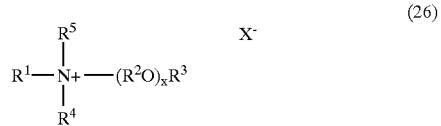

(26)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 30 carbon atoms, x is an average number from 1 to about 60, and X— is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2O$) groups is independently $C_2$–$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x $(R^2O)$ groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x $(R^2O)$ groups is independently ethylene or propylene, $R^3$ is hydrogen or methyl, $R^4$ and $R^5$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x $(R^2O)$ groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(p) quaternary ammonium salts having the formula:

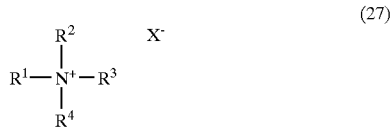

(27)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion. In this context, preferred $R^1$, $R^2$, $R^3$, and $R^4$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to-about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(q) ether amines having the formula:

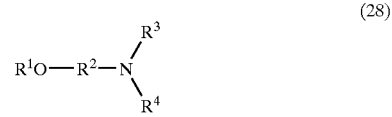

(28)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —$(R^5O)_nR^6$, $R^5$ in each of the x$(R^5$—O) groups is independently $C_2$–$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or —$(R^5O)_x R^6$, $R^5$ in each of the x $(R^5O)$ groups is independently $C_2$–$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or —$(R^5O)R^6$, $R^5$ in each of the x $(R^5O)$ groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or —$(R^5O)_nR^6$, $R^5$ in each of the x $(R^{50})$ groups is independently ethylene or propylene, $R^6$ is hydrogen, and x is an average number from 1 to about 5.

(r) diamines having the formula:

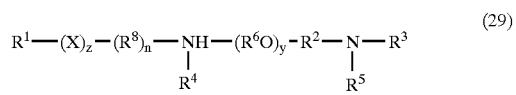

(29)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$; $R^2$ and $R^8$ are independently hydrocarbylene or substituted hydrocarbylene having from 2 to about 30 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —$SO_2$—, y is 0 or an average number from 1 to about 30, n and z are independently 0 or 1, and $R^9$ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^6$ in each of the y ($R^6O$) groups is independently $C_2$–$C_4$ alkylene, y is an average number from 1 to about 20 and n and z are 0; or $R^1$ and $R^3$ are independently a linear or branched alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or —$(R^6O)_xR^7$, $R^6$ in each of the x ($R^6O$) groups is independently $C_2$–$C_4$ alkylene, $R^7$ is hydrogen, or a linear or branched alkyl group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is —C(O)— or —$SO_2$—, n and y are 0 and z is 1. More preferably, $R^1$ and $R^4$ are independently a linear or branched alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or —$(R^6O)_xR^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is —C(O)— or —$SO_2$—, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{12}$, $C_{14}$ or $C_{16}$ ethylene, propylene or butylene N-methyl diamines from Monsanto), Ethoduomeens™, and Jeffamine™ EDR-148.

(s) amine oxides having the formula:

(30)

wherein $R^1$, $R^2$ and $R^3$ are independently hydrogen, hydrocarbyl or substituted hydrocarbyl having from 1 to about 30 carbon atoms, —$(R^4O)_xR^5$, or —$R^6(OR^4)_xOR^5$; $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8. In this context, preferred $R^1$, $R^2$, $R^3$, $R^5$ and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or —$(R^4O)_xR^5$; $R^3$ is a linear or branched alkyl or linear or branched alkenyl group having from about 8 to about 30 carbon atoms, $R^4$ in each of the x ($R^4O$) groups is independently $C_2$–$C_4$ alkylene; $R^5$ is hydrogen or a linear or branched alkyl or linear or branched alkenyl group having from 1 to about 30 carbon atoms, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently —$(R^4)_xR^5$, $R^3$ is a linear or branched alkyl group having from about 8 to about 22 carbon atoms, $R^4$ in each of the x ($R^4O$) groups is ethylene or propylene, $R^5$ is hydrogen or a linear or branched alkyl or linear or branched alkenyl group having from 1 to about 30 carbon atoms, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently —$(R^4O)_xR^5$, $R^3$ is a linear or branched alkyl group having from about 8 to about 18 carbon atoms, $R^4$ in each of the x ($R^4O$) groups is ethylene or propylene, $R^5$ is hydrogen or an alkyl group having from about 8 to about 18 carbon atoms, and x is an average number from 1 to about 5. Commercially available amine oxide surfactants include Chemoxide L70.

(t) alkoxylated amine oxides having the formula:

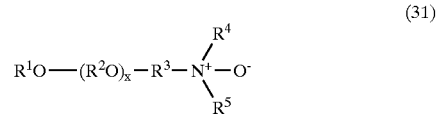

(31)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —(R⁶)ₙ—(R²O)ᵥR⁷; R⁶ is hydrocarbylene or substituted hydrocarbylene containing from 1 to about 6 carbon atoms, R⁷ is hydrogen or a linear or branched alkyl group having 1 to about 4 carbon atoms, n is 0 or 1, and x and y are independently an average number from 1 to about 60. In this context, preferred R¹, R⁴, R⁵ and R⁶ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, R¹ is a linear or branched alkyl or linear or branched alkenyl group having from about 8 to about 25 carbon atoms, R² in each of the x (R²O) groups is independently C₂–C₄ alkylene, R³ is a linear or branched alkylene or alkenylene group having from 2 to about 6 carbon atoms, R⁴ and R⁵ are each independently hydrogen or a linear or branched alkyl group having from 1 to about 6 carbon atoms, and x is an average number from 1 to about 30. More preferably, R¹ is a linear or branched alkyl group having from about 12 to about 22 carbon atoms, R² in each of the x (R²O) groups is independently ethylene or propylene, R³ is a linear or branched alkylene or alkenylene group having from 2 to about 6 carbon atoms, R⁴ and R⁵ are each independently hydrogen, methyl, or tris(hydroxymethyl)methyl, and x is an average number from about 2 to about 30. Even more preferably, R¹ is a linear or branched alkyl group having from about 12 to about 18 carbon atoms, R² in each of the x (R²O) groups is independently ethylene or propylene, R³ is an ethylene, propylene or 2-hydroxypropylene group, R⁴ and R⁵ are each independently hydrogen or methyl, and x is an average number from about 4 to about 20. Most preferably, R¹ is a linear or branched alkyl group having from about 12 to about 18 carbon atoms, R² in each of the x (R²O) groups is independently ethylene or propylene, R³ is an ethylene, propylene, or 2-hydroxypropylene group, R⁴ and R⁵ are methyl, and x is an average number from about 4 to about 20.

(u) dialkoxylated amines having the formula:

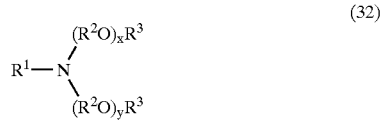

(32)

wherein R¹ is a hydrocarbyl or substituted hydrocarbyl having from about 6 to about 30 carbon atoms, or —R⁴SR⁵. R² in each of the x (R²O) and the y (R²O) groups is independently C₂–C₄ alkylene, R³ is hydrogen, or a linear or branched alkyl group having from 1 to about 4 carbon atoms, R⁴ is a linear or branched alkylene group having from about 6 to about 30 carbon atoms, R⁵ is a linear or branched alkyl group having from about 4 to about 15 carbon atoms, and x and y are independently an average number from 1 to about 40. In this context, preferred R¹ hydrocarbyl groups are linear or branched alkyl, linear or branched alkenyl, linear or branched alkynyl, aryl, or aralkyl groups. Preferably, R¹ is a linear or branched alkyl or linear or branched alkenyl group having from about 8 to about 30 carbon atoms, R² in each of the x (R²O) and the y (R²O) groups is independently C₂–C₄ alkylene, R³ is hydrogen, methyl or ethyl, and x and y are independently an average number from 1 to about 30. More preferably, R¹ is a linear or branched alkyl group having from about 8 to about 25 carbon atoms, R² in each of the x (R²O) and the y (R²O) groups is independently ethylene or propylene, R³ is hydrogen or methyl, and x and y are independently an average number from 1 to about 20. Even more preferably, R¹ is a linear or branched alkyl group having from about 8 to about 22 carbon atoms, R² in each of the x (R²O) and the y (R²O) groups is independently ethylene or propylene, R³ is hydrogen or methyl, and x and y are independently an average number from 1 to about 10 and even more preferably from 1 to about 5. Preferred commercially available dialkoxylated amines include Trymeen™ 6617 (from Cognis) and Ethomeen™ C/12, C/15, C/20, C/25, T/12, T/15, T/20 and T/25 (from Akzo Nobel).

and (v) aminated alkoxylated alcohols having the following chemical structure:

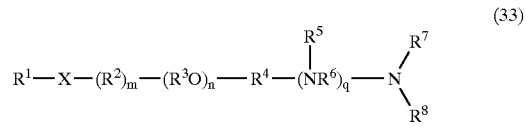

(33)

wherein R¹, R⁷, R⁸, and R⁹ are each independently hydrogen, hydrocarbyl or substituted hydrocarbyl having from 1 to about 30 carbon atoms, or —(R¹¹)ₛ(R³O)ᵥR¹⁰; X is —O—, —OC(O)—, —C(O)O—, —N(R¹²)C(O)—, —C(O)N(R¹²)—, —S—, —SO—, —SO₂— or —N(R⁹)—; R³ in each of the n (R³O) groups and the v (R³O) groups is independently C₂–C₄ alkylene; R¹⁰ is hydrogen, or a linear or branched alkyl group having from 1 to about 30 carbon atoms; n is an average number from 1 to about 60; v is an average number from 1 to about 50; R² and R¹¹ are each independently hydrocarbylene or substituted hydrocarbylene having from 1 to about 6 carbon atoms; R⁴ is hydrocarbylene or substituted hydrocarbylene having from 2 to about 6 carbon atoms; R¹² is hydrogen or hydrocarbyl or substituted hydrocarbyl having from 1 to about 30 carbon atoms; m and s are each independently 0 or 1; R⁶ is hydrocarbylene or substituted hydrocarbylene having from 2 to about 30 carbon atoms, —C(=NR¹²)—, —C(S)—, or —C(O)—; q is an integer from 0 to 5; and R⁵ is hydrogen or hydrocarbyl or substituted hydrocarbyl having from 1 to about 30 carbon atoms. In this context, preferred R¹, R², R⁴, R⁵, R⁶, R⁷, R⁸, R⁹, R¹¹ and R¹² hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

In one embodiment, any of the amine or quaternary ammonium surfactants as described in sections (a)–(v) above are included in liquid glyphosate concentrates other than IPA glyphosate, such as glyphosate concentrates containing potassium, diammonium, ammonium, sodium, monoethanolamine, n-propylamine, methylamine, ethylamine, hexamethylenediamine, dimethylamine, or trimethylsulfonium glyphosate and mixtures thereof, which contain at least about 10 wt. % glyphosate a.e., more preferably at least about 15%, 20%, 25%, 30%, 35%, 40% or more wt. % a.e., or at least about 120 g a.e. glyphosate per liter, more preferably at least 130, 140, 150, 160, 170, 180, 190, 200, 210, 220, 230, 240, 250, 260, 270, 280, 290, 300, 310, 320, 330, 340, 350, 360, 370, 380, 390, or 400 g a.e./l or more.

In another embodiment, any of the cationic surfactants as described in (a)–(v) above are preferably formulated in concentrates that are free of alkyl polyglycosides, or that only contain alkyl polyglycosides having a light color of less than 10, preferably less than 9, 8, 7, 6, or 5 as measured using a Gardner colorimeter. When dye is added to a formulated glyphosate product having a Gardner color greater than about 10, the concentrate remains dark brown in color. Concentrates having a Gardner color value of 10 are difficult to dye blue or green as is often desired to distinguish the glyphosate product from other herbicidal products.

A subclass of such cationic surfactants described above includes a monoalkoxylated amine having the formula:

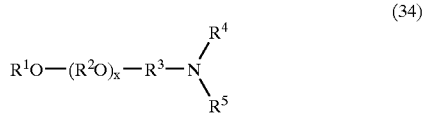

(34)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —$(R^6)_n$—$(R^2O)_y R^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$–$C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is ethylene or propylene, $R^4$ and $R^5$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is ethylene, $R^4$ and $R^5$ are methyl, and x is an average number from about 4 to about 20. Preferred monoalkoxylated amines include PEG13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah) and Surfonic™ AGM-550 from Huntsman.

Quaternary ammonium, sulfonium and sulfoxonium salts are also effective cationic surfactants in forming potassium glyphosate concentrates and have a chemical structure:

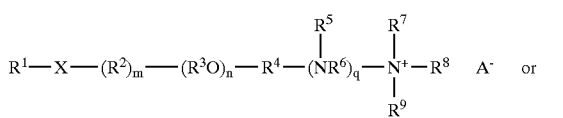

(35)

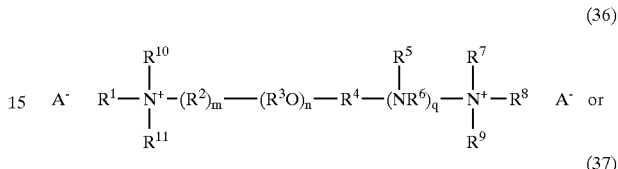

(36)

(37)

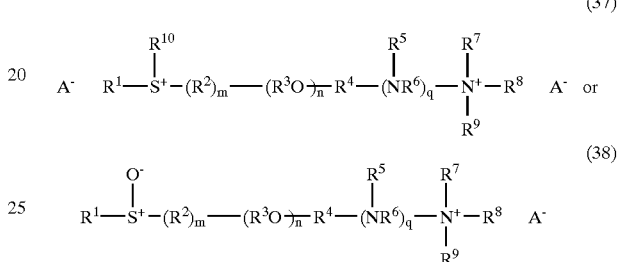

(38)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —$(R^{13})_s(R^3O)_v R^{12}$; X is —O—, —OC(O)—, —N($R^{14}$)C(O)—, —C(O)N($R^{14}$)—, —C(O)O—, or —S—; $R^3$ in each of the n ($R^3O$) groups and v ($R^3O$) groups is independently $C_2$–$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=N$R^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion. In this context, preferred $R^1$, $R^2$, $R^4$, $R^5$, $R^6$, $R^7$, $R^8$, $R^9$, $R^{10}$, $R^{11}$, $R^3$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Another cationic surfactant effective in the formulations of the invention is a diamine or diammonium salt having the formula:

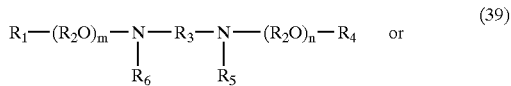

(39)

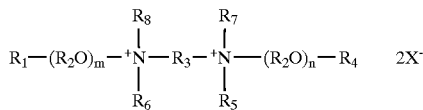

(40)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$–$C_4$ alkylene, $R^3$ is hydrocarbylene or substituted hydrocarbylene having from about 2 to about 6 carbon atoms or —$(R^2O)_p$ $R_9$—, m and n are individually an average number from 0 to about 50, and p is an average number from 0 to about 60. In this context, preferred $R^1$, $R^3$, $R^4$, $R^5$, $R^6$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (40), $R^3$ is hydrocarbylene having from about 2 to about 6 carbon atoms, and the remaining groups are as defined above.

Some preferred cationic surfactants include alkylamine ethoxylates (including etheramines and diamines) such as tallowamine ethoxylate, cocoamine ethoxylate, etheramine ethoxylate, N-tallow ethylenediamine ethoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl) cocoamine N-oxide), nonethoxylated amine oxides (e.g., cethyldimethylamine N-oxide) and amidoamine oxides.

Preferred nonionic surfactants suitable for use in formulating the herbicidal compositions and concentrates of the invention include:

(a) alkoxylated alcohols having the formula:

$$R^1O-(R^2O)_xR \qquad (41)$$

wherein $R^1$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x ($R^2O$) groups is independently $C_2$–$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x ($R^2O$) groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, $R^2$ in each of the x ($R^2O$) groups is independently ethylene or propylene, $R^3$ is hydrogen or methyl, and x is an average number from about 8 to about 30. Preferred commercially available alkoxylated alcohols include Procol™ LA-15 (from Protameen), Brij™ 35, Brij™ 76, Brij™ 78, Brij™ 97 and Brij™ 98 (from Sigma Chemical Co.), Neodol™ 25-12 (from Shell), Hexotol™ CA-10, Hexotol™ CA-20, Hexotol™ CS-9, Hexotol™ CS-15, Hexotol™ CS-20, Hexotol™ CS-25, Hexotol™ CS-30, and Plurafac™ A38 (from BASF), ST-8303 (from Cognis), and Arosurf™ 66 E20 (from Witco/Crompton).

(b) dialkoxylated alcohols having the formula:

$$R^1(OR^2)_xO-R^3-O-(R^2O)_yR^1 \qquad (42)$$

wherein $R^1$ is independently hydrogen, or a linear or branched alkyl group having from 1 to about 4 carbon atoms, $R^2$ in each of the x ($R^2O$) and the y ($R^2O$) groups is independently $C_2$–$C_4$ alkylene, $R^3$ is hydrocarbylene or substituted hydrocarbylene having from 2 to about 30 carbon atoms, and x and y are independently an average number from 1 to about 60. In this context, preferred $R^3$ hydrocarbylene groups are linear or branched alkylene, linear or branched alkenylene, linear or branched alkynylene, arylene, or aralkylene groups. Preferably, $R^1$ is hydrogen, methyl or ethyl, $R^2$ in each of the x ($R^2O$) and the y ($R^2O$) groups is independently $C_2$–$C_4$ alkylene, $R^3$ is a linear or branched alkylene or linear or branched alkenylene group having from about 8 to about 25 carbon atoms, and x and y are independently an average number from about 1 to about 20. More preferably, $R^1$ is hydrogen or methyl, $R^2$ in each of the x ($R^2O$) and the y ($R^2O$) groups is independently ethylene or propylene, $R^3$ is a linear or branched alkylene or linear or branched alkenylene group having from about 8 to about 18 carbon atoms, and x and y are independently an average number from 1 to about 10. Even more preferably, $R^1$ is hydrogen, $R^2$ in each of the x ($R^2O$) and the y ($R^2O$) groups is independently ethylene or propylene, $R^3$ is a linear or branched alkylene group having from about 8 to about 18 carbon atoms, and x and y are independently an average number from 1 to about 5.

(b) alkoxylated dialkylphenols having the formula:

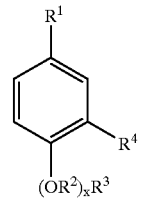

(43)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2O$) groups is independently $C_2$–$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

Other suitable nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol ethoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as Neodols and oxoalcohol ethoxylates; and ethylene oxide/propylene oxide copolymers such as Pluronic type, Tetronic type, or Tergitol XH type.

Additional nonionic surfactants for inclusion in surfactant compositions that may be used in the invention are polyoxyethylene (5–30) $C_{8-22}$ alkylethers and polyoxyethylene (5–30) $C_{8-12}$ alkylphenylethers, wherein "(5–30)" means that the average number of ethylene oxide units in the polyoxyethylene chains of these surfactants is from about 5 to about 30. Examples of such nonionic surfactants include polyoxyethylene nonylphenols, octanols, decanols and trimethylnonanols. Particular nonionic surfactants that have proved useful include NEODOL™ 91-6 of Shell (a polyoxyethylene (6) $C_{9-11}$ linear primary alcohol), NEODOL™ 1-7 of Shell (a polyoxyethylene (7) $C_{11}$ linear primary alcohol), TERGITOL™ 15-S-9 of Union Carbide (a polyoxyethylene (9) $C_{12-15}$ secondary alcohol) and SURFONIC™ NP95 of Huntsman (a polyoxyethylene (9.5) nonylphenol).

The herbicidal compositions of the invention may also include a compound capable of reducing eye irritancy. Such compounds are generally effective in combination with the alkylamine surfactants described herein, and have the formula:

$$R_1O(R_2O)_nX_1 \tag{43A}$$

wherein $R^1$ is a hydrocarbyl group having from about 8 to about 22 carbon atoms, each of the n ($R^2O$) groups is independently $C_2$–$C_4$ alkylene, n is a number from 0 to about 60, and $X_1$ is a carboxylate, sulfate or phosphate. These compounds are described in U.S. Pat. No. 6,063,733, which is incorporated herein by reference.

Suitable amphoteric surfactants include betaines such as simple betaines (e.g., cocodimethylbetaines), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as N-alkyl, N,-bis(2-hydroxyethyl)glycine and alkylaminedipropionates.

Other surfactants for use in herbicidal compositions and concentrates of the invention include compounds of the formula:

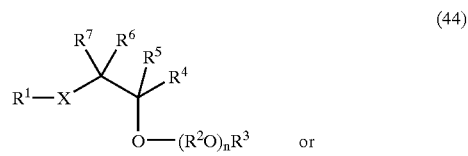
(44)

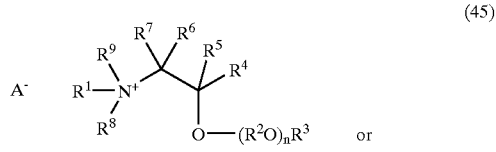
(45)

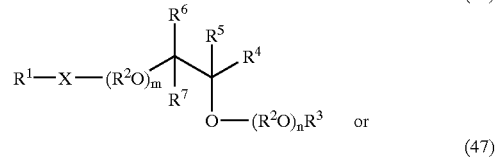
(46)

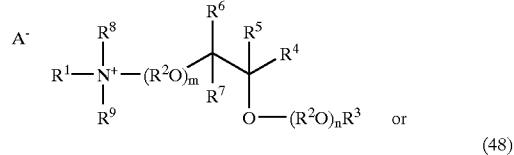
(47)

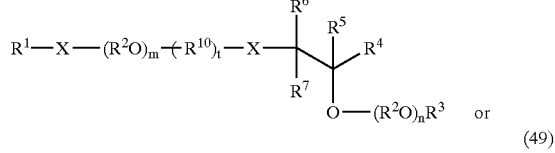
(48)

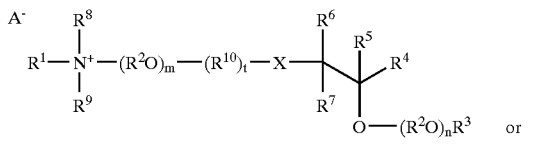
(49)

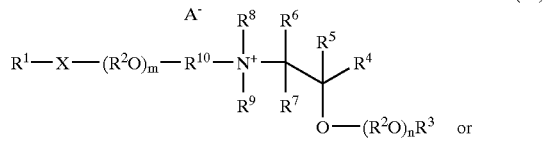
(50)

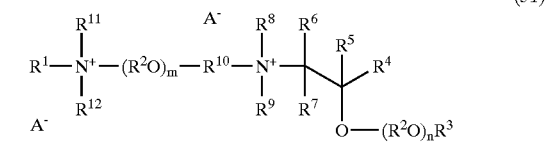
(51)

wherein $R^1$, $R^9$, and $R^{12}$ are independently hydrocarbyl or substituted hydrocarbyl having from 1 to about 30 carbon atoms, or —$(R^2O)_pR^{13}$; $R^2$ in each of the m ($R^2O$), n ($R^2O$), p ($R^2O$) and q ($R^2O$) groups is independently $C_2$–$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —$(CH_2)_yOR^{13}$ or —$(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrocarbyl or substituted hydrocarbyl having from 1 to about 30 carbon atoms, or —$(CH_2)_zO(R^2O)_pR^3$; m, n, p and q are independently an average number from 1 to about 50; X is independently —O—, —N($R^{14}$)—, —C(O)—, —C(O)O—, —OC(O)—, —N($R^{15}$)C(O)—, —C(O)N($R^{15}$)—, —S—, —SO—, or —$SO_2$—; t is 0 or 1; A— is an agriculturally acceptable anion; and y and z are independently an integer from 0 to about 30. In this context, preferred $R^1$, $R^3$, and $R^5$–$R^{15}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^9$, and $R^{12}$ are independently linear or branched alkyl or alkenyl groups having from 1 to about 22 carbon atoms, or —$(R^2O)_pR^{13}$; $R^2$ in each of the m ($R^2O$), n ($R^2O$), p ($R^2O$) and q ($R^2O$) groups is independently $C_2$–$C_4$ alkylene; $R^3$ is hydrogen, methyl or ethyl; $R^4$ is —$(CH_2)_yOR^{13}$ or —$(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^8$, $R^{11}$, $R^{13}$ and $R^{15}$ are independently hydrogen, or linear or branched alkyl or alkenyl groups having from 1 to about 22 carbon atoms; $R^{10}$ is a linear or branched alkylene or alkenylene group having from 2 to about 18 carbon atoms; $R^{14}$ is a linear or branched alkyl or alkenyl group having from 1 to about 22 carbon atoms, or —$(CH_2)_zO(R^2O)_pR^3$; m, n, p and q are independently an average number from 1 to about 30; X is independently —O—, —N($R^{14}$)—, —C(O)—, —C(O)O—, —OC(O)—, —N($R^{15}$)C(O)—, —C(O)N($R^{15}$)—, —S—, —SO—, or —$SO_2$—, t is 0 or 1; A— is an agriculturally acceptable anion; and y and z are independently an integer from 0 to about 30. More preferably, $R^1$ is a linear or branched alkyl or alkenyl groups having from about 8 to about 18 carbon atoms, or —$(R^2O)_pR^{13}$; $R^9$ and $R^{12}$ are independently linear or branched alkyl or alkenyl groups having from 1 to about 22 carbon atoms, or —$(R^2O)_pR^{13}$; $R^2$ in each of the m ($R^2O$), n ($R^2O$), p ($R^2O$) and q ($R^2O$) groups is independently ethylene or propylene; $R^3$ is hydrogen or methyl; $R^4$ is —$(CH_2)_yOR^{13}$ or —$(CH_2)_yO(R^2O)_qR^3$; $R^8$, $R^{11}$, $R^{15}$ are independently hydrogen, or linear or branched alkyl or alkenyl groups having from 1 to about 22 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or —$(CH_2)_zO(R^2O)_pR^3$; m, n, p and q are independently an average number from 1 to about 20; X is independently —O—, —N($R^{14}$)—, —C(O)—, —C(O)O—, —OC(O)—, —N($R^{15}$)C(O)—, —C(O)N($R^{15}$)—, —S—, —SO—, or —$SO_2$—, t is 0 or 1; A— is an agriculturally acceptable anion; and y and z are independently an integer from 0 to about 10. Most preferably, $R^1$ is a linear or branched alkyl or alkenyl groups having from about 12 to about 18 carbon atoms, or —$(R^2O)_pR^{13}$; $R^9$ and $R^{12}$ are independently linear or branched alkyl or alkenyl groups having from 1 to about 6 carbon atoms, or —$(R^2O)_pR^{13}$; $R^2$ in each of the m ($R^2O$), n ($R^2O$), p ($R^2O$) and q ($R^2O$) groups is independently ethylene or propylene; $R^3$ is hydrogen; $R^4$ is —$(CH_2)_yOR^{13}$ or —$(C_2)_yO(R^2O)_qR^3$; $R^8$, $R^{11}$, $R^{15}$ are independently hydrogen, or linear or branched alkyl or alkenyl groups having from 1 to about 6 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to-about 22 carbon atoms, or —$(CH_2)_zO(R^2O)_pR^3$; m, n, p and q are independently an average number from 1 to about 5; X is independently —O— or —N($R^{14}$)—, t is 0 or 1; A— is an agriculturally acceptable anion; and y and z are independently an integer from 1 to about 3.

Preferred anionic surfactants effective in forming formulations of the invention include saturated carboxylic acids such as butyric, caproic, caprylic, capric, lauric, palmitic, myristic or stearic acid, and unsaturated carboxylic acids such as palmitoleic, oleic, linoleic or linolenic acid. Preferred carboxylic acids include palmitic, oleic or stearic acid. Other preferred anionic surfactants include alkyl sulfates such as sodium lauryl sulfate, and alkyl alkoxylated phosphates having the formulae:

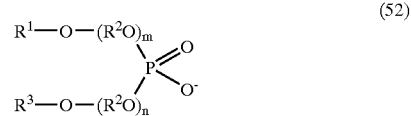

(52)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$–$C_4$ alkylene; and m and n are independently from 1 to about 30; or

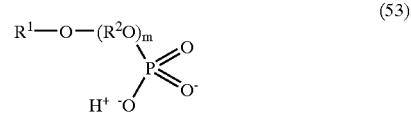

(53)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$–$C_4$ alkylene; and m is from 1 to about 30. Representative alkyl alkoxylated phosphates include oleth-10 phosphate, oleth-20 phosphate and oleth-25 phosphate.

Preferred phosphate ester surfactants include mono- and dialcohol phosphates, mono- and di- (polyoxyalkylene alcohol) phosphates and the mono- and dialcohol phosphates, (polyoxyalkylene alkylphenol) phosphates, and are represented by the formula:

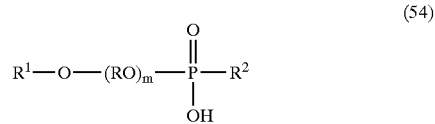

(54)

wherein $R^1$ is $C_8$–$C_{20}$ alkyl or $C_8$–$C_{20}$ alkylphenyl; R is an alkylene having from 2 to about 4 carbon atoms, usually ethylene or propylene, m is zero or a number up to about 60, preferably less than 10 and more preferably about 4, and $R^2$ is hydroxyl or $R^1$—O—$(RO)_m$-radical wherein $R^1$ and R are as just indicated and m is 0 to about 30. If $R^2$ is hydroxyl, then the compound is monoester. If $R^2$ is a $R^1$—O—$(RO)_m$-radical, then the compound is a diester. Mixtures of phosphate esters or diesters of formula (52), (53), and/or (54) and a cationic surfactant, particularly the alkylamine surfactants of formula (61), (62), (63) or (64) are preferred for use in the compositions of the invention. Mixtures of monoesters and diesters are also useful, together with the polyoxyalkylene alkylamines. Where mixtures of monoesters and diesters are present, the weight percentage of the monoester, or monoesters, exceeds that of the diester or diesters.

Other suitable anionic surfactants include fatty soaps such as ammonium tallowate and sodium stearate; alkyl sulfates such as sodium $C_{8-10}$ alcohol sulfate, and sodium oleyl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., sodium dibutylnapthalene sulfonate), alkyl sulfonates (e.g., alpha olefin sulfonates), sulfosuccinates such as dialkylsulfosuccinates (e.g., sodium dioctylsulfosuccinate) and monoalkylsulfosuccinates and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine; and phosphates such as alkylether ethoxylate phosphates and alkylarylether ethoxyated phosphates.

Exemplary surfactants that may be used in accordance with the present invention include the following species:

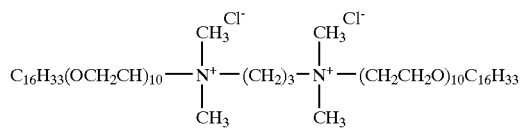
(55)

and

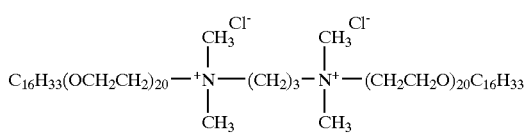
(56)

Other surfactants for use in herbicidal compositions and concentrates of the invention include N-acyl sarcosinates, which are described in U.S. Pat. No. 5,985,798, which is incorporated herein by reference. Such surfactants are represented by the formula:

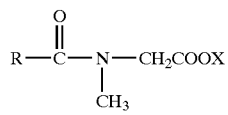
(57)

wherein R is $C_8$ to $C_{22}$ N-acyl, preferably a fatty acid of chain length $C_{10}$ to $C_{18}$, and X is salt forming cation including alkali metal, ammonia or alkanolamine. More preferably R is lauroyl, cocoyl, palmitoyl, myristoyl or oleoyl, and X is sodium, potassium, ammonium, an isopropylamine, or an amino alcohol. Preferred sarcosinates include sodium lauroyl sarcosinate, sodium cocoyl sarcosinate and sodium myristoyl sarcosinate, which are commercially available under the trademark HAMPOSYL from Hampshire Chemical Corp.

Alkylpolyglycosides are also suitable for use in the compositions and concentrates of the invention, and are described, for example, in U.S. Pat. No. 6,117,820. As used herein the term "alkylglycoside" includes mono- and polyalkylglycosides. Glycosides are represented by the formula:

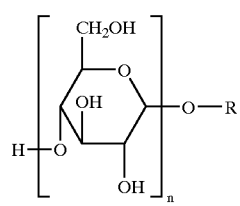
(58)

wherein n is the degree of polymerization, or number of glycose groups, and R is a branched or straight chain alkyl group preferably having from 4 to 18 carbon atoms, or a mixture of alkyl groups having an average value within the given range. The number of glycose groups per alkyl group may vary and alkyl mono- or di-, or polyglucose or saccharide derivatives are possible. Commercial alkylpolyglycosides usually contain a mixture of derivatives with n expressed as an average. Preferably n is between 1 and about 5, and more preferably between 1 and about 3. Typical of alkylglycosides is the product commercially available under the trade names AL2042 (Imperial Chemical Industries PLC) wherein n is an average of 1.7 and R is a mixture of octyl (45%) and decyl (55%), the product commercially available under the trade name AGRIMUL PG2069 (Henkel Corp) wherein n is an average of 1.6 and R is a mixture of nonyl (20%), decyl (40%) and undecyl (40%), and the product commercially available under the trade name BEROL AG6202 (Akzo Nobel) which is 2-ethyl-1-hexylglycoside.

The more preferred surfactant for use in the particulate solid concentrates are of the "superspreading" type. The superspreading surfactants include, but are not limited to organosilicones and fluoro-organic surfactant. The organosilicone surfactants comprise a polysiloxane. More specifically, the organosilicone surfactants comprise a polysiloxane wherein at least one of the siloxane groups possesses a moiety comprising one or more polyalkyleneoxy or polyalkyleneoxyalkyl groups.

The polysiloxane surfactants are represented by the following formula:

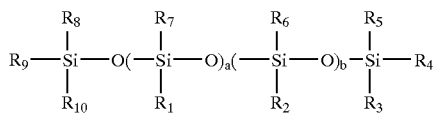

(59)

wherein $R^1$ is —$C_nH_{2n}O(CH_2CH_2O)_m(CH_2CH(CH_3)O)_qX$, n is 0 to 6, a is 0 to about 100, b is 0 to about 10, m is 0 to about 30, q is 0 to about 30, X is hydrogen or a $C_{1-20}$ hydrocarbyl or $C_{2-6}$ acyl group, and $R_2$, $R_3$, $R_4$, $R_5$, $R_6$, $R_7$, $R_8$, $R_9$, $R_{10}$ groups are independently substituted or unsubstituted $C_{1-20}$ hydrocarbyl or nitrogen containing groups.

Generally, in preferred embodiments, n is 0 to 6, a is 1 to about 30, b is 0 to about 10, m is 0 to about 30, q is 0 to about 3, X is hydrogen or a $C_{1-6}$ hydrocarbyl or $C_{2-6}$ acyl group, and $R_2$, $R_3$, $R_4$, $R_5$, $R_6$, $R_7$, $R_8$, $R_9$, $R_{10}$ groups are independently substituted or unsubstituted $C_{1-4}$ hydrocarbyl or nitrogen containing groups.

In one preferred embodiment, the polysiloxane is a polyoxyethylene heptamethyl trisiloxane wherein $R_1$ is —$C_nH_{2n}O(CH_2CH_2O)_m(CH_2CH(CH_3)O)_qX$, n is 3 or 4, a is 1, b is 0, m is 1 to about 30, q is 0, X is hydrogen or a methyl, ethyl or acetyl group, and $R_2$, $R_3$, $R^4$, $R_5$, $R^6$, $R_7$, $R_8$, $R_9$, $R_{10}$ groups are independently substituted or unsubstituted $C_{1-4}$ hydrocarbyl or nitrogen containing groups.

In a preferred embodiment of the invention in the formula for the polysiloxane surfactant(s), a is 1 to 5, b is 0 to 10, n is 3 or 4, m is 1 to about 30, q is 0, X is hydrogen or a methyl, ethyl or acetyl group, and $R_2$, $R_3$, $R_4$, $R_5$, $R_6$, $R_7$, $R_8$, $R_9$, and $R_{10}$ are methyl groups.

In another preferred embodiment of the invention in the formula for said polysiloxane surfactant(s), a is 1 to 5, b is 0 to 10, n is 3 or 4, m is 4 to 12, q is 0, X is hydrogen or a methyl or acetyl group, $R_2$, $R_3$, $R_4$ $R_5$, $R_6$, $R_7$, $R_8$, $R_9$, and $R_{10}$ are methyl groups.

In a more preferred embodiment of the invention in the formula for said polysiloxane surfactant(s), a is 1, b is 0, n is 3 or 4, m is 1 to about 30, b is 0, X is hydrogen or a methyl, ethyl or acetyl group, and $R_2$, $R_3$, $R_4$, $R_5$, $R_6$, $R_7$, $R_8$, $R_9$, and $R_{10}$ are methyl groups.

In a further preferred embodiment of the invention in the formula for said polysiloxane surfactant(s), a is 1, b is 0, n is 3, m is 8, b is 0, X is methyl and $R_2$, $R_3$, $R_4$, $R_5$, $R_6$, $R_7$, $R_8$, $R_9$, and $R_{10}$ are methyl groups.

Trisiloxanes of the above formula are generally described in product literature of Crompton Corporation and in U.S. Pat. No. 3,505,377. Several of such trisiloxanes are ethoxylated organosilicone wetting agents available from Crompton Corporation as Silwet® silicone glycol copolymers. Both liquid organosilicones and dry organosilicones can be used in the surfactant composition; both are included within the scope of the invention.

More preferred trisiloxanes are those sold commercially in the United States or elsewhere by Crompton Corporation as Silwet® L-77, Silwet® 408 and Silwet® 800, by Dow-Corning as Sylgard® 309, by Exacto, Inc., as Qwikwet® 100, and by Goldschmidt as Breakthru S-240™. In the most preferred polyoxyethylene heptamethyl trisiloxanes, $R^2$ is hydrogen.

A preferred surfactant composition useful in this invention contains about 75% to about 100%, more preferably about 80% to about 100% by weight of the polyoxyalkylene trisiloxane. A blend of more than one polyoxyalkylene trisiloxane can be used, in which case the preferred total amount of all polyoxyalkylene trisiloxanes present in the surfactant composition is as above.

The polysiloxane surfactants can be combined with any of the surfactants described herein. In one embodiment, a polysiloxane of formula (59) is combined with an alkyl diphenyloxide sulfonate surfactant having the formula:

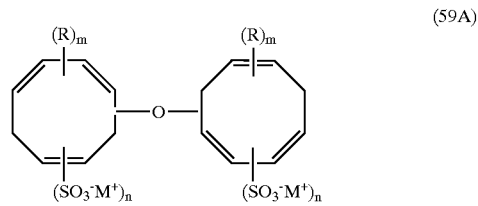

(59A)

wherein each R is independently a hydrocarbyl having 1 to about 30 carbon atoms (preferably 6–10 carbon atoms), each n is independently 0 or 1, each $M^+$ is an agriculturally acceptable cation, and each n is independently 0 or 1, provided that the surfactant include at least one sulfonate group. The cation can be ammonium (including alkylammonium and hydroxyalkylammonium), alkali metal, alkaline earth metal, or hydrogen. Such surfactant combinations generally include from about 5–55 wt. % polysiloxane surfactant and from about 45–95 wt. % diphenyloxide sulfonate, and are described in EP 1064844. Commercially available diphenyloxide sulfonates include sodium alkyl diphenyloxide sulfonates sold as DOWFAX™ from Dow Chemical.

Fluoro-organic wetting agents useful in this invention are organic molecules represented by the formula:

(60)

wherein $R_f$ is a fluoroaliphatic radical and G is a group which contains at least one hydrophilic group such as cationic, anionic, nonionic, or amphoteric groups. $R_f$ is a fluorinated, monovalent, aliphatic organic radical containing at least four carbon atoms. Preferably, it is a saturated perfluoroaliphatic monovalent organic radical. However, hydrogen or chlorine atoms can be present as substituents on the skeletal chain. Although radicals containing a large number of carbon atoms can function adequately, compounds containing not more than about 20 carbon atoms are preferred because large radicals usually represent a less efficient utilization of fluorine than is possible with shorter skeletal chains. Preferably, $R_f$ contains about 5 to 14 carbon atoms.

The cationic groups which are usable in the fluoro-organic wetting agents employed in this invention can include an amine or a quaternary ammonium cationic group. Such amine and quaternary ammonium cationic hydrophilic groups can have formulas such as $NH_2$, $NHR^2$, —$N(R^2)_2$, —$(NH_3)X$, —$NH_2R^2)X$, —$(NH(R^2)_2X)$, or —$(N(R^2)_3)X$, where X is an anionic counterion such as halide, hydroxide, sulfate, bisulfate, acetate or carboxylate, and each $R^2$ is independently a $C_{1-18}$ alkyl group. Preferably, X is halide, hydroxide, or bisulfate. Preferably, the cationic fluoro-organic wetting agents used in this invention contain hydrophilic groups which are quaternary ammonium cationic groups. The anionic groups which are usable in the fluoro-organic wetting agents employed in this invention include groups which by ionization can become radicals of anions. The anionic groups can have formulas such as —COOM, —$SO_3M$, $^-OSO_3M$, —$PO_3M_2$, —$PO_3HM$, —$OPO_3M_2$, or OPO$_3$HM, where M is H, an alkali metal ion, (NR$^1_4$)$^+$, or (SR$^1_3$)$^+$, where each R$^1$ is independently H or substituted or unsubstituted C$_1$–C$_6$ alkyl. Preferably M is Na$^+$ or K$^+$. The preferred anionic groups of the fluoro-organic wetting agents used in this invention have the formula —COOM or —SO$_3$M.

The amphoteric groups which are usable in the fluoro-organic wetting agents employed in this invention include groups which contain at least one cationic group as defined above and at least one anionic group as defined above. Other useful amphoteric groups are amine oxides.

The nonionic groups which are usable in the fluoro-organic wetting agents employed in this invention include groups which are hydrophilic but which under pH conditions of normal agronomic use are not ionized. The nonionic groups can have formulas such as —O(CH2CH2)XH wherein x is greater than zero, preferably 1–30, —SO$_2$NH$_2$, SO$_2$NHCH$_2$CH$_2$OH, SO$_2$N(CH$_2$CH$_2$OH)$_2$, —CONH$_2$, —CONHCH$_2$CH$_2$OH, or —ON(CH$_2$CH$_2$OH)$_2$.

Cationic fluoro-organic wetting agents useful herein include those cationic fluorochemicals described, for example, in U.S. Pat. Nos. 2,764,602, 2,764,603, 3,147,064, and 4,069,158. Amphoteric fluoro-organic wetting agents useful herein include those amphoteric fluorochemicals described, for example, in U.S. Pat. Nos. 2,764,602, 4,042,522, 4,069,158, 4,069,244, 4,090,967, 4,161,590 and 4,161,602. Anionic fluoro-organic wetting agents useful herein include those anionic fluorochemicals described, for example, in U.S. Pat. Nos. 2,803,656, 3,255,131, 3,450,755 and 4,090,967. The pertinent disclosure of the above patents is incorporated herein by reference.

Several fluoro-organic wetting agents suitable for use in the invention are available from 3M under the Fluorad trademark. They include anionic agents Fluorad FC-120, Fluorad FC-129 and Fluorad FC-99, cationic agent Fluorad FC-750, and nonionic agents Fluorad FC-170C, Fluorad FC-171 and Fluorad FC-430.

Preferred alkoxylated alkylamines are generally represented by the following structural formula:

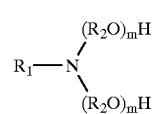
(61)

or

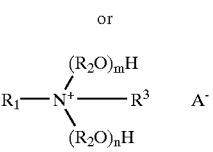
(62)

wherein R$_1$ is a straight or branched alkyl group comprising about 8 to about 22 carbon atoms, R$_2$ in each of the m(R$_2$O) and n(R$_2$O) groups is independently C$_2$–C$_4$ alkylene, R$_3$ is C$_1$–C$_4$ alkyl, and m and n are average numbers such that m+n is about 0 to about 60, preferably 2 to about 20.

In a preferred alkoxylated alkylamine surfactant, R$_1$ is a straight chain alkyl group with an average of about 12 to about 18 carbon atoms. The alkyl chain may be naturally or synthetically derived. Typically it is derived from a natural source such as coconut or soybean oil or tallow. Preferred alkylamines include dodecylamine, stearylamine, cocoamine and tallowamine. R$_2$ in the structure of the alkoxylated alkylamine surfactant is preferably ethylene. M is preferably about 1 to about 19 and n is preferably about 1 to about 19.

Preferred alkoxylated tertiary etheramines are represented by the following structural formula:

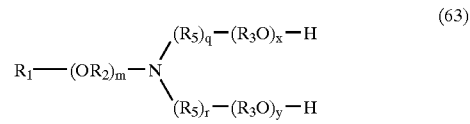
(63)

wherein R$^1$ is a straight or branched chain hydrocarbon having from about 6 to about 22 carbon atoms, m is about 0 to about 10, R$_2$ is independently C$_1$–C$_4$ alkylene, R$_3$ groups are independently C$_1$–C$_4$ alkylene, R$_5$ is independently C$_1$–C$_4$ alkylene, and x and y are average numbers such that x+y is about 2 to about 60, q is 0 or 1, and r is 0 or 1.

Preferred alkoxylated quaternary etheramines are represented by the following structural formula:

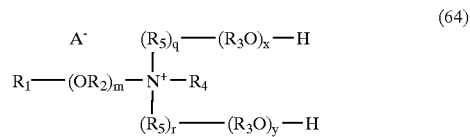
(64)

wherein R$_1$ is a straight or branched chain hydrocarbon having about 6 to about 22 carbon atoms, m is about 0 to about 10, R$_2$ is independently C$_1$–C$_4$ alkylene, R$_3$ groups are independently C$_1$–C$_4$ alkylene, x and y are average numbers such that x+y is 0 to about 60, R$_4$ is C$_1$–C$_4$ alkyl, R$_5$ is independently C$_1$–C$_4$ alkylene, q is 0 or 1, r is 0 or 1, and A$^-$ is an agriculturally acceptable anion.

Preferred alkoxylated etheramine oxide surfactants are represented by the following structural formula:

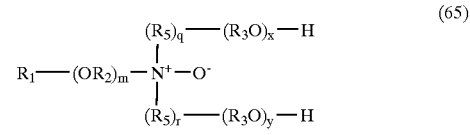
(65)

wherein R$_1$ is a straight or branched chain hydrocarbon having from about 6 to about 22 carbon atoms, m is about 0 to about 10, R$_2$ is independently C$_1$–C$_4$ alkylene, R$_3$ groups are independently C$_1$–C$_4$ alkylene, R$_5$ is independently C$_1$–C$_4$ alkylene, q is 0 or 1, r is 0 or 1, and x and y are average numbers such that x+y is about 2 to about 60.

The straight or branched chain hydrocarbon having from about 6 to about 22 carbon atoms is preferably an alkyl, aryl, or alkylaryl group. Aryl groups, if present in R$_1$ have 5–7, preferably 6 carbon atoms and may or may not be substituted. The alkyl portion in any alkylaryl group comprising R$_1$ has 1–16 carbon atoms. Such an alkylaryl group could be alkylphenyl, for example, nonylphenol.

However, in preferred surfactants of the invention R$^1$ is a straight or branched chain alkyl group having about 8 to about 18, for example about 10-15 carbon atoms, and are derived from the corresponding alcohol. For example, the alkyl group may be naturally derived, from coconut or tallow, for example, or may be derived from a synthetic alcohol such as isodecyl, isotridecyl, linear $C_{12}$–$C_{14}$ or octadecyl alcohols.

The $R_2$ substituent closest to the nitrogen atom (the proximal $R_2$ group) is preferably a linear propylene (—$CH_2CH_2CH_2$—), isopropylene (—$CH_2CH(CH_3)$—) or ethylene (—$CH_2CH_2$—) group. Preferred examples in which the proximal $R_2$ group is linear propylene have m=1. Where the proximal $R_2$ group is isopropylene or ethylene, m is preferably in the range from about 1 to about 5, most preferably from about 2 to about 3, and all $R_2$ groups are the same.

In quaternary etheramines of the invention, $R^4$ is preferably methyl and A— is preferably a halide, for example chloride or bromide. A— can also be a phosphate or a sulfate ion, or alternatively may be a glyphosate ion or may be contributed by an anionic surfactant included with the etheramine in the formulation. It will be recognized by those skilled in the art that at low pH such as may well exist in a glyphosate formulation, tertiary etheramines will most likely be protonated at the nitrogen atom and may be associated with a counterion. In these cases the tertiary etheramine is best represented by the chemical structure shown above for a quaternary etheramine with the exception that $R_4$ is hydrogen. The counterion A— in a low pH glyphosate formulation comprising a tertiary amine will most likely be glyphosate itself.

Representative surfactants of the type mentioned above are described in U.S. Pat. Nos. 5,703,015, 5,750,468 and 5,389,598, the entirety of each being incorporated herein by reference.

The surfactant component of the compositions of the present invention may optionally contain a glycol or glycol ester of formula:

$$HO—(R^4O)_x—R^5 \qquad (66)$$

wherein $R^4$ in each of the x ($R^4O$) groups is independently a linear or branched $C_{2-6}$ alkylene group, x is 1 to about 4, and $R^5$ is hydrogen or a $C_1$–$C_4$ hydrocarbyl group. The total amount of glycol or glycol ester in the surfactant component is from about 50% to about 95% by weight. Contemplated glycols and glycol esters include but are not limited to monoethylene glycol, diethylene glycol, propylene glycol or the methyl, ethyl, n-propyl, n-butyl or t-butyl ethers thereof, dipropylene glycol or the methyl, ethyl, n-propyl, n-butyl or t-butyl ethers thereof, tripropylene glycol, or the methyl, ethyl, n-propyl, n-butyl or t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol. Preferred are glycols having 4 or more carbon atoms. Of these, 2-methyl-1,3-propanediol and 1,4-butanediol are more preferred glycols. A blend or mixture of several glycols may be used, in which case the total amount of all glycols present is as above. In such a case, it is preferred that at least one of the glycols in the blend be a $C_4$ or higher glycol, especially 2-methyl-1,3-propanediol or 1,4-butanediol. In another embodiment, the surfactant composition contains about 50% to about 80% by weight of 2-methyl-1,3-propanediol, 1,4-butanediol or a mixture thereof and about 5% to about 30% by weight of propylene glycol.

A composition of the invention that includes both the glycol or glycol ester and the polysiloxane, such as polyoxyalkylene trisiloxane, exhibits increased penetration of the herbicidal composition into or through the plant, under certain conditions, namely hot, dry conditions.

Other nonionic surfactants may likewise be found useful, including without restriction polyoxyethylene polyoxypropylene block copolymers and alkyl polyglucosides. Cationic, anionic or amphoteric surfactants may also be included if desired.

In one embodiment of the invention, the herbicidal compositions include at least one nonionic surfactant and at least one cationic surfactant such as those described herein. Such surfactant combinations are described in U.S. Pat. No. 5,998,332, which is incorporated herein by reference.

Additional cationic surfactants suitable for use in the herbicidal compositions of the invention are those described in U.S. Pat. Nos. 5,563,111, 5,622,911, 5,849,663, 5,863,909, 5,985,794, 6,030,923 and 6,093,679, which are incorporated herein by reference.

The surfactant compositions typically are intended for mixing with a water soluble herbicide composition. It is preferred that there be substantially no water present in the surfactant composition.

A surfactant composition of the invention comprises any combination of the surfactants as described above. The surfactant composition is particularly preferred for use in formulating compositions or concentrates containing potassium, di-ammonium, ammonium, sodium, monoethanolamine, n-propylamine, methylamine, ethylamine, hexamethylenediamine, dimethylamine and/or trimethylsulfonium glyphosate, and diquat or paraquat. The surfactant composition can be incorporated into a composition or concentrate comprising any combination of these glyphosate salts and diquat and/or paraquat.

The density of any glyphosate-containing formulation of the invention is preferably at least 1.050 grams/liter, more preferably at least about 1.055, 1.060, 1.065, 1.070, 1.075, 1.080, 1.085, 1.090, 1.095, 1.100, 1.105, 1.110, 1.115, 1.120, 1.125, 1.130, 1.135, 1.140, 1.145, 1.150, 1.155, 1.160, 1.165, 1.170, 1.175, 1.180, 1.185, 1.190, 1.195, 1.200, 1.205, 1.210, 1.215, 1.220, 1.225, 1.230, 1.235, 1.240, 1.245, 1.250, 1.255, 1.260, 1.265, 1.270, 1.275, 1.280, 1.285, 1.290, 1.295, 1.300, 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.41.0, 1.415, 1.420, 1.425, 1.430, 1.435, 1.440, 1.445, or 1.450 grams/liter.

As further discussed herein, other additives, adjuvants, or ingredients may be introduced into the formulations of the present invention to improve certain properties of the resulting formulations. Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. Suitable solubilizers for use with the novel formulations of the present invention include, for example, cocoamine (Armeen C), dimethylcocoamine (Arquad DMCD), cocoammonium chloride (Arquad C), PEG 2 cocoamine (Ethomeen C12), PEG 5 tallowamine (Ethomeen T15), and PEG 5 cocoamine (Ethomeen C15), all of which are manufactured by Akzo Nobel (California).

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 ethylene oxide groups. Preferred alkylamine compounds include C₆ to C12 alkylamines having 0 to 2 ethylene oxide groups. Similarly, etheramine compounds having 4 to 12 carbons and 0 to about 5 ethylene oxide groups, as well as the corresponding quaternary ammonium compounds, also enhance the compatibility of such formulations. In one embodiment, the compounds which enhance the compatibility of such surfactants include amines or quaternary ammonium salts having the formula:

 (67)

 (68)

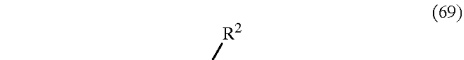 (69)

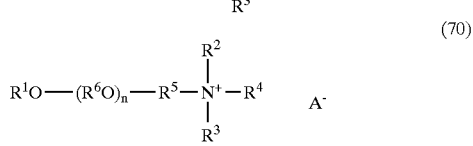 (70)

wherein $R^1$ is linear or branched alkyl or aryl having from about 4 to about 16 carbon atoms, $R^2$ is hydrogen, methyl, ethyl, or —(CH₂CH₂O)ₓH, $R^3$ is hydrogen, methyl, ethyl, or —(CH₂CH₂O)ᵧH wherein the sum of X and y is not more than about 5; $R^4$ is hydrogen or methyl; $R^6$ in each of the n (R⁶O) groups is independently $C_2$–$C_4$ alkylene; $R^5$ is hydrocarbylene or substituted hydrocarbylene having from 2 to about 6 carbon atoms; and A— is an agriculturally acceptable anion.

Also provided by the present invention is a herbicidal method comprising diluting with a suitable volume of water a herbicidally effective volume of a concentrate as provided herein to form an application mixture, and applying the application mixture to foliage of a plant or plants.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl (—CH$_2$OH), and hydroxyethyl (—C$_2$H$_4$OH), bis(hydroxymethyl)methyl (—CH(CH$_2$OH)$_2$), and tris(hydroxymethyl)methyl (—C(CH$_2$OH)$_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is R$^1$, R$^1$O—, R$^1$R$^2$N—, or R$^1$S—, R$^1$ is hydrocarbyl, heterosubstituted hydrocarbyl, or heterocyclo and R$^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number." The presence in a composition of individual surfactant molecules having an integer number of such units outside the stated range in "average number" does not remove the composition from the scope of the present invention, so long as the "average number" is within the stated range and other requirements are met.

By "storage-stable," in the context of a liquid concentrate of the invention, is meant not exhibiting phase separation on exposure to temperatures up to about 50° C. for 14–28 days, and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate aqueous solution concentrate. Ideally the cloud point should be 60° C. or more, and the composition should withstand temperatures as low as about −10° C. for up to about 7 days without crystal growth, even in the presence of seed crystals of the glyphosate salt.

Additional ingredients, including other surfactants for example, may also be utilized in the present invention. It often proves desirable to employ additional surfactants in order, for example, to moderate the spreading properties imparted to the composition by a super spreading surfactant.

Another ingredient that can optionally be added to the compositions of the present invention to further improve the herbicidal effectiveness and related herbicidal properties is a dicarboxylic acid or salt of a dicarboxylic acid. Suitable dicarboxylic acids that may be added to the compositions as described herein include, for example, oxalic acid, malonic acid, succinic acid, glutaric acid, maleic acid, adipic acid, and fumaric acid, and combinations or mixtures thereof, with oxalic acid being preferred. Also, in addition to, or in place of the dicarboxylic acid, salts of the aforementioned dicarboxylic acids may be incorporated into the compositions of the present invention to improve herbicidal performance. Suitable salts include, for example, alkali metal salts such as potassium salts, alkanolamine salts and lower alkylamine salts. Preferred salts include potassium oxalate, dipotassium oxalate, sodium oxalate, disodium oxalate, diammonium oxalate, diethanolamine oxalate, dimethylamine oxalate, alkanolamine salts of oxalic acid, and lower alkylamine salts of oxalic acid. Compositions containing a dicarboxylic acid such as oxalic acid or a dicarboxylic acid salt such as potassium oxalate, typically contain a sufficient amount of dicarboxylic acid/dicarboxylic acid salt to enhance the resulting efficacy of the composition. Typically, the weight ratio of total surfactant to dicarboxylic acid/dicarboxylic acid salt may be from about 1:1 to about 50:1, more preferably 5:1 to 40:1 and most preferably from about 5:1 to about 20:1. This ratio of total surfactant to dicarboxylic acid/dicarboxylic acid salt significantly enhances the herbicidal performance of the resulting composition.

While the herbicidal compositions of the invention include water and water-soluble ingredients, the present invention encompasses compositions additionally containing one or more oils, which may be of vegetable origin (such as methylated vegetable oils) or petroleum derived, together with any standard formulation ingredients such as emulsifiers that might be used to stabilize the oil in the aqueous composition.

The herbicidal compositions of the invention can be formulated as spray compositions or concentrates. The term herbicidal spray composition is used herein to indicate a herbicidal composition that is ready for application to target foliage. Such a herbicidal composition can be obtained by dilution of a liquid concentrate with water, or dissolution or dispersion in water of a dry (e.g. granular, powder, tablet or briquette) formulation such as a particulate solid concentrate which may contain small amounts of water. Spray compositions include tank mixes and ready-to-use formulations.

Herbicidal spray compositions of the present invention typically can be made with a glyphosate concentration from about 2 to about 36 grams acid equivalent per liter, preferably from about 4 to about 18 grams acid equivalent per liter, more preferably from about 6 to about 11 grams acid equivalent per liter.

Herbicidal spray compositions of the present invention typically can be made with a bipyridilium concentration from about 0.025 to about 0.75 grams cation per liter, preferably from about 0.05 to about 0.3 grams cation per liter, more preferably from about 0.07 to about 0.2 grams cation per liter.

Similarly, herbicidal spray compositions of the present invention typically can be made with a surfactant concentration from about 0.2 to about 10.7 grams per liter or from about 0.02 to about 1.0% vol/vol, preferably from about 0.65 to about 6.4 grams per liter or from about 0.06 to about 0.6% vol/vol, more preferably from about 1.33 to about 4.3 grams per liter or from about 0.125 to about 0.4% vol/vol.

Therefore, herbicidal spray compositions of the present invention typically can be made with weight ratios of about 100:1 to about 2:1 glyphosate (a.e.) to bipyridilium (c.e.), preferably from about 80:1 to 20:1, more preferably from about 60:1 to about 30:1. Further, the herbicidal spray composition can be made with weight ratios of about 48:1 to 0.4:1 glyphosate a.e. to surfactant, preferably from about 17:1 to 0.5:1 glyphosate (a.e.) to surfactant, more preferably from about 8:1 to about 1:1. The herbicidal composition can also be made with weight ratios of about 0.002:1 to 0.75:1 bipyridilium (c.e.) to surfactant, preferably from about 0.004:1 to 0.5:1, more preferably from about 0.02:1 to about 0.15:1.

The weight ratio of glyphosate to bipyridilium in the herbicidal spray compositions of the invention preferably is between about 20:1, 21:1, 22:1, 23:1, 24:1, 25:1, 26:1, 27:1, 28:1, 29:1, 30:1, or 35:1 and about 100:1. The weight ratio of glyphosate to surfactant in the herbicidal compositions of the invention preferably is between about 0.5:1, 0.6:1, 0.7:1, 0.8:1, 0.9:1, 1:1, 2:1, 3:1, 4:1, 5:1, 6:1, 7:1 or 8:1 and about 100:1.

The herbicidal spray composition described above can be obtained by dilution of a liquid concentrate with water, or dissolution, dispersion or suspension in water of a dry (e.g. granular, powder, tablet or briquette) formulation, such as a particulate solid concentrate which may contain small amounts of water.

The particulate solid concentrates of the invention yield aqueous solutions when dissolved in water which upon proper dilution are to be used in accordance with the method of the present invention. The particulate solid concentrates of the present invention are storage stable.

This particulate solid concentrate comprises by weight about 50% to 95% glyphosate acid (a.e.) or a herbicidally acceptable salt or ester thereof (a.i.), preferably from about 60% to 90%, more preferably from about 70% to about 85%; or about 65% to 85%; 0.5% to 3% by weight of a bipyridilium (c.e.), preferably from about 1% to 2.5% c.e., more preferably from about 1.3% to 2% c.e.; 5% to 40% by weight of a surfactant, preferably from 7% to 30%, more preferably 10% to 25%; 0 to 1% by weight of an antioxidant, preferably from about 0.2% to 0.8%, more preferably from about 0.3% to 0.5%; 0 to 2.0% by weight of antifoam agent, preferably 0.2% to 1.5%, more preferably from about 0.6% to 1.0%.

Thus, a preferred embodiment contains about 60% to 90% by weight (a.i.) of an alkali metal, ammonium, $C_{1-6}$ alkylammonium, $C_{1-16}$ alkanolammonium or $C_{1-16}$ alkylsulfonium salt of glyphosate; and about 1% to 2.5% by weight of a bipyridilium; about 7% to 30% by weight of one or more surfactant(s); about 0.2% to 0.8% by weight of antioxidant; and about 0.2% to 1.5% by weight antifoam agent.

A more preferred embodiment contains about 65% to 85% by weight (a.i.) of an ammonium or sodium salt of glyphosate; about 1.3% to 2% by weight (c.e.) of a salt of diquat; about 10% to 25% by weight polysiloxane surfactant; about 0.3% to 0.5% by weight antioxidant; and 0.6% to 1.0% by weight antifoam agent.

Therefore, particulate solid concentrates of the present invention typically can be made with weight ratios of about 1:1 to 100:1 glyphosate (a.e.) to bipyridilium (c.e.), preferably from about 22:1 to 90:1, more preferably from about 40:1 to about 50:1. Further, the particulate solid concentrates can be made with weight ratios of about 1:1 to about 40:1 glyphosate (a.e.) to surfactant, preferably from about 1.5:1 to 15:1, more preferably from about 2:1 to about 6:1. The particulate solid concentrates can also be made with weight ratios of about 0.013:1 to 11:1 bipyridilium (c.e.) to surfactant, preferably from about 0.018:1 to 0.5:1, more preferably from about 0.02:1 to about 0.15:1.

The antioxidant is used to prevent the formation of nitrosamine. Examples include, but are not limited to ascorbic acid and sodium sulfite. Sodium sulfite is the preferred antioxidant.

Preferably the antifoam agent used is Antifoam™ or Y-14088 Antifoam™, both available from Crompton Corporation. Preferred organosilicone surfactants include, but are not limited to, Silwet L-77™, Silwet 800™ and Breakthru AF-9903™, Breakthru S-240™ organosilicone surfactants.

The particulate solid concentrate of the invention preferably exhibits a dissolution rate of not more than five minutes, more preferably not more than four minutes, three minutes, two minutes or 1 minute.

The particulate solid concentrate is prepared by combining glyphosate, a bipyridilium, and one or more surfactants. Preferably, the particulate solid concentrate is prepared by combining an antioxidant, a salt of glyphosate, antifoam, organosilicone surfactant and a bipyridilium. More preferably, the particulate solid concentrate is prepared by combining sodium sulfite, ammonium glyphosate, antifoam, organosilicone surfactant and diquat. In the more preferred process for preparing the particulate solid concentrate, sodium sulfite is added to a blender containing ammonium glyphosate and mixed. In a separate container, antifoam is added to an amount of an organosilicone surfactant and blended. This surfactant/antifoam mixture is slowly added to the ammonium glyphosate/sodium sulfite mixture. Diquat is then added to the combined mixture and mixed at room temperature. The combined mixture is then processed through an extruder. The resulting extrudate is then dried. The dried composition is further purified to select for particles of a certain size to produce the desired particulate solid concentrate product. The particulate solid concentrate can be prepared by other processes.

A liquid concentrate containing glyphosate can be diluted with water to yield the herbicidal spray composition described above which is ready for application to foliage. The liquid concentrates of the present invention are storage stable.

Stable liquid concentrate compositions of the present invention typically can be made with a glyphosate concentration from about 5 grams a.e./L to about 550 grams a.e./L preferably from about 50 grams a.e./L to about 450 grams a.e./L, more preferably from about 120 grams a.e./L to about 360 grams a.e./L, and most preferably from about 140 to about 350 grams a.e./L.

Stable liquid concentrate compositions of the present invention typically can be made with a bipyridilium concentration from about 0.1 grams cation/L to about 50 grams cation/L, preferably from about 1 gram cation/L to about 40 grams cation/L, more preferably from about 2 grams cation/L to about 35 grams cation/L, and most preferably 335 grams c.e./L.

Stable liquid concentrate compositions of the present invention typically can be made with weight ratios of about 1:1 to 100:1 glyphosate (a.e.) to bipyridilium (c.e.), preferably from about 8:1 to 60:1, more preferably from about 25:1 to about 50:1. Further, the stable liquid concentrates can be made with ratios of about 0.1:1 to about 50:1 glyphosate (a.e.) to surfactant, preferably from about 0.5:1 to 30:1, more preferably from about 2:1 to about 5:1. The liquid concentrates can also be made with ratios of about 0.001:1 to 1:1 bipyridilium (c.e.) to surfactant, preferably from about 0.01:1 to 0.5:1, more preferably from about 0.06:1 to about 0.3:1.

When an organosilicone surfactant is employed, stable liquid concentrate compositions of the present invention typically can be made with weight ratios of about 1:1 to 100:1 glyphosate (a.e.) to bipyridilium (c.e.), preferably from about 15:1 to 75:1, more preferably from about 25:1 to about 50:1. Further, the stable liquid concentrates can be made with weight ratios of about 0.2:1 to about 45:1 glyphosate (a.e.) to organosilicone surfactant, preferably from about 0.5:1 to 25: 1, more preferably from about 2:1 to about 6:1. The liquid concentrates can also be made with ratios of about 0.002:1 to 0.75:1 bipyridilium (c.e.) to surfactant, preferably from about 0.008:1 to 0.4:1, more preferably from about 0.04:1 to about 0.2:1.

Preferred salts of glyphosate for use in a liquid concentrate of the invention include the IPA salts of glyphosate, monoethanolamine salt of glyphosate, the ammonium salts of glyphosate and the potassium salts of glyphosate. Commercially available sources of glyphosate include Roundup Ultra®, Roundup UltraMAX®, Ranger®, Roundup Full®, and Super-Roundup®, which are from Monsanto Company. Preferred bipyridiliums include diquat. The weight ratio of glyphosate to bipyridilium in the herbicidal compositions of the invention preferably is between about 26:1, 27:1, 28:1, 29:1, 30:1, 31:1, 32:1, 33:1, 34:1, 35:1, 36:1, 37:1, 38:1, 39:1 or 40:1 and about 100:1. The weight ratio of glyphosate to surfactant in the herbicidal compositions of the invention preferably is between about 0.5:1, 0.6:1, 0.7:1, 0.8:1, 0.9:1, 1:1, 2:1, 3:1, 4:1, 5:1, 6:1, 7:1 or 8:1 and about 50:1. The glyphosate concentration is at least about 120 grams a.e./l, or 125, 130, 135, 140, 145, 150, 155, 160, 165, 170, 175, 180, 185, 190, 195 or 200 grams a.e./l.

The liquid concentrate is prepared by combining glyphosate, a bipyridilium, one or more surfactants and water. Preferably, the concentrate is prepared by combining MON 0139, a suitable surfactant, a bipyridilium such as diquat, and water. Concentrates can be prepared by combining commercially available herbicides which include at least one surfactant, a glyphosate salt, a bipyridilium, and water. For example, Roundup Ultra®, Roundup UltraMAX®, Ranger®, Roundup Full® or Super-Roundup® can be mixed with Reglone® and water.

The herbicidal spray composition can be prepared from the liquid concentrate by diluting the liquid concentrate in an appropriate volume of water and agitating as needed. The resulting herbicidal spray composition can then be applied, for example by spraying, to any unwanted vegetation to be killed or controlled. Herbicidal spray compositions can be prepared from particulate solids by dissolving or dispersing the particulate solids in an appropriate volume of water, agitating as needed, and applying to unwanted vegetation. Prepared herbicidal compositions of the present invention containing superspreading surfactants should be used within 24 to 48 hours following preparation, depending upon various conditions.

The herbicidal spray compositions of the present invention are applied as aqueous solutions or dispersions, whether they result from the further dilution of the liquid concentrate or the addition of water to the particulate solid concentrate. The term "aqueous" as used herein is not intended to exclude the presence of some small amount of nonaqueous solvent, so long as the predominant solvent present, other than the glycol or glycol ester component of the surfactant composition, is water. The herbicidal spray compositions included in the present invention can be applied to the foliage of the plants to be treated through any of the appropriate methods that are well known to those having skill in the art.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. The herbicidal effectiveness data set forth herein report "control" as a percentage following a standard procedure in the art which reflects a visual assessment of plant mortality and growth reduction by comparison with untreated plants, made by technicians specially trained to make and record such observations. In all cases, a single technician makes all assessments of percent control within any one experiment or trial. Such measurements are relied upon and regularly reported by Monsanto Company in the course of its herbicide business.

The selection of application rates that are biologically effective for glyphosate is within the skill of the ordinary agricultural scientist. Those of skill in the art will likewise recognize that individual plant conditions, weather and growing conditions, as well as the glyphosate formulation selected, will affect the efficacy achieved in practicing this invention. Useful application rates for glyphosate can depend upon all of the above conditions. With respect to the use of the method of this invention, much information is known about appropriate application rates for glyphosate herbicide. Over two decades of glyphosate use and published studies relating to such use have provided abundant information from which a weed control practitioner can select glyphosate application rates that are herbicidally effective on particular species at particular growth stages in particular environmental conditions.

In general, the herbicidal composition of the present invention is applied to plants at a rate sufficient to give the desired biological effects: control of plant growth and early visual symptoms of treatment. The amount of glyphosate and a bipyridilium applied to plants in combination generally provides a herbicidally-effective amount of herbicide. The amount of glyphosate and a bipyridilium applied to plants further is sufficient to provide early visual symptoms of plant treatment without significantly reducing the desired biological effect of the glyphosate. These application rates are usually expressed as amount of glyphosate per unit area treated, e.g. grams per hectare (g/ha). What constitutes a "desired effect" varies according to the standards and practice of those who investigate, develop, market and use compositions. Typically, the amount of the composition applied per unit area to give 85% control of a plant species as measured by growth reduction or mortality is often used to define a commercially effective rate. Early visual symptoms of treatment generally should appear no later than four days after treatment, preferably no later than three days after treatment, more preferably no later than two days after treatment, and still more preferably no later than one day after treatment.

In the herbicidal composition as applied to the target foliage, for example, the application rate of glyphosate ranges from about 0.5 to about 12 pounds acid equivalent per acre, preferably from about 3.0 to about 9.0, and more preferably from about 4.5 to about 7.5 pounds acid equivalent per acre; the application rate of bipyridilium ranges from about 0.01 to about 0.5 pounds cation per acre, preferably from about 0.025 to about 0.25, and more preferably from about 0.0625 to about 0.15 pounds cation per acre; and the application rate of the surfactant composition ranges from about 0.25 to about 9.0 pounds per acre; preferably from about 0.55 to about 5.5, and more preferably from about 1.0 to about 3.5 pounds per acre.

The herbicidal composition of the present invention can be applied at a carrier volume of between about 20 gallons per acre to about 250 gallons per acre. Preferably, the herbicidal composition of the present invention is applied at between about 50 gallons per acre to about 200 gallons per acre. More preferably, the herbicidal compositions of the present invention are applied at about 75 gallons per acre to about 175 gallons per acre. Still more preferably, the herbicidal compositions of the present invention are applied at between about 80 gallons per acre to about 150 gallons per acre.

Also included in the invention is a method of killing or controlling weeds or unwanted vegetation comprising the steps of diluting the liquid concentrate in a convenient amount of water to form an application mixture and applying a herbicidally effective amount of the application mixture to the foliage of the weeds or unwanted vegetation. Similarly included in the invention is the method of killing or controlling weeds or unwanted vegetation comprising the steps of diluting a solid particulate concentrate in a convenient amount of water to form an application mixture and applying a herbicidally effective amount of the application mixture to the foliage of the weeds or unwanted vegetation. The application mixture is typically a tank mix.

The herbicidal compositions of the present invention can be used to control a very wide variety of plants worldwide such as annual and perennial grass and broadleaf weeds and sedges. These compositions can be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Festuca, Helianthus, Imperata, Ipomoea, Kochia, Lolium, Malva, Oryza, Ottochloa, Panicum, Paspalum, Pennisetum, Phalaris, Phragmites, Poa, Polygonum, Portulaca, Pteridium, Pueraria, Rubus, Salsola, Setaria, Sida, Sinapis, Sorghum, Triticum, Typha, Ulex, Xanthium*, and *Zea*.

Particularly important species for which the compositions are used are exemplified without limitation by the following:

Annual broadleaves including, but not limited to, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*), spurge, chickweed (*Stellaria Media*), and cocklebur (*Xanthium* spp.).

Annual narrowleaves including, but not limited to, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), annual bluegrass (*Poa annua*), wheat (*Triticum aestivum*), and corn (*Zea mays*).

Perennial broadleaves including, but not limited to, mugwort (*Artemisia* spp.), milkweed (*Asclepias* spp.), canada thistle (*Cirsium arvense*), white clover (*trifolium repens*) field bindweed (*Convolvulus arvensis*), and kudzu (*Pueraria* spp.).

Perennial narrowleaves including, but not limited to, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), tall fescue (*Festuca arundinacea*), lalang (*Imperata cylindrica*), perennial ryegrass (*Lolium perenne*), guineagrass (*Panicum maximum*), dallisgrass (*Paspalum dilatatum*), kikuyugrass (*Pennisetum clandestinum*), reed (*Phragmites* spp.), Kentucky bluegrass (*Poa pratensis*), johnsongrass (*Sorghum halepense*), and cattail (*Typha* spp.).

Other perennials including, but not limited to, horsetail (*Equisetum* spp.), bracken (*Pteridium aquilinum*), blackberry (*Rubus* spp.), and gorse (*Ulex europaeus*).

Tree seedlings including oak, maple, and ash.

Thus, the methods of the present invention can be useful on any of the above species.

EXAMPLES

The following examples are provided for illustrative purposes only and are not intended to limit the scope of the present invention defined by the claims. In these examples, percentage amounts refer to percent by weight of tank mix composition as it is applied to target foliage unless otherwise noted. All examples were sprayed at a carrier volume of between about 80 gallons per acre to 150 gallons per acre. In the following examples, experiments were performed using the following materials.

| NO. | FORMULATION |
|---|---|
| 1 | ROUNDUP PRODRY ® |
| 2 | REWARD ® |
| 3 | SCYTHE ® |
| 4 | Surfactant Composition A |
| 5 | KINETIC ™ |
| 6 | SILWET L-77 ® |
| 7 | Formulation A |
| 8 | TRITON AG-98 ™ |

-continued

| NO. | FORMULATION |
|---|---|
| 9 | KERB ™ |
| 10 | Simazine |
| 11 | Ammonium Sulfate |
| 12 | RONSTAR ™ |
| 13 | FINALE ™ |
| 14 | Formulation B |
| 15 | Formulation C |
| 16 | Formulation D |
| 17 | Paraquat |
| 18 | ROUNDUP ® Concentrate |
| 19 | REAL KILL ™ |
| 20 | ROUNDUP ® RTU 2X FATTY ACID |
| 21 | Formulation E |
| 22 | ROUNDUP ULTRA ® |
| 23 | MON 0139 |
| 24 | Surfactant Composition B |
| 25 | BREAKTHRU S-240 ™ |
| 26 | Formulation F |
| 27 | ROUNDUP ® RTU |
| 28 | SPECTRACIDE ™ RTU |
| 29 | SUREFIRE ™ |
| 30 | Formulation G |
| 31 | Formulation H |
| 32 | Formulation I |
| 33 | Formulation J |
| 34 | Formulation K |
| 35 | Formulation L |
| 36 | Formulation M |
| 37 | Formulation N |
| 38 | Formulation O |
| 39 | Formulation P |
| 40 | Formulation Q |
| 41 | Formulation R |
| 42 | Formulation S |
| 43 | FLUAZIFOP |
| 44 | Formulation T |
| 45 | SPECTRACIDE GWK ™ |
| 46 | Eliminator ™ |
| 47 | Kgro ™ Grass & Weed Killer ™ |
| 48 | Super K-Gro SHOOT OUT ™ |
| 49 | Formulation U |
| 50 | Formulation V |
| 51 | Nu-Film-IR ™ |
| 52 | DyneAmic MSO ™ |
| 53 | CIDE-KICK II ™ |
| 54 | ACTIVATOR 90 ™ |
| 55 | MON 0818 |
| 56 | Methylated Seed Oil |
| 57 | FRIGATE ™ |
| 58 | FORMULATION W |
| 59 | FORMULATION X |
| 60 | FORMULATION Y |
| 61 | FORMULATION Z |
| 62 | FORMULATION AA |

ROUNDUP PRODRY® herbicide is a commercially available water soluble granular formulation of Monsanto Company containing 71.4% by weight of the ammonium salt of glyphosate, or about 64.9% by weight of N-phosphonomethylglycine acid equivalent, 28.6% surfactant and other minor ingredients. 1.156 Pounds of ROUNDUP PRODRY™ herbicide contains 0.75 pound of glyphosate acid equivalent.

REWARD® herbicide is a commercially available emulsified concentrate formulation of Syngenta Corporation containing 37.3% of the dibromide salt of dihydrodipyrido(1,2-a:2',1'-c)pyrazinediium. REWARD® herbicide contains two pounds of dihydrodipyrido(1,2-a:2',1'-c)pyrazinediium cation per U.S. gallon as 3.73 pounds of dihydrodipyrido(1,2-a:2',1'-c)pyrazinediium dibromide.

SCYTHE® herbicide is a commercially available emulsified concentrate formulation of Dow Agrosciences containing 57.0% pelargonic acid, 3.0% related $C_6$–$C_{12}$ fatty acids, 30% paraffinic petroleum oil, and 10% inerts. Each U.S. gallon of SCYTHE® herbicide contains 4.2 pounds of pelargonic acid.

Surfactant Composition A is the same as Surfactant Composition A as disclosed in U.S. Pat. No. 6,040,272, the entirety of which has been incorporated by reference.

KINETIC™ is a blend of polyalkylene oxide modified polydimethylsiloxane and a nonionic surfactant and is from Helena Chemical Company.

SILWET L-77™ is an ethoxylated trisiloxane from Crompton.

Formulations A, B, C and D are as prepared in Examples 19–22, respectively.

TRITON AG-98™ is 80% octylphenol ethoxylate and is from Union Carbide Corporation.

KERB™ is 50% pronamide 3,5-dichloro-N-1,1-dimethyl-2-propynyl-benzamide and 50% inerts and is from Rohm & Haas Company.

Simazine is available as Princep® from Novartis Crop Protection, Inc.

RONSTAR™ is a surfactant containing oxadiazon from Rhone Poulenc, Inc.

FINALE™ is 11.33% ammonium glufosinate, less than 20% alkylhydroxy polyoxyethylene sulfate surfactant, and remainder inerts.

QWIKWET® 100 is a polyoxyethylene heptamethyltrisiloxane of Exacto, Inc.

NEODOL™ 1-7 is a polyoxyethylene (7) $C_{11}$ linear primary alcohol of Shell.

MON 0139 is an aqueous solution of 62% by weight of the IPA salt of glyphosate.

MON 0818 is an ethoxylated fatty tallow amine with an average ethylene oxide content of about 15–18 moles.

Formulation E contains 25% a.i. IPA glyphosate, 1.46% a.i. diquat, and 8.8% Surfactant Composition B.

ROUNDUP® Concentrate contains 25% a.i. IPA glyphosate.

REAL KILL™ contains 1.92% a.i. IPA glyphosate.

ROUNDUP RTU 2X FATTY ACID contains 1.92% a.i. IPA glyphosate per gallon.

ROUNDUP ULTRA® contains 41% a.i. IPA glyphosate, 14.5% cationic tallowamine and phosphate ester surfactants, and 44.5% inerts and water.

Surfactant Composition B is a mixture of cationic tallowamines and phosphate esters as described in U.S. Pat. No. 5,703,015.

BREAKTHRU S-240™ is a polyether polymethylsiloxane copolymer from Goldschmidt Chemical Corporation.

Formulation F contains 68.8% a.i. ammonium glyphosate, 2.71% a.i. diquat dibromide, and 23.3% silicone surfactant.

ROUNDUP RTU® contains 0.96% a.i. isopropylamine salt of glyphosate in water.

SPECTRACIDE™ RTU contains 0.18% diquat dibromide and 0.06% fluazifop-p-butyl.

SUREFIRE™ contains 29.42% paraquat dichloride and 10.66% diuron. The remaining 59.92% constitutes other inert ingredients.

Formulation G contains 18.5% a.e. IPA glyphosate, 0.37% a.i. diquat, and 7.3% Surfactant Composition B.

Formulation H contains 18.5% a.e. IPA glyphosate, 0.73% a.i. diquat, and 7.3% Surfactant Composition B.

Formulation I contains 18.5% a.e. IPA glyphosate, 1.46% a.i. diquat, and 7.3% Surfactant Composition B.

Formulation J contains 18.5% a.e. IPA glyphosate, 0.37% a.i. diquat, 2% Breakthru S-240™, and 5.3% Surfactant Composition B.

Formulation K contains 18.5% a.e. IPA glyphosate, 0.73% a.i. diquat, 2% Breakthru S-240™, and 5.3% Surfactant Composition B.

Formulation L contains 18.5% a.e. IPA glyphosate, 1.46% a.i. diquat, 2% Breakthru S-240™, and 5.3% Surfactant Composition B.

Formulation M contains 18% a.i. IPA glyphosate, 1.46% a.i. diquat, and 5.26% Surfactant Composition B.

Formulation N contains 18% a.i. IPA glyphosate, 0.73% a.i. diquat, and 5.26% Surfactant Composition B.

Formulation O contains 18% a.i. IPA glyphosate, 0.37% a.i. diquat, and 5.26% Surfactant Composition B.

Formulation P contains 25% a.i. IPA glyphosate, 1.46% a.i. diquat, and 7.3% Surfactant Composition B.

Formulation Q contains 25% a.i. IPA glyphosate, 0.73% a.i. diquat, and 7.3% Surfactant Composition B.

Formulation R contains 25% a.i. IPA glyphosate, 0.37% a.i. diquat, and 7.3% Surfactant Composition B.

Formulation S contains 25% a.i. IPA glyphosate, 1.46% a.i. diquat, and 8.8% Surfactant Composition B.

Formulation T contains 25% a.i. IPA glyphosate, 0.73% a.i. diquat, and 5.3% Surfactant Composition B.

SPECTRACIDE GWK™ concentrate contains 2.30% a.i. diquat dibromide per gallon and 0.75% a.i. fluazifop per gallon.

ELIMINATOR™ is a water dilutable concentrate containing 1.85% diquat.

Formulation U is a solid particulate concentrate containing 77.3% a.i. ammonium glyphosate, 2.88% a.i. diquat dibromide, and 18.6% silicone surfactant.

Formulation V is a solid particulate concentrate containing 77.3% a.i. ammonium glyphosate, 2.88% a.i. diquat dibromide, and 18.6% silicone surfactant.

KGro Grass & Weed Killer™ contains 0.75% a.i. IPA glyphosate.

Super K-Gro SHOOT OUT™ Spot Weed & Grass Killer contains 0.96% a.i. IPA glyphosate.

Nu-Film-IR™ is 96% poly-1-p-menthene and 4% inert ingredients.

DyneAmic MSO™ contains a proprietary blend of polyalkyleneoxide polydimethylsiloxane, nonionic emulsifiers, and methylated vegetable oils and is from Helena Chemical Co.

CIDE-KICK II™ is a nonionic spray adjuvant containing d,1-limonene, terpine hydrocarbon, and nonylphenol polyethylene glycol ether.

ACTIVATOR 90™ is 90% alkyl polyoxyethylene ether and free fatty acids and 10% inerts from Loveland Industries.

FRIGATE™ is 70% polyethoxylated tallowamine and 30% butanol.

Formulation W is a solid particulate concentrate containing 70.2% a.i. ammonium glyphosate, 1.38% a.i. diquat dibromide, and 23.3% silicone furfactant.

FORMULATION X contains 18% a.i. IPA glyphosate, 2.1% a.i. diquat, and 5.26% Surfactant Composition B.

FORMULATION Y contains 18% a.i. IPA glyphosate, 3.2% a.i. diquat, and 5.26% Surfactant Composition B.

FORMULATION Z contains 18% a.i. IPA glyphosate, 4.2% a.i. diquat, and 5.26% Surfactant Composition B.

FORMULATION AA contains 18% a.i. IPA glyphosate, 5.3% a.i. diquat, and 5.26% Surfactant Composition B.

The formulations of Table 1 were prepared by mixing the components of each formulation specified in Table 1 in water with mild agitation in an amount sufficient to provide the stated application rate based on an application rate of 100 gallons per acre. The resulting tank mix was applied by backpack sprayer using 8008 VS flat fan nozzles calibrated to deliver a spray volume of 100 gallons per acre at a pressure of 12 psi. The herbicidal compositions were applied as post-emergent applications to the foliage of the plants.

At various intervals after treatment, all plants in the test were examined by a single practiced technician to evaluate percent control, which is a visual measurement of the effectiveness of the treatment by comparison with untreated plants. The percent control figures reported represent the average control determined for a sample size of 10-15 treated plants, by comparison with untreated plants. A percent control value of 0% indicates no effect and a percent control value of 100% indicates that all of the specimens are completely dead.

The preparation and application of the formulations of Examples 2, 3, 4 and 5 was carried out in a manner similar to Example 1 using the components in the proportions reported in those Examples. The preparation and application of the formulations of subsequent Examples 6–14 was conducted in a manner similar to Example 1 with the exception that Formulation A was prepared from a particulate solid concentrate in the manner described in Example 19. Similarly, Formulation B was prepared from a particulate solid concentrate in the manner described in Example 20, Formulation C was prepared from a particulate solid concentrate in the manner described in Example 21, and Formulation D was prepared from a particulate solid concentrate in the manner described in Example 22.

The treatment number(s) listed in each table of the examples corresponds to the formulations listed in the above table. The active ingredient (e.g., herbicide or surfactant) application rate or the active ingredient concentration of the spray composition appears in parentheses following the treatment number. For example, 1(6# ae/A) as in Table 1 refers to the application of 6 lbs. glyphosate a.e. per acre of ROUNDUP PRODRY®.

Example 1

A test was conducted in Arkansas to determine the effectiveness of herbicide formulations of Tables 1 and 2 for killing or controlling Bermudagrass (*Cynodon dactylon*, CYNDA). Applications were made in late September and October. Evaluations were made 1, 2, 4, 9, and 32 days after treatment (DAT). Treatments and corresponding percent controls are reported in Tables 1 and 2.

TABLE 1

| TREATMENT (RATE) | PERCENT CONTROL DAYS AFTER APPLICATION | | |
|---|---|---|---|
| | 1 Day | 2 Days | 4 Days |
| 1 (6 # ae/A) | 0 | 0 | 33 |
| 1 (15 # ae/A) | 0 | 0 | 43 |
| 1 (6 # ae/A) + 2 (0.062 qts/A) | 0 | 0 | 37 |
| 1 (6 # ae/A) + 2 (0.125 qts/A) | 0 | 7 | 47 |
| 1 (6 # ae/A) + 2 (0.25 qts/A) | 7 | 13 | 57 |
| 1 (6 # ae/A) + 2 (0.5 qts/A) | 20 | 73 | 83 |
| 1 (15 # ae/A) + 2 (0.062 qts/A) | 0 | 0 | 43 |
| 1 (15 # ae/A) + 2 (0.25 qts/A) | 10 | 27 | 57 |
| 1 (6 # ae/A) + 3 (12 qts/A) | 87 | 93 | 90 |
| 1 (15 # ae/A) + 3 (4 qts/A) | 7 | 7 | 33 |
| 1 (15 # ae/A) + 4 (10% by V) | 20 | 33 | 53 |
| 1 (6 # ae/A) + 4 (5% by V) | 0 | 0 | 30 |
| 1 (6 # ae/A) + 2 (0.125 qts/A) + 4 (5% by V) | 90 | 95 | 95 |

TABLE 1-continued

| TREATMENT (RATE) | PERCENT CONTROL DAYS AFTER APPLICATION | | |
|---|---|---|---|
| | 1 Day | 2 Days | 4 Days |
| 1 (6 # ae/A) + 2 (0.25 qts/A) + 4 (2.5% by V) | 80 | 90 | 90 |
| UNTREATED | 0 | 0 | 0 |

TABLE 2

| TREATMENT (RATE) | PERCENT CONTROL DAYS AFTER APPLICATION | |
|---|---|---|
| | 9 Days | 32 Days |
| 1 (6 # ae/A) | 97 | 100 |
| 1 (15 # ae/A) | 97 | 100 |
| 1 (6 # ae/A) + 2 (0.062 qts/A) | 97 | 100 |
| 1 (6 # ae/A) + 2 (0.125 qts/A) | 95 | 100 |
| 1 (6 # ae/A) + 2 (0.25 qts/A) | 95 | 98 |
| 1 (6 # ae/A) + 2 (0.5 qts/A) | 97 | 98 |
| 1 (15 # ae/A) + 2 (0.062 qts/A) | 97 | 100 |
| 1 (15 # ae/A) + 2 (0.25 qts/A) | 97 | 100 |
| 1 (6 # ae/A) + 3 (12 qts/A) | 100 | 100 |
| 1 (15 # ae/A) + 3 (4 qts/A) | 88 | 100 |
| 1 (15 # ae/A) + 4 (10% by V) | 92 | 100 |
| 1 (6 # ae/A) + 4 (5% by V) | 88 | 100 |
| 1 (6 # ae/A) + 2 (0.125 qts/A) + 4 (5% by V) | 100 | 98 |
| 1 (6 # ae/A) + 2 (0.25 qts/A) + 4 (2.5% by V) | 98 | 98 |
| UNTREATED | 0 | 0 |

Example 2

A test was conducted in Alabama to determine the effectiveness of the herbicide formulations of Tables 3 and 4 for killing or controlling St. Augustinegrass (*Stenotaphrum secundatum*, STPSE). Applications were made in late September and October. Evaluations were made 1, 2, 3, 5, 7, 14 and 28 days after treatment (DAT). Application rates, treatments and corresponding percent control are reported in Tables 3 and 4.

TABLE 3

| TREATMENT (RATE) | PERCENT CONTROL DAYS AFTER APPLICATION | | | |
|---|---|---|---|---|
| | 1 Day | 2 Days | 3 Days | 5 Days |
| 1 (6 # ae/A) | 0 | 1 | 5 | 57 |
| 1 (15 # ae/A) | 0 | 10 | 17 | 65 |
| 1 (6 # ae/A) + 2 (0.062 qts/A) | 0 | 3 | 6 | 60 |
| 1 (6 # ae/A) + 2 (0.125 qts/A) | 2 | 7 | 12 | 67 |
| 1 (6 # ae/A) + 2 (0.25 qts/A) | 3 | 5 | 2 | 78 |
| 1 (6 # ae/A) + 2 (0.5 qts/A) | 3 | 5 | 5 | 87 |
| 1 (15 # ae/A) + 2 (0.062 qts/A) | 4 | 8 | 12 | 65 |
| 1 (15 # ae/A) + 2 (0.25 qts/A) | 0 | 8 | 12 | 67 |
| 1 (6 # ae/A) + 2 (12 qts/A) | 0 | 2 | 3 | 62 |
| 1 (15 # ae/A) + 3 (4 qts/A) | 0 | 5 | 4 | 65 |
| 1 (6 # ae/A) + 4 (10% by V) | 2 | 8 | 10 | 88 |
| 1 (15 # ae/A) + 4 (5% by V) | 2 | 7 | 5 | 72 |
| 1 (6 # ae/A) + 2 (0.125 qts/A) + 4 (5% by V) | 0 | 2 | 4 | 74 |
| 1 (6 # ae/A) + 2 (0.25 qts/A) + 4 (2.5% by V) | 2 | 8 | 7 | 88 |
| UNTREATED | 0 | 3 | 4 | 3 |

TABLE 4

| TREATMENT (RATE) | PERCENT CONTROL DAYS AFTER APPLICATION | | |
|---|---|---|---|
| | 7 Days | 14 Days | 28 Days |
| 1 (6 # ae/A) | 83 | 99 | 100 |
| 1 (15 # ae/A) | 87 | 100 | 100 |
| 1 (6 # ae/A) + 2 (0.062 qts/A) | 88 | 99 | 100 |
| 1 (6 # ae/A) + 2 (0.125 qts/A) | 88 | 99 | 100 |
| 1 (6 # ae/A) + 2 (0.25 qts/A) | 87 | 99 | 100 |
| 1 (6 # ae/A) + 2 (0.5 qts/A) | 90 | 100 | 100 |
| 1 (15 # ae/A) + 2 (0.062 qts/A) | 85 | 99 | 100 |
| 1 (15 # ae/A) + 4 2 (0.25 qts/A) | 82 | 99 | 100 |
| 1 (6 # ae/A) + 3 (12 qts/A) | 58 | 98 | 100 |
| 1 (15 # ae/A) + 3 (4 qts/A) | 88 | 99 | 100 |
| 1 (6 # ae/A) + 4 (10% by V) | 97 | 100 | 100 |
| 1 (15 # ae/A) + 4 (5% by V) | 90 | 99 | 100 |
| 1 (6 # ae/A) + 2 (0.125 qts/A) + 4 (5% by V) | 86 | 99 | 100 |
| 1 (6 # ae/A) + 2 (0.25 qts/A) + 4 (2.5% by V) | 88 | 99 | 100 |
| UNTREATED | 0 | 13 | 0 |

Example 3

A field test was conducted in Rhode Island to determine the effectiveness of the herbicide formulations of Tables 5 and 6 for killing or controlling Kentucky bluegrass (*Poa pratensis*, POAPR). Applications were made in late September and evaluations were made 1, 2, 3, 4 and 5 days after treatment (DAT). Application rates, treatments and corresponding percent control are reported in Tables 5 and 6.

TABLE 5

| TREATMENT (RATE) | PERCENT CONTROL DAYS AFTER APPLICATION | | |
|---|---|---|---|
| | 1 Day | 2 Days | 3 Days |
| 1 (6 # ae/A) | 0 | 0 | 0 |
| 1 (15 # ae/A) | 0 | 0 | 1 |
| 1 (6 # ae/A) + 2 (0.062 # cation/A) | 0 | 4 | 2 |
| 1 (6 # ae/A) + 2 (0.125 # cation/A) | 5 | 6 | 9 |
| 1 (6 # ae/A) + 2 (0.25 # cation/A) | 8 | 12 | 12 |
| 1 (6 # ae/A) + 2 (0.5 # cation/A) | 19 | 25 | 35 |
| 1 (15 # ae/A) + 2 (0.062 # cation/A) | 1 | 6 | 8 |
| 1 (15 # ae/A) + 2 (0.25 # cation/A) | 5 | 9 | 10 |
| 1 (6 # ae/A) + 3 (12 # pelargonic acid/A) | 65 | 74 | 84 |
| 1 (15 # ae/A) + 3 (4 # pelargonic acid/A) | 2 | 11 | 14 |
| 1 (6 # ae/A) + 4 (10% by V) | 20 | 40 | 56 |
| 1( 15 # ae/A) + 4 (5% by V) | 0 | 5 | 10 |
| 1 (6 # ae/A) + 2 (0.125 # cation/A) + 4 (5% by V) | 20 | 30 | 48 |
| 1 (6 # ae/A) + 2 (0.25 # cation/A) + 4 (2.5% by V) | 30 | 58 | 75 |
| UNTREATED | 0 | 0 | 0 |

TABLE 6

| TREATMENT (RATE) | PERCENT CONTROL DAYS AFTER APPLICATION | |
|---|---|---|
| | 4 Days | 5 Days |
| 1 (6 # ae/A) | 4 | 14 |
| 1 (15 # ae/A) | 12 | 21 |
| 1 (6 # ae/A) + 2 (0.062 # cation/A) | 8 | 14 |
| 1 (6 # ae/A) + 2 (0.125 # cation/A) | 11 | 20 |
| 1 (6 # ae/A) + 2 (0.25 # cation/A) | 19 | 26 |

TABLE 6-continued

| TREATMENT (RATE) | PERCENT CONTROL DAYS AFTER APPLICATION | |
|---|---|---|
| | 4 Days | 5 Days |
| 1 (6 # ae/A) + 2 (0.5 # cation/A) | 46 | 55 |
| 1 (15 # ae/A) + 2 (0.062 # cation/A) | 15 | 20 |
| 1 (15 # ae/A) + 2 (0.25 # cation/A) | 19 | 29 |
| 1 (6 # ae/A) + 3 (12 # pelargonic acid/A) | 88 | 90 |
| 1 (15 # ae/A) + 3 (4 # pelargonic acid/A) | 20 | 30 |
| 1 (6 # ae/A) + 4 (10% by V) | 61 | 66 |
| 1 (15 # ae/A) + 4 (5% by V) | 18 | 28 |
| 1 (6 # ae/A) + 2 (0.125 # cation/A) + 4 (5% by V) | 60 | 61 |
| 1 (6 # ae/A) + 2 (0.25 # cation/A) + 4 (2.5% by V) | 84 | 90 |
| UNTREATED | 0 | 0 |

Example 4

A test was conducted in North Carolina to determine the effectiveness of the herbicide formulations of Tables 7 and 8 for killing or controlling tall fescue (*Festuca arundinacea*, FESAR). Evaluations were made 1, 2, 4, 7, 14, 21, 29 and 36 days after treatment (DAT). Application rates, treatments and corresponding percent control are reported in Tables 7 and 8.

TABLE 7

| TREATMENT (RATE) | PERCENT CONTROL DAYS AFTER APPLICATION | | | |
|---|---|---|---|---|
| | 1 Day | 2 Days | 4 Days | 7 Days |
| 1 (6 # ae/A) | 0 | 4 | 8 | 62 |
| 1 (15 # ae/A) | 0 | 8 | 15 | 66 |
| 1 (6 # ae/A) + 2 (0.062 qts/A) | 2 | 6 | 10 | 62 |
| 1 (6 # ae/A) + 2 (0.125 qts/A) | 1 | 6 | 11 | 60 |
| 1 (6 # ae/A) + 2 (0.25 qts/A) | 1 | 15 | 24 | 66 |
| 1 (6 # ae/A) + 2 (0.5 qts/A) | 1 | 20 | 35 | 70 |
| 1 (15 # ae/A) + 2 (0.062 qts/A) | 4 | 7 | 11 | 60 |
| 1 (15 # ae/A) + 2 (0.25 qts/A) | 1 | 8 | 15 | 65 |
| 1 (6 # ae/A) + 3 (12 qts/A) | 46 | 50 | 62 | 71 |
| 1 (15 # ae/A) + 3 (4 qts/A) | 2 | 6 | 10 | 62 |
| 1 (6 # ae/A) + 4 (10% by V) | 6 | 13 | 21 | 59 |
| 1 (15 # ae/A) + 4 (5% by V) | 0 | 5 | 11 | 56 |
| 1 (6 # ae/A) + 2 (0.125 #/A) + 4 (5% by V) | 2 | 40 | 61 | 72 |
| 1 (6 # ae/A) + 2 (0.25 qts/A) + 4 (2.5% by V) | 8 | 40 | 65 | 74 |
| UNTREATED | 0 | 0 | 0 | 0 |

TABLE 8

| TREATMENT (RATE) | PERCENT CONTROL DAYS AFTER APPLICATION | | | |
|---|---|---|---|---|
| | 14 Days | 21 Days | 29 Days | 36 Days |
| 1 (6 # ae/A) | 86 | 99 | 99 | 100 |
| 1 (15 # ae/A) | 86 | 100 | 100 | 100 |
| 1 (6 # ae/A) + 2 (0.062 qts/A) | 85 | 98 | 99 | 100 |
| 1 (6 # ae/A) + 2 (0.125 qts/A) | 82 | 99 | 99 | 100 |
| 1 (6 # ae/A) + 2 (0.25 qts/A) | 89 | 99 | 98 | 100 |
| 1 (6 # ae/A) + 2 (0.5 qts/A) | 85 | 99 | 99 | 100 |
| 1 (15 # ae/A) + 2 (0.062 qts/A) | 80 | 98 | 99 | 100 |
| 1 (15 # ae/A) + 2 (0.25 qts/A) | 84 | 98 | 99 | 100 |
| 1 (6 # ae/A) + 3 (12 qts/A) | 84 | 97 | 97 | 100 |
| 1 (15 # ae/A) + 3 (4 qts/A) | 81 | 98 | 99 | 100 |
| 1 (6 # ae/A) + 4 (10% by V) | 75 | 96 | 99 | 100 |
| 1 (15 # ae/A) + 4 (5% by V) | 80 | 99 | 98 | 100 |
| 1 (6 # ae/A) + 2 (0.125 #/A) + 4 (5% by V) | 82 | 97 | 99 | 100 |
| 1 (6 # ae/A) + 2 (0.25 qts/A) + 4 (2.5% by V) | 86 | 97 | 99 | 100 |
| UNTREATED | 0 | 0 | 0 | 0 |

Example 5

A test-was conducted in California to determine the effectiveness of the herbicide formulations of Tables 9 and 10 for killing or controlling kikuyugrass (*pennisetum* clandestinum, PESCL). Evaluations were made 1, 2, 4, 7, 14 and 28 days after treatment (DAT). Application rates, treatments and corresponding percent inhibitions are reported in Tables 9 and 10.

TABLE 9

| TREATMENT (RATE) | PERCENT CONTROL DAYS AFTER APPLICATION | | |
|---|---|---|---|
| | 1 Day | 2 Days | 4 Days |
| 1 (6 # ae/A) | 0 | 2 | 11 |
| 1 (15 # ae/A) | 0 | 8 | 19 |
| 1 (6 # ae/A) + 2 (0.0625 qts/A) | 0 | 3 | 15 |
| 1 (6 # ae/A) + 2 (0.125 qts/A) | 1 | 13 | 22 |
| 1 (6 # ae/A) + 2 (0.25 qts/A) | 5 | 19 | 31 |
| 1 (6 # ae/A) + 2 (0.5 qts/A) | 7 | 27 | 48 |
| 1 (15 # ae/A) + 2 (0.0625 qts/A) | 0 | 12 | 22 |
| 1 (15 # ae/A) + 2 (0.125 qts/A) | 1 | 17 | 33 |
| 1 (6 # ae/A) + 3 (10% by V) | 72 | 87 | 92 |
| 1 (15 # ae/A) + 3 (1% by V) | 3 | 11 | 22 |
| 1 (6 # ae/A) + 4 (10% by V) | 12 | 24 | 36 |
| 1 (15 # ae/A) + 4 (5% by V) | 7 | 18 | 29 |
| 1 (6 # ae/A) + 2 (0.125 qts/A) + 4 (5% by V) | 23 | 33 | 51 |
| 1 (6 # ae/A) + 2 (0.25 qts/A) + 4 (2.5% by V) | 28 | 42 | 64 |
| UNTREATED | 0 | 0 | 0 |

TABLE 10

| TREATMENT (RATE) | PERCENT CONTROL DAYS AFTER APPLICATION | | |
|---|---|---|---|
| | 7 Days | 14 Days | 28 Days |
| 1 (6 # ae/A) | 35 | 95 | 100 |
| 1 (15 # ae/A) | 37 | 94 | 100 |
| 1 (6 # ae/A) + 2 (0.0625 qts/A) | 41 | 96 | 100 |
| 1 (6 # ae/A) + 2 (0.125 qts/A) | 48 | 96 | 100 |
| 1 (6 # ae/A) + 2 (0.25 qts/A) | 55 | 97 | 100 |
| 1 (6 # ae/A) + 2 (0.5 qts/A) | 79 | 96 | 95 |
| 1 (15 # ae/A) + 2 (0.0625 qts/A) | 42 | 96 | 100 |
| 1 (15 # ae/A) + 2 (0.125 qts/A) | 54 | 97 | 100 |
| 1 (6 # ae/A) + 3 (10% by V) | 94 | 97 | 89 |
| 1 (15 # ae/A) + 3 (1% by V) | 42 | 94 | 100 |
| 1 (6 # ae/A) + 4 (10% by V) | 49 | 95 | 100 |
| 1 (15 # ae/A) + 4 (5% by V) | 42 | 94 | 100 |
| 1 (6 # ae/A) + 2 (0.125 qts/A) + 4 (5% by V) | 74 | 92 | 98 |

TABLE 10-continued

| TREATMENT (RATE) | PERCENT CONTROL DAYS AFTER APPLICATION | | |
|---|---|---|---|
| | 7 Days | 14 Days | 28 Days |
| 1 (6 # ae/A) + 2 (0.25 qts/A) + 4 (2.5% by V) | 85 | 92 | 92 |
| UNTREATED | 0 | 0 | 0 |

Example 6

A test was conducted in North Carolina to determine both the rainfastness and effectiveness of the herbicide formulations of Table 11 for killing or controlling tall fescue, (*Festuca arundinacea*, FESAR). Applications were made in May. Approximately 0.1 inch of rain or irrigation was simulated at 15, 30, 60 minutes and no rain after application. Evaluations were made 2, 5, and 7 days after treatment (DAT). Application rates, treatments and corresponding percent controls are reported in Table 11.

TABLE 11

| TREATMENT (RATE) | PERCENT CONTROL DAYS AFTER APPLICATION | | |
|---|---|---|---|
| | 2 Days | 5 Days | 7 Days |
| UNTREATED | 0 | 0 | 0 |
| 1 (6 # ae/A) | 1 | 14 | 20 |
| 1 (6 # ae/A) + 2 (0.25 qts/A) + 4 (2.5% by V) | 69 | 73 | 69 |
| 1 (6 # ae/A) | 0 | 8 | 11 |
| 1 (6 # ae/A) + 2 (0.25 qts/A) + 4 (2.5% by V) | 71 | 75 | 69 |
| 1 (6 # ae/A) | 0 | 8 | 13 |
| 1 (6 # ae/A) + 2 (0.25 qts/A) + 4 (2.5% by V) | 69 | 74 | 66 |
| 1 (6 # ae/A) | 0 | 9 | 19 |
| 1 (6 # ae/A) + 2 (0.25 qts/A) + 4 (2.5% by V) | 73 | 79 | 72 |

Example 7

A test was conducted in North Carolina to determine both the rainfastness and effectiveness of the herbicide formulations of Table 12 for killing or controlling tall fescue (*Festuca arundinacea*, FESAR). Applications were made in May. Approximately 0.25 inches of rain or irrigation was simulated at 15, 30, 60 minutes and no rain after application. Evaluations were made 2, 5, and 7 days after treatment (DAT). Application rates, treatments and corresponding percent controls are reported in Table 12.

TABLE 12

| TREATMENT (RATE) | PERCENT CONTROL DAYS AFTER APPLICATION | | |
|---|---|---|---|
| | 2 Days | 5 Days | 7 Days |
| UNTREATED | 0 | 0 | 0 |
| 1 (6 # ae/A) | 0 | 8 | 26 |
| 1 (6 # ae/A) + 2 (0.25 qts/A) + 4 (2.5% by V) | 69 | 73 | 71 |
| 1 (6 # ae/A) | 0 | 11 | 30 |
| 1 (6 # ae/A) + 2 (0.25 qts/A) + 4 (2.5% by V) | 74 | 75 | 71 |

TABLE 12-continued

| TREATMENT (RATE) | PERCENT CONTROL DAYS AFTER APPLICATION | | |
|---|---|---|---|
| | 2 Days | 5 Days | 7 Days |
| 1 (6 # ae/A) | 0 | 9 | 19 |
| 1 (6 # ae/A) + 2 (0.25 qts/A) + 4 (2.5% by V) | 71 | 70 | 70 |
| 1 (6 # ae/A) | 0 | 34 | 53 |
| 1 (6 # ae/A) + 2 (0.25 qts/A) + 4 (2.5% by V) | 80 | 79 | 81 |

Example 8

A test was conducted in California to determine the effectiveness of the herbicide formulations of Tables 13 and 14 for killing or controlling kikuyugrass (*Pennisetum clandostinum*, PESCL). Applications were made in July and evaluations were made 1, 2, 4, 7, and 14 days after treatment (DAT). Application rates, treatments and corresponding percent controls are reported in Tables 13 and 14.

TABLE 13

| TREATMENT (RATE) | PERCENT CONTROL DAYS AFTER APPLICATION | | |
|---|---|---|---|
| | 1 Day | 2 Days | 4 Days |
| 1 (6 # ae/A) | 4 | 12 | 22 |
| 1 (6 # ae/A) + 2 (0.25 qts/A) | 22 | 40 | 52 |
| 1 (6 # ae/A) + 2 (0.5 qts/A) | 33 | 51 | 81 |
| 1 (6 # ae/A) + 3 (12 qts/A) | 52 | 64 | 72 |
| 1 (6 # ae/A) + 4 (2.5% by V) | 8 | 13 | 32 |
| 1 (6 # ae/A) + 4 (6% by V) | 12 | 16 | 30 |
| 1 (6 # ae/A) + 2 (0.125 qts/A) + 4 (2.5% by V) | 45 | 61 | 69 |
| 1 (6 # ae/A) + 2 (0.125 qts/A) + 4 (5% by V) | 52 | 64 | 73 |
| 1 (6 # ae/A) + 2 (0.25 qts/A) + 4 (2.5% by V) | 57 | 67 | 73 |
| 1 (6 # ae/A) + 2 (0.25 qts/A) + 4 (5% by V) | 60 | 70 | 81 |
| 1 (6 # ae/A) + 2 (0.25 qts/A) + 4 (1.25% by V) | 38 | 54 | 61 |
| 1 (6 # ae/A) + 2 (0.25 qts/A) + 5 (0.25% by V) | 30 | 50 | 58 |
| 1 (6 # ae/A) + 2 (0.25 qts/A) + 5 (0.5% by V) | 37 | 56 | 65 |
| 1 (6 # ae/A) + 2 (0.25 qts/A) + 6 (0.25% by V) | 37 | 67 | 69 |
| 1 (6 # ae/A) + 2 (0.25 qts/A) + 6 (0.5% by V) | 33 | 54 | 67 |
| 7 (6 # ae/A) | 62 | 72 | 82 |
| 7 (9 # ae/A) | 68 | 77 | 81 |
| UNTREATED | 0 | 0 | 0 |

TABLE 14

| TREATMENT (RATE) | PERCENT CONTROL DAYS AFTER APPLICATION | |
|---|---|---|
| | 7 Days | 14 Days |
| 1 (6 # ae/A) | 51 | 97 |
| 1 (6 # ae/A) + 2 (0.25 qts/A) | 69 | 77 |
| 1 (6 # ae/A) + 2 (0.5 qts/A) | 75 | 79 |
| 1 (6 # ae/A) + 3 (12 qts/A) | 80 | 84 |
| 1 (6 # ae/A) + 4 (2.5% by V) | 55 | 97 |
| 1 (6 # ae/A) + 4 (6% by V) | 53 | 98 |
| 1 (6 # ae/A) + 2 (0.125 qts/A) + 4 (2.5% by V) | 74 | 78 |

TABLE 14-continued

| TREATMENT (RATE) | PERCENT CONTROL DAYS AFTER APPLICATION | |
|---|---|---|
| | 7 Days | 14 Days |
| 1 (6 # ae/A) + 2 (0.125 qts/A) + 4 (5% by V) | 78 | 80 |
| 1 (6 # ae/A) + 2 (0.25 qts/A) + 4 (2.5% by V) | 76 | 78 |
| 1 (6 # ae/A) + 2 (0.25 qts/A) + 4 (5% by V) | 82 | 80 |
| 1 (6 # ae/A) + 2 (0.25 qts/A) + 4 (1.25% by V) | 76 | 86 |
| 1 (6 # ae/A) + 2 (0.25 qts/A) + 5 (0.25% by V) | 75 | 80 |
| 1 (6 # ae/A) + 2 (0.25 qts/A) + 5 (0.5% by V) | 78 | 81 |
| 1 (6 # ae/A) + 2 (0.25 qts/A) + 6 (0.25% by V) | 78 | 70 |
| 1 (6 # ae/A) + 2 (0.25 qts/A) + 6 (0.5% by V) | 76 | 81 |
| 7 (6 # ae/A) | 82 | 77 |
| 7 (9 # ae/A) | 81 | 79 |
| UNTREATED | 0 | 0 |

Example 9

A test was conducted in Arkansas to determine both the rainfastness and effectiveness of the herbicide formulations of Table 15 for killing or controlling bermudagrass (*Cynodon dactylon*, CYNDA). Applications were made in June. Evaluations were made 2, 8, 12 and 21 days after treatment (DAT). Application rates, treatments and corresponding percent controls are reported in Table 15.

TABLE 15

| TREATMENT (RATE) | PERCENT CONTROL DAYS AFTER APPLICATION | | | |
|---|---|---|---|---|
| | 2 Days | 8 Days | 12 Days | 21 Days |
| 1 (6 # ae/A) | 17 | 78 | 83 | 91 |
| 1 (6 # ae/A) + 2 (0.25 qts/A) | 57 | 70 | 70 | 78 |
| 1 (6 # ae/A) + 2 (0.5 qts.A) | 80 | 77 | 75 | 58 |
| 1 (6 # ae/A) | 12 | 70 | 80 | 90 |
| 1 (6 # ae/A) + 4 (2.5% by V) | 22 | 77 | 87 | 93 |
| 1 (6 # ae/A) + 4 (5% by V) | 20 | 73 | 87 | 94 |
| 1 (6 # ae/A) + 2 (0.125 qts/A) + 4 (2.5% by V) | 82 | 87 | 92 | 85 |
| 1 (6 # ae/A) + 2 (0.125 qts/A) + 4 (5% by V) | 85 | 92 | 93 | 83 |
| 1 (6 # ae/A) + 2 (0.25 qts/A) + 4 (2.5% by V) | 88 | 87 | 73 | 62 |
| 1 (6 # ae/A) + 2 (0.25 qts/A) + 4 (5% by V) | 90 | 88 | 87 | 60 |
| 1 (6 # ae/A) + 2 (0.25 qts/A) + 4 (1.25% by V) | 70 | 75 | 73 | 60 |
| 1 (6 # ae/A) + 2 (0.25 qts/A) + 5 (0.25% by V) | 68 | 77 | 77 | 82 |
| 1 (6 # ae/A) + 2 (0.25 qts/A) + 5 (0.5% by V) | 68 | 77 | 77 | 83 |
| 1 (6 # ae/A) + 2 (0.25 qts/A) + 8 (0.25% by V) | 60 | 75 | 73 | 80 |
| 1 (6 # ae/A) + 2 (0.25 qts/A) + 8 (0.5% by V) | 70 | 73 | 73 | 67 |
| 7 (6 # ae/A) | 88 | 85 | 77 | 53 |
| 7 (9 # ae/A) | 95 | 95 | 95 | 70 |
| UNTREATED | 0 | 0 | 0 | 0 |

Example 10

A test was conducted in Florida to determine both the effectiveness of the herbicide formulations of Tables 16 and 17 for killing or controlling St. Augustinegrass (*Stenotaphrum secundatum*, STPSE). Applications were made in May. Evaluations were made 1, 2, 4, 7, 14, 28, and 54 days after treatment (DAT). Application rates, treatments and corresponding percent controls are reported in Tables 16 and 17.

TABLE 16

| TREATMENT (RATE) | PERCENT CONTROL DAYS AFTER APPLICATION | | | |
|---|---|---|---|---|
| | 1 Day | 2 Days | 4 Days | 7 Days |
| 1 (6 # ae/A) | 5 | 8 | 40 | 80 |
| 1 (6 # ae/A) + 2 (0.25 qts/A) | 8 | 10 | 50 | 82 |
| 1 (6 # ae/A) + 2 (0.5 qts/A) | 3 | 8 | 30 | 73 |
| 1 (6 # ae/A) + 3 (12 qts/A) | 40 | 57 | 58 | 72 |
| 1 (6 # ae/A) + 4 (2.5% by V) | 0 | 0 | 5 | 57 |
| 1 (6 # ae/A) + 4 (5% by V) | 0 | 0 | 5 | 60 |
| 1 (6 # ae/A) + 2 (0.125 qts/A) + 4 (2.5% by V) | 8 | 10 | 12 | 53 |
| 1 (6 # ae/A) + 2 (0.125 qts/A) + 4 (5% by V) | 28 | 35 | 38 | 75 |
| 1 (6 # ae/A) + 2 (0.25 qts/A) + 4 (2.5% by V) | 15 | 23 | 32 | 73 |
| 1 (6 # ae/A) + 2 (0.25 qts/A) + 4 (5% by V) | 67 | 78 | 80 | 90 |
| 1 (6 # ae/A) + 2 (0.25 qts/A) + 4 (1.25% by V) | 3 | 3 | 13 | 65 |
| 1 (6 # ae/A) + 2 (0.25 qts/A) + 5 (0.25% by V) | 5 | 3 | 23 | 78 |
| 1 (6 # ae/A) + 2 (0.25 qts/A) + 5 (0.5% by V) | 7 | 3 | 10 | 75 |
| 1 (6 # ae/A) + 2 (0.25 qts/A) + 6 (0.25% by V) | 42 | 57 | 67 | 85 |
| 1 (6 # ae/A) + 2 (0.25 qts/A) + 6 (0.5% by V) | 70 | 80 | 83 | 91 |
| 7 (6 # ae/A) | 43 | 55 | 70 | 90 |
| 7 (9 # ae/A) | 67 | 75 | 82 | 91 |
| UNTREATED | 0 | 0 | 0 | 0 |

TABLE 17

| TREATMENT (RATE) | PERCENT CONTROL DAYS AFTER APPLICATION | | |
|---|---|---|---|
| | 14 Days | 28 Days | 54 Days |
| 1 (6 # ae/A) | 99 | 97 | 96 |
| 1 (6 # ae/A) + 2 (0.25 qts/A) | 98 | 95 | 97 |
| 1 (6 # ae/A) + 2 (0.5 qts/A) | 98 | 96 | 95 |
| 1 (6 # ae/A) + 3 (12 qts/A) | 94 | 87 | 73 |
| 1 (6 # ae/A) + 4 (2.5% by V) | 98 | 98 | 96 |
| 1 (6 # ae/A) + 4 (5% by V) | 99 | 99 | 95 |
| 1 (6 # ae/A) + 2 (0.125 qts/A) + 4 (2.5% by V) | 97 | 98 | 97 |
| 1 (6 # ae/A) + 2 (0.125 qts/A) + 4 (5% by V) | 98 | 98 | 97 |
| 1 (6 # ae/A) + 2 (0.25 qts/A) + 4 (2.5% by V) | 97 | 98 | 93 |
| 1 (6 # ae/A) + 2 (0.25 qts/A) + 4 (5% by V) | 97 | 95 | 80 |
| 1 (6 # ae/A) + 2 (0.25 qts/A) + 4 (1.25% (by V) | 98 | 98 | 94 |
| 1 (6 # ae/A) + 2 (0.25 qts/A) + 5 (0.25% by V) | 99 | 99 | 98 |
| 1 (6 # ae/A) + 2 (0.25 qts/A) + 5 (0.5% by V) | 99 | 98 | 94 |
| 1 (6 # ae/A) + 2 (0.25 qts/A) + 6 (0.25% by V) | 97 | 96 | 93 |
| 1 (6 # ae/A) + 2 (0.25 qts/A) + 6 (0.5% by V) | 96 | 96 | 90 |

TABLE 17-continued

| TREATMENT (RATE) | PERCENT CONTROL DAYS AFTER APPLICATION | | |
|---|---|---|---|
| | 14 Days | 28 Days | 54 Days |
| 7 (6 # ae/A) | 98 | 97 | 88 |
| 7 (9 # ae/A) | 97 | 96 | 83 |
| UNTREATED | 0 | 0 | 0 |

Example 11

A test was conducted in North Carolina to determine the effectiveness of the herbicide formulations of Tables 18 and 19 for killing or controlling tall fescue (*Festuca arundinacea*, FESAR). Applications were made in May. Evaluations were made 1, 2, 4, 7, 14, 21, 28, and 35 days after treatment (DAT). Application rates, treatments and corresponding percent controls are reported in Tables 18 and 19.

TABLE 18

| TREATMENT (RATE) | PERCENT CONTROL DAYS AFTER APPLICATION | | | |
|---|---|---|---|---|
| | 1 Day | 2 Days | 4 Days | 7 Days |
| 1 (6 # ae/A) | 3 | 8 | 14 | 35 |
| 1 (6 # ae/A) + 2 (0.25 qts/A) | 6 | 6 | 19 | 21 |
| 1 (6 # ae/A) + 2 (0.5 qts/A) | 24 | 46 | 56 | 64 |
| 1 (6 # ae/A) + 3 (12 qts/A) | 68 | 66 | 65 | 69 |
| 1 (6 # ae/A) + 4 (2.5% by V) | 1 | 5 | 10 | 41 |
| 1 (6 # ae/A) + 4 (5% by V) | 4 | 11 | 10 | 28 |
| 1 (6 # ae/A) + 2 (0.125 qts/A) + 4 (2.5% by V) | 36 | 56 | 61 | 70 |
| 1 (6 # ae/A) + 2 (0.125 qts/A) + 4 (5% by V) | 66 | 79 | 74 | 75 |
| 1 (6 # ae/A) + 2 (0.25 qts/A) + 4 (2.5% by V) | 66 | 79 | 76 | 76 |
| 1 (6 # ae/A) + 2 (0.25 qts/A) + 4 (5% by V) | 74 | 86 | 79 | 83 |
| 1 (6 # ae/A) + 2 (0.25 qts/A) + 4 (1.25% by V) | 26 | 55 | 61 | 68 |
| 1 (6 # ae/A) + 2 (0.25 qts/A) + 5 (0.25% by V) | 9 | 29 | 30 | 54 |
| 1 (6 # ae/A) + 2 (0.25 qts/A) + 5 (0.5% by V) | 18 | 46 | 45 | 61 |
| 1 (6 # ae/A) + 2 (0.25 qts/A) + 6 (0.25% by V) | 64 | 79 | 70 | 73 |
| 1 (6 # ae/A) + 2 (0.25 qts/A) + 6 (0.5% by V) | 71 | 88 | 75 | 81 |
| 7 (6 # ae/A) | 74 | 85 | 79 | 84 |
| 7 (9 # ae/A) | 83 | 94 | 88 | 88 |
| UNTREATED | 0 | 0 | 0 | 0 |

TABLE 19

| TREATMENT (RATE) | PERCENT CONTROL DAYS AFTER APPLICATION | | | |
|---|---|---|---|---|
| | 14 Days | 21 Days | 28 Days | 35 Days |
| 1 (6 # ae/A) | 94 | 98 | 99 | 100 |
| 1 (6 # ae/A) + 2 (0.25 qts/A) | 88 | 96 | 99 | 100 |
| 1 (6 # ae/A) + 2 (0.5 qts/A) | 83 | 84 | 93 | 93 |
| 1 (6 # ae/A) + 3 (12 qts/A) | 86 | 97 | 98 | 99 |
| 1 (6 # ae/A) + 4 (2.5% by V) | 92 | 98 | 99 | 100 |
| 1 (6 # ae/A) + 4 (5% by V) | 90 | 99 | 100 | 100 |
| 1 (6 # ae/A) + 2 (0.125 qts/A) + 4 (2.5% by V) | 88 | 98 | 98 | 100 |
| 1 (6 # ae/A) + 2 (0.125 qts/A) + 4 (5% by V) | 86 | 95 | 97 | 98 |
| 1 (6 # ae/A) + 2 (0.25 qts/A) + 4 (2.5% by V) | 84 | 91 | 93 | 93 |
| 1 (6 # ae/A) + 2 (0.25 qts/A) + 4 (5% by V) | 81 | 94 | 95 | 96 |
| 1 (6 # ae/A) + 2 (0.25 qts/A) + 4 (1.25% by V) | 89 | 96 | 99 | 99 |
| 1 (6 # ae/A) + 2 (0.25 qts/A) + 5 (0.25% by V) | 86 | 95 | 98 | 97 |
| 1 (6 # ae/A) + 2 (0.25 qts/A) + 5 (0.5% by V) | 89 | 95 | 97 | 97 |
| 1 (6 # ae/A) + 2 (0.25 qts/A) + 6 (0.25% by V) | 81 | 93 | 95 | 96 |
| 1 (6 # ae/A) + 2 (0.25 qts/A) + 6 (0.5% by V) | 85 | 95 | 97 | 96 |
| 7 (6 # ae/A) | 89 | 95 | 96 | 97 |
| 7 (9 # ae/A) | 93 | 97 | 97 | 97 |
| UNTREATED | 0 | 0 | 0 | 0 |

Example 12

A test was conducted in North Carolina to determine the effectiveness of the herbicide formulations of Tables 20 and 21 for killing or controlling annual bluegrass (*Poa annua*, POAAN). Applications were made in February. Evaluations were made 1, 3, 7, 21, 35, 49, 59, and 83 days after treatment (DAT). Application rates, treatments and corresponding percent controls are reported in Tables 20 and 21.

TABLE 20

| TREATMENT (RATE) | PERCENT CONTROL DAYS AFTER APPLICATION | | | | |
|---|---|---|---|---|---|
| | 1 Day | 3 Days | 7 Days | 21 Days | 35 Days |
| 1 (6 # ae/A) | 1 | 3 | 11 | 86 | 98 |
| 1 (6 # ae/A) + 2 (0.125 qts/A) | 1 | 6 | 43 | 93 | 98 |
| 1 (6 # ae/A) + 2 (0.250 qts/A) | 0 | 11 | 68 | 96 | 97 |
| 1 (6 # ae/A) + 2 (0.5 qts/A) | 1 | 15 | 74 | 98 | 98 |
| 1 (6 # ae/A) + 3 (12 qts/A) | 16 | 50 | 66 | 87 | 75 |
| 1 (6 # ae/A) + 4 (2.5% by V) | 4 | 5 | 9 | 89 | 95 |
| 1 (6 # ae/A) + 4 (5% by V) | 1 | 3 | 9 | 84 | 97 |
| 1 (6 # ae/A) + 2 (0.125 qts/A) + 4 (2.5% by V) | 1 | 10 | 56 | 93 | 95 |
| 1 (6 # ae/A) + 2 (0.125 qts/A) + 4 (5% by V) | 9 | 24 | 74 | 94 | 96 |
| 1 (6 # ae/A) + 2 (0.250 qts/A) + 4 (2.5% by V) | 4 | 31 | 79 | 95 | 95 |
| 1 (6 # ae/A) + 2 (0.250 qts/A) + 4 (5% by V) | 0 | 35 | 85 | 97 | 97 |
| 1 (6 # ae/A) + 9 (1% by V) | 6 | 9 | 8 | 86 | 98 |
| 1 (6 # ae/A) + 10 (1 qt/A) | 0 | 0 | 0 | 81 | 99 |
| 1 (6 # ae/A) + 11 (7% by V) | 0 | 6 | 1 | 81 | 97 |
| 1 (6 # ae/A) + 12 (1% by V) | 0 | 0 | 8 | 88 | 99 |
| 1 (6 # ae/A) + 12 (1.5% by V) | 3 | 5 | 9 | 89 | 100 |

TABLE 20-continued

| TREATMENT (RATE) | PERCENT CONTROL DAYS AFTER APPLICATION | | | | |
|---|---|---|---|---|---|
| | 1 Day | 3 Days | 7 Days | 21 Days | 35 Days |
| 1 (6 # ae/A) + 12 (2% by V) | 3 | 3 | 11 | 91 | 98 |
| 1 (6 # ae/A) + 13 (1% by V) | 1 | 4 | 46 | 93 | 95 |
| UNTREATED | 0 | 0 | 0 | 0 | 0 |

TABLE 21

| TREATMENT (RATE) | PERCENT CONTROL DAYS AFTER APPLICATION | | |
|---|---|---|---|
| | 49 Days | 59 Days | 83 Days |
| 1 (6 # ae/A) | 97 | 97 | 96 |
| 1 (6 # ae/A) + 2 (0.125 qts/A) | 96 | 96 | 91 |
| 1 (6 # ae/A) + 2 (0.250 qts/A) | 96 | 96 | 91 |
| 1 (6 # ae/A) + 2 (0.5 qts/A) | 96 | 94 | 95 |
| 1 (6 # ae/A) + 3 (12 qts/A) | 73 | 66 | 58 |
| 1 (6 # ae/A) + 4 (2.5% by V) | 95 | 96 | 95 |
| 1 (6 # ae/A) + 4 (5% by V) | 99 | 97 | 95 |
| 1 (6 # ae/A) + 2 (0.125 qts/A) + 4 (2.5% by V) | 95 | 95 | 95 |
| 1 (6 # ae/A) + 2 (0.125 qts/A) + 4 (5% by V) | 96 | 94 | 95 |
| 1 (6 # ae/A) + 2 (0.250 qts/A) + 4 (2.5% by V) | 89 | 81 | 90 |
| 1 (6 # ae/A) + 2 (0.250 qts/A) + 4 (5% by V) | 91 | 85 | 84 |
| 1 (6 # ae/A) + 9 (1% by V) | 96 | 96 | 99 |
| 1 (6 # ae/A) + 10 (1 qt/A) | 98 | 98 | 98 |
| 1 (6 # ae/A) + 11 (7% by V) | 97 | 96 | 96 |
| 1 (6 # ae/A) + 12 (1% by V) | 97 | 99 | 99 |
| 1 (6 # ae/A) + 12 (1.5% by V) | 97 | 97 | 99 |
| 1 (6 # ae/A) + 12 (2% by V) | 98 | 99 | 99 |
| 1 (6 # ae/A) + 13 (1% by V) | 91 | 89 | 86 |
| UNTREATED | 0 | 0 | 0 |

Example 13

A test was conducted in Nebraska to determine the effectiveness of the herbicide formulations of Table 22 for killing or controlling Kentucky bluegrass (*Poa pratensis*, POAPR). Applications were made in July. Evaluations were made 1, 2, 3, and 4 days after treatment (DAT). Application formulations, rates, treatments and corresponding percent controls are reported in Table 22.

TABLE 22

| TREATMENT (RATE) | PERCENT CONTROL DAYS AFTER APPLICATION | | | |
|---|---|---|---|---|
| | 1 Day | 2 Days | 3 Days | 4 Days |
| 1 (6 # ae/A) | 7 | 17 | 30 | 43 |
| 1 (6 # ae/A) + 2 (0.25 qts/A) | 30 | 33 | 50 | 50 |
| 1 (6 # ae/A) + 3 (12 qts/A) | 70 | 77 | 67 | 73 |
| 1 (6 # ae/A) + 4 (5% by V) | 20 | 23 | 40 | 50 |
| 1 (6 # ae/A) + 2 (0.125 qts/A) + 4 (5% by V) | 60 | 60 | 67 | 70 |
| 1 (6 # ae/A) + 2 (0.250 qts/A) + 4 (2.5% by V) | 57 | 63 | 67 | 83 |
| 1 (6 # ae/A) + 2 (0.250 qts/A) + 4 (5% by V) | 67 | 80 | 70 | 83 |
| 1 (6 # ae/A) + 2 (0.250 qts/A) + 4 (1.25% by V) | 53 | 50 | 53 | 70 |

TABLE 22-continued

| TREATMENT (RATE) | PERCENT CONTROL DAYS AFTER APPLICATION | | | |
|---|---|---|---|---|
| | 1 Day | 2 Days | 3 Days | 4 Days |
| 1 (6 # ae/A) + 2 (0.250 qts/A) + 5 (0.25% by V) | 50 | 80 | 67 | 77 |
| 1 (6 # ae/A) + 2 (0.250 qts/A) + 5 (0.50% by V) | 73 | 80 | 77 | 87 |
| 1 (6 # ae/A) + 2 (0.250 qts/A) + 6 (0.5% by V) | 70 | 80 | 77 | 83 |
| 1 (6 # ae/A) + 6 (2.5% by V) | 80 | 90 | 83 | 97 |
| 7 (6 # ae/A) | 57 | 60 | 63 | 63 |
| 7 (6 # ae/A) | 70 | 70 | 70 | 77 |
| UNTREATED | 0 | 0 | 0 | 0 |

Example 14

A test was conducted in Rhode Island to determine the effectiveness of the herbicide formulations of Table 23 for killing or controlling fine fescue (*Festuca*, spp.). Applications were made in June. Evaluations were made 1, 2, 3, 5, and 11 days after treatment (DAT). Application rates, treatments and corresponding percent controls are reported in Table 23.

TABLE 23

| TREATMENT (RATE) | PERCENT CONTROL DAYS AFTER APPLICATION | | | | |
|---|---|---|---|---|---|
| | 1 Day | 2 Days | 3 Days | 5 Days | 11 Days |
| UNTREATED | 0 | 0 | 0 | 0 | 0 |
| 1 (6 # ae/A) | 0 | 0 | 0 | 10 | 100 |
| 1 (6 # ae/A) + 2 (0.25 qts/A) | 10 | 20 | 20 | 30 | 90 |
| 1 (6 # ae/A) + 3 (12 qts/A) | 60 | 70 | 70 | 70 | 100 |
| 1 (6 # ae/A) + 4 (5% by V) | 0 | 0 | 0 | 10 | 80 |
| 1 (6 # ae/A) + 2 (0.125 qts/A) + 4 (5% by V) | 10 | 30 | 30 | 50 | 90 |
| 1 (6 # ae/A) + 2 (0.25 qts/A) + 4 (2.5% by V) | 40 | 60 | 80 | 80 | 90 |
| 1 (6 # ae/A) + 2 (0.25 qts/A) + 4 (5% by V) | 60 | 80 | 90 | 90 | 100 |
| 1 (6 # ae/A) + 2 (0.25 qts/A) + 4 (1.25% by V) | 20 | 40 | 50 | 60 | 90 |
| 1 (6 # ae/A) + 2 (0.25 qts/A) + 5 (0.25% by V) | 10 | 30 | 40 | 50 | 90 |
| 1 (6 # ae/A) + 2 (0.25 qts/A) + 5 (0.5% by V) | 20 | 30 | 40 | 50 | 90 |
| 1 (6 # ae/A) + 2 (0.25 qts/A) + 6 (0.25% by V) | 20 | 40 | 50 | 60 | 90 |
| 1 (6 # ae/A) + 2 (0.25 qts/A) + 6 (0.5% by V) | 40 | 60 | 80 | 80 | 90 |
| 7 (6 # ae/A) | 50 | 70 | 70 | 80 | 90 |
| 7 (9 # ae/A) | 80 | 90 | 100 | 100 | 100 |

Example 15

A test was conducted in Rhode Island to determine the effectiveness of the herbicide formulations of Table 24 for killing or controlling fine fescue (*Festuca*, spp.). Applications were made in July. Evaluations were made 6 hours, 1 day, 2 days, 3 days, and 14 days after treatment (DAT). Application formulations, rates, treatments and corresponding percent controls are reported in Table 24.

TABLE 24

| TREATMENT (RATE) | PERCENT CONTROL DAYS AFTER APPLICATION | | | | |
|---|---|---|---|---|---|
| | 6 Hours | 1 Day | 2 Days | 3 Days | 14 Days |
| UNTREATED | 0 | 0 | 0 | 0 | 0 |
| 1 (6 # ae/A) | 0 | 0 | 0 | 20 | 100 |
| 1 (6 # ae/A) + 3 (12 qts/A) | 70 | 90 | 90 | 90 | 100 |
| 1 (6 # ae/A) + 2 (0.125 qts/A) + 4 (2.5% by V) | 20 | 50 | 70 | 90 | 100 |
| 1 (6 # ae/A) + 2 (0.125 qts/A) + 4 (5.0% by V) | 20 | 70 | 80 | 100 | 100 |
| 1 (6 # ae/A) + 2 (0.25 qts/A) + 4 (2.5% by V) | 30 | 80 | 100 | 100 | 100 |
| 1 (6 # ae/A) + 2 (0.25 qts/A) + 4 (5% by V) | 30 | 90 | 100 | 100 | 100 |
| 1 (6 # ae/A) + 2 (0.25 qts/A) + 6 (0.25% by V) | 20 | 70 | 90 | 100 | 100 |
| 1 (6 # ae/A) + 2 (0.25 qts/A) | 30 | 90 | 100 | 100 | 100 |
| 7 (6 # ae/A) | 30 | 90 | 100 | 100 | 100 |
| 14 (6 # ae/A) | 20 | 80 | 100 | 100 | 100 |
| 15 (6 # ae/A) | 20 | 80 | 90 | 100 | 100 |
| 16 (6 # ae/A) | 20 | 90 | 100 | 100 | 100 |

Example 16

A series of tests were conducted in North Carolina to determine the effectiveness of the herbicide formulations of Tables 25–29 for killing or controlling tall fescue (*Festuca arundinacea*, FESAR). Applications were made in July. Evaluations were made 1, 2, 3, or 6 days after treatment (DAT) for different formulations. Application formulations, rates, treatments and corresponding percent controls are reported in Table 25–29.

TABLE 25

| TREATMENT (RATE) | PERCENT CONTROL DAYS AFTER APPLICATION | | | | |
|---|---|---|---|---|---|
| | 3 Days | 6 Days | 21 Days | 28 Days | 42 Days |
| 1 (6 # ae/A) | 10 | 69 | 100 | 100 | 100 |
| 1 (6 # ae/A) + 3 (12 qts/A) | 29 | 70 | 100 | 100 | 100 |
| 7 (6 # ae/A) | 80 | 83 | 99 | 100 | 100 |
| 14 (6 # ae/A) | 78 | 81 | 98 | 100 | 100 |
| 15 (6 # ae/A) | 63 | 83 | 96 | 99 | 100 |

TABLE 26

| TREATMENT (RATE) | PERCENT CONTROL DAYS AFTER APPLICATION | | | |
|---|---|---|---|---|
| | 3 Days | 18 Days | 25 Days | 39 Days |
| 1 (6 # ae/A) | 9 | 9 | 98 | 100 |
| 1 (6 # ae/A) + 3 (12 qts/A) | 20 | 88 | 96 | 100 |
| 7 (6 # ae/A) | 65 | 96 | 100 | 100 |
| 14 (6 # ae/A) | 58 | 91 | 96 | 100 |
| 15 (6 # ae/A) | 60 | 89 | 97 | 98 |
| 16 (6 # ae/A) | 66 | 95 | 98 | 100 |

TABLE 27

| TREATMENT (RATE) | PERCENT CONTROL DAYS AFTER APPLICATION | | | |
|---|---|---|---|---|
| | 2 Days | 7 Days | 24 Days | 38 Days |
| 1 (6 # ae/A) | 0 | 74 | 84 | 86 |
| 1 (6 # ae/A) + 3 (12 qts/A) | 1 | 73 | 79 | 89 |
| 7 (6 # ae/A) | 64 | 78 | 81 | 78 |
| 14 (6 # ae/A) | 63 | 78 | 81 | 79 |
| 15 (6 # ae/A) | 55 | 74 | 80 | 75 |
| 16 (6 # ae/A) | 65 | 78 | 83 | 81 |

TABLE 28

| TREATMENT (RATE) | PERCENT CONTROL DAYS AFTER APPLICATION | | | |
|---|---|---|---|---|
| | 1 Day | 16 Days | 23 Days | 37 Days |
| 1 (6 # ae/A) | 0 | 100 | 100 | 100 |
| 1 (6 # ae/A) + 3 (12 qts/A) | 55 | 97 | 99 | 100 |
| 7 (6 # ae/A) | 75 | 88 | 94 | 98 |
| 14 (6 # ae/A) | 75 | 86 | 95 | 97 |
| 15 (6 # ae/A) | 64 | 85 | 91 | 98 |

TABLE 29

| TREATMENT (RATE) | PERCENT CONTROL DAYS AFTER APPLICATION | | |
|---|---|---|---|
| | 15 Days | 22 Days | 36 Days |
| 1 (6 # ae/A) | 100 | 100 | 100 |
| 1 (6 # ae/A) + 3 (12 qts/A) | 96 | 100 | 100 |
| 7 (6 # ae/A) | 94 | 98 | 100 |
| 14 (6 # ae/A) | 96 | 99 | 99 |
| 15 (6 # ae/A) | 95 | 99 | 100 |
| 16 (6 # ae/A) | 96 | 99 | 100 |

Example 17

A test was conducted in Rhode Island to determine the effectiveness of the herbicide formulations of Tables 30 and 31 for killing or controlling fine fescue (*Festuca*, spp.). Applications were made in July. Evaluations were made 6 days, 7 days, 8 days, 13 days, 14 days, and 15 days after treatment (DAT). Application rates, treatments and corresponding percent controls are reported in Tables 30 and 31.

TABLE 30

| TREATMENT (RATE) | PERCENT CONTROL DAYS AFTER APPLICATION | | |
|---|---|---|---|
| | 6 Days | 7 Days | 8 Days |
| 1 (6 #ae/A) | 50 | 50 | 95 |
| 1 (6 #ae/A) + 3 (12 qts/A) | 15 | 50 | 96 |
| 1 (6 #ae/A) + 2 (0.25 qts/A) + 4 (5% by V) | 70 | 90 | 98 |
| 1 (6 #ae/A) + 2 (0.25 qts/A) + 6 (0.5% by V) | 70 | 95 | 99 |
| 7 (6 #ae/A) | 75 | 96 | 97 |
| 14 (6 #ae/A) | 80 | 98 | 99 |
| 15 (6 #ae/A) | 5 | 90 | 96 |
| 16 (6 #ae/A) | 85 | 97 | 99 |
| UNTREATED | 0 | 0 | 0 |

TABLE 31

| TREATMENT (RATE) | PERCENT CONTROL DAYS AFTER APPLICATION | | |
|---|---|---|---|
| | 13 Days | 14 Days | 15 Days |
| 1 (6 #ae/A) | 55 | 99 | 100 |
| 1 (6 #ae/A) + 3 (12 qts/A) | 50 | 100 | 100 |
| 1 (6 #ae/A) + 2 (0.25 qts/A) + 4(5% by V) | 45 | 98 | 100 |
| 1 (6 #ae/A) + 2 (0.25 qts/A) + 6 (0.5% by V) | 45 | 98 | 100 |
| 7 (6 #ae/A) | 85 | 98 | 100 |
| 14 (6 #ae/A) | 85 | 99 | 100 |
| 15 (6 #ae/A) | 25 | 97 | 100 |
| 16 (6 #ae/A) | 90 | 98 | 100 |
| UNTREATED | 0 | 0 | 0 |

Example 18

A test was conducted in Rhode Island to determine the effectiveness of the herbicide formulations of Table 32 for killing or controlling bermudagrass (*Cynodon dactylon*, CYNDA). Applications were made in September. Evaluations were made 2 days and 5 days. Application formulations, rates, treatments and corresponding percent controls are reported in Table 32.

TABLE 32

| TREATMENT (RATE) | PERCENT CONTROL DAYS AFFER APPLICATION | |
|---|---|---|
| | 2 Days | 5 Days |
| 1 (6 #ae/A) | 3 | 28 |
| 1 (6 #ae/A) + 3 (12 qts/A) | 36 | 57 |
| 1 (6 #ae/A) + 2 (0.25 qts/A) + 6 (0.25% by V) | 58 | 75 |
| 1 (6 #ae/A) + 17 (0.062 qts/A) + 6 (0.25% by V) | 58 | 80 |
| 1 (6 #ae/A) + 17 (2.5 qts/A) + 6 (0.25% by V) | 66 | 81 |
| 1 (6 #ae/A) + 17 (2.5 qts/A) + 6 (0.25% by V) | 74 | 85 |
| 1 (6 #ae/A) + 2 (0.25 qts/A) + 6 (0.5% by V) | 61 | 76 |
| 7 (6 #ae/A) | 75 | 80 |
| 14 (6 #ae/A) | 64 | 80 |
| 15 (6 #ae/A) | 60 | 80 |
| 16 (6 #ae/A) | 69 | 80 |
| 16 (4.5 #ae/A) | 63 | 75 |
| 16 (3 #ae/A) | 45 | 66 |
| 14 (3 #ae/A) | 55 | 75 |
| 15 (3 #ae/A) | 56 | 69 |
| 16 (3 #ae/A) | 64 | 78 |
| UNTREATED | 0 | 0 |

Example 19

Preparation of Formulation A 867.6 grams of ammonium glyphosate was placed in the bowl of a 4 quart Hobart blender and 4.8 grams of sodium sulfite was added and mixed in the blender at low speed and at ambient temperature for 5 minutes. In a separate glass beaker, 279.6 grams of Silwet 800™ and 12.0 grams of Y-14088 antifoam added to the Silwet 800™ and blended using a stirring rod. This surfactant/antifoam mixture was slowly poured into the dry ingredients in the Hobart blender with the blender set on low speed. 88.8 grams of REWARD® was then added to the mixture and mixed at ambient temperature for 5 minutes. A second batch of material was prepared as above and combined with the first batch. The combined mixture was then processed through a twin screw EXS-60 extruder fitted with a 1.0 mm screen. The resulting extrudate was dried for 10 minutes in a fluid bed dryer at 60 degrees Celsius. The dried composition was passed through a 12 mesh screen to sieve off any agglomerated clumps and placed on a 40 mesh screen to remove any fine materials. Mild agitation is used to promote product flow through the screens. The material on the 40 mesh screen is collected as product and the over and undersize material is discarded. Approximately 1.9 kilograms of product was produced.

Example 20

Preparation of Formulation B 924 grams of ammonium glyphosate was placed in the bowl of a 4 quart Hobart blender and 4.8 grams of sodium sulfite was added and mixed in the blender at low speed and at ambient temperature for 5 minutes. In a separate glass beaker, 223.6 grams of Silwet 800™ and 9.4 grams of Y-14088 antifoam added to the Silwet 800™ and blended using a stirring rod. This surfactant/antifoam mixture was slowly poured into the dry ingredients in the Hobart blender with the blender set on low speed. 94.6 grams of REWARD® was then added to the mixture and mixed at ambient temperature for 3 minutes and then 42 grams of deionized water was slowly added and then blended for an additional 5 minutes. A second batch of material was prepared as above and combined with the first batch. The combined mixture was then processed through a twin screw EXD-60 extruder fitted with a 1.0 mm screen. The resulting extrudate was dried for 10 minutes in a fluid bed dryer at 60 degrees Celsius. The dried composition was passed through a 12 mesh screen to sieve off any agglomerated clumps and placed on a 40 mesh screen to remove any fine materials. Mild agitation is used to promote product flow through the screens. The material on the 40 mesh screen is collected as product and the over and undersize material is discarded. Approximately 2.0 kilograms of product was produced.

Example 21

Preparation of Formulation C 988.1 grams of ammonium glyphosate was placed in the bowl of a 4 quart Hobart blender and 4.8 grams of sodium sulfite was added and mixed in the blender at low speed and at ambient temperature for 5 minutes. In a separate glass beaker, 159.4 grams of Silwet 800™ and 6.6 grams of Y-14088 antifoam added to the Silwet 800™ and blended using a stirring rod. This surfactant/antifoam mixture was slowly poured into the dry ingredients in the Hobart blender with the blender set on low speed. 101.1 grams of REWARD® was then added to the mixture and mixed at ambient temperature for 3 minutes and then 66 grams of deionized water was slowly added and then blended for an additional 5 minutes. A second batch of material was prepared as above and combined with the first batch. The combined mixture was then processed through a twin screw EXD-60 extruder fitted with a 1.0 mm screen. The resulting extrudate was dried for 10 minutes in a fluid bed dryer at 60 degrees Celsius. The dried composition was passed through a 12 mesh screen to sieve off any agglomerated clumps and placed on a 40 mesh screen to remove any fine materials. Mild agitation is used to promote product flow through the screens. The material on the 40 mesh screen is collected as product and the over and undersize material is discarded. Approximately 2.1 kilograms of product was produced.

Example 22

Preparation of Formulation D 867.6 grams of ammonium glyphosate was placed in the bowl of a 4 quart Hobart blender and 4.8 grams of sodium sulfite was added and mixed in the blender at low speed and at ambient temperature for 5 minutes. In a separate glass beaker, 279.6 grams of Breakthru S-240™ and 12.0 grams of Breakthru™ AF-9903 antifoam added to the Breakthru S-240™ and blended using a stirring rod. This surfactant/antifoam mixture was slowly poured into the dry ingredients in the Hobart blender with the blender set on low speed. 88.8 grams of REWARD® was then added to the mixture and mixed at ambient temperature for 5 minutes. A second batch of material was prepared as above and combined with the first batch. The combined mixture was then processed through a twin screw EXD-60 extruder fitted with a 1.0 mm screen. The resulting extrudate was dried for 10 minutes in a fluid bed dryer at 60 degrees Celsius. The dried composition was passed through a 12 mesh screen to sieve off any agglomerated clumps and placed on a 40 mesh screen to remove any fine materials. Mild agitation is used to promote product flow through the screens. The material on the 40 mesh screen is collected as product and the over and undersize material is discarded. Approximately 1.9 kilograms of product was produced.

Example 23

Liquid Concentrate Compositions

The following formulations can be prepared using the proportions of the compounds listed in the following table:

| LIQUID FORMU-LATION | COMPONENTS | AI Ratio 12:1 | | AI Ratio 25:1 | |
|---|---|---|---|---|---|
| | | % w/w | % ai | % w/w | % ai |
| 1 | Roundup Ultra ® (41% ai IPA glyphosate) | 61.0 | 25.0 | 61.0 | 25.0 |
| | Reglone (37.3% ai diquat) | 5.6 | 2.1 | 2.7 | 1.0 |
| | Water | 33.4 | 0 | 36.3 | 0 |
| 2 | Roundup UltraMAX ® (50.2% ai IPA glyphosate) | 49.8 | 25.0 | 49.8 | 25.0 |
| | Reglone (37.3% ai diquat) | 5.6 | 2.1 | 5.6 | 2.1 |
| | Water | 44.6 | 0 | 44.6 | 0 |
| 3 | Ranger (28.6% ai glyphosate) | 87.4 | 25.0 | 87.4 | 25.0 |
| | Reglone (37.3% ai diquat) | 5.6 | 2.1 | 2.7 | 1.0 |
| | Water | 7.0 | 0 | 9.9 | 0 |
| 4 | Roundup Full (52% MEA Glyphosate) | 48 | 25.0 | 48 | 25.0 |
| | Reglone (37.3% ai diquat) | 5.6 | 2.1 | 2.7 | 1.0 |
| | Water | 46 | 0 | 49 | 0 |
| 5 | Super-Roundup (46.2% ai glyphosate) | 54 | 25.0 | 54 | 25.0 |
| | Reglone (37.3% ai diquat) | 5.6 | 2.1 | 2.7 | 1.0 |
| | Water | 40 | 0 | 43 | 0 |
| 6 | Potassium Glyphosate salt (62% ai) | 40.3 | 25.0 | 40.3 | 25.0 |
| | Surfonic AGM 550 ether-amine surfactant | 5.0 | 0 | 5.0 | 0 |
| | Reglone (37.3% ai diquat) | 5.6 | 2.1 | 2.7 | 1.0 |
| | Water | 49.1 | 0 | 52.0 | 0 |

Example 24

A test was conducted in Missouri to determine both the rainfastness and effectiveness of the herbicide formulations of Tables 33 and 34 for killing or controlling velvetleaf (*Abutilon theophrasti*, ABUTH) and barnyardgrass (*Echinocloa crus-galli*, ECHCG). Applications were made in April. Approximately 0.25 inch of rain or irrigation was simulated at 1 hour, 2 hours and no rain after application. Evaluations were made at 1, 14, and 18 days after application. Application and treatments and corresponding percent controls are reported for velvetleaf in Table 33 and for barnyardgrass in Table 34. Spray volume was 145 gals/A.

TABLE 33

ABUTH PERCENT CONTROL DAYS AFTER APPLICATION

| | 1 Day | | | 14 Days | | | 18 Days | | |
|---|---|---|---|---|---|---|---|---|---|
| TREATMENT (CONC.) | No Rain | 1 Hour Rain | 2 Hours Rain | No Rain | 1 Hour Rain | 2 Hours Rain | No Rain | 1 Hour Rain | 2 Hours Rain |
| 1 (3 oz/gal) | 5.0 | 3.0 | 3.0 | 100.0 | 66.7 | 80.0 | 100.0 | 66.7 | 80.0 |
| 1 (6 oz/gal) | 10.0 | 3.0 | 3.0 | 100.0 | 77.7 | 87.0 | 100.0 | 77.7 | 87.0 |
| 19 (1.92% gly a.e.) | 7.0 | 3.0 | 3.0 | 100.0 | 85.3 | 95.0 | 100.0 | 85.3 | 95.0 |
| 20 (1.92% gly a.e.) | 20.0 | 8.7 | 7.0 | 100.0 | 94.3 | 87.7 | 100.0 | 94.3 | 87.7 |
| 21 (3 oz/gal) | 60.0 | 36.7 | 46.7 | 85.3 | 63.3 | 77.0 | 85.3 | 63.3 | 77.0 |
| 21 (6 oz/gal) | 75.0 | 50.0 | 63.3 | 94.0 | 76.0 | 88.7 | 94.0 | 76.0 | 88.7 |

TABLE 34

| | ECHCG PERCENT CONTROL DAYS AFTER APPLICATION | | | | | | | | |
|---|---|---|---|---|---|---|---|---|---|
| | 1 Day | | | 14 Days | | | 18 Days | | |
| TREATMENT (CONC.) | No Rain | 1 Hour Rain | 2 Hours Rain | No Rain | 1 Hour Rain | 2 Hours Rain | No Rain | 1 Hour Rain | 2 Hours Rain |
| 1 (3 oz/gal) | 3.7 | 3.0 | 3.0 | 99.3 | 91.0 | 100.0 | 99.3 | 91.0 | 100.0 |
| 1 (6 oz/gal) | 9.0 | 3.0 | 5.0 | 100.0 | 100.0 | 96.0 | 100.0 | 100.0 | 96.0 |
| 19 (1.92% gly a.e.) | 9.0 | 3.7 | 5.0 | 100.0 | 98.3 | 100.0 | 100.0 | 98.3 | 100.0 |
| 20 (1.92% gly a.e) | 87.7 | 80.0 | 85.3 | 95.3 | 92.0 | 93.0 | 95.3 | 92.0 | 93.0 |
| 21 (3 oz/gal) | 72.0 | 60.0 | 60.0 | 76.0 | 61.7 | 63.3 | 76.0 | 61.7 | 63.3 |
| 21 (6 oz/gal) | 75.3 | 77.7 | 75.0 | 80.3 | 73.3 | 69.3 | 80.3 | 73.3 | 69.3 |

Example 25

A test was conducted in Missouri to determine the effectiveness of the herbicide formulations of Tables 35 and 36 for killing or controlling velvetleaf (*Abutilon theophrasti*, ABUTH) and barnyardgrass (*Echinocloa crus-galli*, ECHCG). Applications were made in July and evaluations were made at 2 and 16 days after application. Application treatments and corresponding percent controls are reported for velvetleaf in Tables 35 and for barnyardgrass in Table 36.

TABLE 35

| TREATMENT (RATE) | ABUTH PERCENT CONTROL DAYS AFTER APPLICATION | |
|---|---|---|
| | 2 Days | 16 Days |
| 22(4.40 #ae/A) | 13.3 | 100.0 |
| 22(6.15 #ae/A) | 16.7 | 100.0 |
| 22(8.85 #ae/A) | 25.0 | 100.0 |
| 22(12.30 #ae/A) | 31.7 | 100.0 |
| 23(4.40 #ae/A) + 2(0.18 #AI/A) + 24(0.15% V/V) | 50.7 | 85.3 |
| 23(4.40 #ae/A) + 2(0.27 #AI/A) + 24(0.15% V/V) | 58.3 | 85.7 |
| 23(4.40 #ae/A) + 2(0.36 #AI/A) + 24(0.15% V/V) | 68.0 | 81.3 |
| 23(6.15 #ae/A) + 2(0.180 #AI/A) + 24(0.15% V/V) | 69.3 | 95.7 |
| 23(6.15 #ae/A) + 2(0.27 #AI/A) + 24(0.15% V/V) | 66.3 | 95.0 |
| 23(6.15 #ae/A) + 2(0.36 #AI/A) + 24(0.15% V/V) | 69.7 | 92.0 |
| 23(8.85 #ae/A) + 2(0.137 #AI/A) + 24(0.15% V/V) | 70.0 | 100.0 |
| 23(8.85 #ae/A) + 2(0.180 #AI/A) + 24(0.15% V/V) | 69.3 | 100.0 |
| 23(8.85 #ae/A) + 2(0.27 #AI/A) + 24(0.15% V/V) | 62.0 | 99.7 |
| 23(8.85 #ae/A) + 2(0.36 #AI/A) + 24(0.15% V/V) | 68.3 | 96.7 |
| 23(12.30 #ae/A) + 2(0.137 #AI/A) + 24(0.15% V/V) | 66.0 | 100.0 |
| 23(12.30 #ae/A) + 2(0.180 #AI/A) + 24(0.15% V/V) | 70.0 | 100.0 |
| 23(12.30 #ae/A) + 2(0.27 #AI/A) + 24(0.15% V/V) | 71.7 | 100.0 |
| 23(12.30 #ae/A) + 2(0.36 #AI/A) + 24(0.15% V/V) | 74.0 | 96.7 |
| 23(4.40 #ae/A) + 2(0.180 #AI/A) + 24(0.3% V/V) | 77.3 | 88.0 |
| 23(4.40 #ae/A) + 2(0.27 #AI/A) + 24(0.3% V/V) | 78.3 | 91.7 |
| 23(4.40 #ae/A) + 2(0.36 #AI/A) + 24(0.3% V/V) | 78.0 | 80.0 |
| 23(6.15 #ae/A) + 2(0.180 #AI/A) + 24(0.3% V/V) | 71.3 | 90.7 |
| 23(6.15 #ae/A) + 2(0.27 #A/IA) + 24(0.3% V/V) | 78.3 | 92.0 |
| 23(6.15 #ae/A) + 2(0.27 #AI/A) + 24(0.3% V/V) | 77.3 | 96.7 |
| 23(8.85 #ae/A) + 2(0.137 #AI/A) + 24(0.3% V/V) | 70.0 | 100.0 |
| 23(8.85 #ae/A) + 2(0.180 #AI/A) + 24(0.3% V/V) | 73.3 | 98.0 |
| 23(8.85 #ae/A) + 2(0.27 #AI/A) + 24(0.3% V/V) | 77.3 | 89.0 |
| 23(8.85 #ae/A) + 2(0.36 #AI/A) + 24(0.3% V/V) | 81.3 | 100.0 |
| 23(12.30 #ae/A) + 2(0.137 #AI/A) + 24(0.3% V/V) | 66.0 | 100.0 |
| 23(12.30 #ae/A) + 2(0.180 #AI/A) + 24(0.3% V/V) | 70.0 | 97.3 |
| 23(12.30 #ae/A) + 2(0.27 #AI/A) + 24(0.3% V/V) | 76.7 | 100.0 |
| 23(12.30 #ae/A) + 2(0.36 #AI/A) + 24(0.3% V/V) | 80.3 | 97.3 |
| 23(4.40 #ae/A) + 2(0.180 #AI/A) + 25(0.15% V/V) | 86.3 | 99.3 |
| 23(4.40 #ae/A) + 2(0.27 #AI/A) + 25(0.15% V/V) | 89.3 | 94.0 |
| 23(4.40 #ae/A) + 2(0.36 #AI/A) + 25(0.15% V/V) | 87.7 | 100.0 |
| 23(6.15 #ae/A) + 2(0.180 #AI/A) + 25(0.15% V/V) | 80.3 | 96.0 |
| 23(6.15 #ae/A) + 2(0.27 #AI/A) + 25(0.15% V/V) | 88.0 | 100.0 |
| 23(6.15 #ae/A) + 2(0.36 #AI/A) + 25(0.15% V/V) | 90.3 | 100.0 |
| 23(8.85 #ae/A) + 2(0.137 #AI/A) + 25(0.15% V/V) | 81.0 | 96.7 |
| 23(8.85 #ae/A) + 2(0.180 #AI/A) + 25(0.15% V/V) | 69.3 | 83.7 |
| 23(8.85 #ae/A) + 2(0.27 #AI/A) + 25(0.15% V/V) | 87.0 | 100.0 |
| 23(8.85 #ae/A) + 2(0.36 #AI/A) + 25(0.15% V/V) | 90.7 | 100.0 |
| 23(12.30 #ae/A) + 2(0.137 #AI/A) + 25(0.15% V/V) | 70.0 | 94.0 |
| 23(12.30 #ae/A) + 2(0.18 #AI/A) + 25(0.15% V/V) | 83.7 | 100.0 |
| 23(12.30 #ae/A) + 2(0.27 #AI/A) + 25(0.15% V/V) | 75.7 | 92.7 |
| 23(12.30 #ae/A) + 2(0.36 #AI/A) + 25(0.15% V/V) | 89.0 | 100.0 |
| 23(4.40 #ae/A) + 2(0.180 #AI/A) + 25(0.3% V/V) | 81.3 | 95.0 |
| 23(4.40 #ae/A) + 2(0.27 #AI/A) + 25(0.3% V/V) | 90.3 | 100.0 |

TABLE 35-continued

| TREATMENT (RATE) | ABUTH PERCENT CONTROL DAYS AFTER APPLICATION | |
|---|---|---|
| | 2 Days | 16 Days |
| 23(4.40 #ae/A) + 2(0.36 #AI/A) + 25(0.3% V/V) | 67.7 | 80.7 |
| 23(6.15 #ae/A) + 2(0.180 #AI/A) + 25(0.3% V/V) | 91.0 | 100.0 |
| 23(6.15 #ae/A) + 2(0.27 #AI/A) + 25(0.3% V/V) | 92.5 | 100.0 |
| 23(6.15 #ae/A) + 2(0.36 #AI/A) + 25(0.3% V/V) | 90.7 | 100.0 |
| 23(8.85 #ae/A) + 2(0.137 #AI/A) + 25(0.3% V/V) | 86.3 | 95.7 |
| 23(8.85 #ae/A) + 2(0.180 #AI/A) + 25(0.3% V/V) | 89.3 | 100.0 |
| 23(8.85 #ae/A) + 2(0.27 #AI/A) + 25(0.3% V/V) | 92.0 | 100.0 |
| 23(8.85 #ae/A) + 2(0.36 #AI/A) + 25(0.3% V/V) | 97.7 | 100.0 |
| 23(12.30 #ae/A) + 2(0.137 #AI/A) + 25(0.3% V/V) | 88.3 | 100.0 |
| 23(12.30 #ae/A) + 2(0.180 #AI/A) + 25(0.3% V/V) | 93.3 | 100.0 |
| 23(12.30 #ae/A) + 2(0.27 #AI/A) + 25(0.3% V/V) | 91.7 | 100.0 |
| 23(12.30 #ae/A) + 2(0.36 #AI/A) + 25(0.3% V/V) | 94.7 | 100.0 |
| 26(4.40 #ae/A) | 67.0 | 75.0 |
| 26(6.15 #ae/A) | 76.7 | 93.3 |
| 26(8.85 #ae/A) | 89.7 | 100.0 |
| 26(12.30 #ae/A) | 91.7 | 100.0 |
| 27(0.96% AI/A @ 140 GPA) | 72.7 | 96.0 |
| 28(140 GPA) | 91.3 | 100.0 |
| 29(140 GPA) | 67.0 | 100.0 |
| UNTREATED | 0 | 0 |

TABLE 36

| TREATMENT (RATE) | ECHCF PERCENT CONTROL DAYS AFTER APPLICATION | |
|---|---|---|
| | 2 Days | 16 Days |
| 22(4.40 #ae/A) | 15.0 | 100.0 |
| 22(6.15 #ae/A) | 15.0 | 100.0 |
| 22(8.85 #ae/A) | 21.7 | 100.0 |
| 22(12.30 #ae/A) | 21.7 | 100.0 |
| 23(4.40 #ae/A) + 2(0.18 #AI/A) + 24(0.15% V/V) | 86.3 | 100.0 |
| 23(4.40 #ae/A) + 2(0.27 #AI/A) + 24(0.15% V/V) | 87.7 | 100.0 |
| 23(4.40 #ae/A) + 2(0.36 #AI/A) + 24(0.15% V/V) | 87.7 | 100.0 |
| 23(6.15 #ae/A) + 2(0.180 #AI/A) + 24(0.15% V/V) | 88.0 | 100.0 |
| 23(6.15 #ae/A) + 2(0.27 #AI/A) + 24(0.15% V/V) | 88.0 | 100.0 |
| 23(6.15 #ae/A) + 2(0.36 #AI/A) + 24(0.15% V/V) | 91.3 | 100.0 |
| 23(8.85 #ae/A) + 2(0.137 #AI/A) + 24(0.15% V/V) | 82.3 | 100.0 |
| 23(8.85 #ae/A) + 2(0.180 #AI/A) + 24(0.15% V/V) | 87.0 | 100.0 |
| 23(8.85 #ae/A) + 2(0.27 #AI/A) + 24(0.15% V/V) | 88.3 | 100.0 |
| 23(8.85 #ae/A) + 2(0.36 #AI/A) + 24(0.15% V/V) | 90.0 | 100.0 |
| 23(12.30 #ae/A) + 2(0.137 #AI/A) + 24(0.15% V/V) | 83.3 | 99.7 |
| 23(12.30 #ae/A) + 2(0.180 #AI/A) + 24(0.15% V/V) | 87.3 | 100.0 |
| 23(12.30 #ae/A) + 2(0.27 #AI/A) + 24(0.15% V/V) | 92.0 | 100.0 |
| 23(12.30 #ae/A) + 2(0.36 #AI/A) + 24(0.15% V/V) | 92.0 | 100.0 |
| 23(4.40 #ae/A) + 2(0.180 #AI/A) + 24(0.3% V/V) | 89.7 | 100.0 |
| 23(4.40 #ae/A) + 2(0.27 #AI/A) + 24(0.3% V/V) | 93.0 | 100.0 |
| 23(4.40 #ae/A + 2(0.36 #AI/A) + 24(0.3% V/V) | 94.0 | 100.0 |
| 23(6.15 #ae/A) + 2(0.180 #AI/A) + 24(0.3% V/V) | 91.3 | 100.0 |
| 23(6.15 #ae/A) + 2(0.27 #AI/A) + 24(0.3% V/V) | 92.7 | 100.0 |
| 23(6.15 #ae/A) + 2(0.27 #AI/A) + 24(0.3% V/V) | 96.0 | 100.0 |
| 23(8.85 #ae/A) + 2(0.137 #AI/A) + 24(0.3% V/V) | 89.3 | 100.0 |
| 23(8.85 #ae/A) + 2(0.180 #AI/A) + 24(0.3% V/V) | 90.3 | 100.0 |
| 23(8.85 #ae/A) + 2(0.27 #AI/A) + 24(0.3% V/V) | 92.7 | 100.0 |
| 23(8.85 #ae/A) + 2(0.36 #AI/A) + 24(0.3% V/V) | 95.0 | 100.0 |
| 23(12.30 #ae/A) + 2(0.137 #AI/A) + 24(0.3% V/V) | 91.3 | 100.0 |
| 23(12.30 #ae/A) + 2(0.180 #AI/A) + 24(0.3% V/V) | 90.0 | 100.0 |
| 23(12.30 #ae/A) + 2(0.27 #AI/A) + 24(0.3% V/V) | 93.3 | 100.0 |
| 23(12.30 #ae/A) + 2(0.36 #AI/A) + 24(0.3% V/V) | 91.7 | 100.0 |
| 23(4.40 #ae/A) + 2(0.180 #AI/A) + 25(0.15% V/V) | 89.7 | 100.0 |
| 23(4.40 #ae/A) + 2(0.27 #AI/A) + 25(0.15% V/V) | 92.0 | 100.0 |
| 23(4.40 #ae/A) + 2(0.36 #AI/A) + 25(0.15% V/V) | 92.3 | 100.0 |
| 23(6.15 #ae/A) + 2(0.180 #AI/A) + 25(0.15% V/V) | 89.7 | 100.0 |
| 23(6.15 #ae/A) + 2(0.27 #AI/A) + 25(0.15% V/V) | 92.0 | 100.0 |
| 23(6.15 #ae/A) + 2(0.36 #AI/A) + 25(0.15% V/V) | 94.0 | 100.0 |
| 23(8.85 #ae/A) + 2(0.137 #AI/A) + 25(0.15% V/V) | 90.0 | 100.0 |
| 23(8.85 #ae/A) + 2(0.180 #AI/A) + 25(0.15% V/V) | 90.0 | 100.0 |
| 23(8.85 #ae/A) + 2(0.27 #AI/A) + 25(0.15% V/V) | 92.7 | 100.0 |
| 23(8.85 #ae/A) + 2(0.36 #AI/A) + 25(0.15% V/V) | 91.3 | 100.0 |
| 23(12.30 #ae/A) + 2(0.137 #AI/A) + 25(0.15% V/V) | 89.5 | 100.0 |
| 23(12.30 #ae/A) + 2(0.18 #AI/A) + 25(0.15% V/V) | 92.0 | 100.0 |
| 23(12.30 #ae/A) + 2(0.27 #AI/A) + 25(0.15% V/V) | 91.3 | 100.0 |
| 23(12.30 #ae/A) + 2(0.36 #AI/A) + 25(0.15% V/V) | 95.3 | 100.0 |
| 23(4.40 #ae/A) + 2(0.180 #AI/A) + 25(0.3% V/V) | 97.3 | 100.0 |
| 23(4.40 #ae/A) + 2(0.27 #AI/A) + 25(0.3% V/V) | 97.3 | 100.0 |
| 23(4.40 #ae/A) + 2(0.36 #AI/A) + 25(0.3% V/V) | 45.0 | 100.0 |
| 23(6.15 #ae/A) + 2(0.180 #AI/A) + 25(0.3% V/V) | 89.7 | 100.0 |
| 23(6.15 #ae/A) + 2(0.27 #AI/A) + 25(0.3% V/V) | 92.0 | 100.0 |
| 23(6.15 #ae/A) + 2(0.36 #AI/A) + 25(0.3% V/V) | 92.7 | 100.0 |

TABLE 36-continued

| TREATMENT (RATE) | ECHCF PERCENT CONTROL DAYS AFTER APPLICATION | |
|---|---|---|
| | 2 Days | 16 Days |
| 23(12.30 #ae/A) + 2(0.27 #AI/A) + 24(0.15% V/V) | 92.0 | 100.0 |
| 23(12.30 #ae/A) + 2(0.36 #AI/A) + 24(0.15% V/V) | 92.0 | 100.0 |

TABLE 36-continued

| TREATMENT (RATE) | ECHCF PERCENT CONTROL DAYS AFTER APPLICATION | |
|---|---|---|
| | 2 Days | 16 Days |
| 23(8.85 #ae/A) + 2(0.137 #AI/A) + 25(0.3% V/V) | 90.0 | 100.0 |
| 23(8.85 #ae/A) + 2(0.180 #AI/A) + 25(0.3% V/V) | 91.0 | 100.0 |
| 23(8.85 #ae/A) + 2(0.27 #AI/A) + 25(0.3% V/V) | 98.0 | 100.0 |
| 23(8.85 #ae/A) + 2(0.36 #AI/A) + 25(0.3% V/V) | 93.5 | 100.0 |
| 23(12.30 #ae/A) + 2(0.137 #AI/A) + 25(0.3% V/V) | 94.0 | 100.0 |
| 23(12.30 #ae/A) + 2(0.180 #AI/A) + 25(0.3% V/V) | 88.0 | 100.0 |
| 23(12.30 #ae/A) + 2(0.27 #AI/A) + 25(0.3% V/V) | 94.7 | 100.0 |
| 23(12.30 #ae/A) + 2(0.36 #AI/A) + 25(0.3% V/V) | 90.3 | 100.0 |
| 26(4.40 #ae/A) | 82.0 | 96.3 |
| 26(6.15 #ae/A) | 88.7 | 100.0 |
| 26(8.85 #ae/A) | 92.3 | 100.0 |
| 26(12.30 #ae/A) | 96.3 | 100.0 |
| 27(0.96% AI/A @ 140 GPA) | 86.0 | 100.0 |
| 28(140 GPA) | 97.3 | 100.0 |
| 29(140 GPA) | 55.0 | 100.0 |
| UNTREATED | 0 | 0 |

Example 26

A test was conducted in Missouri to determine the effectiveness of the herbicide formulations of Tables 37 and 38 for killing or controlling velvetleaf (*Abutilon theophrasti*, ABUTH) and barnyardgrass (*Echinocloa crus-galli*, ECHCG). Applications were made in August and evaluations were made at 2 and 17 days after application. Application treatments and corresponding percent controls are reported for velvetleaf in Table 37 and for barnyardgrass in Table 38.

TABLE 37

| TREATMENT (RATE) | ABUTH PERCENT CONTROL DAYS AFTER APPLICATION | |
|---|---|---|
| | 2 Days | 17 Days |
| 22(6.15 #ae/A) | 31.7 | 100.0 |
| 22(12.30 #ae/A) | 38.3 | 100.0 |
| 23(6.15 #ae/A) + 2(0.90 #AI) + 24(0.15% V/V) | 55.0 | 96.7 |
| 23(6.15 #ae/A) + 2(0.18 #AI/A) + 24(0.15% V/V) | 59.3 | 86.3 |
| 23(6.15 #ae/A) + 2(0.36 AI/A) + 24(0.15% V/V) | 71.7 | 92.7 |
| 23(12.30 ae/A) + 2(0.18 #AI/A) + 24(0.3% V/V) | 59.3 | 92.7 |
| 23(12.30 #ae/A) + 2(0.36 #AI/A) + 24(0.3% V/V) | 77.7 | 100.0 |
| 23(12.30 #ae/A) + 2(0.72 #AI/A) + 24(0.3% V/V) | 89.3 | 100.0 |
| 23(6.15 #ae/A) + 2(0.09 #AI/A) + 24(0.08% V/V) + 25(0.70% V/V) | 48.0 | 100.0 |
| 23(6.15 #ae/A) + 2(0.18 #AI/A) + 24(0.08% V/V) + 25(0.07% V/V) | 57.7 | 94.0 |
| 23(6.15 #ae/A) + 2(0.36 #AI/A) + 24(0.08% V/V) + 25(0.07% V/V) | 68.7 | 95.7 |
| 23(12.30 #ae/A) + 2(0.18 #AI/A) + 24(0.16% V/V) + 25(0.14% V/V) | 68.3 | 100.0 |
| 23(12.30 #ae/A) + 2(0.36 #AI/A) + 24(0.16% V/V) + 25(0.14% V/V) | 79.0 | 100.0 |
| 23(12.30 #ae/A) + 2(0.72 #AI/A) + 24(0.16% V/V) + 25(0.14% V/V) | 87.7 | 100.0 |
| 30 (6.15 #ae/A) | 57.7 | 99.7 |

TABLE 37-continued

| TREATMENT (RATE) | ABUTH PERCENT CONTROL DAYS AFTER APPLICATION | |
|---|---|---|
| | 2 Days | 17 Days |
| 30 (12.30 #ae/A) | 81.7 | 100.0 |
| 31(6.15 #ae/A) | 74.3 | 100.0 |
| 31(12.30#ae/A) | 90.7 | 100.0 |
| 32 (6.15 #ae/A) | 77.7 | 93.7 |
| 32 (12.30 #ae/A) | 94.3 | 100.0 |
| 33 (6.15 #ae/A) | 55.0 | 100.0 |
| 33(12.30 #ae/A) | 82.7 | 100.0 |
| 34 (6.15 #ae/A) | 69.7 | 92.7 |
| 34 (12.30 #ae/A) | 87.3 | 100.0 |
| 35 (6.15 #ae/A) | 69.3 | 98.3 |
| 35 (12.30 #ae/A) | 89.3 | 100.0 |
| 27 (0.96 #AI @ 145 GPA) | 53.3 | 100.0 |
| 20 (1.92 #AI/A @ 145 GPA) | 63.3 | 100.0 |
| 28 (145 GPA) | 81.3 | 98.7 |
| 29 (145 GPA) | 68.3 | 100.0 |
| UNTREATED | 0 | 0 |

TABLE 38

| TREATMENT (RATE) | ECHCG PERCENT CONTROL DAYS AFTER APPLICATION | |
|---|---|---|
| | 2 Days | 17 Days |
| 22(12.30 #ae/A) | 31.5 | 100.0 |
| 23(6.15 #ae/A) + 2(0.90 #AI) + 24(0.15% V/V) | 73.0 | 97.7 |
| 23(6.15 #ae/A) + 2(0.18 #AI/A) + 24(0.15% V/V) | 77.7 | 97.3 |
| 23(6.15 #ae/A) + 2(0.36 A1/A) + 24(0.15% V/V) | 80.0 | 91.3 |
| 23 12.30 ae/A) + 2(0.18 #AI/A) + 24(0.3% V/V) | 79.3 | 99.3 |
| 23(12.30 #ae/A) + 2(0.36 #AI/A) + 24(0.3% V/V) | 81.7 | 96.0 |
| 23(12.30 #ae/A) + 2(0.72 #AI/A) + 24(0.3% V/V) | 83.3 | 100.0 |
| 23(6.15 #ae/A) + 2(0.09 #AI/A) + 24(0.08% V/V) + 25(0.70% V/V) | 78.0 | 99.7 |
| 23(6.15 #ae/A) + 2(0.18 #AI/A) + 24(0.08% V/V) + 25(0.07% V/V) | 87.0 | 96.0 |
| 23(6.15 #ae/A) + 2(0.36 #AI/A) + 24(0.08% V/V) + 25(0.07% V/V) | 87.0 | 100.0 |
| 23(12.30 #ae/A) + 2(0.18 #AI/A) + 24(0.16% V/V) + 25(0.14% V/V) | 89.3 | 100.0 |
| 23(12.30 #ae/A) + 2(0.36 #AI/A) + 24(0.16% V/V) + 25(0.14% V/V) | 90.0 | 100.0 |
| 23(12.30 #ae/A) + 2(0.72 #AI/A) + 24(0.16% V/V) + 25(0.14% V/V) | 89.3 | 100.0 |
| 30(6.15 #ae/A) | 74.3 | 99.7 |
| 30(12.30 #ae/A) | 83.3 | 100.0 |
| 31(6.15 #ae/A) | 88.3 | 100.0 |
| 31(12.30 #ae/A) | 91.7 | 100.0 |
| 32(6.15 #ae/A) | 98.7 | 100.0 |
| 32(12.30 #ae/A) | 92.7 | 100.0 |
| 33(6.15 #ae/A) | 83.0 | 99.3 |
| 33(12.30 #ae/A) | 88.7 | 99.3 |
| 34(6.15 #ae/A) | 78.3 | 96.7 |
| 34(12.30 #ae/A) | 86.0 | 100.0 |
| 35(6.15 #ae/A) | 88.0 | 100.0 |
| 35(12.30 #ae/A) | 89.3 | 100.0 |
| 27(11.6 #AI/A) | 72.7 | 96.0 |
| 20(23.2 #AI/A) | 75.0 | 100.0 |
| 28(145 GPA) | 92.7 | 100.0 |
| 29(145 GPA) | 65.7 | 100.0 |
| UNTREATED | 0 | 0 |

Example 27

A test was conducted in Missouri to determine both the effectiveness of the herbicide formulations of Tables 39 and 40 for killing or controlling buckhorn plantain (*Plantago* lanceolata, PLALA) and tall fescue (Festuca arundinacea, FESAR). Applications were made in December and evaluations were made at 2 and 18 days after application. Treatments and corresponding percent controls are reported for buckhorn plantain in Tables 39 and for tall fescue in Table 40. Spray volume was 145 gals/A.

TABLE 39

| TREATMENT (CONC.) | PLALA PERCENT CONTROL DAYS AFTER APPLICATION | |
|---|---|---|
| | 2 Days | 18 Days |
| 36 (3.00 oz/gal) | 80.0 | 96.7 |
| 36 (6.00 oz/gal) | 88.3 | 100.0 |
| 37 (3.00 oz/gal) | 53.3 | 88.3 |
| 37 (6.00 oz/gal) | 76.7 | 100.0 |
| 38 (3.00 oz/gal) | 43.2 | 99.3 |
| 38 (6.00 oz/gal) | 55.0 | 95.3 |
| 39 (3.00 oz/gal) | 80.0 | 98.3 |
| 36 (6.00 oz/gal) | 86.7 | 100.0 |
| 40 (3.00 oz/gal) | 63.3 | 96.0 |
| 40 (6.00 oz/gal) | 76.7 | 100.0 |
| 41 (3.00 oz/gal) | 43.3 | 98.3 |
| 41 (6.00 oz/gal) | 53.3 | 100.0 |
| 21 (3.00 oz/gal) | 90.0 | 98.3 |
| 21 (6.00 oz/gal) | 91.7 | 100.0 |
| 27 (11.6 #AI/A) | 55.0 | 100.0 |
| 20 (23.2 #AI/A) | 76.0 | 100.0 |
| 28 (145 GPA) | 96.0 | 95.0 |
| 18 (3.00 oz/gal) | 16.0 | 98.0 |
| 18 (6.00 oz/gal) | 20.0 | 100.0 |
| 29 (145 GPA) | 31.7 | 100.0 |
| UNTREATED | 0 | 0 |

TABLE 40

| TREATMENT (CONC.) | FESAR PERCENT CONTROL DAYS AFTER APPLICATION | |
|---|---|---|
| | 2 Days | 18 Days |
| 36 (3.00 oz/gal) | 50.0 | 80.0 |
| 36 (6.00 oz/gal) | 60.0 | 83.3 |
| 37 (3.00 oz/gal) | 30.0 | 80.0 |
| 37 (6.00 oz/gal) | 40.0 | 83.3 |
| 38 (3.00 oz/gal) | 28.3 | 86.7 |
| 38 (6.00 oz/gal) | 31.7 | 85.0 |
| 39 (3.00 oz/gal) | 50.0 | 85.0 |
| 36 (6.00 oz/gal) | 63.3 | 87.7 |
| 40 (3.00 oz/gal) | 40.0 | 81.7 |
| 40 (6.00 oz/gal) | 55.0 | 86.7 |
| 41 (3.00 oz/gal) | 25.0 | 85.0 |
| 41 (6.00 oz/gal) | 35.0 | 87.0 |
| 21 (3.00 oz/gal) | 53.3 | 85.0 |
| 21 (6.00 oz/gal) | 60.0 | 91.7 |
| 27 (11.6 #AI/A)) | 46.7 | 91.0 |
| 20 (23.2 #AI/A) | 61.7 | 91.7 |
| 28 (145 GPA) | 75.0 | 91.0 |
| 18 (3.00 oz/gal) | 5.0 | 90.0 |
| 18 (6.00 oz/gal) | 10.0 | 95.0 |
| 29 (145 GPA) | 13.3 | 100.0 |
| UNTREATED | 0 | 0 |

Example 28

A test was conducted in Missouri to determine the effectiveness of the herbicide formulations of Tables 41 and 42 for killing or controlling velvetleaf (Abutilon theophrasti, ABUTH) and barnyardgrass (Echinocloa crus-galli, ECHCG). Applications were made in August and evaluations were made at 1 and 15 days after application. Treatments and corresponding percent controls are reported for velvetleaf in Table 41 and for barnyardgrass in Table 42.

TABLE 41

| TREATMENT (RATE) | ABUTH PERCENT CONTROL DAYS AFTER APPLICATION | |
|---|---|---|
| | 1 Day | 15 Days |
| 22 (6.15 #ae/A) | 10.0 | 100.0 |
| 22 (8.85 #ae/A) | 13.3 | 100.0 |
| 22 (12.30 #ae/A) | 20.0 | 100.0 |
| 23 (6.15 #ae/A) + 2 (0.180 #AI/A) + 24 (0.15% V/V) | 42.0 | 99.7 |
| 23 (6.15 #ae/A) + 2 (0.27 #AI/A) + 24 (0.15% V/V) | 66.7 | 100.0 |
| 23 (6.15 #ae/A) + 2 (0.36 #AI/A) + 24 (0.15% V/V) | 71.3 | 100.0 |
| 23 (6.15 #ae/A) + 2 (0.45 #AI/A) + 24 (0.15% V/V) | 74.7 | 96.3 |
| 23 (6.15 #ae/A) + 2 (0.72 #AI/A) + 24 (0.15% V/V) | 85.0 | 100.0 |
| 23 (8.85 #ae/A) + 2 (0.180 #AI/A) + 24 (0.15% V/V) | 65.0 | 100.0 |
| 23 (8.85 #ae/A) + 2 (0.27 #AI/A) + 24 (0.15% V/V) | 64.3 | 100.0 |
| 23 (8.85 #ae/A) + 2 (0.36 #AI/A) + 24 (0.15% V/V) | 72.7 | 100.0 |
| 23 (8.85 #ae/A) + 2 (0.45 #AI/A) + 24 (0.15% V/V) | 75.0 | 95.0 |
| 23 (8.85 #ae/A) + 2 (0.72 #AI/A) + 24 (0.15% V/V) | 80.0 | 96.0 |
| 23 (12.30 #ae/A) + 2 (0.180 #AI/A) + 24 (0.15% V/V) | 70.0 | 100.0 |
| 23 (12.30 #ae/A) + 2 (0.27 #AI/A) + 24 (0.15% V/V) | 71.7 | 100.0 |
| 23 (12.30 #ae/A) + 2 (0.36 #AI/A) + 24 (0.15% V/V) | 78.0 | 100.0 |
| 23 (12.30 #ae/A) + 2 (0.45 #AI/A) + 24 (0.15% V/V) | 73.3 | 100.0 |
| 23 (12.30 #ae/A) + 2 (0.72 #AI/A) + 24 (0.15% V/V) | 83.3 | 100.0 |
| 23 (12.30 #ae/A) + 2 (0.18 #AI/A) + 24 (0.3% V/V) | 86.7 | 100.0 |
| 23 (6.15 #ae/A) + 2 (0.27 #AI/A) + 24 (0.3% V/V) | 74.7 | 96.7 |
| 23 (6.15 #ae/A) + 2 (0.36 #AI/A) + 24 (0.3% V/V) | 73.3 | 95.0 |
| 23 (6.15 #ae/A) + 2 (0.45 #AI/A) + 24 (0.3% V/V) | 76.7 | 95.7 |
| 23 (6.15 #ae/A) + 2 (0.72 #AI/A) + 24 (0.3% V/V) | 85.3 | 100.0 |
| 23 (8.85 #ae/A) + 2 (0.180 #AI/A) + 24 (0.3% V/V) | 68.3 | 100.0 |
| 23 (8.85 #ae/A) + 2 (0.27 #AI/A) + 24 (0.3% V/V) | 70.0 | 100.0 |
| 23 (8.85 #ae/A) + 2 (0.36 #AI/A) + 24 (0.3% V/V) | 71.7 | 100.0 |
| 23 (8.85 #ae/A) + 2 (0.45 #AI/A) + 24 (0.3% V/V) | 78.7 | 100.0 |
| 23 (8.85 #ae/A) + 2 (0.72 #AI/A) + 24 (0.3% V/V) | 82.0 | 100.0 |
| 23 (12.30 #ae/A) + 2 (0.180 #AI/A) + 24 (0.3% V/V) | 63.3 | 100.0 |
| 23 (12.30 #ae/A) + 2 (0.27 #AI/A) + 24 (0.3% V/V) | 69.3 | 100.0 |
| 23 (12.30 #ae/A) + 2 (0.36 #AI/A) + 24 (0.3% V/V) | 74.0 | 100.0 |
| 23 (12.30 #ae/A) + 2 (0.45 #AI/A) + 24 (0.3% V/V) | 78.7 | 100.0 |
| 23 (12.30 #ae/A) + 2 (0.72 #AI/A) + 24 (0.3% V/V) | 85.0 | 100.0 |
| 23 (6.15 #ae/A) + 2 (0.103 #AI/A) + 25 (0.15% V/V) | 81.3 | 94.0 |
| 23 (6.15 #ae/A) + 2 (0.137 #AI/A) + 25 (0.15% V/V) | 84.0 | 91.3 |
| 23 (6.15 #ae/A) + 2 (0.180 #AI/A) + 25 (0.15% V/V) | 84.0 | 94.7 |
| 23 (6.15 #ae/A) + 2 (0.27 #AI/A) + 25 (0.15% V/V) | 86.3 | 96.0 |
| 23 (6.15 #ae/A) + 2 (0.36 #AI/A) + 25 (0.15% V/V) | 86.7 | 95.7 |

TABLE 41-continued

| TREATMENT (RATE) | ABUTH PERCENT CONTROL DAYS AFTER APPLICATION | |
|---|---|---|
| | 1 Day | 15 Days |
| 23 (8.85 #ae/A) + 2 (0.103 #AI/A) + 25 (0.15% V/V) | 80.0 | 97.3 |
| 23 (8.85 #ae/A) + 2 (0.137 #AI/A) + 25 (0.15% V/V) | 82.0 | 96.7 |
| 23 (8.85 #ae/A) + 2 (0.180 #AI/A) + 25 (0.15% V/V) | 82.0 | 100.0 |
| 23 (8.85 #ae/A) + 2 (0.27 #AI/A) + 25 (0.15% V/V) | 85.3 | 100.0 |
| 23 (8.85 #ae/A) + 2 (0.36 #AI/A) + 25 (0.15% V/V) | 82.0 | 100.0 |
| 23 (12.30 #ae/A) + 2 (0.103 #AI/A) + 25 (0.15% V/V) | 80.0 | 100.0 |
| 23 (12.30 #ae/A) + 2 (0.137 #AI/A) + 25 (0.15% V/V) | 79.3 | 95.3 |
| 23 (12.30 #ae/A) + 2 (0.180 #AI/A) + 25 (0.15% V/V) | 80.7 | 96.0 |
| 23 (12.30 #ae/A) + 2 (0.27 #AI/A) + 25 (0.15% V/V) | 87.3 | 100.0 |
| 23 (12.30 #ae/A) + 2 (0.36 #AI/A) + 25 (0.15% V/V) | 90.0 | 100.0 |
| 23 (6.15 #ae/A) + 2 (0.103 #AI/A) + 25 (0.3% V/V) | 81.7 | 96.0 |
| 23 (6.15 #ae/A) + 2 (0.137 #AI/A) + 25 (0.3% V/V) | 85.0 | 92.0 |
| 23 (6.15 #ae/A) + 2 (0.180 #AI/A) + 25 (0.3% V/V) | 88.7 | 100.0 |
| 23 (6.15 #ae/A) + 2 (0.27 #AI/A) + 25 (0.3% V/V) | 86.3 | 97.7 |
| 23 (6.15 #ae/A) + 2 (0.36 #AI/A) + 25 (0.3% V/V) | 93.0 | 100.0 |
| 23 (8.85 #ae/A) + 2 (0.103 #AI/A) + 25 (0.3% V/V) | 88.0 | 100.0 |
| 23 (8.85 #ae/A) + 2 (0.137 #AI/A) + 25 (0.3% V/V) | 83.3 | 100.0 |
| 23 (8.85 #ae/A) + 2 (0.180 #AI/A) + 25 (0.3% V/V) | 80.0 | 100.0 |
| 23 (8.85 #ae/A) + 2 (0.27 #AI/A) + 25 (0.3% V/V) | 93.3 | 100.0 |
| 23 (8.85 #ae/A) + 2 (0.36 #AI/A) + 25 (0.3% V/V) | 95.0 | 100.0 |
| 23 (12.30 #ae/A) + 2 (0.103 #AI/A) + 25 (0.3% V/V) | 80.7 | 100.0 |
| 23 (12.30 #ae/A) + 2 (0.137 #AI/A) + 25 (0.3% V/V) | 92.0 | 100.0 |
| 23 (12.30 #ae/A) + 2 (0.180 #AI/A) + 25 (0.3% V/V) | 90.3 | 100.0 |
| 23 (12.30 #ae/A) + 2 (0.27 #AI/A) + 25 (0.3% V/V) | 89.0 | 100.0 |
| 23 (12.30 #ae/A) + 2 (0.36 #AI/A) + 25 (0.3% V/V) | 95.0 | 100.0 |
| 26 (4.40 #gly ae/A) + (0.10# diguat cation/A) | 82.0 | 92.3 |
| 26 (6.15 #aegly/A) + (0.14# diguat cation/A) | 87.3 | 100.0 |
| 26 (8.85 #aegly/A) + (0.20# diguat cation/A) | 92.3 | 100.0 |
| 26 (12.30 #aegly/A) + (0.29# diguat cation/A) | 98.0 | 100.0 |
| 27 (11.3# AI/A) | 65.0 | 100.0 |
| 28 (140 GPA) | 92.3 | 100.0 |
| 29 (140 GPA) | 55.0 | 100.0 |
| UNTREATED | 0 | 0 |

TABLE 42

| TREATMENT (RATE) | ECHCG PERCENT CONTROL DAYS AFTER APPLICATION | |
|---|---|---|
| | 1 Day | 15 Days |
| 22 (6.15 #ae/A) | 5.0 | 100.0 |
| 22 (8.85 #ae/A) | 5.0 | 100.0 |
| 22 (12.30 #ae/A) | 5.0 | 100.0 |

TABLE 42-continued

| TREATMENT (RATE) | ECHCG PERCENT CONTROL DAYS AFTER APPLICATION | |
|---|---|---|
| | 1 Day | 15 Days |
| 23 (6.15 #ae/A) + 2 (0.180 #AI/A) + 24 (0.15% V/V) | 80.0 | 98.3 |
| 23 (6.15 #ae/A) + 2 (0.27 #AI/A) + 24 (0.15% V/V) | 88.7 | 99.0 |
| 23 (6.15 #ae/A) + 2 (0.36 #AI/A) + 24 (0.15% V/V) | 86.0 | 91.3 |
| 23 (6.15 #ae/A) + 2 (0.45 #AI/A) + 24 (0.15% V/V) | 90.0 | 100.0 |
| 23 (6.15 #ae/A) + 2 (0.72 #AI/A) + 24 (0.15% V/V) | 82.0 | 100.0 |
| 23 (8.85 #ae/A) + 2 (0.180 #AI/A) + 24 (0.15% V/V) | 85.3 | 100.0 |
| 23 (8.85 #ae/A) + 2 (0.27 #AI/A) + 24 (0.15% V/V) | 86.0 | 99.7 |
| 23 (8.85 #ae/A) + 2 (0.36 #AI/A) + 24 (0.15% V/V) | 80.0 | 100.0 |
| 23 (8.85 #ae/A) + 2 (0.45 #AI/A) + 24 (0.15% V/V) | 85.3 | 100.0 |
| 23 (8.85 #ae/A) + 2 (0.72 #AI/A) + 24 (0.15% V/V) | 90.0 | 100.0 |
| 23 (12.30 #ae/A) + 2 (0.180 #AI/A) + 24 (0.15% V/V) | 80.0 | 100.0 |
| 23 (12.30 #ae/A) + 2 (0.27 #AI/A) + 24 (0.15% V/V) | 82.7 | 100.0 |
| 23 (12.30 #ae/A) + 2 (0.36 #AI/A) + 24 (0.15% V/V) | 88.0 | 100.0 |
| 23 (12.30 #ae/A) + 2 (0.45 #AI/A) + 24 (0.15% V/V) | 90.0 | 100.0 |
| 23 (12.30 #ae/A) + 2 (0.72 #AI/A) + 24 (0.15% V/V) | 90.0 | 100.0 |
| 23 (12.30 #ae/A) + 2 (0.18 #AI/A) + 24 (0.3% V/V) | 86.0 | 99.7 |
| 23 (6.15 #ae/A) + 2 (0.27 #AI/A) + 24 (0.3% V/V) | 87.3 | 100.0 |
| 23 (6.15 #ae/A) + 2 (0.36 #AI/A) + 24 (0.3% V/V) | 88.7 | 100.0 |
| 23 (6.15 #ae/A) + 2 (0.45 #AI/A) + 24 (0.3% V/V) | 90.7 | 100.0 |
| 23 (6.15 #ae/A) + 2 (0.72 #AI/A) + 24 (0.3% V/V) | 92.0 | 100.0 |
| 23 (8.85 #ae/A) + 2 (0.180 #AI/A) + 24 (0.3% V/V) | 83.3 | 100.0 |
| 23 (8.85 #ae/A) + 2 (0.27 #AI/A) + 24 (0.3% V/V) | 85.0 | 100.0 |
| 23 (8.85 #ae/A) + 2 (0.36 #AI/A) + 24 (0.3% V/V) | 89.3 | 100.0 |
| 23 (8.85 #ae/A) + 2 (0.45 #AI/A) + 24 (0.3% V/V) | 89.3 | 100.0 |
| 23 (8.85 #ae/A) + 2 (0.72 #AI/A) + 24 (0.3% V/V) | 92.0 | 100.0 |
| 23 (12.30 #ae/A) + 2 (0.180 #AI/A) + 24 (0.3% V/V) | 84.0 | 100.0 |
| 23 (12.30 #ae/A) + 2 (0.27 #AI/A) + 24 (0.3% V/V) | 86.7 | 100.0 |
| 23 (12.30 #ae/A) + 2 (0.36 #AI/A) + 24 (0.3% V/V) | 88.0 | 100.0 |
| 23 (12.30 #ae/A) + 2 (0.45 #AI/A) + 24 (0.3% V/V) | 92.0 | 100.0 |
| 23 (12.30 #ae/A) + 2 (0.72 #AI/A) + 24 (0.3% V/V) | 91.3 | 100.0 |
| 23 (6.15 #ae/A) + 2 (0.103 #AI/A) + 25 (0.15% V/V) | 79.3 | 100.0 |
| 23 (6.15 #ae/A) + 2 (0.137 #AI/A) + 25 (0.15% V/V) | 81.3 | 99.3 |
| 23 (6.15 #ae/A) + 2 (0.180 #AI/A) + 25 (0.15% V/V) | 88.7 | 100.0 |
| 23 (6.15 #ae/A) + 2 (0.27 #AI/A) + 25 (0.15% V/V) | 89.7 | 100.0 |
| 23 (6.15 #ae/A) + 2 (0.36 #AI/A) + 25 (0.15% V/V) | 92.0 | 100.0 |
| 23 (8.85 #ae/A) + 2 (0.103 #AI/A) + 25 (0.15% V/V) | 78.7 | 100.0 |

TABLE 42-continued

| TREATMENT (RATE) | ECHCG PERCENT CONTROL DAYS AFTER APPLICATION | |
|---|---|---|
| | 1 Day | 15 Days |
| 23 (8.85 #ae/A) + 2 (0.137 #AI/A) + 25 (0.15% V/V) | 85.0 | 100.0 |
| 23 (8.85 #ae/A) + 2 (0.180 #AI/A) + 25 (0.15% V/V) | 86.0 | 100.0 |
| 23 (8.85 #ae/A) + 2 (0.27 #AI/A) + 25 (0.15% V/V) | 86.7 | 100.0 |
| 23 (8.85 #ae/A) + 2 (0.36 #AI/A) + 25 (0.15% V/V) | 90.0 | 100.0 |
| 23 (12.30 #ae/A) + 2 (0.103 #AI/A) + 25 (0.15% V/V) | 78.0 | 99.3 |
| 23 (12.30 #ae/A) + 2 (0.137 #AI/A) + 25 (0.15% V/V) | 82.0 | 100.0 |
| 23 (12.30 #ae/A) + 2 (0.180 #AI/A) + 25 (0.15% V/V) | 86.7 | 100.0 |
| 23 (12.30 #ae/A) + 2 (0.27 #AI/A) + 25 (0.15% V/V) | 89.3 | 100.0 |
| 23 (12.30 #ae/A) + 2 (0.36 #AI/A) + 25 (0.15% V/V) | 90.7 | 100.0 |
| 23 (6.15 #ae/A + 2 (0.103 #AI/A) + 25 (0.3% V/V) | 81.3 | 100.0 |
| 23 (6.15 #ae/A) + 2 (0.137 #AI/A) + 25 (0.3% V/V) | 97.7 | 100.0 |
| 23 (6.15 #ae/A) + 2 (0.180 #AI/A) + 25 (0.3% V/V) | 87.0 | 100.0 |
| 23 (6.15 #ae/A) + 2 (0.27 #AI/A) + 25 (0.3% V/V) | 90.0 | 100.0 |
| 23 (6.15 #ae/A) + 2 (0.36 #AI/A) + 25 (0.3% V/V) | 90.3 | 100.0 |
| 23 (8.85 #ae/A) + 2 (0.103 #AI/A) + 25 (0.3% V/V) | 76.0 | 100.0 |
| 23 (8.85 #ae/A) + 2 (0.137 #AI/A) + 25 (0.3% V/V) | 82.0 | 100.0 |
| 23 (8.85 #ae/A) + 2 (0.180 #AI/A) + 25 (0.3% V/V) | 87.3 | 100.0 |
| 23 (8.85 #ae/A) + 2 (0.27 #AI/A) + 25 (0.3% V/V) | 90.0 | 100.0 |
| 23 (8.85 #ae/A) + 2 (0.36 #AI/A) + 25 (0.3% V/V) | 90.7 | 100.0 |
| 23 (12.30 #ae/A) + 2 (0.103 #AI/A) + 25 (0.3% V/V) | 75.0 | 100.0 |
| 23 (12.30 #ae/A) + 2 (0.137 #AI/A) + 25 (0.3% V/V) | 75.0 | 100.0 |
| 23 (12.30 #ae/A) + 2 (0.180 #AI/A) + 25 (0.3% V/V) | 82.0 | 100.0 |
| 23 (12.30 #ae/A) + 2 (0.27 #AI/A) + 25 (0.3% V/V) | 89.3 | 100.0 |
| 23 (12.30 #ae/A) + 2 (0.36 #AI/A) + 25 (0.3% V/V) | 92.0 | 100.0 |
| 26 (4.40 #aegly/A) + (0.10# diguat cation/A) | 72.0 | 89.0 |
| 26 (6.15 #aegly/A) + (0.14# diguat cation/A) | 70.7 | 100.0 |
| 26 (8.85 #aegly/A) + (0.20# diguat cation/A) | 88.7 | 100.0 |
| 26 (12.30 #aegly/A) + (0.29# diguat cation/A) | 90.0 | 100.0 |
| 27 (11.3# AI/A) | 70.0 | 100.0 |
| 28 (140 GPA) | 97.0 | 100.0 |
| 29 (140 GPA) | 92.0 | 100.0 |
| UNTREATED | 0 | 0 |

Example 29

A test was conducted in Missouri to determine the effectiveness of the herbicide formulations of Tables 43 and 44 for killing or controlling velvetleaf (*Abutilon theophrasti*, ABUTH) and barnyardgrass (*Echinocloa crus-galli*, ECHCG). Applications were made in October and evaluations were made at 2 and 17 days after application. Application treatments and corresponding percent controls are reported for velvetleaf in Table 43 and for barnyardgrass in Table 44. Spray volume was 145 gals/A.

TABLE 43

| TREATMENT (CONC.) | ABUTH PERCENT CONTROL DAYS AFTER APPLICATION | |
|---|---|---|
| | 2 Days | 17 Days |
| 37 (3.00 oz/gal) | 65.0 | 88.7 |
| 37 (6.00 oz/gal) | 78.3 | 90.0 |
| 36 (3.00 oz/gal) | 77.3 | 89.3 |
| 36 (6.00 oz/gal) | 87.0 | 89.3 |
| 59 (3.00 oz/gal) | 87.0 | 87.0 |
| 59 (6.00 oz/gal) | 87.0 | 100.0 |
| 60 (3.00 oz/gal) | 88.0 | 89.3 |
| 60 (6.00 oz/gal) | 90.0 | 99.7 |
| 61 (3.00 oz/gal) | 89.3 | 100.0 |
| 61 (6.00 oz/gal) | 92.0 | 100.0 |
| 62 (3.00 oz/gal) | 91.7 | 99.3 |
| 62 (6.00 oz/gal) | 93.3 | 100.0 |
| 27 (0.96% AI/A/gal) | 36.7 | 100.0 |
| 20 (1.92% AI/gal) | 33.3 | 81.7 |
| 28 (145 GPA) | 68.3 | 96.0 |
| UNTREATED | 0 | 0 |

TABLE 44

| TREATMENT (CONC.) | ECHCF PERCENT CONTROL DAYS AFTER APPLICATION | |
|---|---|---|
| | 2 Days | 17 Days |
| 37 (3.00 oz/gal) | 84.7 | 87.0 |
| 37 (6.00 oz/gal) | 89.3 | 95.0 |
| 36 (3.00 oz/gal) | 90.0 | 91.7 |
| 36 (6.00 oz/gal) | 95.0 | 96.7 |
| 59 (3.00 oz/gal) | 90.3 | 76.0 |
| 59 (6.00 oz/gal) | 98.0 | 98.3 |
| 60 (3.00 oz/gal) | 88.0 | 76.0 |
| 60 (6.00 oz/gal) | 98.0 | 98.3 |
| 61 (3.00 oz/gal) | 91.7 | 78.7 |
| 61 (6.00 oz/gal) | 98.0 | 100.0 |
| 62 (3.00 oz/gal) | 94.0 | 91.0 |
| 62 (6.00 oz/gal) | 95.0 | 100.0 |
| 27 (0.96% AI/A/gal) | 91.0 | 97.7 |
| 20 (1.92% AI/gal) | 94.3 | 94.3 |
| 28 (145 GPA) | 98.0 | 100.0 |
| UNTREATED | 0 | 0 |

Example 30

A test was conducted in Missouri to determine the effectiveness of the herbicide formulations of Table 45 for killing or controlling bermudagrass (*Cynodon dactylon*, CYNDA). Applications were made in January and evaluations were made at 3 and 18 days after application. Application treatments and corresponding percent controls arc reported in Table 45. Spray volume was 145 gals/A.

TABLE 45

| TREATMENT (CONC.) | CYNDA PERCENT CONTROL DAYS AFTER APPLICATION | |
|---|---|---|
| | 3 Days | 18 Days |
| 36 (3.00 oz/gal) | 66.7 | 40.0 |
| 36 (6.00 oz/gal) | 76.7 | 53.3 |
| 37 (3.00 oz/gal) | 56.7 | 43.3 |
| 37 (6.00 oz/gal) | 73.3 | 55.0 |
| 38 (3.00 oz/gal) | 46.7 | 55.0 |
| 38 (6.00 oz/gal) | 60.0 | 65.0 |
| 42 (3.00 oz/gal) | 66.7 | 46.7 |
| 42 (6.00 oz/gal) | 80.0 | 63.3 |
| 27 (0.96% AI/A/gal) | 35.0 | 81.7 |

TABLE 45-continued

| TREATMENT | CYNDA PERCENT CONTROL DAYS AFTER APPLICATION | |
|---|---|---|
| (CONC.) | 3 Days | 18 Days |
| 20 (1.92% AI/gal) | 38.3 | 89.3 |
| 28 (145 GPA) | 90.7 | 95.0 |
| 18 (3.00 oz/gal) | 18.3 | 83.3 |
| 18 (6.00 oz/gal) | 26.7 | 95.0 |
| 29 (145 GPA) | 50.0 | 100.0 |
| UNTREATED | 0 | 0 |

Example 31

A test was conducted in Missouri to determine the effectiveness of the herbicide formulations of Table 46 for killing or controlling dandelion (*Taraxacum officinale*, TAROF). Applications were made in January and evaluations were made at 3 and 18 days after application. Application treatments and corresponding percent controls are reported in Table 46. Spray volume was 145 gals/A.

TABLE 46

| TREATMENT | PERCENT CONTROL DAYS AFTER APPLICATION | |
|---|---|---|
| (CONC.) | 3 Days | 18 Days |
| 36 (3.00 oz/gal) | 91.7 | 95.0 |
| 36 (6.00 oz/gal) | 96.0 | 96.7 |
| 37 (3.00 oz/gal) | 76.7 | 83.3 |
| 37 (6.00 oz/gal) | 86.0 | 96.7 |
| 38 (3.00 oz/gal) | 81.0 | 79.3 |
| 38 (6.00 oz/gal) | 76.7 | 86.7 |
| 42 (3.00 oz/gal) | 89.3 | 99.3 |
| 42 (6.00 oz/gal) | 97.0 | 100.0 |
| 27 (0.96% AI/gal) | 45.0 | 100.0 |
| 20 (1.92% AI/gal) | 51.7 | 100.0 |
| 28 (145 GPA) | 98.0 | 71.0 |
| 18 (3.00 oz/gal) | 11.7 | 100.0 |
| 18 (6.00 oz/gal) | 13.3 | 100.0 |
| 29 (145 GPA) | 51.7 | 100.0 |
| UNTREATED | 0 | 0 |

Example 32

A test was conducted in Missouri to determine the effectiveness of the herbicide formulations of Tables 47 and 48 for killing or controlling velvetleaf (*Abutilon theophrasti*, ABUTH) and barnyardgrass (*Echinocloa crus-galli*, ECHCG). Applications were made in January and evaluations were made at 3 and 18 days after application. Application formulations and Treatments and corresponding percent controls are reported for velvetleaf in Table 47 and for barnyardgrass in Table 48. Spray volume was 145 gals/A.

TABLE 47

| TREATMENT | ABUTH PERCENT CONTROL DAYS AFTER APPLICATION | |
|---|---|---|
| (CONC.) | 3 Days | 18 Days |
| 36 (3.00 oz/gal) | 80.3 | 88.3 |
| 36 (6.00 oz/gal) | 90.7 | 96.0 |
| 37 (3.00 oz/gal) | 66.7 | 88.3 |

TABLE 47-continued

| TREATMENT | ABUTH PERCENT CONTROL DAYS AFTER APPLICATION | |
|---|---|---|
| (CONC.) | 3 Days | 18 Days |
| 37 (6.00 oz/gal) | 76.7 | 96.7 |
| 38 (3.00 oz/gal) | 63.3 | 91.7 |
| 38 (6.00 oz/gal) | 68.3 | 99.3 |
| 42 (3.00 oz/gal) | 84.3 | 91.0 |
| 42 (6.00 oz/gal) | 90.0 | 98.3 |
| 27 (0.96% AI/gal) | 40.0 | 100.0 |
| 20 (1.92% AI/gal) | 46.7 | 88.3 |
| 28 (145 GPA) | 93.7 | 94.3 |
| 18 (3.00 oz/gal) | 18.3 | 200.0 |
| 18 (6.00 oz/gal) | 40.0 | 100.0 |
| 29 (145 GPA) | 69.3 | 97.7 |
| UNTREATED | 0 | 0 |

TABLE 48

| TREATMENT (Conc.) | ECHCG PERCENT CONTROL DAYS AFTER APPLICATION | |
|---|---|---|
|  | 3 Days | 18 Days |
| 36 (3.00 oz/gal) | 70.0 | 53.7 |
| 36 (6.00 oz/gal) | 79.3 | 86.0 |
| 37 (3.00 oz/gal) | 61.7 | 60.0 |
| 37 (6.00 oz/gal) | 71.7 | 79.3 |
| 38 (3.00 oz/gal) | 55.0 | 64.3 |
| 38 (6.00 oz/gal) | 66.7 | 85.0 |
| 42 (3.00 oz/gal) | 71.0 | 71.7 |
| 42 (6.00 oz/gal) | 85.3 | 93.3 |
| 27 (0.96% AI/gal) | 87.7 | 96.7 |
| 20 (1.92% AI/gal) | 90.0 | 96.7 |
| 28 (145 GPA) | 96.0 | 100.0 |
| 18 (3.00 oz/gal) | 40.0 | 100.0 |
| 18 (6.00 oz/gal) | 50.0 | 100.0 |
| 29 (145 GPA) | 61.7 | 100.0 |
| UNTREATED | 0 | 0 |

Example 33

A test was conducted in Oregon to determine the effectiveness of the herbicide formulations of Tables 49 and 50 for killing or controlling perennial ryegrass (*Lolium multiflorum*, LOLMU) and fine fescue (*Festuca* spp.). Applications were made in March and evaluations were made at 1 hour, 4 hours, 1 day, 2 days, 3 days, and 7 days after application. Application treatments and corresponding percent turf dessication are reported for perennial ryegrass in Table 49 and for fine fescue in Table 50. Spray volume was 145 gals/A.

TABLE 49

PERENNIAL RYEGRASS DAYS AFTER APPLICATION

| TREATMENT (CONC.) | % Dessic. 14 Days | % Dessic. 20 days | % Regrowth 20 days | % Regrowth 29 Days | % Regrowth 43 Days | % Regrowth 86 Days |
|---|---|---|---|---|---|---|
| 37 (3 oz/gal) | 0.0 | 0.0 | 0.0 | 0.0 | 10.0 | 71.7 |
| 37 (6 oz/gal) | 0.0 | 0.0 | 0.0 | 0.0 | 23.3 | 78.3 |
| 44 (3 oz/gal) | 0.0 | 0.0 | 0.0 | 0.0 | 8.3 | 60.0 |
| 44 (6 oz/gal) | 0.0 | 0.0 | 0.0 | 0.0 | 28.3 | 78.3 |
| 22 (3 oz/gal) | 0.0 | 0.0 | 0.0 | 0.0 | 3.0 | 63.3 |
| 22 (6 oz/gal) | 0.0 | 0.0 | 0.0 | 0.0 | 6.7 | 73.3 |
| 18 (3 oz/gal) | 0.0 | 0.0 | 0.0 | 0.0 | 4.0 | 65.0 |
| 18 (6 oz/gal) | 0.0 | 0.0 | 0.0 | 0.0 | 15.0 | 73.3 |
| 45 (3 oz/gal) | 0.0 | 2.0 | 8.3 | 8.3 | 78.3 | 91.7 |
| 45 (6 oz/gal) | 1.7 | 5.0 | 18.3 | 18.3 | 90.0 | 95.0 |
| 45 (9 oz/gal) | 5.0 | 9.3 | 30.0 | 30.0 | 95.0 | 98.3 |
| UNTREATED | 0 | 0 | 0 | 0 | 0 | 0 |

TABLE 50

FINE FESCUE PERCENT TURF DESSICATION DAYS AFTER APPLICATION

| TREATMENT (CONC.) | 14 Days | 20 Days | 20 Days | 29 Days | 43 Days | 86 Days |
|---|---|---|---|---|---|---|
| 37 (3 oz/gal) | 90.7 | 97.3 | 0.0 | 1.3 | 1.3 | 3.7 |
| 37 (6 oz/gal) | 92.0 | 97.7 | 0.0 | 0.0 | 0.0 | 1.0 |
| 44 (3 oz/gal) | 85.0 | 95.0 | 0.0 | 0.7 | 0.7 | 3.0 |
| 44 (6 oz/gal) | 94.0 | 98.7 | 0.0 | 0.0 | 0.0 | 1.0 |
| 22 (3 oz/gal) | 87.7 | 96.3 | 0.0 | 0.0 | 0.0 | 1.0 |
| 22 (6 oz/gal) | 91.7 | 98.7 | 0.0 | 0.0 | 0.0 | 0.3 |
| 18 (3 oz/gal) | 87.7 | 97.3 | 0.0 | 0.7 | 0.3 | 0.7 |
| 18 (6 oz/gal) | 91.3 | 98.7 | 0.0 | 0.0 | 0.3 | 0.0 |
| 45 (3 oz/gal) | 90.7 | 80.0 | 15.0 | 48.3 | 75.0 | 95.0 |
| 45 (6 oz/gal) | 98.3 | 96.3 | 1.3 | 15.0 | 26.7 | 65.0 |
| 45 (9 oz/gal) | 99.0 | 97.3 | 0.7 | 13.3 | 16.7 | 45.0 |
| UNTREATED | 0 | 0 | 0 | 0 | 0 | 0 |

Example 34

A test was conducted in Oregon to determine the effectiveness of the herbicide formulations of Tables 51A and 51B for killing or controlling groundsel (*Senecio vulgaris*, SENVU). Applications were made in March and evaluations were made at 2 hours, 4 hours, 1 day, 2 days, 3 days, 6 days, 13 days, 19 days, 28 days and 55 days after application. Application formulations and treatments and corresponding percent dessication or regrowth are reported in Tables 51A and 51B. Spray volume was 145 gals/A.

TABLE 51A

PERCENT GROUNDSEL DESSICATION DAYS AFTER APPLICATION

| TREATMENT (CONC.) | % Cover 0 Days | 2 Hours | 4 Hours | 1 Day | 2 Days | 3 Days | 6 Days |
|---|---|---|---|---|---|---|---|
| 37 (3 oz/gal) | 11.7 | 0.0 | 0.0 | 0.0 | 2.0 | 5.0 | 15.0 |
| 37 (6 oz/gal) | 21.7 | 0.0 | 0.0 | 3.3 | 5.7 | 11.7 | 26.7 |
| 44 (3 oz/gal) | 16.7 | 0.0 | 0.0 | 1.7 | 3.0 | 5.7 | 10.0 |
| 44 (6 oz/gal) | 20.0 | 0.0 | 0.0 | 0.7 | 6.7 | 10.7 | 23.3 |
| 22 (3 oz/gal) | 23.3 | 0.0 | 0.0 | 0.0 | 1.3 | 1.7 | 8.3 |
| 22 (6 oz/gal) | 14.0 | 0.0 | 0.0 | 0.0 | 5.0 | 8.3 | 15.0 |
| 18 (3 oz/gal) | 11.7 | 0.0 | 0.0 | 0.0 | 5.0 | 8.3 | 13.3 |
| 18 (6 oz/gal) | 11.7 | 0.0 | 0.0 | 0.7 | 8.3 | 10.0 | 20.0 |
| 45 (3 oz/gal) | 18.3 | 0.0 | 0.0 | 6.7 | 40.0 | 53.3 | 68.3 |
| 45 (6 oz/gal) | 18.3 | 0.0 | 0.0 | 21.7 | 83.3 | 93.3 | 96.3 |
| 45 (9 oz/gal) | 10.3 | 0.0 | 0.0 | 41.7 | 93.3 | 99.0 | 99.0 |
| UNTREATED | 16.7 | 0.0 | 0.0 | 0.0 | 0.0 | 0.0 | 0.0 |

TABLE 51B

| | | DAYS AFTER APPLICATION | | | | |
|---|---|---|---|---|---|---|
| TREATMENT | CONC. | % Turf Dessication 3 Days | % Turf Dessication 19 Days | % Groundsel Regrowth 19 Days | % Groundsel Regrowth 28 Days | % Groundsel Regrowth 55 Days |
| 37 | 3 oz/gal | 86.7 | 97.0 | 0.0 | 0.0 | 0.0 |
| 37 | 6 oz/gal | 93.3 | 98.0 | 0.0 | 0.0 | 0.0 |
| 44 | 3 oz/gal | 86.7 | 98.3 | 0.0 | 0.0 | 0.0 |
| 44 | 6 oz/gal | 93.3 | 98.0 | 0.0 | 0.0 | 0.0 |
| 22 | 3 oz/gal | 83.3 | 98.0 | 0.0 | 0.0 | 0.0 |
| 22 | 6 oz/gal | 91.7 | 98.0 | 0.0 | 0.0 | 0.0 |
| 18 | 3 oz/gal | 88.3 | 98.0 | 0.0 | 0.0 | 0.0 |
| 18 | 6 oz/gal | 88.3 | 98.3 | 0.0 | 0.0 | 0.0 |
| 45 | 3 oz/gal | 81.7 | 80.0 | 13.3 | 20.0 | 18.3 |
| 45 | 6 oz/gal | 97.3 | 92.7 | 6.7 | 13.3 | 10.0 |
| 45 | 9 oz/gal | 98.7 | 0.7 | 0.7 | 0.7 | 0.7 |
| UNTREATED | UNTREATED | 0.0 | 0.0 | 100.0 | 100.0 | 100.0 |

Example 35

A test was conducted in Florida to determine the effectiveness of the herbicide formulations of Tables 52, 53, 54, 55, 56 and 57 for killing or controlling mini-flower pennywort (*Hydrocotyle umbellata*, HYDUM), bitblue St. Augustine grass (*Stenotaphrum secundatim*, STSE), hybrid bermudagrass (*Tifway*) and ryegrass (*Lolium multiflorum*, LOLMU). Applications were made in March and evaluations were made at 2 hours, 2 days, 2 weeks, 3 weeks, 4 weeks, 5 weeks, 6 weeks, and 8 weeks after application. Application treatments and corresponding percent controls are reported in Tables 52, 53, 54, 55, 56 and 57. Spray volume was 145 gals/A.

TABLE 52

| | | PERCENT CONTROL | | | | |
|---|---|---|---|---|---|---|
| TREATMENT | Conc. | HYDUM Activity 2 Hours After Application | Bitblue Activity 2 Hours After Application | 419/rye Activity 2 Hours After Application | HYDUM Activity 2 Days After Application | Bitblue Activity 2 Days After Application |
| 37 | 3 oz/gal | 2.0 | 0.0 | 0.0 | 7.0 | 1.0 |
| 37 | 6 oz/gal | 2.0 | 0.0 | 0.0 | 8.0 | 2.3 |
| 22 | 3 oz/gal | 0.0 | 0.0 | 0.0 | 0.0 | 0.0 |
| 22 | 6 oz/gal | 0.0 | 0.0 | 0.0 | 0.0 | 0.7 |
| 49 | 3 oz/gal | 0.3 | 0.0 | 0.0 | 0.0 | 1.3 |
| 49 | 6 oz/gal | 2.3 | 0.0 | 0.3 | 8.0 | 1.0 |
| 18 | 3 oz/gal | 0.0 | 0.0 | 0.0 | 0.0 | 0.7 |
| 18 | 6 oz/gal | 0.3 | 0.0 | 0.0 | 0.3 | 0.7 |
| 46 | 3.5 oz/gal | 0.0 | 0.0 | 0.0 | 0.0 | 0.3 |
| 46 | 6.5 oz/gal | 0.0 | 0.0 | 0.0 | 0.0 | 0.7 |
| 28 | 3 oz/gal | 1.7 | 2.0 | 0.3 | 9.0 | 7.7 |
| 28 | 6 oz/gal | 4.0 | 4.0 | 3.0 | 10.0 | 8.7 |
| 28 | 12 oz/gal | 5.7 | 6.7 | 3.7 | 10.0 | 9.3 |
| 47 | 3.5 oz/gal | 0.0 | 0.0 | 0.0 | 0.3 | 0.3 |
| 47 | 6.5 oz/gal | 0.0 | 0.0 | 0.0 | 0.7 | 0.3 |
| 48 | 3 oz/gal | 2.7 | 1.3 | 1.3 | 9.7 | 7.3 |
| 48 | 6 oz/gal | 4.7 | 3.0 | 2.3 | 9.3 | 8.0 |
| 48 | 12 oz/gal | 5.7 | 6.7 | 5.0 | 10.0 | 9.3 |
| UNTREATED | UNTREATED | 0.0 | 0.0 | 0.0 | 0.0 | 0.0 |

TABLE 53

| | | PERCENT CONTROL | | | | |
|---|---|---|---|---|---|---|
| TREATMENT | Conc. | 419/rye Activity 2 Days After Application | HYDUM Activity 2 Weeks After Application | Bitblue Activity 2 Weeks After Application | Rye Activity 2 Weeks After Application | Tifway Activity 2 Weeks After Application |
| 37 | 3 oz/gal | 4.7 | 9.0 | 8.0 | 10.0 | 8.0 |
| 37 | 6 oz/gal | 6.3 | 8.7 | 8.7 | 10.0 | 9.0 |
| 22 | 3 oz/gal | 1.0 | 6.0 | 8.7 | 10.0 | 9.0 |
| 22 | 6 oz/gal | 1.0 | 5.7 | 9.3 | 10.0 | 9.3 |
| 49 | 3 oz/gal | 5.3 | 8.7 | 8.0 | 10.0 | 9.0 |
| 49 | 6 oz/gal | 5.0 | 9.0 | 9.3 | 10.0 | 9.3 |
| 18 | 3 oz/gal | 1.0 | 5.7 | 9.0 | 10.0 | 9.3 |

TABLE 53-continued

| | | PERCENT CONTROL | | | | |
|---|---|---|---|---|---|---|
| TREATMENT | Conc. | 419/rye Activity 2 Days After Application | HYDUM Activity 2 Weeks After Application | Bitblue Activity 2 Weeks After Application | Rye Activity 2 Weeks After Application | Tifway Activity 2 Weeks After Application |
| 18 | 6 oz/gal | 1.0 | 6.0 | 9.7 | 10.0 | 9.3 |
| 46 | 3.5 oz/gal | 1.0 | 6.0 | 8.0 | 10.0 | 9.3 |
| 46 | 6.5 oz/gal | 1.0 | 6.0 | 9.3 | 10.0 | 9.3 |
| 28 | 3 oz/gal | 8.7 | 7.0 | 5.3 | 8.3 | 8.0 |
| 28 | 6 oz/gal | 9.7 | 7.7 | 6.7 | 9.7 | 9.3 |
| 28 | 12 oz/gal | 10.0 | 8.7 | 7.7 | 10.0 | 9.7 |
| 47 | 3.5 oz/gal | 0.7 | 5.3 | 9.3 | 10.0 | 8.7 |
| 47 | 6.5 oz/gal | 2.7 | 6.3 | 9.7 | 10.0 | 9.3 |
| 48 | 3 oz/gal | 8.7 | 8.0 | 2.2 | 9.0 | 8.7 |
| 48 | 6 oz/gal | 9.3 | 8.0 | 6.7 | 9.0 | 9.0 |
| 48 | 12 oz/gal | 10.0 | 8.3 | 7.7 | 9.7 | 9.3 |
| UNTREATED | UNTREATED | 0.0 | 0.0 | 0.0 | 0.0 | 0.0 |

TABLE 54

| | | PERCENT CONTROL | | | | |
|---|---|---|---|---|---|---|
| TREATMENT | Conc. | Bitblue Activity 3 Weeks After Application | Rye Activity 3 Weeks After Application | Tifway Activity 3 Weeks After Application | Bitblue Activity 4 Weeks After Application | Rye Activity 4 Weeks After Application |
| 37 | 3 oz/gal | 9.3 | 10.0 | 8.7 | 9.0 | 10.0 |
| 37 | 6 oz/gal | 10.0 | 10.0 | 8.7 | 10.0 | 10.0 |
| 22 | 3 oz/gal | 9.7 | 10.0 | 9.0 | 10.0 | 10.0 |
| 22 | 6 oz/gal | 10.0 | 10.0 | 10.0 | 10.0 | 10.0 |
| 49 | 3 oz/gal | 9.7 | 10.0 | 9.3 | 10.0 | 10.0 |
| 49 | 6 oz/gal | 10.0 | 10.0 | 10.0 | 10.0 | 10.0 |
| 18 | 3 oz/gal | 10.0 | 10.0 | 9.7 | 9.0 | 10.0 |
| 18 | 6 oz/gal | 10.0 | 10.0 | 10.0 | 10.0 | 10.0 |
| 46 | 3.5 oz/gal | 10.0 | 10.0 | 10.0 | 10.0 | 10.0 |
| 46 | 6.5 oz/gal | 10.0 | 10.0 | 9.3 | 10.0 | 10.0 |
| 28 | 3 oz/gal | 4.3 | 10.0 | 8.7 | 3.0 | 10.0 |
| 28 | 6 oz/gal | 5.0 | 10.0 | 9.0 | 3.7 | 10.0 |
| 28 | 12 oz/gal | 6.7 | 10.0 | 9.7 | 4.7 | 10.0 |
| 47 | 3.5 oz/gal | 10.0 | 10.0 | 9.0 | 9.0 | 10.0 |
| 47 | 6.5 oz/gal | 10.0 | 10.0 | 10.0 | 10.0 | 10.0 |
| 48 | 3 oz/gal | 5.3 | 10.0 | 9.3 | 3.3 | 10.0 |
| 48 | 6 oz/gal | 5.0 | 10.0 | 9.3 | 3.7 | 10.0 |
| 48 | 12 oz/gal | 6.0 | 10.0 | 9.7 | 5.0 | 10.0 |
| UNTREATED | UNTREATED | 0.0 | 0.0 | 0.0 | 0.0 | 0.0 |

TABLE 55

| | | PERCENT CONTROL | | | | |
|---|---|---|---|---|---|---|
| TREATMENT | Conc. Unit | Tifway Activity 4 Weeks After Application | HYDUM Activity 4 Weeks After Application | Bitblue Activity 5 Weeks After Application | Rye Activity 5 Weeks After Application | Tifway Activity 5 Weeks After Application |
| 37 | 3 oz/gal | 9.0 | 9.0 | 10.0 | 10.0 | 10.0 |
| 37 | 6 oz/gal | 9.3 | 9.3 | 10.0 | 10.0 | 9.3 |
| 22 | 3 oz/gal | 7.7 | 7.7 | 10.0 | 10.0 | 9.0 |
| 22 | 6 oz/gal | 8.3 | 8.3 | 10.0 | 10.0 | 9.7 |
| 49 | 3 oz/gal | 8.7 | 8.7 | 9.9 | 10.0 | 9.7 |
| 49 | 6 oz/gal | 9.0 | 9.0 | 10.0 | 10.0 | 10.0 |
| 18 | 3 oz/gal | 9.0 | 9.0 | 9.7 | 10.0 | 9.0 |
| 18 | 6 oz/gal | 8.7 | 8.7 | 10.0 | 10.0 | 10.0 |
| 46 | 3.5 oz/gal | 7.7 | 7.7 | 10.0 | 10.0 | 9.7 |
| 46 | 6.5 oz/gal | 8.7 | 8.7 | 10.0 | 10.0 | 9.3 |
| 28 | 3 oz/gal | 4.3 | 4.3 | 2.0 | 10.0 | 8.7 |
| 28 | 6 oz/gal | 5.0 | 5.0 | 2.3 | 10.0 | 9.3 |
| 28 | 12 oz/gal | 6.0 | 6.0 | 4.0 | 10.0 | 9.7 |
| 47 | 3.5 oz/gal | 8.0 | 8.0 | 10.0 | 10.0 | 10.0 |
| 47 | 6.5 oz/gal | 8.7 | 8.7 | 0.0 | 10.0 | 10.0 |
| 48 | 3 oz/gal | 5.3 | 5.3 | 2.3 | 10.0 | 9.0 |

TABLE 55-continued

| | | PERCENT CONTROL | | | | |
|---|---|---|---|---|---|---|
| TREATMENT | Conc. Unit | Tifway Activity 4 Weeks After Application | HYDUM Activity 4 Weeks After Application | Bitblue Activity 5 Weeks After Application | Rye Activity 5 Weeks After Application | Tifway Activity 5 Weeks After Application |
| 48 | 6 oz/gal | 5.0 | 5.0 | 2.3 | 10.0 | 9.7 |
| 48 | 12 oz/gal | 5.7 | 5.7 | 5.0 | 10.0 | 10.0 |
| UNTREATED | UNTREATED | 0.0 | 0.0 | 0.0 | 0.0 | 0.0 |

TABLE 56

| | | PERCENT CONTROL | | | | |
|---|---|---|---|---|---|---|
| TREATMENT | Conc. | HYDUM Activity 5 Weeks After Application | Bitblue Activity 6 Weeks After Application | Rye Activity 6 Weeks After Application | Tifway Activity 6 Weeks After Application | HYDUM Activity 6 Weeks After Application |
| 37 | 3 oz/gal | 8.3 | 10.0 | 10.0 | 9.0 | 7.7 |
| 37 | 6 oz/gal | 9.3 | 10.0 | 10.0 | 9.3 | 8.7 |
| 22 | 3 oz/gal | 9.0 | 10.0 | 10.0 | 9.0 | 9.0 |
| 22 | 6 oz/gal | 9.7 | 10.0 | 10.0 | 9.7 | 9.0 |
| 49 | 3 oz/gal | 8.3 | 9.7 | 10.0 | 9.7 | 8.0 |
| 49 | 6 oz/gal | 8.7 | 10.0 | 10.0 | 10.0 | 8.7 |
| 18 | 3 oz/gal | 9.7 | 9.7 | 10.0 | 9.0 | 9.0 |
| 18 | 6 oz/gal | 8.7 | 10.0 | 10.0 | 10.0 | 8.7 |
| 46 | 3.5 oz/gal | 8.0 | 10.0 | 10.0 | 9.7 | 7.7 |
| 46 | 6.5 oz/gal | 9.3 | 10.0 | 10.0 | 9.3 | 8.7 |
| 28 | 3 oz/gal | 4.0 | 0.0 | 10.0 | 8.3 | 0.0 |
| 28 | 6 oz/gal | 4.7 | 0.0 | 10.0 | 9.0 | 2.0 |
| 28 | 12 oz/gal | 6.7 | 0.0 | 10.0 | 9.7 | 2.7 |
| 47 | 3.5 oz/gal | 9.3 | 10.0 | 10.0 | 10.0 | 8.0 |
| 47 | 6.5 oz/gal | 10.0 | 10.0 | 10.0 | 10.0 | 8.7 |
| 48 | 3 oz/gal | 5.0 | 0.0 | 10.0 | 8.7 | 2.0 |
| 48 | 6 oz/gal | 6.0 | 0.0 | 10.0 | 9.0 | 2.7 |
| 48 | 12 oz/gal | 6.0 | 0.0 | 10.0 | 9.7 | 3.0 |
| UNTREATED | UNTREATED | 0.0 | 0.0 | 0.0 | 0.0 | 0.0 |

TABLE 57

| | | PERCENT CONTROL | | | |
|---|---|---|---|---|---|
| TREATMENT | Conc. | Bitblue Activity 8 Weeks After Application | Rye Activity 8 Weeks After Application | Tifway Activity 8 Weeks After Application | HYDUM Activity 8 Weeks After Application |
| 37 | 3 oz/gal | 10.0 | 10.0 | 8.7 | 7.7 |
| 37 | 6 oz/gal | 10.0 | 10.0 | 9.0 | 8.7 |
| 22 | 3 oz/gal | 10.0 | 10.0 | 8.7 | 9.0 |
| 22 | 6 oz/gal | 10.0 | 10.0 | 9.7 | 9.0 |
| 49 | 3 oz/gal | 9.3 | 10.0 | 9.7 | 8.0 |
| 49 | 6 oz/gal | 10.0 | 10.0 | 10.0 | 8.7 |
| 18 | 3 oz/gal | 9.7 | 10.0 | 8.7 | 9.0 |
| 18 | 6 oz/gal | 10.0 | 10.0 | 10.0 | 8.7 |
| 46 | 3.5 oz/gal | 10.0 | 10.0 | 9.7 | 7.7 |
| 46 | 6.5 oz/gal | 10.0 | 10.0 | 9.3 | 8.7 |
| 28 | 3 oz/gal | 0.0 | 10.0 | 8.3 | 0.0 |
| 28 | 6 oz/gal | 0.0 | 10.0 | 9.0 | 0.0 |
| 28 | 12 oz/gal | 0.0 | 10.0 | 9.3 | 0.0 |
| 47 | 3.5 oz/gal | 10.0 | 10.0 | 10.0 | 7.7 |
| 47 | 6.5 oz/gal | 10.0 | 10.0 | 10.0 | 8.3 |
| 48 | 3 oz/gal | 0.0 | 10.0 | 7.7 | 0.0 |
| 48 | 6 oz/gal | 0.0 | 10.0 | 8.0 | 0.0 |
| 48 | 12 oz/gal | 0.0 | 10.0 | 9.0 | 0.0 |
| UNTREATED | UNTREATED | 0.0 | 0.0 | 0.0 | 0.0 |

Example 36

A test was conducted in Oregon to determine the effectiveness of the herbicide formulations of Tables 58A, 58B, 59A and 59B for killing or controlling fireweed (*Erechtites hieraciifolia*, EREHI) and prickly lettuce (*Lactuca canadensis*, LACCA). Applications were made in March and evaluations were made at 2 hours and 4 hours after treatment, and 1 day, 2 days, 3 days, 6 days, 13 days, 19 days, 28 days, and 55 days after application. Application formulations and treatments and corresponding percent controls are reported for prickly lettuce in Tables 58A and 58B and for fireweed in Table 59A and 59B. Spray volume was 145 gals/A.

TABLE 58A

PLETTUCE PERCENT DESSICATION HOURS OR DAYS AFTER APPLICATION

| TREATMENT (CONC.) | % Cover 0 Days | 2 Hours | 4 Hours | 1 Day | 2 Days | 3 Days | 6 Days |
|---|---|---|---|---|---|---|---|
| 37 (3 oz/gal) | 11.7 | 0.0 | 0.0 | 0.0 | 2.0 | 5.0 | 15.0 |
| 37 (6 oz/gal) | 21.7 | 0.0 | 0.0 | 3.3 | 5.7 | 11.7 | 26.7 |
| 44 (3 oz/gal) | 16.7 | 0.0 | 0.0 | 1.7 | 3.0 | 5.7 | 10.0 |
| 44 (6 oz/gal) | 20.0 | 0.0 | 0.0 | 0.7 | 6.7 | 10.7 | 23.3 |
| 22 (3 oz/gal) | 23.3 | 0.0 | 0.0 | 0.0 | 1.3 | 1.7 | 8.3 |
| 22 (6 oz/gal) | 14.0 | 0.0 | 0.0 | 0.0 | 5.0 | 8.3 | 15.0 |
| 18 (3 oz/gal) | 11.7 | 0.0 | 0.0 | 0.0 | 5.0 | 8.3 | 13.3 |
| 18 (6 oz/gal) | 11.7 | 0.0 | 0.0 | 0.7 | 8.3 | 10.0 | 20.0 |
| 45 (3 oz/gal) | 18.3 | 0.0 | 0.0 | 6.7 | 40.0 | 53.3 | 68.3 |
| 45 (6 oz/gal) | 18.3 | 0.0 | 0.0 | 21.7 | 83.3 | 93.3 | 96.3 |
| 45 (9 oz/gal) | 10.3 | 0.0 | 0.0 | 41.7 | 93.3 | 99.0 | 99.0 |
| UNTREATED | 16.7 | 0.0 | 0.0 | 0.0 | 0.0 | 0.0 | 0.0 |

TABLE 58B

PLETTUCE DAYS AFTER APPLICATION

| TREATMENT | Conc. | % Dessication 13 Days | % Dessication 19 Days | % Regrowth 19 Days | % Regrowth 28 Days | % Regrowth 55 Days |
|---|---|---|---|---|---|---|
| 37 | 3 oz/gal | 86.7 | 97.0 | 0.0 | 0.0 | 0.0 |
| 37 | 6 oz/gal | 93.3 | 98.0 | 0.0 | 0.0 | 0.0 |
| 44 | 3 oz/gal | 86.7 | 98.3 | 0.0 | 0.0 | 0.0 |
| 44 | 6 oz/gal | 93.3 | 98.0 | 0.0 | 0.0 | 0.0 |
| 22 | 3 oz/gal | 83.3 | 98.0 | 0.0 | 0.0 | 0.0 |
| 22 | 6 oz/gal | 91.7 | 98.0 | 0.0 | 0.0 | 0.0 |
| 18 | 3 oz/gal | 88.3 | 98.0 | 0.0 | 0.0 | 0.0 |
| 18 | 6 oz/gal | 88.3 | 98.3 | 0.0 | 0.0 | 0.0 |
| 45 | 3 oz/gal | 81.7 | 80.0 | 13.3 | 20.0 | 18.3 |
| 45 | 6 oz/gal | 97.3 | 92.7 | 6.7 | 13.3 | 10.0 |
| 45 | 9 oz/gal | 98.7 | 0.7 | 0.7 | 0.7 | 0.7 |
| UNTREATED | UNTREATED | 0.0 | 0.0 | 100.0 | 100.0 | 100.0 |

TABLE 59A

FIREWEED PERCENT DESSICATION DAYS AFTER APPLICATION

| TREATMENT (CONC.) | % Cover 0 Days | 2 Hours | 4 Hours | 1 Day | 2 Days | 3 Days | 6 Days |
|---|---|---|---|---|---|---|---|
| 37 (3 oz/gal) | 6.7 | 0.0 | 0.0 | 0.0 | 5.0 | 18.3 | 35.0 |
| 37 (6 oz/gal) | 3.7 | 0.0 | 0.0 | 0.7 | 7.3 | 25.0 | 46.7 |
| 44 (3 oz/gal) | 5.7 | 0.0 | 0.0 | 0.0 | 1.7 | 20.0 | 48.3 |
| 44 (6 oz/gal) | 6.3 | 0.0 | 0.0 | 0.0 | 10.0 | 28.3 | 63.3 |
| 22 (3 oz/gal) | 7.7 | 0.0 | 0.0 | 0.0 | 0.7 | 3.3 | 40.0 |
| 22 (6 oz/gal) | 8.3 | 0.0 | 0.0 | 0.0 | 0.7 | 10.0 | 56.7 |
| 18 (3 oz/gal) | 5.7 | 0.0 | 0.0 | 0.0 | 0.7 | 5.0 | 35.0 |
| 18 (6 oz/gal) | 8.3 | 0.0 | 0.0 | 0.7 | 4.0 | 13.3 | 68.3 |
| 45 (3 oz/gal) | 11.7 | 0.0 | 0.0 | 23.3 | 43.3 | 71.0 | 88.3 |
| 45 (6 oz/gal) | 4.7 | 0.0 | 0.0 | 33.3 | 75.0 | 90.0 | 97.0 |
| 45 (9 oz/gal) | 10.3 | 0.0 | 0.0 | 50.0 | 88.3 | 97.7 | 97.3 |
| UNTREATED | 2.7 | 0.0 | 0.0 | 0.0 | 0.0 | 0.0 | 0.0 |

TABLE 59B

| | | FIREWEED DAYS AFTER APPLICATION | | | | |
|---|---|---|---|---|---|---|
| TREATMENT | Conc. | % Dessication 13 Days | % Dessication 19 Days | % Regrowth 19 Days | % Regrowth 28 Days | % Regrowth 55 Days |
| 37 | 3 oz/gal | 78.3 | 97.0 | 0.0 | 0.0 | 0.0 |
| 37 | 6 oz/gal | 86.7 | 98.0 | 0.0 | 0.0 | 0.0 |
| 44 | 3 oz/gal | 83.3 | 98.3 | 0.0 | 0.0 | 0.0 |
| 44 | 6 oz/gal | 88.3 | 98.0 | 0.0 | 0.0 | 0.0 |
| 22 | 3 oz/gal | 81.7 | 97.0 | 0.0 | 0.0 | 0.0 |
| 22 | 6 oz/gal | 86.7 | 98.0 | 0.0 | 0.0 | 0.0 |
| 18 | 3 oz/gal | 88.3 | 98.0 | 0.0 | 0.0 | 0.0 |
| 18 | 6 oz/gal | 85.0 | 98.0 | 0.0 | 0.0 | 0.0 |
| 45 | 3 oz/gal | 90.0 | 86.7 | 10.0 | 16.7 | 26.7 |
| 45 | 6 oz/gal | 97.3 | 94.0 | 3.3 | 7.3 | 15.0 |
| 45 | 9 oz/gal | 99.0 | 97.7 | 0.3 | 0.3 | 3.3 |
| UNTREATED | UNTREATED | 0.0 | 0.0 | 100.0 | 100.0 | 100.0 |

Example 37

A test was conducted in Indiana to determine the effectiveness of the herbicide formulations of Tables 60 and 61 for killing or controlling dandelion (*Taraxacum officinale*, TAROF) and white clover (*Trifolium repens*, TRFRE). Applications were made in June. Evaluations were made at 1, 2, 3 and 10 days after application. Application formulations and treatments and corresponding percent controls are reported for dandelion in Table 60 and for white clover in Table 61.

TABLE 60

| | Rate | PERCENT DANDELION CONTROL DAYS AFTER APPLICATION | | | |
|---|---|---|---|---|---|
| TREATMENT | (Units/A) | 1 Day | 2 Days | 3 Days | 10 Days |
| 49 | 6 lb. Ae | 96 | 96 | 88 | 67 |
| 44 | 6 lb. ae | 88 | 75 | 84 | 75 |
| 1 | 6 lb. Ae | 0 | 59 | 88 | 100 |
| 1+3 | 6 lb. Ae + 12 qt | 92 | 96 | 84 | 71 |
| UNTREATED | UNTREATED | 0 | 0 | 0 | 0 |

TABLE 61

| | Rate | PERCENT WHITE CLOVER CONTROL DAYS AFTER APPLICATION | | | |
|---|---|---|---|---|---|
| TREATMENT | (Units/A) | 1 Day | 2 Days | 3 Days | 10 Days |
| 49 | 6 lb. ae | 88 | 84 | 88 | 83 |
| 44 | 6 lb. ae | 80 | 63 | 67 | 79 |
| 1 | 6 lb. ae | 4 | 13 | 13 | 29 |
| 1+3 | 6 lb. ae + 12 qt | 84 | 71 | 67 | 92 |
| UNTREATED | UNTREATED | 0 | 0 | 0 | 0 |

Example 38

A test was conducted in Nebraska to determine the effectiveness of the herbicide formulations of Tables 62, 63 and 64 for killing or controlling white clover (*Trifolium repens*, TRFRE), dandelion (*Taraxacum officinale*, TAROF) and knotweed (*Polygonum aviculare*, POLAV). Applications were made in June. Evaluations were made at 1, 2, 3, 6, 9 and 15 days after application. Application treatments and corresponding percent controls are reported for white clover in Table 62, dandelion in Table 63 and for knotweed in Table 64.

TABLE 62

| | Rate | PERCENT WHITE CLOVER CONTROL DAYS AFTER APPLICATION | | | | | |
|---|---|---|---|---|---|---|---|
| TREATMENT | (Units/A) | 1 Day | 2 Days | 3 Days | 6 Days | 9 Days | 15 Days |
| 49 | 6 lb. Ae | 30 | 43 | 67 | 43 | 70 | 83 |
| 44 | 6 lb. ae | 20 | 27 | 50 | 57 | 63 | 80 |
| 1 | 6 lb. Ae | 3 | 13 | 23 | 40 | 57 | 87 |
| 1+3 | 6 lb. Ae + 12 qt | 23 | 33 | 50 | 53 | 63 | 67 |
| UNTREATED | UNTREATED | 0 | 0 | 0 | 0 | 0 | 0 |

TABLE 63

| | | PERCENT DANDELION CONTROL DAYS AFTER APPLICATION | | | | | |
|---|---|---|---|---|---|---|---|
| TREATMENT | Rate (Units/A) | 1 Day | 2 Days | 3 Days | 6 Days | 9 Days | 15 Days |
| 49 | 6 lb. ae | 33 | 57 | 30 | 50 | 33 | 77 |
| 44 | 6 lb. ae | 17 | 33 | 20 | 53 | 37 | 73 |
| 1 | 6 lb. ae | 3 | 7 | 10 | 27 | 40 | 67 |
| 1+3 | 6 lb. ae + 12 qt | 20 | 30 | 20 | 33 | 43 | 63 |
| UNTREATED | UNTREATED | 0 | 0 | 0 | 0 | 0 | 0 |

TABLE 64

| | | PERCENT KNOTWEED CONTROL DAYS AFTER APPLICATION | | | | | |
|---|---|---|---|---|---|---|---|
| TREATMENT | Rate (Units/A) | 1 Day Dande | 2 Days Knotwd | 3 Days Clover | 6 Days Dande | 9 Days Knotwd | 15 Days Clover |
| 49 | 6 lb. ae | 33 | 37 | 50 | 63 | 83 | 83 |
| 44 | 6 lb. ae | 33 | 33 | 40 | 67 | 83 | 83 |
| 1 | 6 lb. ae | 10 | 13 | 40 | 73 | 77 | 87 |
| 1+3 | 6 lb. ae + 12 qt | 37 | 43 | 53 | 73 | 87 | 90 |
| UNTREATED | UNTREATED | 0 | 0 | 0 | 0 | 0 | 0 |

Example 39

A test was conducted in Rhode Island to determine the effectiveness of the herbicide formulations of Tables 65 and 66 for killing or controlling curly dock (*Rumex crispus*, RUMCR), lambs quarters (*Chenopodium album*, CHEAL), chickweed (*Stellaria media*, STEME), broadleaf plantain (*Plantago major*, PLAMA), peregrina (*Sargula arusmis*, SPRAR) and fleabane (*Erigeron annuus*, ERIAN). Applications were made in May. Evaluations were made at 1, 2, 3, 7 days and 2, 4 and 7 weeks after application. Application treatments and corresponding percent controls are reported in Tables 65 and 66.

TABLE 65

| | PERCENT CONTROL | | | | |
|---|---|---|---|---|---|
| TREATMENT (RATE) | BRDLEAF 1 Day After Application | BRDLEAF 2 Days After Application | BRDLEAF 3 Days After Application | BRDLEAF 7 Days After Application | RUMCR 2 Weeks After Application |
| UNTREATED | 0 | 0 | 0 | 0 | 0 |
| 49 (6.0 #ae/A) | 49 | 75 | 88 | 85 | 47.5 |
| 44 (4.5 #ae/A) | 40 | 18 | 60 | 78 | 55.0 |
| 1 (6.0 #ae/A) | 0 | 0 | 6 | 63 | 72.0 |
| 1 (6.0 #ae/A) + 3 (12 qt/A) | 33 | 50 | 74 | 70 | 47.5 |

TABLE 66

| | PERCENT CONTROL | | | | |
|---|---|---|---|---|---|
| TREATMENT (RATE) | PLAMA 2 Weeks After Application | BRIAN 2 Weeks After Application | RUMCR 4 Weeks After Application | GRASSES 4 Weeks After Application | RUMCR 7 Weeks After Application |
| UNTREATED | 0.0 | 0.0 | 0.0 | 0.0 | 0.0 |
| 49 (6.0 #ae/A) | 100.0 | 100.0 | 60.0 | 100.0 | 41.3 |
| 44 (4.5 #ae/A) | 100.0 | 100.0 | 76.3 | 100.0 | 95.3 |
| 1 (6.0 #ae/A) | 91.3 | 95.0 | 96.3 | 100.0 | 98.3 |
| 1 (6.0 #ae/A) + 3 (12 qt/A) | 100.0 | 98.8 | 60.0 | 96.3 | 66.3 |

Example 40

A test was conducted in Georgia to determine the effectiveness of the herbicide formulations of Tables 67, 68, 69, 70, 71, 72 and 73 for killing or controlling redstem filaree (*Erodium cicutarium*, EROCI), parsley-piert (*Aphanes arvensis*, APHAR), perennial ryegrass (*Lolium multiflorum*, LOLPE), corn speedwell (*Veronica arvensis*, VERAR), cutleaf eveningprimrose (*Oenothera laciniata*, OEOLA), annual bluegrass (*Poa annua*, POANN) and white clover (*Trifolium repens*, TRFRE. Applications were made in April. Evaluations were made at 1, 2, 3, 6, 13 and 28 days after application. Application formulations, treatments and corresponding percent controls are reported for redstem filaree in Table 67, parsley-piert in Table 68, perennial ryegrass in Table 69, corn speedwell in Table 70, cutleaf eveningprimrose in Table 71, annual bluegrass in Table 72 and for white clover in Table 73.

TABLE 67

| TREATMENT | Rate (Units/A) | PERCENT REDSTEM FILAREE CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 10.0 | 40.0 | 78.7 | 86.0 | 88.8 | 95.1 |
| 44 | 6 lb. ae | 0.0 | 10.0 | 43.3 | 73.3 | 81.7 | 97.0 |
| 1 | 6 lb. ae | 0.0 | 0.0 | 0.0 | 36.7 | 100.0 | 100.0 |
| 1+3 | 6 lb. ae + 12 qt | 90.0 | 95.0 | 97.0 | 97.3 | 88.3 | 10.0 |
| UNTREATED | UNTREATED | 0.0 | 0.0 | 0.0 | 0.0 | 0.0 | 0.0 |

TABLE 68

| TREATMENT | Rate (Units/A) | PERCENT PARSLEY PIERT CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 21.7 | 43.3 | 66.7 | 73.3 | 91.7 | 98.3 |
| 44 | 6 lb. ae | 0.0 | 10.0 | 33.3 | 48.3 | 80.0 | 95.0 |
| 1 | 6 lb. ae | 0.0 | 1.7 | 28.3 | 36.7 | 85.0 | 98.3 |
| 1+3 | 6 lb. ae + 12 qt | 91.7 | 97.0 | 97.0 | 98.7 | 98.0 | 98.3 |
| UNTREATED | UNTREATED | 0.0 | 0.0 | 0.0 | 0.0 | 0.0 | 0.0 |

TABLE 69

| TREATMENT | Rate Units/A | PERCENT PERENNIAL RYEGRASS CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 15.0 | 25.0 | 51.7 | 68.3 | 94.3 | 100.0 |
| 44 | 6 lb. ae | 0.0 | 5.0 | 31.7 | 40.0 | 91.7 | 99.7 |
| 1 | 6 lb. ae | 0.0 | 1.7 | 25.0 | 43.3 | 96.0 | 100.0 |
| 1+3 | 6 lb. ae + 12 qt | 73.3 | 80.0 | 91.0 | 91.0 | 63.3 | 10.0 |
| UNTREATED | UNTREATED | 0.0 | 0.0 | 0.0 | 0.0 | 0.0 | 0.0 |

TABLE 70

| TREATMENT | Rate Units/A | PERCENT CORN SPEEDWELL CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 21.7 | 46.7 | 71.7 | 86.7 | 99.3 | 98.3 |
| 44 | 6 lb. ae | 0.0 | 10.0 | 23.3 | 66.7 | 99.3 | 100.0 |
| 1 | 6 lb. ae | 0.0 | 1.7 | 16.7 | 26.7 | 99.7 | 100.0 |
| 1+3 | 6 lb. ae + 12 qt | 90.0 | 97.0 | 99.3 | 100.0 | 100.0 | 100.0 |
| UNTREATED | UNTREATED | 0.0 | 0.0 | 0.0 | 0.0 | 0.0 | 0.0 |

TABLE 71

| TREATMENT | Rate Units/A | PERCENT CUTLEAF EVENINGPRIMROSE CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 5.0 | 6.7 | 10.0 | 16.7 | 75.0 | 96.3 |
| 44 | 6 lb. ae | 0.0 | 1.7 | 5.0 | 11.7 | 55.0 | 91.7 |
| 1 | 6 lb. ae | 0.0 | 1.7 | 8.3 | 21.7 | 63.3 | 91.7 |
| 1+3 | 6 lb. ae + 12 qt | 85.0 | 95.0 | 96.7 | 96.9 | 98.3 | 98.2 |
| UNTREATED | UNTREATED | 0.0 | 0.0 | 0.0 | 0.0 | 0.0 | 0.0 |

TABLE 72

| TREATMENT | Rate Units/A | PERCENT ANNUAL BLUEGRASS CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 6.7 | 10.0 | 50.0 | 80.0 | 98.3 | 100.0 |
| 44 | 6 lb. ae | 0.0 | 3.3 | 10.0 | 68.3 | 100.0 | 100.0 |
| 1 | 6 lb. ae | 0.0 | 0.0 | 6.7 | 43.3 | 100.0 | 100.0 |
| 1+3 | 6 lb. ae + 12 qt | 90.0 | 95.0 | 98.3 | 98.7 | 98.3 | 50.0 |
| UNTREATED | UNTREATED | 0.0 | 0.0 | 0.0 | 0.0 | 0.0 | 0.0 |

TABLE 73

| TREATMENT | Rate Units/A | PERCENT WHITE CLOVER CONTROL DAYS AFTER APPLICATION | | | | | |
|---|---|---|---|---|---|---|---|
| | | 1 Day | 2 Days | 3 Days | 6 Days | 13 Days | 28 Days |
| 49 | 6 lb. ae | 20.0 | 63.3 | 78.3 | 73.3 | 70.0 | 78.3 |
| 44 | 6 lb. ae | 0.0 | 15.0 | 31.7 | 63.3 | 83.3 | 90.0 |
| 1 | 6 lb. ae | 0.0 | 0.0 | 6.7 | 53.3 | 96.0 | 99.0 |
| 1+3 | 6 lb. ae + 12 qt | 90.0 | 91.0 | 92.7 | 78.3 | 60.0 | 10.0 |
| UNTREATED | UNTREATED | 0.0 | 0.0 | 0.0 | 0.0 | 0.0 | 0.0 |

Example 41

A test was conducted in South Carolina to determine the effectiveness of the herbicide formulations of Tables 74–84 for killing or controlling white clover (*Trifolium repens*, TRFRE), annual bluegrass (*Poa annua*, POAAN), purple deadnettle (*Lamium purpureum*, LANPU), common chickweed (*Stellaria media*, STEME), hairy buttercup (*Ranunculus sardous*, RANSA), Carolina geranium (*Geranium carolinianum*, GRECA), Mouseear chickweed (*Cerastium vulgatum*, CERVU), common dandelion (*Taraxacum officinale*, TAROF), Buckhorn plantain (*Plantago lanceolta*, PLALA), Johnny jump-up (*Viola rafinesquii*, VIORA), and corn speedwell (*Veronica ahensis*, VERAR). Applications were made in March. Evaluations were made at 2, 9, 18 and 25 days after application. Application formulations, treatments and corresponding percent controls are reported for white clover in Table 74, annual bluegrass in Table 75, purple deadnettle in Table 76, common chickweed in Table 77, hairy buttercup in Table 78, Carolina geranium in Table 79, Mouseear chickweed in Table 80, common dandelion in Table 81 Buckhorn plantain in Table 82, Johnny jump-up in Table 83, and corn speedwell in Table 84.

TABLE 74

| TREATMENT | Rate Units/A | PERCENT WHITE CLOVER CONTROL DAYS AFTER APPLICATION | | | |
|---|---|---|---|---|---|
| | | 2 Days | 9 Days | 18 Days | 25 Days |
| UNTREATED | UNTREATED | 0.0 | 0.0 | 0.0 | 0.0 |
| 44 | 6lb.ae | 13.3 | 36.7 | 46.7 | 68.3 |
| 49 | 6lb.ae | 15.0 | 31.7 | 40.0 | 50.0 |
| 1 | 6lb.ae | 3.3 | 31.7 | 75.0 | 93.3 |
| 1 + 3 | 6 lb. ae + 12 qt | 20.0 | 48.3 | 23.3 | 36.7 |
| 13 | 6lb.ae | 16.7 | 83.3 | 83.3 | 83.3 |

TABLE 75

| TREATMENT | Rate Units/A | PERCENT ANNUAL BLUGRASS CONTROL DAYS AFTER APPLICATION | | | |
|---|---|---|---|---|---|
| | | 2 Days | 9 Days | 18 Days | 25 Days |
| UNTREATED | UNTREATED | 0.0 | 0.0 | 0.0 | 0.0 |
| 44 | 6lb.ae | 11.7 | 35.0 | 85.0 | 93.3 |
| 49 | 6lb.ae | 18.3 | 41.7 | 76.7 | 90.0 |
| 1 | 6lb.ae | 5.0 | 23.3 | 83.3 | 100.0 |
| 1 + 3 | 6 lb. ae + 12 qt | 46.7 | 48.3 | 70.0 | 86.7 |
| 13 | 6lb.ae | 11.7 | 78.3 | 61.7 | 61.7 |

TABLE 76

| | | PERCENT PURPLE DEADNETTLE CONTROL | | | |
|---|---|---|---|---|---|
| TREATMENT | Rate Units/A | 2 Days After Application | 9 Days After Application | 18 Days After Application | 25 Days After Application |
| UNTREATED | UNTREATED | 0.0 | 0.0 | 0.0 | 0.0 |
| 44 | 6lb.ae | 5.0 | 15.0 | 65.0 | 98.3 |
| 49 | 6lb.ae | 8.3 | 13.3 | 40.0 | 100.0 |
| 1 | 6lb.ae | 1.7 | 13.3 | 88.3 | 96.7 |
| 1 + 3 | 6 lb. ae + 12 qt | 15.0 | 16.7 | 35.0 | 100.0 |
| 13 | 6lb.ae | 3.3 | 75.0 | 38.3 | 73.3 |

TABLE 77

| | | PERCENT COMMON CHICKWEED CONTROL | | | |
|---|---|---|---|---|---|
| TREATMENT | Rate Units/A | 2 Days After Application | 9 Days After Application | 18 Days After Application | 25 Days After Application |
| UNTREATED | UNTREATED | 0.0 | 0.0 | 0.0 | 0.0 |
| 44 | 6lb.ae | 16.7 | 71.7 | 95.0 | 100.0 |
| 49 | 6lb.ae | 20.0 | 81.7 | 95.0 | 100.0 |
| 1 | 6lb.ae | 5.0 | 28.3 | 95.0 | 100.0 |
| 1 + 3 | 6 lb. ae + 12 qt | 16.7 | 73.3 | 95.0 | 100.0 |
| 13 | 6lb.ae | 10.0 | 85.0 | 95.0 | 100.0 |

TABLE 78

| | | PERCENT HAIRY BUTTERCUP CONTROL | | | |
|---|---|---|---|---|---|
| TREATMENT | Rate Units/A | 2 Days After Application | 9 Days After Application | 18 Days After Application | 25 Days After Application |
| UNTREATED | UNTREATED | 0.0 | 0.0 | 0.0 | 0.0 |
| 44 | 6lb.ae | 3.3 | 30.0 | 90.0 | 100.0 |
| 49 | 6lb.ae | 15.0 | 23.3 | 91.7 | 100.0 |
| 1 | 6lb.ae | 3.3 | 26.7 | 95.0 | 100.0 |
| 1 + 3 | 6 lb. ae + 12 qt | 30.0 | 43.3 | 93.3 | 100.0 |
| 13 | 6lb.ae | 5.0 | 48.3 | 91.7 | 100.0 |

TABLE 79

| | | PERCENT CAROLINA GERANIUM CONTROL | | | |
|---|---|---|---|---|---|
| TREATMENT | Rate Units/A | 2 Days After Application | 9 Days After Application | 18 Days After Application | 25 Days After Application |
| UNTREATED | UNTREATED | 0.0 | 0.0 | 0.0 | 0.0 |
| 44 | 6lb.ae | 5.0 | 10.0 | 21.7 | 53.3 |
| 49 | 6lb.ae | 11.7 | 13.3 | 21.7 | 40.0 |
| 1 | 6lb.ae | 1.7 | 8.3 | 93.3 | 100.0 |
| 1 + 3 | 6 lb. ae + 12 qt | 13.3 | 10.0 | 20.0 | 41.7 |
| 13 | 6lb.ae | 6.7 | 41.7 | 100.0 | 100.0 |

TABLE 80

| | | PERCENT MOUSEEAR CHICKWEED CONTROL | | | |
|---|---|---|---|---|---|
| TREATMENT | Rate Units/A | 2 Days After Application | 9 Days After Application | 18 Days After Application | 25 Days After Application |
| UNTREATED | UNTREATED | 0.0 | 0.0 | 0.0 | 0.0 |
| 44 | 6lb.ae | 10.0 | 35.0 | 95.0 | 100.0 |
| 49 | 6lb.ae | 13.3 | 66.7 | 95.0 | 100.0 |
| 1 | 6lb.ae | 3.3 | 15.0 | 95.0 | 100.0 |
| 1 + 3 | 6 lb. ae + 12 qt | 18.3 | 18.3 | 95.0 | 100.0 |
| 13 | 6lb.ae | 5.0 | 73.3 | 95.0 | 100.0 |

TABLE 81

PERCENT COMMON DANDELION CONTROL

| TREAT-MENT | Rate Units/A | 2 Days After Application | 9 Days After Application | 18 Days After Application | 25 Days After Application |
|---|---|---|---|---|---|
| UNTREATED | UNTREATED | 0.0 | 0.0 | 0.0 | 0.0 |
| 44 | 6 lb. ae | 8.3 | 28.3 | 41.7 | 91.7 |
| 49 | 6 lb. ae | 31.7 | 41.7 | 45.0 | 88.3 |
| 1 | 6 lb. ae | 0.0 | 3.3 | 63.3 | 100.0 |
| 1 + 3 | 6 lb. ae + 12 qt | 36.7 | 51.7 | 63.3 | 98.3 |
| 13 | 6 lb. ae | 11.7 | 80.0 | 95.0 | 100.0 |

TABLE 82

PERCENT BUCKHORN PLANTAIN CONTROL

| TREAT-MENT | Rate Units/A | 2 Days After Application | 9 Days After Application | 18 Days After Application | 25 Days After Application |
|---|---|---|---|---|---|
| UNTREATED | UNTREATED | 0.0 | 0.0 | 0.0 | 0.0 |
| 44 | 6 lb. ae | 1.7 | 10.0 | 25.0 | 85.0 |
| 49 | 6 lb. ae | 8.3 | 10.0 | 38.3 | 75.3 |
| 1 | 6 lb. ae | 1.7 | 3.3 | 56.7 | 100.0 |
| 1 + 3 | 6 lb. ae + 12 qt | 20.0 | 23.3 | 56.7 | 81.7 |
| 13 | 6 lb. ae | 6.7 | 60.0 | 26.7 | 18.3 |

TABLE 83

PERCENT JOHNNY JUMP-UP CONTROL

| TREAT-MENT | Rate Units/A | 2 Days After Application | 9 Days After Application | 18 Days After Application | 25 Days After Application |
|---|---|---|---|---|---|
| UNTREATED | UNTREATED | 0.0 | 0.0 | 0.0 | 0.0 |
| 44 | 6 lb. ae | 0.0 | 26.7 | 100.0 | 100.0 |
| 49 | 6 lb. ae | 13.3 | 50.0 | 100.0 | 100.0 |
| 1 | 6 lb. ae | 0.0 | 23.3 | 100.0 | 100.0 |
| 1 + 3 | 6 lb. ae + 12 qt | 33.3 | 70.0 | 100.0 | 100.0 |
| 13 | 6 lb. ae | 8.3 | 88.3 | 100.0 | 100.0 |

TABLE 84

PERCENT CORN SPEEDWELL CONTROL

| TREAT-MENT | Rate Units/A | 2 Days After Application | 9 Days After Application | 18 Days After Application | 25 Days After Application |
|---|---|---|---|---|---|
| UNTREATED | UNTREATED | 0.0 | 0.0 | 0.0 | 0.0 |
| 44 | 6 lb. ae | 3.3 | 13.3 | 100.0 | 100.0 |
| 49 | 6 lb. ae | 3.3 | 16.7 | 100.0 | 100.0 |
| 1 | 6 lb. ae | 0.0 | 1.7 | 100.0 | 100.0 |
| 1 + 3 | 6 lb. ae + 12 qt | 16.7 | 25.0 | 100.0 | 100.0 |
| 13 | 6 lb. ae | 6.7 | 78.3 | 100.0 | 100.0 |

Example 42

A test was conducted in North Carolina to determine the effectiveness of the herbicide formulations of Table 85 for killing or controlling henbit (*Lamium amplexicaule*, LAMAM). Applications were made in March. Evaluations were made at 1, 2, 3, 7, 13, 28, 38, and 44 days after application. Application formulations and treatments and corresponding percent controls are reported in Table 85.

TABLE 85

| TREATMENT | Rate Units/A | PERCENT CONTROL DAYS AFTER APPLICATION | | | | | | | |
|---|---|---|---|---|---|---|---|---|---|
| | | 1 Day | 2 Days | 3 Days | 7 Days | 13 Days | 28 Days | 38 Days | 44 Days |
| 49 | 6 lb. ae | 0.0 | 10.0 | 12.5 | 32.5 | 98.3 | 100.0 | 100.0 | 100.0 |
| 44 | 6 lb. ae | 0.0 | 17.5 | 20.0 | 27.5 | 100.0 | 100.0 | 100.0 | 100.0 |
| 1 | 6 lb. ae | 0.0 | 3.8 | 3.8 | 10.0 | 100.0 | 100.0 | 100.0 | 100.0 |
| 1+3 | 6 lb. ae + 12 qt | 35.0 | 81.3 | 82.5 | 95.0 | 100.0 | 100.0 | 100.0 | 100.0 |
| UNTREATED | UNTREATED | 0.0 | 0.0 | 0.0 | 0.0 | 0.0 | 0.0 | 0.0 | 0.0 |

Example 43

A test was conducted in Alabama to determine the effectiveness of the herbicide formulations of Table 86 for killing or controlling common centipede (*Eremochloa ophiuroides*, ERLOP). Applications were made in June and evaluations were made at 1, 2, 3, 7, 27 and 56 days after application. Application formulations and treatments and corresponding percent controls are reported for common centipede in Table 86.

TABLE 86

| TREATMENT (RATE) | PERCENT CONTROL DAYS AFTER APPLICATION | | | | | |
|---|---|---|---|---|---|---|
| | 1 Day | 2 Days | 3 Days | 7 Days | 27 Days | 56 Days |
| 49 (3 #ae/A) | 4.3 | 10.0 | 11.7 | 53.3 | 81.7 | 88.3 |
| 1 (3 #ae/A) | 0.0 | 8.3 | 10.0 | 75.0 | 95.3 | 97.7 |
| 49 (6 #ae/A) | 21.7 | 25.0 | 33.3 | 69.3 | 94.0 | 96.7 |
| 1 (6 #ae/A) | 0.0 | 8.3 | 10.0 | 84.3 | 98.7 | 99.3 |
| 49 (6 #ae/A) + 51 (0.5% V/V) | 10.7 | 20.0 | 20.0 | 56.7 | 95.0 | 95.7 |
| 49 (6 #ae/A) + 56 (0.25% V/V) | 6.7 | 10.0 | 13.3 | 58.3 | 90.3 | 97.3 |
| 49 (6 #ae/A) + 53 (0.5% V/V) | 9.3 | 11.7 | 16.7 | 55.0 | 91.7 | 97.3 |
| 49 (6 #ae/A) + 54 (0.5% V/V) | 3.3 | 13.3 | 13.3 | 51.7 | 95.7 | 97.0 |
| 49 (6 #ae/A) + 24 (0.5% V/V) | 3.3 | 16.7 | 20.0 | 58.3 | 97.7 | 97.3 |
| 1 (6 #ae/A) + 3 (12 QT/A) | 78.3 | 83.3 | 83.3 | 79.3 | 85.0 | 84.7 |
| UNTREATED | 0.0 | 0.0 | 0.0 | 0.0 | 0.0 | 0.0 |

Example 44

A test was conducted in Mississippi to determine the effectiveness of the herbicide formulations of Tables 87 and 88 for killing or controlling common dandelion (*Taraxacum officionale*, TAROF) and Carolina geranium (*Geranium carolinianum*, GERCA). Applications were made in April and evaluations were made at 1, 2, 3, 6 days, 4 and 8 weeks after application. Treatments and corresponding percent controls are reported for common dandelion in Table 87 and for Carolina geranium in Table 88.

TABLE 87

| TREATMENT (RATE) | PERCENT DANDELION CONTROL | | | | | |
|---|---|---|---|---|---|---|
| | 1 Day After Application | 2 Days After Application | 3 Days After Application | 6 Days After Application | 4 Weeks After Application | 8 Weeks After Application |
| 49 (6 #ae/A) | 42.7 | 86.2 | 86.8 | 80.5 | 90.0 | 61.6 |
| 49 (4 #ae/A) | 15.0 | 37.5 | 47.5 | 55.0 | 90.0 | 47.5 |
| 49 (2 #ae/A) | 0.0 | 0.0 | 0.0 | 17.5 | 55.0 | 57.5 |
| 44 (6 #ae/A) | 0.0 | 0.0 | 0.0 | 32.5 | 90.0 | 65.0 |
| 44 (4 #ae/A) | 0.0 | 0.0 | 0.0 | 25.0 | 72.5 | 32.5 |
| 44 (2 #ae/A) | 0.0 | 0.0 | 0.1 | 13.8 | 63.3 | 48.2 |
| 1 (6 #ae/A) | 0.0 | 0.0 | 5.0 | 30.0 | 87.5 | 62.5 |
| 1 (4 #ae/A) | 0.0 | 0.0 | 0.0 | 27.5 | 77.5 | 37.5 |
| 1 (2 #ae/A) | 0.0 | 0.0 | 0.0 | 12.5 | 77.5 | 35.0 |
| 1 (6 #ae/A) + 3 (12 QT/A) | 52.5 | 85.0 | 85.0 | 87.5 | 80.0 | 40.0 |
| UNTREATED | 0.0 | 0.0 | 0.0 | 0.0 | 0.0 | 0.0 |

TABLE 88

| TREATMENT (RATE) | PERCENT CAROLINA GERANIUM CONTROL | | | | |
|---|---|---|---|---|---|
| | 1 Day After Application | 2 Days After Application | 3 Days After Application | 6 Days After Application | 4 Weeks After Application |
| 49 (6 #ae/A) | 70.7 | 91.3 | 91.3 | 89.2 | 89.5 |
| 49 (4 #ae/A) | 70.0 | 90.0 | 90.0 | 90.0 | 90.0 |
| 49 (2 #ae/A) | 7.5 | 10.0 | 17.5 | 45.0 | 82.5 |
| 44 (6 #ae/A) | 32.5 | 50.0 | 60.0 | 77.5 | 90.0 |

TABLE 88-continued

PERCENT CAROLINA GERANIUM CONTROL

| TREAT-MENT (RATE) | 1 Day After Application | 2 Days After Application | 3 Days After Application | 6 Days After Application | 4 Weeks After Application |
|---|---|---|---|---|---|
| 44 (4 #ae/A) | 0.0 | 0.0 | 2.5 | 52.5 | 90.0 |
| 44 (2 #ae/A) | 0.7 | 1.3 | 1.3 | 59.2 | 89.9 |
| 1 (6 #ae/A) | 0.0 | 5.0 | 10.0 | 42.5 | 90.0 |
| 1 (4 #ae/A) | 0.0 | 0.0 | 5.0 | 42.5 | 90.0 |
| 1 (2 #ae/A) | 0.0 | 0.0 | 0.0 | 32.5 | 90.0 |
| 1 (6 # ae/A) + 3 (12 QT/A) | 70.0 | 90.0 | 90.0 | 90.0 | 90.0 |
| UNTREATED | 0.0 | 0.0 | 0.0 | 0.0 | 0.0 |

Example 45

A test was conducted in North Carolina to determine the effectiveness of the herbicide formulations of Table 89 for killing or controlling bermuda grass (*Cynodon dactylon*, CYNDA). Applications were made in September and evaluations were made at 2, 5, 7 days, 2 and 4 weeks after application. Application formulations and treatments and corresponding percent controls are reported for bermuda grass in Table 89.

TABLE 89

PERCENT CONTROL

| TREAT-MENT (RATE) | 2 Days After Application | 5 Days After Application | 7 Days After Application | 2 Weeks After Application | 4 Weeks After Application |
|---|---|---|---|---|---|
| 1 (6 #ae/A) | 2.5 | 27.5 | 70.0 | 95.0 | 99.0 |
| 1 (6 # ae/A) + 3 (12.0 qt/A) | 36.3 | 57.5 | 81.3 | 95.0 | 99.0 |
| 1 (6 # ae/A) + 2 (0.250 qt/A) + 6 (0.25% V/V) | 57.5 | 75.0 | 85.0 | 95.0 | 98.0 |
| 1 (6 # ae/A) + 17 (0.0625 AI/A) + 6 (0.25% V/V) | 57.5 | 80.0 | 86.3 | 95.0 | 96.8 |
| 1 (6 # ae/A) + 17 (0.125 AI/A) + 6 (0.25% V/V) | 66.3 | 81.3 | 88.8 | 95.0 | 95.8 |
| 1 (6 # ae/A) + 17 (0.25 AI/A) + 6 (0.25% V/V) | 73.8 | 85.0 | 90.0 | 95.0 | 89.8 |
| 1 (6 # ae/A) + 2 (0.250 qt/A) + 6 (0.5% V/V) | 61.3 | 76.3 | 83.8 | 95.0 | 94.8 |
| 7 (6 #ae/A) | 65.0 | 80.0 | 82.5 | 95.0 | 93.8 |
| 14 (6 #ae/A) | 63.8 | 80.0 | 86.3 | 95.0 | 98.0 |
| 15 (6 #ae/A) | 60.0 | 80.0 | 85.0 | 95.0 | 97.0 |
| 26 (6 #ae/A) | 68.8 | 80.0 | 85.0 | 95.0 | 94.8 |
| 26 (4.5 # ae/A) | 62.5 | 75.0 | 82.5 | 95.0 | 95.8 |
| 26 (3 #ae/A) | 45.0 | 66.3 | 80.0 | 95.0 | 95.8 |
| 6 (6 #ae/A) | 55.0 | 75.0 | 82.5 | 95.0 | 95.8 |
| 58 (6 #ae/A) | 56.3 | 68.8 | 82.5 | 95.0 | 97.0 |
| 49 (6 #ae/A) | 63.8 | 77.5 | 83.8 | 95.0 | 97.0 |
| 50 (6 #ae/A) | 61.3 | 73.8 | 86.3 | 95.0 | 99.0 |
| UNTREATED | 0.0 | 0.0 | 0.0 | 0.0 | 0.0 |

Example 46

A test was conducted in North Carolina to determine the effectiveness of the herbicide formulations of Table 90 for killing or controlling tall fescue (*Festuca arundinacea*, FESAR). Applications were made in May and evaluations were made at 7, 9, 12, 15, 20 and 28 days after application. Application formulations and treatments and corresponding percent controls are reported for tall fescue in Table 90.

TABLE 90

| TREATMENT (RATE) | PERCENT TALL FESCUE CONTROL DAYS AFTER APPLICATION | | | | | | |
|---|---|---|---|---|---|---|---|
| | 7 Days | 9 Days | 12 Days | 15 Days | 20 Days | 28 Days | 35 Days |
| 49 (6 #ae/A) | 0.0 | 71.3 | 75.0 | 78.8 | 82.5 | 82.5 | 86.3 |
| 49 (6 #ae/A) | 0.0 | 0.0 | 66.3 | 72.5 | 82.5 | 89.8 | 93.8 |
| 49 (6 #ae/A) | 0.0 | 0.0 | 0.0 | 21.3 | 61.3 | 63.8 | 72.5 |
| 49 (6 #ae/A) | 0.0 | 0.0 | 0.0 | 10.0 | 75.0 | 75.0 | 82.5 |
| 1 (6 #ae/A) | 58.8 | 83.8 | 91.3 | 92.5 | 97.3 | 99.3 | 100.0 |
| 1 (6 #ae/A) | 0.0 | 0.0 | 13.8 | 42.5 | 83.8 | 90.0 | 97.0 |
| 1 (6 #ae/A) | 0.0 | 0.0 | 0.0 | 0.0 | 13.8 | 48.8 | 67.5 |
| 1 (6 #ae/A) + 3 (12.0 qt/A) | 0.0 | 27.5 | 41.3 | 58.8 | 68.8 | 78.8 | 89.8 |
| 1 (6 #ae/A) + 3 (12.0 qt/A) | 0.0 | 0.0 | 25.0 | 52.5 | 66.3 | 77.5 | 87.5 |

TABLE 90-continued

| TREATMENT | PERCENT TALL FESCUE CONTROL DAYS AFTER APPLICATION | | | | | | |
|---|---|---|---|---|---|---|---|
| (RATE) | 7 Days | 9 Days | 12 Days | 15 Days | 20 Days | 28 Days | 35 Days |
| 1 (6 #ae/A) + 3 (12 qt/A) | 0.0 | 0.0 | 0.0 | 2.5 | 10.0 | 23.8 | 30.0 |
| 1 (6 #ae/A) + 3 (12.0 qt/A) | 0.0 | 0.0 | 0.0 | 2.5 | 22.5 | 28.8 | 38.8 |
| UNTREATED | 0.0 | 0.0 | 0.0 | 0.0 | 0.0 | 0.0 | 0.0 |

Example 47

A test was conducted in North Carolina to determine the effectiveness of the herbicide formulations of Table 91 for killing or controlling bermuda grass (*Cynodon dactylon*, CYNDA). Applications were made in May and evaluations were made at 1, 2, 3, 7, 14 and 21 days after application. Application formulations and treatments and corresponding percent controls are reported for bermuda grass in Table 91.

TABLE 91

| TREATMENT | PERCENT BERMUDA GRASS CONTROL DAYS AFTER APPLICATION | | | | | | | |
|---|---|---|---|---|---|---|---|---|
| (RATE) | 1 Day | 2 Days | 3 Days | 7 Days | 14 Days | 21 Days | 28 Days | 35 Days |
| 49 (3 #ae/A) | 3.8 | 10.0 | 28.8 | 92.3 | 99.0 | 96.3 | 95.0 | 93.8 |
| 1 (3 #ae/A) | 0.0 | 0.0 | 5.0 | 90.0 | 99.0 | 96.3 | 95.0 | 95.0 |
| 49 (6 #ae/A) | 75.0 | 83.8 | 85.0 | 93.8 | 99.0 | 95.0 | 93.8 | 91.3 |
| 1 (6 #ae/A) | 0.0 | 0.0 | 8.8 | 99.0 | 99.0 | 97.5 | 95.0 | 96.3 |
| 49 (6 #ae/A) + 51 (0.5% V/V) + | 70.0 | 80.0 | 82.5 | 97.0 | 99.0 | 95.0 | 91.3 | 88.8 |
| 49 (6 #ae/A) + 52 (0.25% V/V) | 72.5 | 82.5 | 85.0 | 94.8 | 99.0 | 95.0 | 91.3 | 90.0 |
| 49 (6 #ae/A) + 53 (0.5% V/V) | 75.0 | 85.0 | 86.3 | 98.0 | 99.0 | 95.0 | 88.8 | 90.0 |
| 49 (6 #ae/A) + 54 (0.5% V/V) | 60.0 | 77.5 | 77.5 | 94.8 | 99.0 | 95.0 | 92.5 | 90.0 |
| 49 (6 #ae/A) + 55 (0.5% V/V) | 31.3 | 63.8 | 71.3 | 97.0 | 99.0 | 97.5 | 95.0 | 92.5 |
| 49 (6 #ae/A) + 3 (12 qt/A) | 78.8 | 87.5 | 88.8 | 93.5 | 99.0 | 78.8 | 68.8 | 77.5 |
| UNTREATED | 0.0 | 0.0 | 0.0 | 0.0 | 0.0 | 0.0 | 0.0 | 0.0 |

Example 48

A test was conducted in Mississippi to determine the effectiveness of the herbicide formulations of Table 92 for killing or controlling bermuda grass (*Cynodon dactylon*, CYNDA). Applications were made in June and evaluations were made at 1, 2, 3, 6 and 13 days after application. Application formulations and treatments and corresponding percent controls are reported for bermuda grass in Table 92.

TABLE 92

| TREATMENT (RATE) | PERCENT BERMUDA GRASS CONTROL | | | | |
|---|---|---|---|---|---|
| | 1 Day After Application | 2 Days After Application | 3 Days After Application | 6 Days After Application | 13 Days After Application |
| 49 (3 #ae/A) | 7.5 | 45.0 | 62.5 | 82.5 | 90.0 |
| 1 (3 #ae/A) | 0.0 | 10.0 | 10.0 | 85.0 | 90.0 |
| 49 (6 #ae/A) | 67.5 | 87.5 | 90.0 | 90.0 | 90.0 |
| 1 (6 #ae/A) | 0.0 | 10.0 | 10.0 | 87.5 | 90.0 |
| 49 (6 #ae/A) + 51 (0.5% V/V) | 65.0 | 87.5 | 90.0 | 90.0 | 90.0 |
| 49 (6 #ae/A) + 56 (0.25% V/V) | 67.5 | 87.5 | 90.0 | 90.0 | 90.0 |
| 49 (6 #ae/A) + 53 (0.5% V/V) | 80.0 | 90.0 | 90.0 | 90.0 | 90.0 |
| 49 (6 #ae/A) + 54 (0.5% V/V) | 57.5 | 87.5 | 90.0 | 90.0 | 87.5 |

TABLE 92-continued

PERCENT BERMUDA GRASS CONTROL

| TREAT-MENT (RATE) | 1 Day After Application | 2 Days After Application | 3 Days After Application | 6 Days After Application | 13 Days After Application |
|---|---|---|---|---|---|
| 49 (6 # ae/A) + 55 (0.55% V/V) | 32.5 | 72.5 | 85.0 | 90.0 | 90.0 |
| 1 (6 # ae/A) + 3 (12 qt/A) | 67.5 | 82.5 | 87.5 | 90.0 | 90.0 |
| UNTREATED | 0.0 | 0.0 | 0.0 | 0.0 | 0.0 |

Example 49

A test was conducted in North Carolina to determine the effectiveness of the herbicide formulations of Table 93 for killing or controlling bermuda grass (*Cynodon dactylon*, CYNDA). Applications were made in May and evaluations were made at 1, 2, 3, 7, 14 and 21 days after application. Application formulations and treatments and corresponding percent controls are reported for bermuda grass in Table 93.

TABLE 93

| TRATMENT (RATE) | PERCENT BERMUDA GRASS CONTROL DAYS AFTER APPLICATION | | | | | | | |
|---|---|---|---|---|---|---|---|---|
|  | 1 Day | 2 Days | 3 Days | 7 Days | 14 Days | 21 Days | 28 Days | 35 Days |
| 49 (6 # ae/A) | 81.3 | 88.8 | 88.8 | 99.0 | 99.0 | 95.0 | 90.0 | 90.0 |
| 49 (4.5 # ae/A) | 78.8 | 85.0 | 86.3 | 99.0 | 99.0 | 95.0 | 88.8 | 90.0 |
| 49 (3 # ae/A) | 26.3 | 47.5 | 61.3 | 98.0 | 99.0 | 95.0 | 93.8 | 91.3 |
| 44 (4.5 # ae/A) | 2.5 | 18.8 | 50.0 | 98.0 | 99.0 | 96.3 | 95.0 | 95.0 |
| 44 (6 #ae/A) | 11.3 | 37.5 | 66.3 | 98.0 | 99.0 | 97.5 | 95.0 | 95.0 |
| 2 (1.5 PT/A) | 70.0 | 92.5 | 83.8 | 15.0 | 0.0 | 0.0 | 0.0 | 0.0 |
| 1 (6 # ae/A) | 0.0 | 0.0 | 6.3 | 99.0 | 99.0 | 97.5 | 95.0 | 95.0 |
| 1 (6 # ae/A) | 76.3 | 82.5 | 85.0 | 98.0 | 99.0 | 93.8 | 92.5 | 93.8 |
| UNTREATED | 0.0 | 0.0 | 0.0 | 0.0 | 0.0 | 0.0 | 0.0 | 0.0 |

Example 50

A test was conducted in Georgia to determine the effectiveness of the herbicide formulations of Table 94 for killing or controlling bermuda grass (*Cynodon dactyon*, CYNDA). Applications were made in June and evaluations were made at 1, 3, and 7 days after application. Application formulations and treatments and corresponding percent controls are reported for bermuda grass in Table 94.

TABLE 94

| TREATMENT (RATE) | PERCENT BERMUDA GRASS CONTROL DAYS AFTER APPLICATION | | |
|---|---|---|---|
|  | 1 Day | 3 Days | 7 Days |
| 49 (3 #ae/A) | 5.0 | 53.3 | 50.0 |
| 1 (3 #ae/A) | 0.0 | 16.7 | 48.3 |
| 49 (6 #ae/A) | 66.7 | 83.3 | 75.0 |
| 1 (6 #ae/A) | 0.0 | 16.7 | 48.3 |
| 49 (6 #ae/A) + 51 (0.5% V/V) | 55.0 | 73.3 | 75.0 |
| 49 (6 #ae/A) + 56 (0.25% V/V) | 51.7 | 68.3 | 76.7 |
| 49 (6 #ae/A) + 53 (0.5% V/V) | 63.3 | 76.7 | 75.0 |
| 49 (6 #ae/A) + 54 (0.5% V/V) | 53.3 | 71.7 | 71.7 |

TABLE 94-continued

| TREATMENT (RATE) | PERCENT BERMUDA GRASS CONTROL DAYS AFTER APPLICATION | | |
|---|---|---|---|
|  | 1 Day | 3 Days | 7 Days |
| 49 (6 #ae/A) + 55 (0.5% V/V) | 13.3 | 70.0 | 58.3 |
| 1 (6 #ae/A) + 3 (12 A/A) | 95.0 | 98.3 | 0.0 |
| UNTREATED | 0.0 | 0.0 | 0.0 |

Example 51

A test was conducted in New Jersey to determine the effectiveness of the herbicide treatments of Tables 95, 96, 97 and 98 for killing or controlling woodsorrel (*Oxalis stricta*, OXAST), horseweed (*Erigeron canadensis*, ERICA), filaree (*Erodium cicutarium*, EROCI), and speedwell (*Veronica peregrina*, VERPG). Applications were made in May and evaluations were made at 1, 5, 9 and 33 days after application. Treatments and corresponding percent controls are reported for woodsorell in Table 95, horseweed in Table 96, filaree in Table 97 and speedwell in Table 98.

TABLE 95

| TREATMENT (RATE) | PERCENT WOODSORREL CONTROL | | | |
|---|---|---|---|---|
|  | 1 Day After Application | 5 Days After Application | 9 Days After Application | 33 Days After Application |
| 49 (6 #ae/A) | 5 | 37 | 99 | 99 |
| 44 (6 #ae/A) | 2 | 30 | 99 | 99 |
| 1 (6 #ae/A) | 2 | 40 | 99 | 99 |
| 1 (6 #ae/A) + 3 (12 #ae/A) | 85 | 90 | 99 | 99 |
| UNTREATED | 0.0 | 0.0 | 0.0 | 0.0 |

TABLE 96

| TREATMENT (RATE) | PERCENT HORSEWEED CONTROL | | | |
|---|---|---|---|---|
|  | 1 Day After Application | 5 Days After Application | 9 Days After Application | 33 Days After Application |
| 49 (6 #ae/A) | 23 | 53 | 88 | 99 |
| 44 (6 #ae/A) | 0 | 33 | 87 | 99 |

TABLE 96-continued

PERCENT HORSEWEED CONTROL

| TREATMENT (RATE) | 1 Day After Application | 5 Days After Application | 9 Days After Application | 33 Days After Application |
|---|---|---|---|---|
| 1 (6 #ae/A) | 0 | 35 | 95 | 99 |
| 1 (6 #ae/A) + 3 (12 #ae/A) | 85 | 90 | 92 | 99 |
| UNTREATED | 0.0 | 0.0 | 0.0 | 0.0 |

TABLE 97

PERCENT FILAREE CONTROL

| TREATMENT (RATE) | 1 Day After Application | 5 Days After Application | 9 Days After Application | 33 Days After Application |
|---|---|---|---|---|
| 49 (6 #ae/A) | 18 | 55 | 82 | 94 |
| 44 (6 #ae/A) | 0 | 35 | 98 | 98 |
| 1 (6 #ae/A) | 0 | 50 | 99 | 99 |
| 1 (6 #ae/A) + 3 (12 #ae/A) | 87 | 87 | 95 | 55 |
| UNTREATED | 0.0 | 0.0 | 0.0 | 0.0 |

TABLE 98

PERCENT SPEEDWELL CONTROL

| TREATMENT (RATE) | 1 Day After Application | 5 Days After Application | 9 Days After Application | 33 Days After Application |
|---|---|---|---|---|
| 49 (6 #ae/A) | 15 | 37 | 95 | 99 |
| 44 (6 #ae/A) | 3 | 23 | 95 | 99 |
| 1 (6 #ae/A) | 8 | 47 | 95 | 99 |
| 1 (6 #ae/A) + 3 (12 #ae/A) | 63 | 37 | 96 | 99 |
| UNTREATED | 0.0 | 0.0 | 0.0 | 0.0 |

Example 52

Fast Symptomology and Long-Term Control In Perennial Turfgrass A test was conducted in Rhode Island to determine the effectiveness of the herbicide formulations of Tables 99 and 100 for killing or controlling perennial turfgrass white clover (*Trifolium repens*, TRFRE), broadleaf plantain (*Plantago major*, PLAMA). Applications were made in May. Evaluations were made at 1, 2, 3, 9 days and 2, 4 and 7 weeks after application. Application treatments and corresponding percent controls are reported in Tables 99 and 100.

TABLE 99

| TREATMENT (RATE) | TURF 1 Day After Application | TURF 2 Days After Application | TURF 3 Days After Application | BRDLEAF 3 Days After Application | TURF 9 Days After Application |
|---|---|---|---|---|---|
| UNTREATED | 0.0 | 0.0 | 0.0 | 0.0 | 0.0 |
| 49 (3.0 # ae/A) | 1.4 | 3.5 | 5.1 | 5.1 | 9.7 |
| 49 (4.5 # ae/A) | 1.3 | 4.3 | 6.1 | 6.1 | 9.8 |
| 49 (6.0 # ae/A) | 3.4 | 6.1 | 8.1 | 8.1 | 9.9 |
| 44 (4.5 # ae/A) | 1.8 | 2.9 | 5.6 | 5.6 | 9.9 |
| 44 (6.0 # ae/A) | 1.9 | 4.4 | 6.4 | 6.4 | 9.9 |
| 2 | 5.6 | 8.5 | 9.1 | 9.1 | 0.5 |
| 1 (6.0 lb ae/A) | 0.0 | 1.1 | 3.6 | 3.6 | 10.0 |
| 1 (6.0 # ae/A) + (12 qt paraquat/A) | 4.8 | 7.3 | 7.9 | 7.9 | 9.7 |

TABLE 100

PERCENT CONTROL

| TREATMENT (RATE) | TURF 9 Days After Application | BRDLEAF 9 Days After Application | TURF 2 Weeks After Application | TURF 4 Weeks After Application | PLALA 4 Weeks After Application | TRFRE 4 Weeks After Application |
|---|---|---|---|---|---|---|
| UNTREATED | 0.0 | 0.0 | 0.0 | 0.0 | 0.0 | 0.0 |
| 49 (3.0 # ae/A) | 9.3 | 7.1 | 9.6 | 9.7 | 8.9 | 6.8 |
| 49 (4.5 # ae/A) | 9.5 | 6.9 | 9.5 | 9.8 | 8.4 | 5.6 |
| 49 (6.0 # ae/A) | 9.7 | 8.5 | 9.8 | 9.9 | 9.1 | 7.3 |
| 44 (4.5 # ae/A) | 9.7 | 7.4 | 9.8 | 9.9 | 9.8 | 9.5 |
| 44 (6.0 # ae/A) | 9.7 | 7.8 | 9.9 | 9.9 | 9.9 | 9.1 |
| 2 | 6.9 | 5.9 | 4.9 | 0.5 | 0.0 | 0.0 |
| 1 (6.0 # ae/A) | 9.6 | 5.9 | 9.9 | 10.0 | 9.8 | 9.8 |
| 1 (6.0 # ae/A) + (12 qt paraquat/A) | 9.7 | 8.0 | 9.8 | 9.7 | 8.0 | 5.3 |

Example 53

A test was conducted in Indiana to determine the effectiveness of the herbicide formulations of Table 101 for killing or controlling perennial ryegrass (*Lolium perenne*, LOLPE). Applications were made in June. Evaluations were made at 1, 2, 3, and 10 days after application. Treatments and corresponding percent controls are reported in Table 101.

TABLE 101

% Perennial Ryegrass Control

| TREATMENT (RATE) | 1 Day After Application | 2 Days After Application | 3 Days After Application | 10 Days After Application |
|---|---|---|---|---|
| 49 (6.0 #ae/A) | 59 | 88 | 88 | 100 |
| 49 (4.5 #ae/A) | 42 | 75 | 79 | 100 |
| 49 (3.0 #ae/A) | 21 | 63 | 75 | 100 |
| 44 (4.5 #ae/A) | 4 | 13 | 42 | 100 |
| 44 (6.0 #ae/A) | 13 | 34 | 67 | 100 |
| 2 (1.5 pints/A) | 17 | 30 | 46 | 17 |
| 1 (6.0 #ae/A) | 0 | 13 | 46 | 100 |
| 1 (6.0 #ae/A) + 3 (12 qt/A) | 17 | 29 | 50 | 100 |
| UNTREATED | 0 | 0 | 0 | 0 |

Example 54

A test was conducted in Indiana to determine the effectiveness of the herbicide formulations of Tables 102 and 103 for killing or controlling dandelion (*Taraxacum officinale*, TAROF) and white clover (*Trifolium repens*, TRFRE). Applications were made in June. Evaluations were made at 1, 2, 3 and 10 days after application. Application treatments and corresponding percent controls are reported for white clover in Table 102 and for dandelion in Table 103.

TABLE 102

% White Clover Control

| TREATMENT (RATE) | 1 Day After Application | 2 Days After Application | 3 Days After Application | 10 Days After Application |
|---|---|---|---|---|
| 49 (6 #ae/A) | 96 | 96 | 88 | 67 |
| 49 (6 #ae/A) | 88 | 75 | 84 | 75 |
| 1 (6 #ae/A) | 0 | 59 | 88 | 100 |
| 1 (6 #ae/A) + 3 (12 qt/A) | 92 | 96 | 84 | 71 |
| UNTREATED | 0 | 0 | 0 | 0 |

TABLE 103

% Dandelion Control

| TREATMENT (RATE) | 1 Day After Application | 2 Days After Application | 3 Days After Application | 10 Days After Application |
|---|---|---|---|---|
| 49 (6#ae/A) | 33 | 57 | 30 | 50 |
| 44 (6#ae/A) | 17 | 33 | 20 | 53 |
| 1 (6#ae/A) | 3 | 7 | 10 | 27 |
| 1 (6#ae/A) + 3 (12 qt/A) | 20 | 30 | 20 | 33 |
| UNTREATED | 0 | 0 | 0 | 0 |

Example 55

A test was conducted in Nebraska to determine the effectiveness of the herbicide formulations of Tables 104 and 105 for killing or controlling dandelion (*Taraxacum officinale*, TAROF), white clover (*Trifolium repens*, TRFRE) and knotweed (*Polygonum aviculare*, POLAV). Applications were made in June. Evaluations were made at 1, 2, 3, 6, 9, and 15 days after application. Application treatments and corresponding percent controls are reported in Tables 104 and 105.

TABLE 104

% White Clover Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6 # ae/A) | 30 | 43 | 67 | 43 | 70 | 83 |
| 44 (6 # ae/A) | 20 | 27 | 50 | 57 | 63 | 80 |
| 1 (6 # ae/A) | 3 | 13 | 23 | 40 | 57 | 87 |
| 1 (6 # ae/A) + 3 (12 qt/A) | 23 | 33 | 50 | 53 | 63 | 67 |
| UNTREATED | 0 | 0 | 0 | 0 | 0 | 0 |

TABLE 105

% Dandelion Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6 # ae/A) | 33 | 57 | 30 | 50 | 33 | 77 |
| 44 (6 # ae/A) | 17 | 33 | 20 | 53 | 37 | 73 |
| 1 (6 # ae/A) | 3 | 7 | 10 | 27 | 40 | 67 |

TABLE 105-continued

% Dandelion Control

| TREATMENT (RATE) | 1 Day After Application | 2 Days After Application | 3 Days After Application | 6 Days After Application | 9 Days After Application | 15 Days After Application |
|---|---|---|---|---|---|---|
| 1 (6 # ae/A) + 3 (12 qt/A) | 20 | 30 | 20 | 33 | 43 | 63 |
| UNTREATED | 0 | 0 | 0 | 0 | 0 | 0 |

Example 56

A test was conducted in Indiana to determine the effectiveness of the herbicide formulations of Table 106 for killing or controlling Kentucky bluegrass. Applications were made in June. Evaluations were made at 1, 2, 3, 6, 9, and 15 days after application. Treatments and corresponding percent controls are reported in Table 106.

TABLE 106

% Kentucky Bluegrass Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6.0 # ae/A) | 7 | 37 | 47 | 57 | 67 | 77 |
| 49 (4.5 # ae/A) | 10 | 40 | 47 | 63 | 67 | 73 |
| 49 (3.0 # ae/A) | 0 | 7 | 20 | 20 | 33 | 57 |
| 44 (4.5 # ae/A) | 3 | 7 | 20 | 27 | 33 | 63 |
| 44 (6.0 # ae/A) | 7 | 23 | 40 | 50 | 67 | 73 |
| 2 (1.5 pints/A) | 37 | 70 | 77 | 77 | 73 | 43 |
| 1 (6.0 # ae/A) | 0 | 3 | 0 | 13 | 53 | 73 |
| 1 (6.0 # ae/A) + 3 (12 qt/A) | 0 | 3 | 13 | 27 | 47 | 83 |
| UNTREATED | 0 | 0 | 0 | 0 | 0 | 0 |

Example 57

A test was conducted in Nebraska to determine the effectiveness of the herbicide formulations of Tables 107, 108 and 109 for killing or controlling dandelion (*Taraxacum officinale*, TAROF), white clover (*Trifolium repens*, TRFRE) and knotweed (*Polygonum aviculare*, POLAV). Applications were made in June. Evaluations were made at 1, 2, 3, 6, 9, and 15 days after application. Application treatments and corresponding percent controls are reported in Tables 107, 108 and 109.

TABLE 107

% White Clover Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6 # ae/A) | 30 | 43 | 67 | 43 | 70 | 83 |
| 44 (6 # ae/A) | 20 | 27 | 50 | 57 | 63 | 80 |
| 1 (6 # ae/A) | 3 | 13 | 23 | 40 | 57 | 87 |
| 1 (6 # ae/A) + 3 (12 qt/A) | 23 | 33 | 50 | 53 | 63 | 67 |
| UNTREATED | 0 | 0 | 0 | 0 | 0 | 0 |

TABLE 108

% Dandelion Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6 # ae/A) | 33 | 57 | 30 | 50 | 33 | 77 |
| 44 (6 #ae/A) | 17 | 33 | 20 | 53 | 37 | 73 |
| 1 (6 # ae/A) | 3 | 7 | 10 | 27 | 40 | 67 |
| 1 (6 # ae/A) + 3 (12 qt/A) | 20 | 30 | 20 | 33 | 43 | 63 |
| UNTREATED | 0 | 0 | 0 | 0 | 0 | 0 |

TABLE 109

% Knotweed Control

| TREATMENT (RATE) | 1 Day After Application | 2 Days After Application | 3 Days After Application | 6 Days After Application | 9 Days After Application | 15 Days After Application |
|---|---|---|---|---|---|---|
| 49 (6 # ae/A) | 33 | 33 | 50 | 63 | 83 | 83 |
| 44 (6 # ae/A) | 33 | 33 | 40 | 67 | 83 | 83 |
| 1 (6 # ae/A) | 10 | 10 | 40 | 73 | 77 | 87 |
| 1 (6 # ae/A) + 3 (12 qt/A) | 37 | 37 | 53 | 73 | 87 | 90 |
| UNTREATED | 0 | 0 | 0 | 0 | 0 | 0 |

Example 58

A test was conducted in Arkansas to determine the effectiveness of the herbicide formulations of Tables 110 and 111 for killing or controlling buttercup (*Ranuculus repens*, RANRE), and bittercress (*Cardamine hirsuta*, CARHI). Applications were made in April. Evaluations were made at 1, 3, 4, and 8 days after application. Treatments and corresponding percent controls are reported for buttercup in Table 108 and bittercress in Table 109.

TABLE 110

% Control Buttercup

| TREATMENT | Rate Units/A | 1 Day After Application | 3 Days After Application | 4 Days After Application | 8 Days After Application |
|---|---|---|---|---|---|
| 49 | 6 # ae | 5 | 5 | 83 | 100 |
| 44 | 6 # ae | 0 | 5 | 65 | 94 |
| 1 | 6 # ae | 0 | 4 | 59 | 95 |
| 1 + 3 | 6 # ae + 12 qt | 90 | 91 | 80 | 99 |
| UNTREATED | 0 | 0 | 0 | 0 | 0 |

TABLE 111

% Control Bittercress

| TREATMENT | Rate Units/A | 1 Day After Application | 3 Days After Application | 4 Days After Application | 8 Days After Application |
|---|---|---|---|---|---|
| 49 | 6 lb. ae | 40 | 58 | 55 | 96 |
| 44 | 6 lb. ae | 23 | 25 | 60 | 94 |
| 1 | 6 lb. ae | 23 | 23 | 58 | 95 |
| 1 + 3 | 6 lb. ae + 12 qt | 60 | 65 | 94 | 96 |
| UNTREATED | 0 | 5 | 0 | 0 | 0 |

Example 59

A test was conducted in Arkansas to determine the effectiveness of the herbicide formulations of Table 112 for bermudagrass (*Cynodon dactylon*, CYNDA). Applications were made in June. Evaluations were made at 1, 2, 3, 7, 16 and 31 days after application. Treatments and corresponding percent controls are reported for bermudagrass in Table 112.

TABLE 112

% Control Bermudagrass

| TREATMENT | Rate | 1 Day After Application | 2 Days After Application | 3 Days After Application | 7 Days After Application | 16 Days After Application | 31 Days After Application |
|---|---|---|---|---|---|---|---|
| 49 | 3 # ae/A | 63 | 60 | 67 | 82 | 80 | 98 |
| 1 | 3 # ae/A | 0 | 0 | 0 | 90 | 100 | 100 |
| 49 | 6 # ae/A | 87 | 88 | 88 | 93 | 95 | 100 |
| 1 | 6 # ae/A | 0 | 0 | 0 | 88 | 98 | 100 |
| 49 + 57 | 6 # ae/A 0.5% V/V | 77 | 87 | 87 | 93 | 93 | 100 |
| 49 + 56 | 6 # ae/A 0.25% V/V | 80 | 88 | 88 | 92 | 92 | 100 |
| 49 + 53 | 6 # ae/A 0.5% V/V | 83 | 88 | 87 | 90 | 92 | 100 |
| 1 + 54 | 6 # ae/A 0.5% V/V | 83 | 88 | 88 | 92 | 90 | 100 |
| 1 + 24 | 6 # ae/A 0.5% V/V | 90 | 92 | 88 | 90 | 92 | 100 |
| 1 + 3 | 6 # ae/A 12 qt/A | 88 | 90 | 92 | 93 | 93 | 93 |
| UNTREATED | 0 | 0 | 0 | 0 | 0 | 0 | 0 |

Example 60

A test was conducted in Nebraska to determine the effectiveness of the herbicide formulations of Table 113 for killing or controlling Kentucky bluegrass (*Trifoliam repens*, TRFRE). Applications were made in June. Evaluations were made at 1, 2, 3, 6, 9, and 15 days after application. Treatments and corresponding percent controls are reported in Table 113.

TABLE 113

| | % Kentucky Bluegrass Control | | | | | |
|---|---|---|---|---|---|---|
| TREATMENT (RATE) | 1 Day After Application | 2 Days After Application | 3 Days After Application | 6 Days After Application | 9 Days After Application | 15 Days After Application |
| 49 (6.0 # ae/A) | 7 | 37 | 47 | 57 | 67 | 77 |
| 49 (4.5 # ae/A) | 10 | 40 | 47 | 63 | 67 | 73 |
| 49 (3.0 # ae/A) | 0 | 7 | 20 | 20 | 33 | 57 |
| 44 (4.5 # ae/A) | 3 | 7 | 20 | 27 | 33 | 63 |
| 44 (6.0 # ae/A) | 7 | 23 | 40 | 50 | 67 | 73 |
| 2 (1.5 pints/A) | 37 | 70 | 77 | 77 | 73 | 43 |
| 1 (6.0 lb ae/A) | 0 | 3 | 0 | 13 | 53 | 73 |
| 1 (6.0 # ae/A) + 3 (12 qt/A) | 0 | 3 | 13 | 27 | 47 | 83 |
| UNTREATED | 0 | 0 | 0 | 0 | 0 | 0 |

In view of the above, it will be seen that the several objects of the invention are achieved. As various changes could be made in the above methods, combinations and compositions of the present invention without departing from the scope of the invention, it is intended that all matter contained in the above description be interpreted as illustrative and not in a limiting sense. All documents mentioned in this application are expressly incorporated by reference as if fully set forth at length.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An aqueous herbicidal composition useful for killing or controlling the growth of unwanted plants, comprising:
   an active component consisting essentially of glyphosate or a herbicidal derivative thereof and a bipyridilium or a herbicidal derivative thereof; and
   at least one surfactant in a concentration sufficient to enhance glyphosate absorption and translocation within a plant before leaf damage induced by the bipyridilium would interfere with further absorption and translocation of glyphosate;
   wherein the glyphosate (acid equivalent basis) and the bipyridilium (cation equivalent basis) are present in a weight ratio of between 26:1 and about 100:1.

2. An aqueous herbicidal composition useful for killing or controlling the growth of unwanted plants, comprising:
   an active component consisting essentially of glyphosate or a herbicidal derivative thereof and a bipyridilium or a herbicidal derivative thereof; and
   at least one surfactant;
   wherein the glyphosate (acid equivalent basis) and the bipyridilium (cation equivalent basis) are present in a weight ratio of between about 26:1 and about 100:1, and the glyphosate (acid equivalent basis) and the surfactant are present in a weight ratio of between about 0.7:1 and about 48:1.

3. An aqueous herbicidal composition useful for killing or controlling the growth of unwanted plants, comprising:
   an active component consisting essentially of glyphosate or a herbicidal derivative thereof and a bipyridilium or a herbicidal derivative thereof; and
   at least one surfactant in a concentration sufficient to enhance glyphosate absorption and translocation within a plant before leaf damage induced by the bipyridilium would interfere with further absorption and translocation of glyphosate;
   wherein the glyphosate (acid equivalent basis) and the bipyridilium (cation equivalent basis) are present in a weight ratio of between 16:1 and about 100:1, and the composition optionally contains an alkylpolyglycoside, the nature and concentration of said alkylpolyglycoside by itself being insufficient to enhance glyphosate absorption and translocation within a plant before leaf damage induced by the bipyridilium would interfere with further absorption and translocation of glyphosate.

4. An aqueous herbicidal liquid concentrate which may be diluted with water to provide an aqueous herbicidal application mixture for application to the foliage of a plant, said concentrate comprising:
   an active component consisting essentially of glyphosate or a herbicidal derivative thereof in a concentration of at least 120 grams acid equivalent per liter and a bipyridilium or a herbicidal derivative thereof; and
   at least one surfactant, the nature and concentration of said surfactant being such that, upon applying said application mixture to the foliage of a plant, glyphosate absorption and translocation within the plant is enhanced before leaf damage induced by the bipyridilium would interfere with further absorption and translocation of glyphosate;
   wherein the glyphosate (acid equivalent basis) and the bipyridilium (cation equivalent basis) are present in a weight ratio of between about 1:1 and about 100:1.

5. An aqueous herbicidal liquid concentrate which may be diluted with water to provide an aqueous herbicidal application mixture for application to the foliage of a plant, said concentrate comprising:
   an active component consisting essentially of glyphosate or a herbicidal derivative thereof and a bipyridilium or a herbicidal derivative thereof; and at least one surfactant, the nature and concentration of said surfactant being such that, upon applying said application mixture to the foliage of a plant, glyphosate absorption and translocation within the plant is enhanced before leaf damage induced by the bipyridilium would interfere with further absorption and translocation of glyphosate;

wherein the glyphosate (acid equivalent basis) and the bipyridilium (cation equivalent basis) are present in a weight ratio of between 26:1 and about 100:1.

6. An aqueous herbicidal liquid concentrate which may be diluted with water to provide an aqueous herbicidal application mixture for application to the foliage of a plant, said concentrate comprising:

an active component consisting essentially of glyphosate or a herbicidal derivative thereof in a concentration of at least 120 grams acid equivalent per liter and a bipyridilium or a herbicidal derivative thereof; and at least one surfactant;

wherein the glyphosate (acid equivalent basis) and the bipyridilium (cation equivalent basis) are present in a weight ratio of between about 1:1 and about 100: 1, and the glyphosate (acid equivalent basis) and the surfactant are present in a weight ratio of between about 0.5:1 and about 50:1.

7. An aqueous herbicidal liquid concentrate which may be diluted with water to provide an aqueous herbicidal application mixture for application to the foliage of a plant, said concentrate comprising:

an active component consisting essentially of glyphosate or a herbicidal derivative thereof and a bipyridilium or a herbicidal derivative thereof; and at least one surfactant, the nature and concentration of said surfactant being such that, upon applying said application mixture to the foliage of a plant, glyphosate absorption and translocation within the plant is enhanced before leaf damage induced by the bipyridilium would interfere with further absorption and translocation of glyphosate;

wherein the glyphosate (acid equivalent basis) and the bipyridilium (cation equivalent basis) are present in a weight ratio of between about 1:1 and about 100: 1, and the concentrate optionally contains an alkylpolyglycoside, the nature and concentration of said alkylpolyglycoside by itself being insufficient to enhance glyphosate absorption and translocation within a plant before leaf damage induced by the bipyridilium would interfere with further absorption and translocation of glyphosate.

8. An aqueous herbicidal liquid concentrate which may be diluted with water to provide an aqueous herbicidal application mixture for application to the foliage of a plant, said concentrate comprising:

an active component consisting essentially of glyphosate or a herbicidal derivative thereof and a bipyridilium or a herbicidal derivative thereof; and at least one surfactant, the nature and concentration of said surfactant being such that, upon applying said application mixture to the foliage of a plant, glyphosate absorption and translocation within the plant is enhanced before leaf damage induced by the bipyridilium would interfere with further absorption and translocation of glyphosate; wherein the glyphosate (acid equivalent basis) and the bipyridilium (cation equivalent basis) are present in a weight ratio of between about 1:1 and about 100:1, and the concentrate when free of dye or a coloring agent has a Gardner color value of not more than 10.

9. A herbicidal particulate solid concentrate which may be dissolved or dispersed in water to provide an aqueous herbicidal application mixture for application to the foliage of a plant, said concentrate comprising:

an active component consisting essentially of glyphosate or a herbicidal derivative thereof in a concentration of at least about 50% by weight of said concentrate and a bipyridilium or a herbicidal derivative thereof; and at least one surfactant, the nature and concentration of said surfactant being such that, upon applying said application mixture to the foliage of a plant, glyphosate absorption and translocation within the plant is enhanced before leaf damage induced by the bipyridilium would interfere with further absorption and translocation of glyphosate;

wherein the glyphosate (acid equivalent basis) and the bipyridilium (cation equivalent basis) are present in a weight ratio of between about 1:1 and about 100:1.

10. A herbicidal particulate solid concentrate which may be dissolved or dispersed in water to provide an aqueous herbicidal application mixture for application to the foliage of a plant, said concentrate comprising:

glyphosate or a herbicidal derivative thereof in a concentration of at least about 50% by weight of said concentrate;

an active component consisting essentially of glyphosate or a herbicidal derivative thereof and a bipyridilium or a herbicidal derivative thereof; and at least one surfactant;

wherein the glyphosate (acid equivalent basis) and the bipyridilium (cation equivalent basis) are present in a weight ratio of between about 1:1 and about 100: 1, and the glyphosate (acid equivalent basis) and the surfactant are present in a weight ratio of between about 1:1 and about 40:1.

11. The composition of claim 2 wherein the glyphosate and the bipyridilium are present in a weight ratio of between about 20:1 and about 80:1.

12. The composition of claim 11 wherein the glyphosate and the bipyridilium are present in a weight ratio of between about 30:1 and about 60:1.

13. The composition of claim 3 wherein the glyphosate and the surfactant are present in a weight ratio of between about 0.4:1 and about 48:1.

14. The composition of claim 13 wherein the glyphosate and the surfactant are present in a weight ratio of between about 0.5:1 and about 17:1.

15. The composition of claim 14 wherein the glyphosate and the surfactant are present in a weight ratio of between about 1:1 and about 8:1.

16. The concentrate of claim 4 wherein the glyphosate and the bipyridilium are present in a weight ratio of between about 8:1 and about 60:1.

17. The concentrate of claim 16 wherein the glyphosate and the bipyridilium are present in a weight ratio of between about 25:1 and about 50:1.

18. The concentrate of claim 4 wherein the glyphosate and the surfactant are present in a weight ratio of between about 0.1:1 and about 50:1.

19. The concentrate of claim 6 wherein the glyphosate and the surfactant are present in a weight ratio of between about 0.5:1 and about 30:1.

20. The concentrate of claim 19 wherein the glyphosate and the surfactant are present in a weight ratio of between about 2:1 and about 5:1.

21. The concentrate of claim 9 wherein the glyphosate and the bipyridilium are present in a weight ratio of between about 22:1 and about 90:1.

22. The concentrate of claim 21 wherein the glyphosate and the bipyridilium are present in a weight ratio of between about 40:1 and about 50:1.

23. The concentrate of claim 9 wherein the glyphosate and the surfactant are present in a weight ratio of between about 1:1 and about 40:1.

24. The concentrate of claim 10 wherein the glyphosate and the surfactant are present in a weight ratio of between about 1.5:1 and about 15:1.

25. The concentrate of claim 24 wherein the glyphosate and the surfactant are present in a weight ratio of between about 2:1 and about 6:1.

26. The concentrate of claim 4 wherein the liquid concentrate has a cloud point of at least about 50° C. and a crystallization point not higher than about 0° C.

27. The concentrate of claim 26 wherein the liquid concentrate has a cloud point of at least about 60° C. and a crystallization point not higher than about −10° C.

28. The concentrate of claim 27 wherein the liquid concentrate has a density of at least about 1.05 grams/liter.

29. The composition of claim 2 wherein the surfactant and the bipyridilium comprised therein are not substantially antagonistic to the herbicidal activity of the glyphosate.

30. The composition of claim 2 further including a dicarboxylic acid.

31. The composition of claim 30 wherein the dicarboxylic acid is the dicarboxylic acid is selected from the group consisting of oxalic acid, malonic acid, succinic acid, glutaric acid, maleic acid, adipic acid, and fumaric acid, and combinations or mixtures thereof.

32. The composition of claim 2 wherein the glyphosate or herbicidal derivative thereof comprises a salt of glyphosate.

33. The concentrate of claim 4 wherein the surfactant contains no effective amount of an alkylpolyglycoside.

34. The concentrate of claim 4 wherein the surfactant contains an alkylpolyglycoside in combination with at least one additional surfactant.

35. The composition of claim 2 wherein the spray composition or application mixture controls plant growth to a greater extent than a similarly loaded composition consisting essentially of trimesium glyphosate, a diquat or paraquat, and an alkylpolyglycoside surfactant.

36. The composition of claim 3 wherein said surfactant further comprises one or more amine or quaternary ammonium salt compounds, each of which comprises an alkyl or aryl substituent having from about 4 to about 16 carbon atoms and not more than ten ethylene oxide linkages within the compound, said compounds being present in an amount which enhances the compatibility of said surfactant with said glyphosate.

37. The composition of claim 36 wherein said compounds are selected from the group consisting of amines or quaternary ammonium salts having the formula:

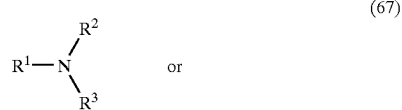

(67)

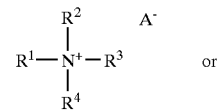

(68)

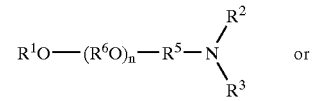

(69)

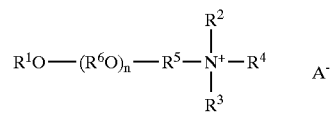

(70)

wherein $R^1$ is linear or branched alkyl or aryl having from about 4 to about 16 carbon atoms, $R^2$ is hydrogen, methyl, ethyl, or —(CH$_2$CH$_2$O)$_x$H, $R^3$ is hydrogen, methyl, ethyl, or —(CH$_2$CH$_2$O)$_y$H wherein the sum of X and y is not more than about 5; $R^4$ is hydrogen or methyl; $R^6$ in each of the n (R$^6$O) groups is independently $C_2$–$C_4$ alkylene; $R^5$ is hydrocarbylene or substituted hydrocarbylene having from 2 to about 6 carbon atoms; and A— is an agriculturally acceptable anion.

38. The composition of claim 3 wherein said surfactant is selected from the group consisting of alkoxylated alkylamines, etheramines, and etheramine oxides.

39. The composition of claim 38 wherein said alkoxylated alkylamine comprises a compound having the formula:

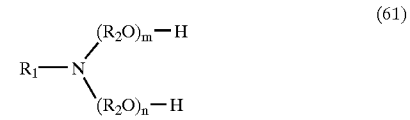

(61)

wherein $R^1$ is a straight or branched alkyl group having from about 8 to about 22 carbon atoms, $R_2$ in each ($R_2$O) group is independently a $C_2$–$C_4$ alkylene group, and m+n is an average number from 0 to about 60.

40. The composition of claim 39 wherein $R_1$ is a straight chain alkyl group having from about 12 to about 18 carbon atoms, and m+n is an average number from about 2 to about 20.

41. The composition of claim 40 wherein m+n is an average number from about 2 to about 10.

42. The composition of claim 39 wherein said alkoxylated alkylamine comprises an alkoxylated dodecylamine, alkoxylated stearylamine, alkoxylated cocoamine, or alkoxylated tallowamine.

43. The composition of claim 3 wherein said surfactant is present in a concentration of about 0.02 to about 10.7 grams per liter of said herbicidal composition.

44. The composition of claim 43 wherein said surfactant is present in a concentration of about 0.65 to about 6.4 grams per liter of said herbicidal composition.

45. The composition of claim 44 wherein said surfactant is present in a concentration of about 1.33 to about 4.3 grams per liter of said herbicidal composition.

46. The composition of claim 2 wherein said herbicidal composition comprises from about 2 to about 36 grams a.e. per liter of the glyphosate, about 0.02 to about 10.7 grams per liter of surfactant, and about 0.025 to about 0.75 grams c.e. per liter of the bipyridilium.

47. The composition of claim 46 wherein said herbicidal composition comprises from about 4 to about 18 grams a.e. per liter of glyphosate, about 0.65 to about 6.4 grams per liter of surfactant, and about 0.05 to about 0.3 grams c.e. per liter of the bipyridilium.

48. The composition of claim 47 wherein said herbicidal composition comprises from about 6 to about 11 grams a.e. per liter of glyphosate, about 1.33 to about 4.3 grams per liter of surfactant, and about 0.07 to about 0.2 grams c.e. per liter of the bipyridilium.

49. The composition of claim 2 wherein the glyphosate or herbicidal derivative thereof is present in a concentration of about 2 to about 36 grams a.e. per liter of said herbicidal composition.

50. The composition of claim 49 wherein the glyphosate or herbicidal derivative thereof is present in a concentration of about 4 to about 18 grams a.e. per liter of said herbicidal composition.

51. The composition of claim 50 wherein the glyphosate or herbicidal derivative thereof is present in a concentration of about 6 to about 11 grams acid equivalent per liter of said herbicidal composition.

52. The composition of claim 2 wherein the bipyridilium or herbicidal derivative thereof comprises diquat, paraquat or a mixture thereof.

53. The composition of claim 52 wherein the diquat comprises a salt of diquat.

54. The composition of claim 53 wherein the salt of diquat comprises a diquat halide.

55. The composition of claim 52 wherein the paraquat comprises a salt of paraquat.

56. The composition of claim 2 wherein the bipyridilium is present at a concentration ranging from about 0.025 to about 0.75 grams c.e. per liter of said herbicidal composition.

57. The composition of claim 56 wherein the bipyridilium is present at a concentration ranging from about 0.05 to about 0.3 grams c.e. per liter of said herbicidal composition.

58. The composition of claim 57 wherein the bipyridilium is present at a concentration ranging from about 0.07 to about 0.2 grams c.e. per liter of said herbicidal composition.

59. The composition of claim 2 wherein the glyphosate or herbicidal derivative thereof comprises a salt of glyphosate, and the bipyridilium or herbicidal derivative thereof comprises a salt of diquat.

60. The composition of claim 59 wherein the glyphosate or herbicidal derivative thereof comprises an alkali metal, ammonium, $C_{1-16}$ alkylammonium, $C_{1-16}$ alkanolammonium or $C_{1-16}$ alkylsulfonium salt of glyphosate, and the bipyridilium or herbicidal derivative thereof comprises a diquat halide.

61. The composition of claim 2 wherein the glyphosate or herbicidal derivative thereof is present in a concentration of about 2 to about 36 grams a.e. per liter of said herbicidal composition, and the bipyridilium or herbicidal derivative thereof is present in a concentration of about 0.025 to about 0.75 grams c.e. per liter of said herbicidal composition.

62. The composition of claim 61 wherein the glyphosate or herbicidal derivative thereof is present in a concentration of about 4 to about 18 grams a.e. per liter of said herbicidal composition, and the bipyridilium or herbicidal derivative thereof is present in a concentration of about 0.05 to about 0.3 grams c.e. per liter of said herbicidal composition.

63. The composition of claim 62 wherein the glyphosate or herbicidal derivative thereof is present in a concentration of about 6 to about 11 grams a.e. per liter of said herbicidal composition, and the bipyridilium or herbicidal derivative thereof is present in a concentration of about 0.07 to about 0.2 grams c.e. per liter of said herbicidal composition.

64. The concentrate of claim 9 wherein the particulate solid concentrate is water soluble.

65. The concentrate of claim 9 further comprising a superspreading surfactant which is present in a proportion sufficient that the surface tension of the application mixture obtained by dissolving or dispersing said solid concentrate in water to a convenient concentration is less than about 25 dynes/cm$^2$.

66. The concentrate of claim 9 wherein the glyphosate or herbicidal derivative thereof is present in a concentration of about 50% to about 95% by weight of said particulate solid.

67. The concentrate of claim 66, wherein the glyphosate or herbicidal derivative thereof is present in a concentration of about 60% to about 90% by weight of said particulate solid.

68. The concentrate of claim 67 wherein the glyphosate or herbicidal derivative thereof is present in a concentration of about 65% to about 85% by weight of said particulate solid.

69. The concentrate of claim 9 wherein the bipyridilium is present at about 0.5% to about 3% by weight (c.e.) of said particulate solid.

70. The concentrate of claim 69 wherein the bipyridilium is present at about 1% to about 2.5% by weight (c.e.) of said particulate solid.

71. The concentrate of claim 70 wherein the bipyridilium is present at about 1.3% to about 2% by weight (c.e.) of said particulate solid.

72. The concentrate of claim 9 wherein the glyphosate or herbicidal derivative thereof is present at a concentration of about 50% to about 95% by weight of said herbicidal composition, and the bipyridilium or herbicidal derivative thereof is present at a concentration of about 0.5% to about 3% by weight (c.e.) of said particulate solid.

73. The concentrate of claim 72 wherein the glyphosate or herbicidal derivative thereof is present at a concentration of about 60% to about 90% by weight of said herbicidal composition, and the bipyridilium or herbicidal derivative thereof is present at a concentration of about 1% to about 2.5% by weight (c.e.) of said particulate solid.

74. The concentrate of claim 73 wherein the glyphosate or herbicidal derivative thereof is present at a concentration of about 65% to about 85% by weight of said herbicidal composition, and the bipyridilium or herbicidal derivative thereof is present at a concentration of about 1.3% to about 2% by weight (c.e.) of said particulate solid.

75. The concentrate of claim 9 wherein said particulate solid concentrate comprises about 50% to about 90% by weight of the glyphosate, 0 to about 1% by weight of an antioxidant, 0 to about 2% by weight of an antifoam agent, about 5% to about 40% by weight of a surfactant and about 0.5% to about 3% by weight of the bipyridilium.

76. The concentrate of claim 75 wherein said particulate solid concentrate comprises about 60% to about 90% by weight of the glyphosate, about 0.2% to about 0.8% by weight of an antioxidant, about 0.2% to about 1.5% by weight of an antifoam agent, about 7% to about 30% by weight of a surfactant and about 1% to about 2.5% by weight of the bipyridilium.

77. The concentrate of claim 76 wherein said particulate solid concentrate comprises 70% to 85% by weight of the glyphosate, 0.3% to 0.5% by weight of an antioxidant, 0.6% to 1.0% by weight of an antifoam, 10% to 25% by weight of a surfactant, and 1.3% to 2% by weight of the bipyridilium.

78. The concentrate of claim 4 wherein surfactant is present in a proportion sufficient that the surface tension of the herbicidal composition is less than about 25 dynes/cm².

79. The concentrate of claim 4 wherein the glyphosate or herbicidal derivative thereof is present in a concentration of about 5 grams a.e. per liter to about 550 grams a.e. per liter of said liquid concentrate.

80. The concentrate of claim 79 wherein the glyphosate or herbicidal derivative thereof is present in a concentration of about 50 grams a.e. per liter to about 450 grams a.e. per liter of said liquid concentrate.

81. The concentrate of claim 80 wherein the glyphosate or herbicidal derivative thereof is present in a concentration of about 120 grams a.e. per liter to about 350 grams a.e. per liter of said liquid concentrate.

82. The concentrate of claim 4 wherein the bipyridilium is present at a concentration of about 0.1 grams c.e. per liter to about 50 grams c.e. per liter of said liquid concentrate.

83. The concentrate of claim 82 wherein the bipyridilium is present at a concentration of about 1 gram c.e. per liter to about 40 grams c.e. per liter of said liquid concentrate.

84. The concentrate of claim 83 wherein the bipyridilium is present at a concentration of about 3 grams c.e. per liter to about 35 grams c.e. per liter of said liquid concentrate.

85. The concentrate of claim 4 wherein the glyphosate or herbicidal derivative thereof is present in a concentration of about 5 grams a.e. per liter to about 550 grams a.e. per liter of said liquid concentrate, and the bipyridilium or herbicidal derivative thereof is present in a concentration of about 0.1 grams c.e. per liter to about 50 grams c.e. per liter of said liquid concentrate.

86. The concentrate of claim 85 wherein the glyphosate or herbicidal derivative thereof is present in a concentration of about 50 grams a.e. per liter to about 450 grams a.e. per liter of said liquid concentrate, and the bipyridilium or herbicidal derivative thereof is present in a concentration of about 1 grams c.e. per liter to about 40 grams c.e. per liter of said liquid concentrate.

87. The concentrate of claim 86 wherein the glyphosate or herbicidal derivative thereof is present in a concentration of about 120 grams a.e. per liter to about 350 grams a.e. per liter of said liquid concentrate, and the bipyridilium or herbicidal derivative thereof is present in a concentration of about 3 grams c.e. per liter to about 35 grams c.e. per liter of said liquid concentrate.

88. The concentrate of claim 7 wherein said surfactant comprises an alkoxylated alkylamine.

89. A method for killing or controlling the growth of unwanted plants comprising the step of contacting the foliage of said plants with the herbicidal composition of claim 2.

90. A method of killing or controlling weeds or unwanted vegetation comprising the steps of
   (a) diluting the liquid concentrate of claim 4 in a convenient amount of water to form an application mixture; and
   (b) applying a herbicidally effective amount of the application mixture to the foliage of the weeds or unwanted vegetation.

91. A method of killing or controlling weeds or unwanted vegetation comprising the steps of
   (a) diluting a solid particulate concentrate of claim 9 in a convenient amount of water to form an application mixture; and
   (b) applying a herbicidally effective amount of the application mixture to the foliage of the weeds or unwanted vegetation.

92. The method of claim 89 wherein the glyphosate or herbicidal derivative thereof comprises a salt of glyphosate.

93. The method of claim 89 wherein said composition or application mixture is applied to a field of vegetation at a rate effective to apply glyphosate at about 0.5 to about 12 pounds a.e. per acre of said field.

94. The method of claim 93 wherein said composition or application mixture is applied to a field of vegetation at a rate effective to apply glyphosate at about 3 to about 9 pounds a.e. per acre of said field.

95. The method of claim 94 wherein said composition or application mixture is applied to a field of vegetation at a rate effective to apply glyphosate at about 4.5 to about 7.5 pounds a.e. per acre of said field.

96. The method of claim 89 wherein the bipyridilium or herbicidal derivative thereof comprises diquat or paraquat.

97. The method of claim 96 wherein the diquat comprises a salt of diquat.

98. The method of claim 97 wherein the diquat salt comprises a diquat halide.

99. The method of claim 96 wherein the paraquat comprises a salt of paraquat.

100. The method of claim 89 wherein said composition or application mixture is applied to a field of vegetation at a rate effective to apply bipyridilium at about 0.01 to about 0.5 pounds c.e. per acre of said field.

101. The method of claim 100 wherein said composition or application mixture is applied to a field of vegetation at a rate effective to apply bipyridilium at about 0.025 to about 0.25 pounds c.e. per acre of said field.

102. The method of claim 101 wherein said composition or application mixture is applied to a field of vegetation at a rate effective to apply bipyridilium at about 0.0625 to about 0.15 pounds c.e. per acre of said field.

103. The method of claim 89 wherein the glyphosate or herbicidal derivative thereof comprises a salt of glyphosate, and the bipyridilium or herbicidal derivative thereof comprises a salt of diquat.

104. The method of claim 89 wherein said composition or application mixture is applied to a field of vegetation at a rate effective to apply glyphosate at about 0.5 to about 12 pounds a.e. per acre of said field, and bipyridilium at about 0.01 to about 0.5 pounds c.e. per acre of said field.

105. The method of claim 104 wherein said composition or application mixture is applied to a field of vegetation at a rate effective to apply glyphosate at about 3 to about 9 pounds a.e. per acre of said field, and bipyridilium at about 0.025 to about 0.25 pounds c.e. per acre of said field.

106. The method of claim 105 wherein said composition or application mixture is applied to a field of vegetation at a rate effective to apply glyphosate at about 4.5 to about 7.5 pounds a.e. per acre of said field, and bipyridilium at about 0.0625 to about 0.15 pounds c.e. per acre of said field.

107. The composition of claim 3 wherein the surfactant is selected from the group consisting of:
   (a) alkoxylated poly(hydroxyalkyl)amines having the formula:

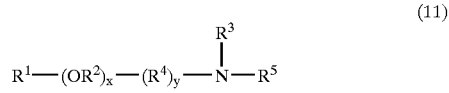

(11)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1;

(b) alkyl alkoxylated phosphates having the formulae:

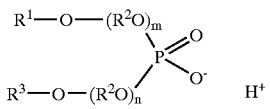

(52)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$–$C_4$ alkylene; and m and n are independently from 1 to about 30; or

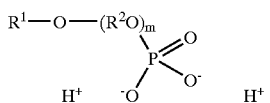

(53)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$–$C_4$ alkylene; and m is from 1 to about 30;

(c) an alkoxylated amine oxide having the formula:

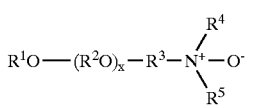

(54)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —($R^6$)$_n$—($R^2O$)$_y$$R^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60;

(d) dialkoxylated alcohols having the formula:

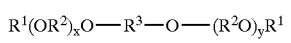

(42)

wherein $R^1$ is independently hydrogen, or a linear or branched alkyl group having from 1 to about 4 carbon atoms, $R^2$ in each of the x ($R^2O$) and the y ($R^2O$) groups is independently $C_2$–$C_4$ alkylene, $R^3$ is hydrocarbylene or substituted hydrocarbylene having from 2 to about 30 carbon atoms, and x and y are independently an average number from 1 to about 60; and (e) compounds of the formula:

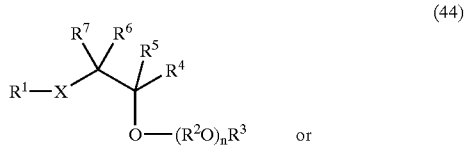

(44)

or

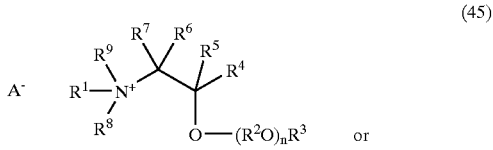

(45)

or

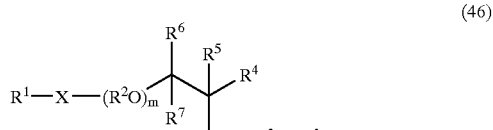

(46)

or

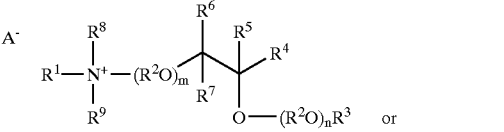

(47)

or

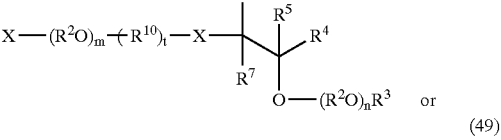

(48)

or

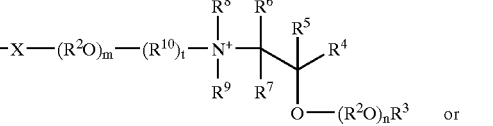

(49)

or

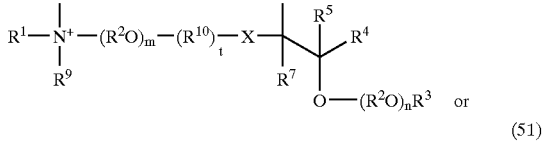

(50)

or

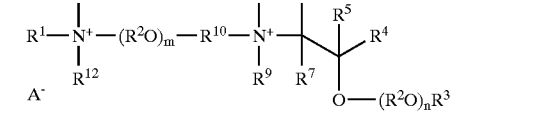

(51)

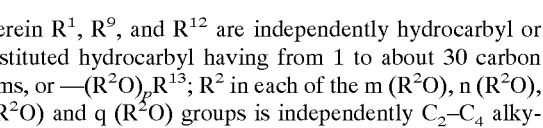

wherein $R^1$, $R^9$, and $R^{12}$ are independently hydrocarbyl or substituted hydrocarbyl having from 1 to about 30 carbon atoms, or —($R^2O$)$_p$$R^{13}$; $R^2$ in each of the m ($R^2O$), n ($R^2O$), p ($R^2O$) and q ($R^2O$) groups is independently $C_2$–$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —(CH$_2$)$_y$OR$^{13}$ or —(CH2)$_y$O ($R^2O$)$_q$$R^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrocarbyl or substituted hydrocarbyl having from 1 to about 30 carbon atoms, or —(CH$_2$)$_z$O(R$^2$O)$_p$R$^3$; m, n, p and q are independently an average number from 1 to about 50; X is independently —O—, —N(R$^{14}$)—, —C(O)—, —C(O)O—, —OC(O)—, —N(R$^{15}$)C(O)—, —C(O)N(R$^{15}$)—, —S—, —SO—, or —SO$_2$—; t is 0 or 1; A— is an agriculturally acceptable anion; and y and z are independently an integer from 0 to about 30;

(f) aminated alkoxylated alcohol having the formula:

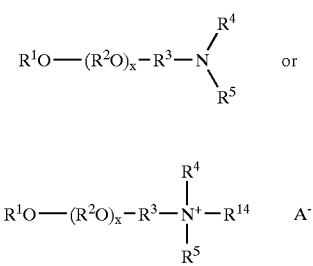

wherein R$^1$ is hydrogen or hydrocarbyl or substituted hydrocarbyl having from 1 to about 30 carbon atoms; R$^2$ in each of the x (R$^2$O) and y (R$^2$O) groups is independently C$_2$–C$_4$ alkylene; R$^3$ and R$^6$ are each independently hydrocarbylene or substituted hydrocarbylene having from 1 to about 6 carbon atoms; R$^4$ is hydrogen, hydrocarbyl or substituted hydrocarbyl having from 1 to about 30 carbon atoms, hydroxy substituted hydrocarbyl, —(R$^6$)$_n$—(R$^2$O)$_y$R$^7$, —C(=NR$^{11}$)NR$^{12}$R$^{13}$, —C(=O)NR$^{12}$R$^{13}$, —C(=S)NR$^{12}$R$^{13}$ or together with R$^5$ and the nitrogen atom to which they are attached, form a cyclic or heterocyclic ring; R$^5$ is hydrogen, hydrocarbyl or substituted hydrocarbyl having from 1 to about 30 carbon atoms, hydroxy substituted hydrocarbyl, —(R$^6$)$_n$—(R$^2$O)$_y$R$^7$, —C(=NR$^{11}$)NR$^{12}$R$^{13}$, —C(=O)NR$^{12}$R$^{13}$, —C(=S)NR$^{12}$R$^{13}$, or together with R$^4$ and the nitrogen atom to which they are attached, form a cyclic or heterocyclic ring; R$^7$ is hydrogen or a linear or branched alkyl group having 1 to about 4 carbon atoms; R$^{11}$, R$^{12}$ and R$^{13}$ are hydrogen, hydrocarbyl or substituted hydrocarbyl, R$^{14}$ is hydrogen, hydrocarbyl or substituted hydrocarbyl having from 1 to about 30 carbon atoms, hydroxy substituted hydrocarbyl, —(R$^6$)$_n$—(R$^2$O)$_y$R$^7$, —C(=NR$^{11}$)NR$^{12}$R$^{13}$, —C(=O)NR$^{12}$R$^{13}$, or —C(=S)NR$^{12}$R$^{13}$, n is 0 or 1, x and y are independently an average number from 1 to about 60, and A— is an agriculturally acceptable anion;

(g) hydroxylated amines having the formula:

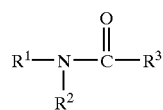

wherein R$^1$ is hydrocarbyl or substituted hydrocarbyl having from about 4 to about 30 carbon atoms, R$^2$ is hydrogen or hydrocarbyl or substituted hydrocarbyl having from 1 to about 30 carbon atoms, and R$^3$ is hydroxyalkyl, polyhydroxyalkyl, or poly(hydroxyalkyl)alkyl;

(h) diamines having the formula:

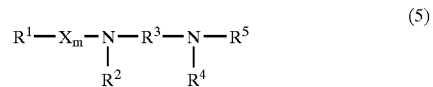

wherein R$^1$, R$^2$ and R$^5$ are independently hydrogen or hydrocarbyl or substituted hydrocarbyl having from 1 to about 30 carbon atoms or —R$^8$(OR$^9$)$_n$OR$^{10}$, R$^3$ is hydrocarbylene or substituted hydrocarbylene having from 2 to about 18 carbon atoms, R$^8$ and R$^9$ are individually hydrocarbylene or substituted hydrocarbylene having from 2 to about 4 carbon atoms, R$^4$ and R$^{10}$ are independently hydrogen or hydrocarbyl or substituted hydrocarbyl having from 1 to about 30 carbon atoms, m is 0 or 1, n is an average number from 0 to about 40, and X is —C(O)— or —SO$_2$—;

(i) mono- or di-ammonium salts having the formula:

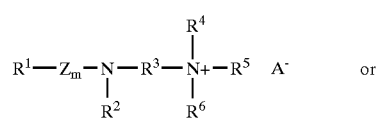

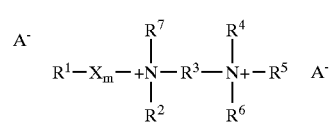

wherein R$^1$, R$^2$, R$^4$, R$^5$ and R$^7$ are independently hydrogen or hydrocarbyl or substituted hydrocarbyl having from 1 to about 30 carbon atoms or —R$^8$(OR$^9$)$_n$OR$^{10}$, R$^6$ is hydrocarbyl or substituted hydrocarbyl having from 1 to about 30 carbon atoms, R$^3$ is hydrocarbylene or substituted hydrocarbylene having from 2 to about 18 carbon atoms, R$^8$ and R$^9$ are individually hydrocarbylene or substituted hydrocarbylene having from 2 to about 4 carbon atoms, R$^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A— is an agriculturally acceptable anion;

(j) poly(hydroxyalkyl)amines having the formula:

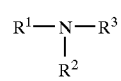

wherein R$^1$ is hydrocarbyl or substituted hydrocarbyl having from about 4 to about 30 carbon atoms or —R$^4$OR$^5$, R$^2$ is hydrogen or hydrocarbyl or substituted hydrocarbyl having from 1 to about 30 carbon atoms, R$^3$ is hydroxyalkyl, polyhydroxyalkyl, or poly(hydroxyalkyl)alkyl, R$^4$ is hydrocarbylene or substituted hydrocarbylene having from 2 to about 18 carbon atoms, and R$^5$ is hydrogen or hydrocarbyl or substituted hydrocarbyl having from 1 to about 30 carbon atoms.

(k) di-poly(hydroxyalkyl)amine having the formula:

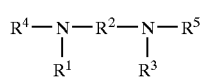
(14)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl;

(l) quaternary poly(hydroxyalkyl)amine salts having the formula:

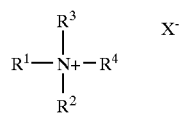
(16)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, and $R^4$ is hydroxyalkyl, polyhydroxyalkyl, or poly(hydroxyalkyl)alkyl;

(m) diamines having the formula:

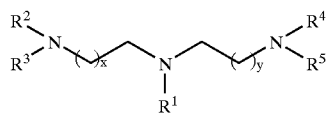
(19)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or $-(R^8)_s(R^7O)_nR^6$; $R^6$ is hydrogen or a linear or branched alkyl group having from 1 to about 4 carbon atoms, $R^7$ in each of the n $(R^7O)$ groups is independently $C_2-C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4;

(n) a secondary or tertiary amine having the formula:

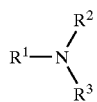
(23)

wherein $R^1$ and $R^2$ are hydrocarbyl having from 1 to about 30 carbon atoms, and $R^3$ is hydrogen or hydrocarbyl having from 1 to about 30 carbon atoms;

(o) monoalkoxylated amines having the formula:

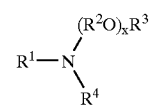
(24)

wherein $R^1$ and $R^4$ are independently hydrocarbyl or substituted hydrocarbyl groups having from 1 to about 30 carbon atoms or $-R^5SR^6$, $R^2$ in each of the x $(R^2O)$ groups is independently $C_2-C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60;

(p) dialkoxylated quaternary ammonium salt having the formula:

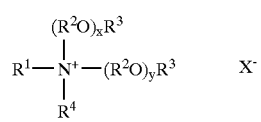
(25)

wherein $R^1$ is hydrocarbyl or substituted hydrocarbyl having from 1 to about 30 carbon atoms, $R^2$ in each of the x $(R^2O)$ and y $(R^2O)$ groups is independently $C_2-C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion;

(q) monoalkoxylated quaternary ammonium salts having the formula:

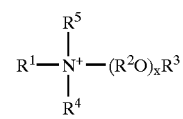
(26)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x $(R^2O)$ groups is independently $C_2-C_4$ alkylene, $R^3$ is hydrogen, or a linear or branched alkyl group having from 1 to about 30 carbon atoms, x is an average number from 1 to about 60, and X— is an agriculturally acceptable anion;

(r) quaternary ammonium salts having the formula:

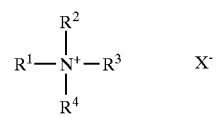
(27)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion;

(s) ether amines having the formula:

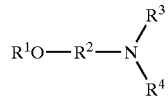

(28)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —$(R^5O)_xR^6$, $R^5$ in each of the x$(R^5O)$ groups is independently $C_2$–$C_4$ alkylene, $R^6$ is hydrogen, or a linear or branched alkyl group having from 1 to about 4 carbon atoms, and x is an average number from 1 to about 50;

(t) diamines having the formula:

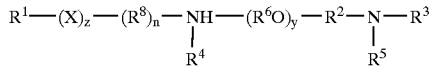

(29)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$; $R^2$ and $R^8$ are independently hydrocarbylene or substituted hydrocarbylene having from 2 to about 30 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —SO$_2$—, y is 0 or an average number from 1 to about 30, n and z are independently 0 or 1, and $R^9$ is hydrogen or hydrocarbyl or substituted hydrocarbyl;

(u) amine oxides having the formula:

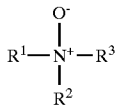

(30)

wherein $R^1$, $R^2$ and $R^3$ are independently hydrogen, hydrocarbyl or substituted hydrocarbyl, —$(R^4O)_nR^5$, or —$R^6$($OR^4)_xOR^5$; $R^4$ in each of the x $(R^4O)$ groups is independently $C_2$–$C_4$ alkylene, $R^5$ is hydrogen, hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8;

(v) dialkoxylated amines having the formula:

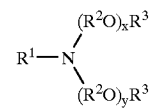

(32)

wherein $R^1$ is a hydrocarbyl or substituted hydrocarbyl having from about 6 to about 30 carbon atoms, or —$R^4SR^5$, $R^2$ in each of the x $(R^2O)$ and the y $(R^2O)$ groups is independently $C_2$–$C_4$ alkylene, $R^3$ is hydrogen, or a linear or branched alkyl group having from 1 to about 4 carbon atoms, $R^4$ is a linear or branched alkylene group having from about 6 to about 30 carbon atoms, $R^5$ is a linear or branched alkyl group having from about 4 to about 15 carbon atoms, and x and y are independently an average number from 1 to about 40;

(w) aminated alkoxylated alcohols having the following chemical structure:

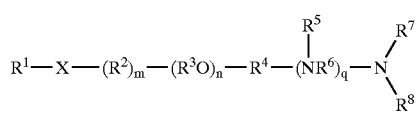

(33)

wherein $R^1$, $R^7$, $R^8$, and $R^9$ are each independently hydrogen, hydrocarbyl or substituted hydrocarbyl having from 1 to about 30 carbon atoms, or —$(R^{11})_s(R^3O)_vR^{10}$; X is —O—, —OC(O)—, —C(O)O—, —N($R^{12}$)C(O)—, —C(O)N($R^{12}$)—, —S—, —SO—, —SO$_2$— or —N($R^9$)—; $R^3$ in each of the n $(R^3O)$ groups and the v $(R^3O)$ groups is independently $C_2$–$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=$NR^{12}$)—, —C(S)—, or —C(O)—; q is an integer from 0 to 5; and $R^5$ is hydrogen or hydrocarbyl or substituted hydrocarbyl having from 1 to about 30 carbon atoms;

(x) a monoalkoxylated amine having the formula:

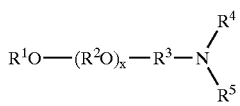

(34)

wherein $R^1$ is hydrogen or hydrocarbyl or substituted hydrocarbyl having from 1 to about 30 carbon atoms; $R^2$ in each of the x $(R^2O)$ and y $(R^2O)$ groups is independently $C_2$–$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60;

(y) quaternary ammonium, sulfonium and sulfoxonium salts having the formula:

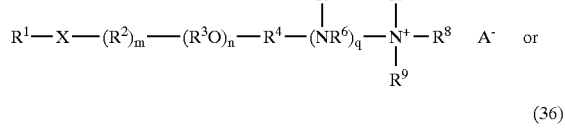

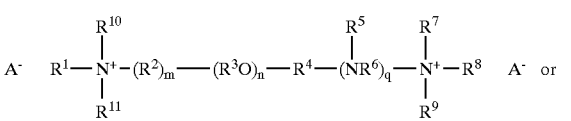

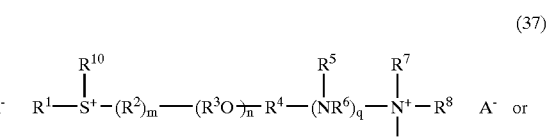

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —$(R^{13})(R^3O)_vR^{12}$; X is —O—, —OC(O)—, —N($R^{14}$)C(O)—, —C(O)N($R^{14}$)—, —C(O)O—, or —S—; $R^3$ in each of the n ($R^3O$) groups and v ($R^3O$) groups is independently $C_2$–$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=$NR^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion;

(z) a diamine or diammonium salt having the formula:

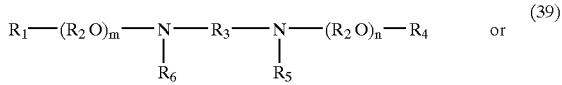

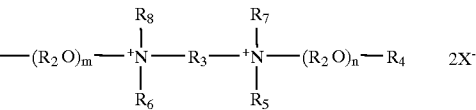

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$–$C_4$ alkylene, $R^3$ is hydrocarbylene or substituted hydrocarbylene having from about 2 to about 6 carbon atoms or —$(R^2O)_p R_9$—, m and n are individually an average number from 0 to about 50, and p is an average number from 0 to about 60;

(aa) alkoxylated alcohols having the formula:

wherein $R^1$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60;

(bb) alkoxylated dialkylphenols having the formula:

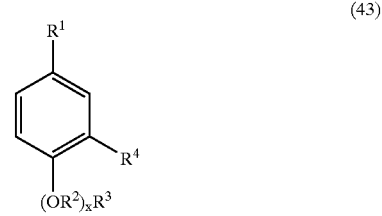

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60;

(cc) diamines having the formula:

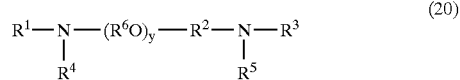

wherein $R^1$, $R^3$, $R^4$ and $R^5$ are independently hydrogen, hydrocarbyl or substituted hydrocarbyl having from 1 to about 30 carbon atoms, or —$(R^6O)_x R^7$, $R^2$ is hydrocarbylene or substituted hydrocarbylene having from 2 to about 30 carbon atoms, C(=$NR^{11}$)$NR^{12}R^{13}$—, —C(=O)$NR^{12}R^{13}$—, —C(=S)$NR^{12}R^{13}$—, —C(=$NR^{12}$)—, —C(S)—, or —C(O)—, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60; and (dd) mono- or di-quaternary ammonium salts having the formula:

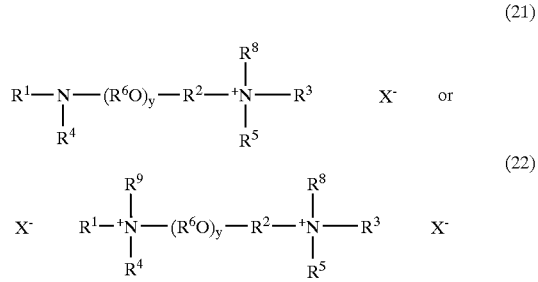

(21)

(22)

wherein $R^1$, $R^3$, $R^4$, $R^5$, $R^8$ and $R^9$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion.

108. The composition of claim 2 wherein the composition is adapted for application to foliage of a plant.

109. The composition of claim 108 wherein the composition is a spray composition.

110. The composition of claim 2 wherein the glyphosate concentration is sufficient to provide at least 70% control of plant regrowth within 50 days after application of the composition to a plant.

111. The composition of claim 2 wherein the bipyridilium concentration is sufficient to provide visual symptoms of herbicidal treatment within 3 days after application of the composition to a plant.

112. The composition of claim 110 wherein the bipyridilium concentration is sufficient to provide visual symptoms of herbicidal treatment within 3 days after application of the composition to a plant.

113. The concentrate of claim 4 wherein, upon dilution of the concentrate with water to form an application mixture, the glyphosate concentration is sufficient to provide at least 70% control of plant regrowth within 50 days after application of the application mixture to a plant.

114. The concentrate of claim 4 wherein, upon dilution of the concentrate with water to form an application mixture, the bipyridilium concentration is sufficient to provide visual symptoms of herbicidal treatment within 3 days after application of the application mixture to a plant.

115. The concentrate of claim 113 wherein, upon dilution of the concentrate with water to form an application mixture, the bipyridilium concentration is sufficient to provide visual symptoms of herbicidal treatment within 3 days after application of the application mixture to a plant.

* * * * *

UNITED STATES PATENT AND TRADEMARK OFFICE
CERTIFICATE OF CORRECTION

PATENT NO.        : 7,008,904 B2
APPLICATION NO.   : 10/204094
DATED             : March 7, 2006
INVENTOR(S)       : Crockett et al.

It is certified that error appears in the above-identified patent and that said Letters Patent is hereby corrected as shown below:

On the title page, Item 22, PCT Filed: "Feb. 13, 2001" should read -- Sept. 13, 2001 --.

Column 5, line 10: "$C_{1-6}$" should read -- $C_{1-16}$ --.

Column 5, line 14: "$C_{1-6}$" should read -- $C_{1-16}$ --.

Column 8, line 13: "$-C(-O)NR^{12}R^{13}$" should read -- $-C(=O)NR^{12}R^{13}$ --.

Column 8, line 20: "$-(6)_n-(R^2O)_yR^7$" should read -- $-(R^6)_n-(R^2O)_yR^7$ --.

Column 9, Formula (4):

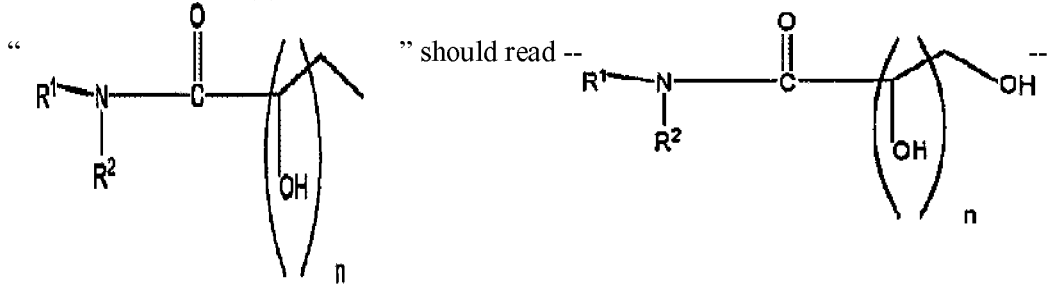

Column 10, line 45: "C(O)–" should read -- –C(O)– --.

Column 16, line 27: "$(R^{70})$" should read -- $(R^7O)$ --.

Column 16, line 51: "$-C(S)NR^{12}R^{13}$" should read -- $-C(=S)NR^{12}R^{13}$ --.

Column 17, line 48: "$X^{31}$" should read -- $X^-$ --.

Column 18, line 47: "$R_1$" should read -- $R^1$ --.

Column 19, line 61: "$R^1$" should read -- $R^3$ --.

Column 20, line 5: "R" should read -- $R^2$ --.

Column 20, line 16: "$R^1$" should read -- $R^2$ --.

Column 21, line 50: "to-about" should read -- to about --.

Column 22, line 30: "$-(R^5O)R^6$" should read -- $-(R^5O)_xR^6$ --.

UNITED STATES PATENT AND TRADEMARK OFFICE
CERTIFICATE OF CORRECTION

PATENT NO. : 7,008,904 B2
APPLICATION NO. : 10/204094
DATED : March 7, 2006
INVENTOR(S) : Crockett et al.

It is certified that error appears in the above-identified patent and that said Letters Patent is hereby corrected as shown below:

Column 22, line 36: "–$(R^5O)_nR^6$" should read -- –$(R^5O)_xR^6$ --.

Column 22, line 36: "$(R^{5O})$" should read -- $(R^5O)$ --.

Column 23, line 65: "$(C_{12},$" should read -- $(C_{10},$ --.

Column 33, line 65: "–$(C_2)_yO(R^2O)_qR^3$" should read -- –$(CH_2)_yO(R^2O)_qR^3$ --.

Column 34, line 7: "to-about" should read -- to about --.

Column 34, Formula (53):

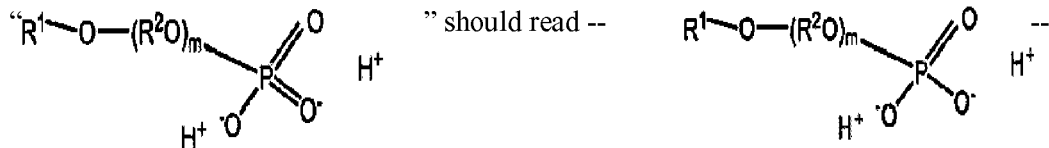 should read --

Column 37, line 26: "$R^4$" should read -- $R_4$ --.

Column 37, line 26: "$R^6$" should read -- $R_6$ --.

Column 39, Formula (61):

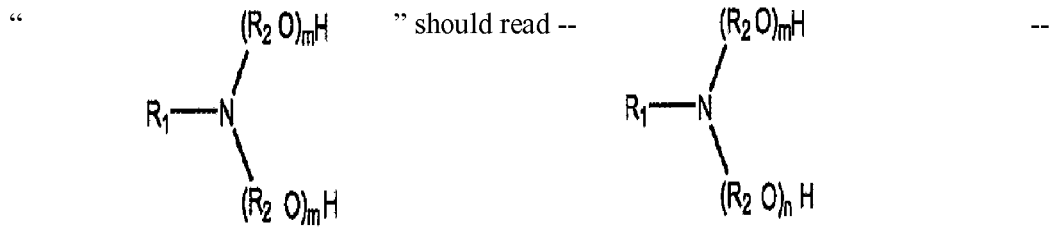 should read --

Column 48, lines 4-5: "$C_{1-6}$ alkylammonium" should read -- $C_{1-16}$ alkylammonium --.

Column 49, line 13: "335" should read -- 3-35 --.

Column 57, line 58, Table 3: "+2" should read -- +3 --.

Column 58, line 14, Table 4: "+4 2" should read -- +2 --.

Column 83, line 48, Table 41: "#gly ae/A)" should read -- #aegly/A) --.

UNITED STATES PATENT AND TRADEMARK OFFICE
CERTIFICATE OF CORRECTION

PATENT NO.      : 7,008,904 B2
APPLICATION NO. : 10/204094
DATED           : March 7, 2006
INVENTOR(S)     : Crockett et al.

It is certified that error appears in the above-identified patent and that said Letters Patent is hereby corrected as shown below:

Column 86, line 51: "arc" should read -- are --.

Column 91, line 27: "STSE" should read -- STPSE --.

Column 99, line 42, Table 60: "Ae" should read -- ae --.

Column 99, line 44, Table 60: "Ae" should read -- ae --.

Column 99, line 45, Table 60: "Ae" should read -- ae --.

Column 100, line 56, Table 62: "Ae" should read -- ae --.

Column 100, line 58, Table 62: "Ae" should read -- ae --.

Column 100, line 59, Table 62: "Ae" should read -- ae --.

Column 114, line 46: "7, 9, 12, 15, 20 and 28 days" should read -- 7, 9, 12, 15, 20, 28 and 35 days --.

Column 122, line 9, Table 102: "49" should read -- 44 --.

Column 125, lines 23-24: "Table 108" should read -- Table 110 --.

Column 125, line 24: "Table 109" should read -- Table 111 --.

UNITED STATES PATENT AND TRADEMARK OFFICE
CERTIFICATE OF CORRECTION

PATENT NO. : 7,008,904 B2
APPLICATION NO. : 10/204094
DATED : March 7, 2006
INVENTOR(S) : Crockett et al.

It is certified that error appears in the above-identified patent and that said Letters Patent is hereby corrected as shown below:

Column 138, claim 107, Formula (49):

"
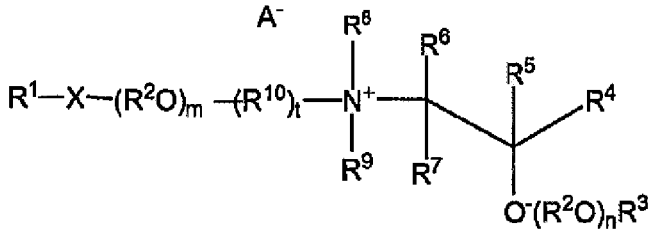
"

should read

--
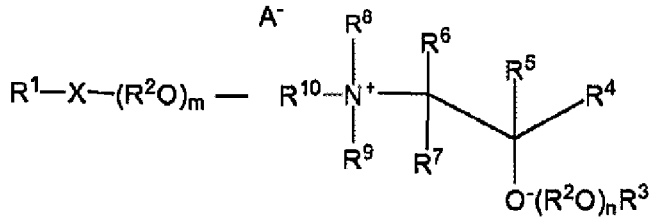
--.

Signed and Sealed this

Seventh Day of August, 2007

JON W. DUDAS
*Director of the United States Patent and Trademark Office*